(12) United States Patent
Brugliera et al.

(10) Patent No.: US 6,774,285 B1
(45) Date of Patent: Aug. 10, 2004

(54) NUCLEIC ACID SEQUENCES ENCODING FLAVONOID 3'-HYDROXYLASE AND METHODS OF ALTERING FLOWER COLOR THEREWITH

(75) Inventors: Filippa Brugliera, Preston (AU); Timothy Albert Holton, Elwood (AU); Michael Zenon Michael, Belair (AU)

(73) Assignee: Florigene Limited, Collingwood (AU)

( * ) Notice: Subject to any disclaimer, the term of this patent is extended or adjusted under 35 U.S.C. 154(b) by 0 days.

(21) Appl. No.: 09/142,108

(22) PCT Filed: Feb. 28, 1997

(86) PCT No.: PCT/AU97/00124

§ 371 (c)(1),
(2), (4) Date: Mar. 29, 1999

(87) PCT Pub. No.: WO97/32023

PCT Pub. Date: Sep. 4, 1997

(30) Foreign Application Priority Data

Mar. 1, 1996 (AU) .............................................. PN8386

(51) Int. Cl.$^7$ ............................. A01H 5/00; A01H 5/10; C12N 15/29; C12N 15/52; C12N 15/82
(52) U.S. Cl. .................... 800/298; 435/320.1; 536/23.2; 536/23.6; 800/282
(58) Field of Search .......................... 435/69.1, 320.1, 435/419, 463; 536/23.2, 23.6; 800/282, 286, 298, 323, 323.1, 323.2, 323.3

(56) References Cited

FOREIGN PATENT DOCUMENTS

WO     WO 93/20206     11/1992     ............ H05K/7/14

OTHER PUBLICATIONS

Altschul, et al. (1990) *J. Mol. Biol 215*:403–410.
Ashikari, et al. (1989) *Appl. Microbiol Biotechnol. 30*:515–520.
Baird, et al. (1987) *EMBO Journal 6*:3223–3231.
Bechtold, et al. (1993) *Scineces de la vir 316*:1194–1199.
Bethesda Research Laboratories (1986) "BRLpUC host: *E. Coli* DH5α™ competent cells." *Bethesda Res. Lab. Focus, 8*(2):9.
Brugliera, et al. (1994) *Plant J. 5(1)*:81–92.
Church, et al. *PNAS USA 81*:1991–1995 (1984).
Chomczynski, et al. (1987) *Anal. Biochem 162*:156–159.
Comai, et al. (1990) *Plant Mol. Biol. 15*:373–381.
Cornu, et al. (1989) *Petunia Hybrida 2(14)*:6.113–6.124.
Davies, et al. (1993) *Plant Science 95*:67–77.
D'Alessio, et al. (1992) *Focus 14*:76–79.
De Greve, et al., *Mol. Appl Genet 1*:499–511 (1983).
Dellaporta, et al. (1983) *Plant Mol. Biiol. Rep. 1*:19–21.
Doodeman, et al. (1984) *Appl. Genet. 67*:357–366.
Dooner, et al. (1991) *Ann. Rev. Genet 25*:173–199.
Fritsch, et al. (1975) Biosynthesis of cyanidin in cell cultures of *Haplopappus gracillus*. *Phytochemistry, 14*:2437–2442.

Frohman, et al. (1988) *Proc. Natl. Acad. Sci. USA 85*:8998–9002.
Gamborg, et al. (1988) *Exp. Cell Res. 50*:151–158.
Garfinkel, et al. (1980) *J. Bacteriol. 144(2)*:732–743.
Forkman, et al. (1980) Anthocyanin biosynthesis on flowers of *Matthiola incana*. Flavanone 3– and flavanoid 3' hydroxylases. *Z. Naturforsch 35c*:691–695.
Forkman, et al. (1981) Genetic control of flavanone 3–hydroxylase activity and flavanoid 3'hydroxylase activity in *Antirrhinium majus*(snapdragon). *Z. Naturforsch 36c*:411–416.
Forkman, G. (1991) *Plant Breeding 106*:1–26.
Franck, et al. (1980) *Cell 21*:285–294.
Gleave, A.P. (1992) *Plant Molecular Biology 20*:1203–1207.
Guilley, et al. (1982) *Cell 30*:763–773.
Hahlbrock, et al. (1979) *Annu. Rev. Plant Physiol. 30*:105–130.
Hanahan, D. (1983) *J. Mol. Biol. 166*:557–580.
Haughn, et al. (1986) *Molecular and General Genetics 204*:430–434.
Holton, et al. (1993) *Nature 366*:276–279.
Holton, et al. (1995) *Plant Cell 7*:1071–1083.
Inoue, et al. (1990) *Gene 96*:23–28.
Ito, et al. (1983) *J. Bacteriol 153(1)*:163–168.
Jefferson, et al. (1987) *Plant Molecular Biology Reporter 5(4)*:387–405.
Jefferson, et al. (1987) *EMBO J. 6*:3901–3907.
Koornneef, et al. (1982) *Arabidopsis Information Service 19*:113–115.
Kozak, M. (1989) *J. Cell Biol. 108*:229–241.
Lander, et al. (1987) *Genomics 121*:185–199.
Lazo, et al. (1991) *Bio/technology 9*:963–967.
Ledger, et al. (1991) *Plant Cell Reports 10*:195–199.
Liang, et al. (1993) *Science 257*:967–971.
Liang, et al. (1993) *Nucl. Acids Res. 21*:3269–3275.
Marchuk, et al. (1990) *Nucl. Acids Res. 19(5)*:1154.
Markham, et al. *Phytochem. 34*:679–685 (1993).
Martin, et al. (1993) *The Molecular biology of flowering*. (Jordan, B.R. ed), UK, CAB International: 219–255.
McLean, et al. (1990) *Heredity 61*:341–346.
Merrifield, J. (1964) J. Am Chem. Soc. 85:2149–2154.
Mizutani, et al. (1993) *Biochem. Biophys. Res.Commun. 190*:875–880.
Murashige, et al. (1962) *Physiol. Plant 15*:473–497.
Nelson, et al. (1996) "P450 superfamily: update on new sequences, gene mapping, accession numbers and nomenclature", *Pharmacogentics,* 6:1–42.
Newman, et al. (1994) *Plant Physiol. 106*:1241–1255.
Pearson, et al. (1988) *Proc. Natl. Acad. Sci. USA 85*:2444–2448.

(List continued on next page.)

*Primary Examiner*—Amy J. Nelson
(74) *Attorney, Agent, or Firm*—Scully, Scott, Murphy & Presser

(57) ABSTRACT

The present invention relates generally to nucleic acid sequences encoding flavonoid 3'-hydroxylase (hereinafter referred to as "F3'H") and their use in the manipulation of pigmentation in flowers of plants.

30 Claims, 25 Drawing Sheets

OTHER PUBLICATIONS

Sato, et al. (1997) "Structural analysis of *Arabidopsis thaliana* chromosomes 5.I. Sequence features of the 1.6Mb regions covered by twenty physically assigned P1 clones." *DNA Res. 4:*215–230.

Schenk, et al. (1972) *Can. J. Bot. 50:*199–204.

Spribille, et al. (1982) Chalcone synthesis and hydroxylation of flavonoids in 3"–positions with enzyme preparations from flowers of *Dianthis caryophyllus* L. (carnation). *Planta 155:* 176–182.

Stafford, H.A., (1990) *Flavonoid Mebabolism,* CRC Press, Inc. Boca Raton, Florida, USA.

Stotz, et al. (1982) *Naturforsch 37c:*19–23.

Tabak, et al. (1978) *Planta 139:*67–71.

Tanaka, et al. (1988) *Biochem 103:*954–961.

Tanaka, et al. (1996) *Plant Cell Physiol. 37*(5):711–716.

Wallroth, et al. (1986) *Mol. Gen. Genet 202:*6–15.

Wiering, et al. (1984) "Inheritance and Biochemistry of Pigments." In: *Petunia Sink,* K.C. (ed.), Springer–Verlag, Berlin, Germany:49–65.

Figure 20 (iii)

```
A 228 qLnWLDIQGVAAKMKKLHARFDAFLTdILE 257
B 214 aLEcLDLQGVASKMKKLHHkRlDnFMSnILE 243
C 234 pLEkLDLQGVIAKMKKLHlRFDSFLSkILg 263
D 225 sLDWLDLQGVAgKMKRLHkRFDAFLSsILk 254
E 226 sLEWLDLQGVASKMKKLHkRFDdFLTaIVE 255
F 223 vLDlfDLQGITkKMKKLHvRFDSFLSkIVE 252
G 227 fLEpLDLQGVASKMKKLHARFDAFLTeIVr 256
H 225 vLgWfDVQGIvgKMKKLHARFDAFLntILE 254
I 187 vLDWfDLQGIAgKMKKLHARFDkFLngILE 216
J  75 aLDWfDLQGITAKMKKVHARFDAFLdaILE 104
K 225 fLEkIDpQGIkrRMtnnfTKFlglISgLID 254
```

```
A 258 EHKgk-----ifgemkDLLSTLISLKndda 282
B 244 EHKsva----hqqnggDLLSiLISLK-dnc 268
C 264 DHKiNss-detkgHs-DLLnmLISLKdadd 291
D 255 EHemNg----qdqKhtDMLSTLISLKgtdl 280
E 256 DHKkGs----gtaghvDMLTTLLSLK-eda 280
F 253 EHKtap----gglghtDLLSTLISLKddad 278
G 257 ERchGqi-nnsgaHqdDLLSTLISfKgldd 285
H 255 EHKcvnnqhttlsKdvDtLSTLIrLKdnga 284
I 217 DRKsNgsn--gaeQyvDLLSvLISLQdsni 244
J 105 EHKsNgsr--gakQhvDLLSmLISLQdnni 132
K 255 DRlkern--lrdnaniDVLdALLnIsqenp 282
```

```
A 283 DNdg--GKLTDTEIKALLLNLFvAGTDTSS 310
B 269 DG--eGGKfSaTEIKALLLdLFTAGTDTSS 296
C 292 ae---GGRLTDvEIKALLLNLFAAGTDTTS 318
D 281 DG--dGGsLTDTEIKALLLNMFTAGTDTSA 308
E 281 DG--eGGKLTDTEIKALLLNMFTAGTDTSS 308
F 279 ie---GGKLTDTEIKALLLNLFAAGTDTSS 305
G 286 gd---CsRLTDTEIKALLLNLl----DTTS 308
H 285 DmdceeGKLTDTEIKALLLNLFTAGTDTSS 314
I 245 DGgdeGtKLTDTEIKALLLNLFiAGTDTSS 274
J 133 DG-esGaKLTDTEIKALLLNLFTAGTDTSS 161
K 283 Ee-----IdrNQIeqLcLdLFAAGTDTTS 306
```

```
A 311 STVEWAIAELIRNPKILaQAQQEIDkVVGR 340
B 297 STtEWAIAELIRHPKILaQvQQEMDsVVGR 326
C 319 STVEWCIAELVRHPeILaQvQkELDsVVGK 348
D 309 STVDWAIAELIRHPdIMvKAQEELDiVVGR 338
E 309 STVEWAIAELIRHPHMLaRvQkELDdfVGH 338
F 306 STVEWAIAELIRHPQILkQAREIDaVVGQ 335
G 309 STVEWAVAELLRHPKtLaQvRQELDsVVGK 338
H 315 STVEWAIALLRNPKILnQAQQELDlVVGQ 344
I 275 STVEWAMAELIRNPKLLvQAQEELDrVVGp 304
J 162 STVEWAIAELIRNPeVLvQAQQELDrVVGp 191
K 307 nTLEWAMAELLQNPHtLqKAQEELaqVIGK 336
```

Figure 20 (iv)

```
A  341  d RLVgElDL aQLtYLEAIVKETFRLHPSTP  370
B  327  d RLIAEADI pNLtfQAVIKEvFRLHPSTP  356
C  349  n RVVkEADL agLPPLQAVVKENFRLHPSTP  378
D  339  d RpVnESDI aQLPYLQAVIKENFRLHPpTP  368
E  339  d RLVTESDI pNLPYLQAVIKETFRLHPSTP  368
F  336  d RLVTEIDL sQLtYLQALVKEvFRLHPSTP  365
G  339  n RLVSETDL nQLPYLQAVVKETFRLHPpTP  368
H  345  n QLVTESDL tdLPFLQAIVKETFRLHPSTP  374
I  305  n RfVTESDL pQLtFLQAVIKETFRLHPSTP  334
J  192  s RLVTESDL pQLaPLQAVIKETFRLHPSTP  221
K  337  g KqVeEADV grLPYLrCIVKETlRIHPAAP  366

A  371  LSLPRIASESCEINGY fIPKGSTLLLNVWA  400
B  357  LSLPRVAnESCEINGY hIPKNTTLLVNVWA  386
C  379  LSLPRIAhESCEVNGY lIPKGSTLLVNVWA  408
D  369  LSLPHIASESCEINGY hIPKGSTLLtNIWA  398
E  369  LSLPRMAAESCEINGY hIPKGSTLLVNVWA  398
F  366  LSLPRISSESCEVdGY yIPKGSTLLVNVWA  395
G  369  LSLPRLAeddCEIdGY lIPKGSTLLVNVWA  398
H  375  LSLPRMgAQgCEINGY fIPKGATLLVNVWA  404
I  335  LSLPRMAAEdCEINGY yVseGSTLLVNVWA  364
J  222  LSLPRMASEgCEINGY sIPKGSTLLVNVWS  251
K  367  LlIPRkveEdvELstY iIPKdsqVLVNVWA  396

A  401  IARDPn aWADPLEFRPERFLPGGEKPkVDV  430
B  387  IARDPe VWADPLEFKPERFLPGGEKPNVDV  416
C  409  IARDPn VWdEPLEFRPERFLkGGEKPNVDV  438
D  399  IARDPd qWSDPLaPKPERFLPGGEKsGVDV  428
E  399  ISRDPa eWADPLEFKPERFLPGGEKPNVDI  428
F  396  IARDPk MWADPLEFRPsRFLPGGEKPGaDV  425
G  399  IARDPk VWADPLEFRPERFLtGGEKadVDV  428
H  405  IARDPn VWTnPLEFnPhRFLPGGEKPNVDI  434
I  365  IARDPn aWAnPLDFnPtRFLaGGEKPNVDV  394
J  252  IARDPs IWADPLEFRPaRFLPGGEKPNVDV  281
K  397  IgRnsdLWenPLvFKPERFwes----eIDI  422

A  431  RGNDPEVIPFGAGRRICAGMnLGIRMVQLM  460
B  417  KGNDPELIPFGAGRRICAGLSLGLRMVQLM  446
C  439  RGNDPELIPFGAGRRICAGMSLGIRMVQLL  468
D  429  KGsDPELIPFGAGRRICAGLSLGLRtIQfL  458
E  429  RGNDPEVIPFGAGRRICAGMSLGLRMVHLM  458
F  426  RGNDPEVIPFGAGRRICAGMSLGLRMVQLL  455
G  429  KGNDPEVIPFGAGRRICAGVgLGIRMVQLL  458
H  435  KGNDPEVIPFGAGRRICSGMSLGIRMVHLL  464
I  395  KGNDPEVIPFGAGRRICAGMSLGIRMVQLV  424
J  282  RGNDPEVIPFGAGRRICAGMSLGLRMVQLs  311
K  423  RGrDPELIPFGAGRRICpGLpLaMRMIpVa  452
```

NUCLEIC ACID SEQUENCES ENCODING FLAVONOID 3'-HYDROXYLASE AND METHODS OF ALTERING FLOWER COLOR THEREWITH

FIELD OF THE INVENTION

The present invention relates generally to genetic sequences encoding flavonoid pathway metabolising enzymes and more particularly to flavonoid 3'-hydroxylase (hereinafter referred to as "F3'H") or derivatives thereof and their use in the manipulation of pigmentation in plants and other organisms.

Bibliographic details of the publications referred to by the author in this specification are collected at the end of the description. Sequence Identity Numbers (SEQ ID NOs) for the nucleotide and amino acid sequences referred to in the specification and claims are defined following the bibliography. A summary of the SEQ ID NOs, and the sequences to which they relate, is provided prior to the Examples.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

DESCRIPTION OF THE RELATED ART

The rapidly developing sophistication of recombinant DNA technology is greatly facilitating research and development in a range of biotechnology related industries. The horticultural industry has become a recent beneficiary of this technology which has contributed to developments in disease resistance in plants and flowers exhibiting delayed senescence after cutting. Some attention has also been directed to manipulating flower colour.

The flower industry strives to develop new and different varieties of flowering plants. An effective way to create such novel varieties is through the manipulation of flower colour. Classical breeding techniques have been used with some success to produce a wide range of colours for most of the commercial varieties of flowers. This approach has been limited, however, by the constraints of a particular species' gene pool and for this reason it is rare for a single species to have a full spectrum of coloured varieties. In addition, traditional breeding techniques lack precision. The aesthetic appeal of the flower is a combination of many factors such as form, scent and colour; modification of one character through hybridization can often be at the expense of an equally valuable feature. The ability to genetically engineer precise colour changes in cutflower and ornamental species would offer significant commercial opportunities in an industry which has rapid product turnover and: where novelty is an important market characteristic.

Flower colour is predominantly due to two types of pigment: flavonoids and carotenoids. Flavonoids contribute to a range of colours from yellow to red to blue. Carotenoids impart an orange or yellow tinge and are commonly the major pigment in yellow or orange flowers. The flavonoid molecules which make the major contribution to flower colour are the anthocyanins which are glycosylated derivatives of cyanidin, delphinidin, petunidin, peonidin, malvidin and pelargonidin, and are localised in the vacuole. The different anthocyanins can produce marked differences in colour. Flower colour is also influenced by co-pigmentation with colourless flavonoids, metal complexation, glycosylation, acylation and vacuolar pH (Forkmann, 1991).

The biosynthetic pathway for the flavonoid pigments (hereinafter referred to as the "flavonoid pathway") is well established and is shown in FIGS. 1a and 1b (Ebel and Hahlbrock, 1988; Hahlbrock and Grisebach, 1979; Wiering and De Vlaming, 1984; Schram et al., 1984; Stafford, 1990; Van Tunen and Mol, 1990; Dooner et al, 1991; Martin and Gerats, 1993; Holton and Cornish, 1995). The first committed step in the pathway involves the condensation of three molecules of malonyl-CoA with one molecule of peoumaroyl-CoA. This reaction is catalysed by the enzyme chalcone synthase (CHS). The product of this reaction, 2',4,4',6', tetrahydroxy-chalcone, is normally rapidly isomerized to produce naringenin by the enzyme chalcone flavanone isomerase (CHI). Naringenin is subsequently hydroxylate at the 3 position of the central ring by flavanone 3-hydroxylase (F3H) to produce dihydrokaempferol (DHK).

The pattern of hydroxylation of the B-ring of DHK plays a key role in determining petal colour. The B-ring can be hydroxylated at either the 3', or both the 3' and 5' positions, to produce dihydroquercetin (DHQ) and dihydromyricetin (DHM), respectively. Two key enzymes involved in this pathway are flavonoid 3'-hydroxylase and flavonoid 3',5'-hydroxylase, both of the cytoclrome P450 class. Cytochrome P450 enzymes are widespread in nature and genes have been isolated and sequenced from vertebrates, insects, yeasts, fungi, bacteria and plants.

Flavonoid 3'-hydroxylase acts on DHK to produce DHQ and on naringenin to produce eriodictyol. Reduction and glycosylation of DHQ produces the cyanidin-glycoside and peonidin-glycoside pigments which, in many plant species (for example rose, carnation and chrysanthemum), contribute to red and pink flower colour. The synthesis of these anthocanins can also result in other flower colours. For example, blue cornflowers contain emcyan. The ability to control flavonoid 3'-hydroxylase activity, or other enzymes involved in the flavonoid pathway, in flowering plants would provide a means to manipulate petal colour. Different coloured versions of a single cultivar could thereby be generated and in some instances a single species would be able to produce a broader spectrum of colours.

A nucleotide sequence (referred to herein as SEQ ID NO:26) encoding a petunia flavonoid 3'-hydroxylase has been cloned (see International Patent Application No. PCT/AU93/00127 [WO 93/120206]). However, this sequence was inefficient in its ability to modulate the production of 3'-hydroxylated anhocyanins in plants There is a need, therefore, to identify further genetic sequences encoding flavonoid 3'-hydroxylases which efficiently modulate the hydroxylation of flavonoid compounds in plants. More particularly, there is a need to identify further genetic sequences encoding flavonoid 3'-hydroxylases which efficiently modulate the production of 3'-hydroxylated anthocyanins in plants.

SUMMARY OF THE INVENTION

In accordance with the present invention, genetic sequences encoding flavonoid 3'-hydroxylase have been identified and cloned. The recombinant genetic sequences of the present invention permit the modulation of expression of genes encoding this enzyme by, for example, de novo expression, over-expression, suppression, antisense inhibition and ribozyme activity. The ability to control flavonoid 3'-hydroxylase synthesis in plants permits modulation of the composition of individual anthocyanins as well as alteration of relative levels of flavonols and anthocyanins, thereby enabling the manipulation of tissue colour, such as petals, leaves, seeds and fruit. The present invention is hereinafter described in relation to the manipulation of flower colour but this is done with the understanding that it extends to manipulation of other plant tissues, such as leaves, seeds and fruit.

DETAILED DESCRIPTION OF THE INVENTION

Accordingly, one aspect of the present invention provides an isolated nucleic acid molecule comprising a sequence of nucleotides encoding a flavonoid 3'-hydroxylase or a derivative thereof wherein said flavonoid 3'-hydroxylase or its derivative is capable of more efficient modulation of hydroxylation of flavonoid compounds in plants than is a flavonoid 3'-hydroxylase encoded by the nucleotide sequence set forth in SEQ ID NO:26.

Efficiency as used herein relates to the capability of the flavonoid 3'-hydroxylase enzyme to hydroxylate flavonoid compounds in a plant cell. This provides the plant with additional substrates for other enzymes of the flavonoid pathway able to further modify this molecule, via, for example, glycosylation, acylation and rhamnosylation, to produce various anthocyanins which contribute to the production of a range of colours. The modulation of 3'-hydroxylated anthocyanins is thereby permitted. Efficiency is conveniently assessed by one or more parameters selected from: extent of transcription, as determined by the amount of mRNA produced; extend of hydroxylation of naringenin and/or DHK; extent of translation of mRNA, as determined by the amount of translation product produced; extent of production of anthocyanin derivatives of DHQ or DHM; the extent of effect on tissue colour, such as flowers, seeds, leaves or fruits.

Another aspect of the present invention is directed to an isolated nucleic acid molecule comprising a sequence of nucleotides which maps to the genetic locus designated Ht1 or Ht2 in petunia, or to equivalent such loci in other flowering plant species, and wherein said isolated nucleic acid molecule encodes, or is complementary to a sequence which encodes, a flavonoid 3'-hydroxylase.

A further aspect of the present invention contemplates an isolated nucleic acid molecule comprising a sequence of nucleotides which corresponds to the genetic locus designated Ht1 or Ht2 in petunia, or to loci in other flowering plant species which contain sequences which control production of 3'-hydroxylated flavonoids, and wherein said isolated nucleic acid molecule encodes a flavonoid 3'-hydroxylase or a derivative thereof which is capable of more efficient conversion of DHK to DHQ in plants than is the flavonoid 3'-hydroxylase set forth in SEQ ID NO:26.

In accordance with the above aspects of the present invention there is provided a nucleic acid molecule comprising a nucleotide sequence or complementary nucleotide sequence substantially as set forth in SEQ ID NO:1 or having at least about 60% similarity thereto or capable of hybridising to the sequence set forth in SEQ ID NO:1 under low stringency conditions.

In a related embodiment, there is provided a nucleic acid molecule comprising a nucleotide sequence or complementary nucleotide sequence substantially as set forth in SEQ ID NO:3 or having at least about 60% similarity thereto or capable of hybridising to the sequence set forth in SEQ ID NO:3 under low stringency conditions.

In another related embodiment, the present invention is directed to a nucleic acid molecule comprising a nucleotide sequence or complementary nucleotide sequence substantially as set forth in SEQ ID NO:5 or having at least about 60% similarity thereto or capable of hybridising to the sequence set forth in SEQ ID, NO:5 under low stringency conditions.

Yet another related embodiment provides a nucleic acid molecule comprising a nucleotide sequence or complementary nucleotide sequence substantially as set forth in SEQ ID NO:7 or having at least about 60% similarity thereto or capable of hybridising to the sequence set forth in SEQ ID NO:7 under low stringency conditions.

Still yet a further embodiment of the present invention relates to a nucleic acid molecule comprising a nucleotide sequence or complementary nucleotide sequence substantially as set forth in SEQ ID NO:9 or having at least about 60% similarity to the coding region thereof or capable of hybridising to the sequence set forth in SEQ ID NO:9 under low stringency conditions.

In another further embodiment, there is provided a nucleic acid molecule comprising a nucleotide sequence or complementary nucleotide sequence substantially as set forth in SEQ ID NO:14 or having at least about 60% similarity thereto or capable of hybridising to the sequence set forth in SEQ ID NO:14 under low stringency conditions.

In yet another further embodiment, the present invention is directed to a nucleic acid molecule comprising a nucleotide sequence or complementary nucleotide sequence substantially as set forth in SEQ ID NO:16 or having at least about 60% similarity thereto or capable of hybridising to the sequence set forth in SEQ ID NO:16 under low stringency conditions.

Still yet another further embodiment provides a nucleic acid molecule comprising a nucleotide sequence or complementary nucleotide sequence substantially as set forth in SEQ ID NO:18 or having at least about 60% similarity thereto or capable of hybridising to the sequence set forth in SEQ ID NO:18 under low stringency conditions.

Moreover, yet a further embodiment of the present invention relates to a nucleic acid molecule comprising a nucleotide sequence or complementary nucleotide sequence substantially as set forth in SEQ ID NO:20 or having at least about 60% similarity thereto or capable of hybridising to the sequence set forth in SEQ ID NO:20 under low stringency conditions.

Still yet another further embodiment is directed to a nucleic acid molecule comprising a nucleotide sequence or complementary nucleotide sequence substantially as set forth in SEQ ID NO:22 or having at least about 60% similarity thereto or capable of hybridising to the sequence set forth in SEQ ID NO:22 under low stringency conditions.

In still yet another further embodiment, the present invention provides a nucleic acid molecule comprising a nucleotide sequence or complementary nucleotide sequence substantially as set forth in SEQ ID NO:24 or having at least about 60% similarity thereto or capable of hybridising to the sequence set forth in SEQ ID NO:24 under low stringency conditions.

In a particularly preferred embodiment there is provided an isolated nucleic acid molecule comprising a nucleotide sequence or complementary nucleotide sequence substantially as set forth in SEQ ID NO:1 or having at least about 60% similarity thereto or capable of hybridising to the sequence set forth in SEQ ID NO:1 under low stringency conditions, wherein said nucleotide sequence maps to the genetic locus designated Ht1 or Ht2 in petunia, or to equivalent such loci in other flowering plant species, and wherein said isolated nucleic acid molecule encodes, or is complementary to a sequence which encodes, a flavonoid 3'-hydroxylase.

Reference herein to a low stringency at 42° C. includes and encompasses from at least about 1% to at least about 15% formamide and from at least about 1M to at least about 2M salt for hybridization, and at least about 1M to at least about 2M salt for washing conditions. Alternative stringency conditions may be applied where necessary, such as medium stringency, which includes and encompasses from at least about 16% to at least about 30% formamide and from at least about 0.5M to at least about 0.9M salt for hybridization, and at least about 0.5M to at least about 0.9M salt for washing conditions, or high stringency, which includes and encompasses from at least about 31% to at least about 50% formamide and from at least about 0.01M to at least about 0.15M salt for hybridization, and at least about 0.01M to at least about 0.15M salt for washing conditions. Hybridization may be carried out at different temperatures and, where this occurs, other conditions may be adjusted accordingly.

Another aspect of the present invention provides a nucleic acid molecule comprising a sequence of nucleotides encoding or complementary to a sequence encoding an amino acid sequence substantially as set forth in SEQ ID NO:2 or an amino acid sequence, having at least about 50% similarity thereto.

In a related embodiment, there is provided a nucleic acid molecule comprising a sequence of nucleotides encoding or complementary to a sequence encoding an amino acid sequence substantially as set forth in SEQ ID NO:4 or an amino acid sequence having at least about 50% similarity thereto.

A further related embodiment of the present invention is directed to a nucleic acid molecule comprising a sequence of nucleotides encoding or complementary toga sequence encoding an amino acid sequence substantially as set forth in SEQ ID NO:6 or an amino acid sequence having at least about 50% similarity thereto.

Still another related embodiment provides a nucleic acid molecule comprising a sequence of nucleotides encoding or complementary to a sequence encoding an amino acid sequence substantially as set forth in SEQ ID NO:8 or an amino acid sequence having at least about 50% similarity thereto.

Yet still another related embodiment relates to a nucleic acid molecule comprising a sequence of nucleotides encoding or complementary to a sequence encoding an amino acid sequence substantially as set forth in SEQ ID NO:10 or SEQ ID NO:11 or SEQ ID NO:12 or SEQ ID NO:13 or an amino acid sequence having at least about 50% similarity thereto.

In another further embodiment, there is provided a nucleic acid molecule comprising a sequence of nucleotides encoding or complementary to a sequence encoding an amino acid sequence substantially as set forth in SEQ ID NO:15 or an amino acid sequence having at least about 50% similarity thereto.

In yet another further embodiment, the present invention is directed to a nucleic acid molecule-comprising a sequence of nucleotides encoding or complementary to a sequence encoding an amino acid sequence substantially as set forth in SEQ ID NO:17 or an amino acid sequence having at least about 50% similarity thereto.

Still yet another further embodiment provides a nucleic acid molecule comprising a sequence of nucleotides encoding or complementary to a sequence encoding an amino acid sequence substantially as set forth in SEQ ID NO:19 or an amino acid sequence having at least about 50% similarity thereto.

Moreover, yet a further embodiment of the present invention relates to:: a nucleic acid molecule comprising a sequence of nucleotides encoding or complementary to a sequence encoding an amino acid sequence substantially as set forth in SEQ ID NO:21 or an amino acid sequence having at least about 50% similarity thereto.

Still yet another further embodiment is directed to a nucleic acid molecule comprising a sequence of nucleotides encoding or complementary to a sequence encoding an amino acid sequence substantially as set forth in SEQ ID NO:23 or an amino acid sequence having at least about 50% similarity thereto.

In still yet another further embodiment, the present invention provides a nucleic acid molecule comprising a sequence of nucleotides encoding or complementary to a sequence encoding an amino acid sequence substantially as set forth in SEQ ID NO:25 or an amino acid sequence having at least about 50% similarity thereto.

In a particularly preferred embodiment there is provided an isolated nucleic acid molecule comprising a sequence of nucleotides encoding or complementary to a sequence encoding an amino acid sequence substantially as set forth in SEQ ID NO:2 or an amino acid sequence having at least about 50% similarity thereto, wherein said sequence of nucleotides maps to the genetic locus designated Ht1 or Ht2 in petunia, or to equivalent such loci in other flowering plant species, and wherein said isolated nucleic acid molecule encodes, or is complementary to a sequence which encodes, a flavonoid 3'-hydroxylase or a derivative therof.

The term "similarity" as used herein includes exact identity between compared sequences, at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels.

The nucleic acid molecule defined by SEQ ID NO:1 encodes a flavonoid 3'-hydroxylase from petunia. Examples of other suitable F3'H genes are from carnation (SEQ ID NO:3), snapdragon (SEQ ID NO:5), arabidopsis (SEQ ID NO:7), arabidopsis genomic DNA clone (SEQ ID NO:9), rose (SEQ ID NO:14), chrysanthemum (SEQ ID NO:16), torenia (SEQ ID NO:18), Japanese morning glory (SEQ ID NO:20), gentian (SEQ ID NO:22) and lisianthus (SEQ ID NO:24). Although the present invention is particularly exemplified by the aforementioned F3'H genes, the subject invention extends to F3'H genes from any species of plant provided that the F3'H gene has at least about 60% similarity at the nucleotide level to a nucleic acid molecule selected from SEQ ID NO:1 or 3 or 5 or 7 or 14 or 16 or 18 or 20 or 22 or 24, or at least about 50% similarity at the amino acid level to an amino acid molecule selected from SEQ ID NO:2 or 4 or 6 or 8 or 10, 11, 12, 13 or 15 or 17 or 19 or 21 or 23 or 25. The subject invention further extends to F3'H genes from any species of plant provided that the F3'H gene has at least about 60% similarity at the nucleotide level to the coding region of SEQ ID NO:9.

The nucleic acid molecules of the present invention are generally genetic sequences in a non-naturally-occurring condition. Generally, this means isolated away from its natural state or synthesized or derived in a non-naturally-occurring environment. More specifically, it includes nucleic acid molecules formed or maintained in vitro, including genomic DNA fragments, recombinant or synthetic molecules and nucleic acids in combination with heterologous nucleic acids. It also extends to the genomic DNA or cDNA or part thereof encoding F3'H or part thereof in reverse orientation relative to its or another promoter. It further extends to naturally-occurring sequences following at least a partial purification relative to other nucleic acid sequences.

The term "nucleic acid molecule" includes a nucleic acid isolate and a genetic sequence and is used herein in its most general sense and encompasses any contiguous series of nucleotide bases specifying directly, or via a complementary series of bases, a sequence of amino acids in a F3'H. Such a sequence of amino acids may constitute a full-length F3'H or an active truncated form thereof or may correspond to a particular region such as an N-terminal, C-terminal or internal portion of the enzyme. The nucleic acid molecules contemplated herein also encompass oligonucleotides useful as genetic probes or as "antisense" molecules capable of regulating expression of the corresponding gene in a plant. An "antisense molecule" as used herein may also encompass a gene construct comprising the structural genomic or cDNA gene or part thereof in reverse orientation relative to its own or another promoter. Accordingly, the nucleic acid molecules of the present invention may be suitable for use as cosuppression molecules, ribozyme molecules, sense molecules and antisense molecules to modulate levels of 3'-hydroxylated anthocyanins.

In one embodiment, the nucleic acid molecule encoding F3'H or various derivatives thereof is used to reduce the activity of an endogenous F3'H, or alternatively the nucleic acid molecule encoding this enzyme or various derivatives thereof is used in the antisense orientation to reduce activity of the F3'H. Although not wishing to limit the present invention to any one theory, it is possible that the introduction of the nucleic acid molecule into a cell results in this outcome either by decreasing transcription of the homologous endogenous gene or by increasing turnover of the corresponding mRNA. This may be achieved using gene constructs containing F3'H nucleic acid molecules or various derivatives thereof in either the sense or the antisense orientation. In a further alternative, ribozymes could be used to inactivate target nucleic acid molecules. Alternatively, the nucleic acid molecule encodes a functional F3'H and this is used to elevate levels of this enzyme in plants.

Reference herein to the altering of flavonoid F3'H activity relates to an elevation or reduction in activity of up to 30% or more preferably of 30–50%, or even more preferably 50–75% or still more preferably 75% or greater above or below the normal endogenous or existing levels of activity. The level of activity can be readily assayed using a modified version of the method described by Stotz and Forkmann (1982) (see Example 7) or by assaying for the amount of F3'H product such as quercetin, cyanidin or peonidin as set forth in Example 5.

The present invention further extends to nucleic acid molecules in the form of oligonucleotide primers or probes capable of hybridizing to a portion of the nucleic acid molecules contemplated above, and in particular those selected from the nucleic acid molecules set forth in SEQ ID NOs: 1, 3, 5, 7, 9, 14, 16, 18, 20, 22 or 24 under high, preferably under medium and most preferably under low stringency conditions. Preferably the portion corresponds to the 5' or the 3' end of the F3'H gene. For convenience the 5' end is considered herein to define a region substantially between the 5' end of the primary transcript to a centre portion of the gene, and the 3' end is considered herein to define a region substantially between the centre portion of the gene and the 3' end of the primary transcript. It is clear, therefore, that oligonucleotides or probes may hybridize to the 5' end or the 3' end or to a region common to both the 5' and the 3' ends.

The nucleic acid molecule or its complementary form may encode the fill-length enzyme or a part or derivative thereof. By "derivative" is meant any single or multiple amino acid substitutions, deletions, and/or additions relative to the naturally-occurring enzyme and includes parts, fragments, portions, fusion molecules, homologues and analogues. In this regard, the nucleic acid includes the naturally-occurring nucleotide sequence encoding F3'H or may contain single or multiple nucleotide substitutions, deletions and/or additions to said naturally-occurring sequence. A fusion molecule may be a fusion between nucleotide sequences encoding two or more F3'Hs, or a fusion between a nucleotide sequence encoding an F3'H and a nucleotide sequence encoding any other proteinaceous molecule. Fusion molecules are useful in altering substrate specificity.

A derivative of the nucleic acid molecule or its complementary form, or of a F3'H, of the present invention may also include a "part", whether active or inactive. An active or functional nucleic acid molecule is one which encodes an enzyme with F3'H activity. An active or functional molecule further encompasses a partially-active molecule; for example, an F3'H with reduced substrate specificity would be regarded as partially active A derivative of a nucleic acid molecule may be useful as an oligonucleotide probe, as a primer for polymerase chain reactions or in various mutagenic techniques, for the generation of antisense molecules or in the construction of ribozymes. They may also be useful in developing co-suppression constructs. The nucleic acid molecule according to this aspect of the present invention may or may not encode a functional F3'H. A "part" may be derived from the 5' end or the 3' end or a region common to both the 5' and the 3' ends of the nucleic acid molecule.

Amino acid insertional derivatives of the F3'H of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence Substitutional amino acid variants are those in which at least one residue in the sequence has been removed and a different residue inserted in its place. Typical substitutions are those made in accordance with Table 1 below.

TABLE 1

Suitable residues for amino add substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |

TABLE 1-continued

Suitable residues for amino add substitutions

| Original Residue | Exemplary Substitutions |
|---|---|
| Phe | Met; Leu; Tyr |
| Ser | Thr |
| Thr | Ser |
| Trp | Tyr |
| Tyr | Trp; Phe |
| Val | Ile; Leu |

Where the F3'H is derivatised by amino acid substitution, the amino acids are generally replaced by other amino acids having lie properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (1989).

Other examples of recombinant or synthetic mutants and derivatives of the F3'H of the present invention include single or multiple substitutions, deletions and/or additions of any molecule associated with the enzyme such as carbohydrates, lipids and/or proteins or polypeptides.

The terms "analogues" and "derivatives" also extend to any chemical equivalents of the F3'H, whether functional or not, and also to any amino acid derivative described above. Where the "analogues" and "derivatives" of this aspect of the present invention are non-functional, they may act as agonists or antagonists of F3'H activity. For convenience, reference to "F3'H" herein includes reference to any derivatives, including parts, mutants, fragments, homologues or analogues thereof.

The present invention is exemplified using nucleic acid sequences derived from petunia, carnation, rose, snapdragon, arabidopsis, chrysanthemum, lisianthus, torenia, morning glory and gentian, since these represent the most convenient and preferred sources of material to date. However, one skill(A in the art will immediately appreciate that similar: sequences can be isolated from any number of sources such as other plants or certain microorganisms. Examples of other plants include, but are not limited to, maize, tobacco, cornflower, pelargonium, apple, gerlera and african violet. All such nucleic acid sequences encoding directly or indirectly a flavonoid pathway enzyme and in particular F3'H, regardless of their source, are encompassed by the present invention.

The nucleic acid molecules contemplated herein may exist in either orientation alone or in combination with a vector molecule, for example an expression-vector. The term vector molecule is used in its broadest sense to include any intermediate vehicle for the nucleic acid molecule, capable of facilitating transfer of the nucleic acid into the plant cell and/or facilitating integration into the plant genome. An intermediate vehicle may, for example, be adapted for use in electroporation, microprojectile bombardment, Agrobacterium-mediated transfer or insertion via DNA or RNA viruses. The intermediate vehicle and/or the nucleic acid molecule contained therein may or may not need to be stably integrated into the plant genome. Such vector molecules may also replicate and/or express in prokaryotic cells. Preferably, the vector molecules or parts thereof are capable of integration into the plant genome. The nucleic acid molecule may additionally contain a promoter sequence capable of directing expression of the nucleic acid molecule in a plant cell. The nucleic acid molecule and promoter may also be introduced into the cell by any number of means such as those described above.

In accordance with the present invention, a nucleic acid molecule encoding a F3'H or a derivative or part thereof may be introduced into a plant in either orientation to allow, permit or otherwise facilitate manipulation of levels of production of mRNA in the cytoplasm and/or production of enzyme from the mRNA, thereby providing a means either to convert DHK and/or other suitable substrates, if synthesised in the plant cell, ultimately into anthocyanin derivatives of anthocyanidins such as cyanidin and/or peonidin, or alternatively to inhibit such conversion of metabolites by reducing or eliminating endogenous or existing F3'H activity. The production of mRNA in the cytoplasm and/or production of enzyme from the mRNA, is referred to herein as "expression". The production of anthocyanins contributes to the production of a red or blue flower colour. Expression of the nucleic acid molecule in either orientation in the plant may be constitutive, inducible or developmental, and may also be tissue-specific.

According to this aspect of the present invention there is provided a method for producing a transgenic plant capable of synthesizing F3'H or functional derivatives thereof, said method comprising stably transforming a cell of a suitable plant with a nucleic acid molecule which comprises a sequence of nucleotides encoding said F3'H, under conditions permitting the eventual expression of said nucleic acid molecule, regenerating a transgenic plant from the cell and growing said transgenic plant for a time and under conditions sufficient to permit the expression of the nucleic acid molecule. The transgenic plant may thereby produce elevated levels of F3'H activity relative to the amount expressed in a comparable non-transgenic plant.

Another aspect of the present invention contemplates a method for producing a transgenic plant with reduced endogenous or existing F3'H activity, said method comprising stably transforming a cell of a suitable plant with a nucleic acid molecule which comprises a sequence of nucleotides encoding or complementary to a sequence encoding F3'H, regenerating a transgenic plant from the cell and where necessary growing said transgenic plant under conditions sufficient to permit the expression of the nucleic acid molecule.

Yet another aspect of the present invention contemplates a method for producing a genetically modified plant with reduced endogenous or existing F3'H activity, said method comprising altering the F3'H gene through modification of the endogenous sequences via homologous recombination from an appropriately altered F3'H gene or derivative or part thereof introduced into the plant cell, and regenerating the genetically modified plant from the cell.

In accordance with these aspects of the present invention the preferred nucleic acid molecules are substantially as set forth in SEQ ID NO:1, 3, 5, 7, 14. 16, 18, 20, 22, 24 or the coding region of 9, or have at least about 60% similarity thereto, or are capable of hybridising thereto under low stringency conditions.

In a preferred embodiment, the present invention contemplates a method for producing a transgenic flowering plant exhibiting altered flower colour, said method comprising stably transforming a cell of a suitable plant with a nucleic acid molecule of the present invention, regenerating a transgenic plant from the cell and growing said transgenic plant for a time and under conditions sufficient to permit the expression of the nucleic acid molecule into the F3'H enzyme. Alternatively, said method may comprise stably transforming a cell of a suitable plant with a nucleic acid molecule of the present invention or its complementary sequence, regenerating a transgenic plant from the cell and growing said transgenic plant for a time and under conditions sufficient to alter the level of activity of the endogenous or existing F3'H. Preferably, the altered level would be less than the endogenous or existing level of F3'H activity in a comparable non-transgenic plant.

In a related embodiment, the present invention contemplates a method for producing a flowering plant exhibiting altered flower colour, said method comprising alteration of the F3'H gene through modification of the endogenous sequences via homologous recombination from an appropriately altered F3'H gene or derivative thereof introduced into the plant cell and regenerating the genetically modified plant from the cell.

The nucleic acid molecules of the present invention may or may not be developmentally regulated. Preferably, the modulation of levels of 3'-hydroxylated anthocyanins leads to altered flower colour which includes the production of red flowers or other colour shades depending on the physiological conditions of the recipient plant. By "recipient plant" is meant a plant capable of producing a substrate for the F3'H enzyme, or producing the F3'H enzyme itself, and possessing the appropriate physiological properties and genotype required for the development of the colour desired. This may include but is not limited to petunia, carnation, chrysanthemum, rose, snapdragon, tobacco, cornflower, pelargonium, lisianthus, gerbera, apple, iris, lily, african violet, gentian, torenia and Japanese morning glory.

Accordingly, the present invention extends to a method for producing a transgenic plant capable of modulating levels of 3'-hydroxylated anthocyanins, said method comprising stably transforming a cell or group of cells of a suitable plant with a nucleic acid molecule comprising a sequence of nucleotides encoding, or complementary to a sequence encoding, F3'H or a derivative thereof, and regenerating a transgenic plant from said cell or cells.

One skilled in the art will immediately recognise the variations applicable to the methods of the present invention, such as increasing or decreasing the level of enzyme activity of the enzyme naturally present in a target plant leading to differing shades of colours.

The present invention, therefore, extends to all transgenic plants containing all or part of the nucleic acid module of the present invention and/or any homologues or related forms thereof or antisense forms of any of these and in particular those transgenic plants which exhibit altered flower colour. The transgenic plants may contain an introduced nucleic acid molecule comprising a nucleotide sequence encoding or complementary to a sequence encoding F3'H. Generally, the nucleic acid would be stably introduced into the plant genome, although the present invention also extends to the introduction of the F3'H nucleotide sequence within an autonomously-replicating nucleic acid sequence such as a DNA or RNA virus capable of replicating within the plant cell. The invention also extends to seeds from such transgenic plants. Such seeds, especially if coloured, will be useful as proprietary tags for plants.

A further aspect of the present invention is directed to recombinant forms of F3'H. The recombinant forms of the enzymes will provide a source of material for research to develop, for example, more active enzymes and may be useful in developing in vitro systems for production of coloured compounds.

Still a further aspect of the present invention contemplates the use of the genetic sequences described herein in the manufacture of a genetic construct capable of use in modulating levels of 3'-hydroxylated anthocyanins in a plant or cells of a plant.

Yet a further aspect of the present invention provides flowers and in particular cut flowers, from the transgenic plants herein described, exhibiting altered flower colour.

Another aspect of the present invention is directed to a nucleic acid molecule comprising a sequence of nucleotides encoding or complementary to a sequence encoding, a F3'H or a derivative thereof wherein said nucleic acid molecule is capable of being expressed in a plant cell. The term "expressed" is equivalent to the term "expression" as defined above.

The nucleic acid molecules according to this and other aspects of the invention allow, permit or otherwise facilitate increased efficiency in modulation of 3'-hydroxylated anthocyanins relative to the efficency of the pCGP619 cDNA insert contained in plasmid pCGP809, disclosed in International Patent Application No. PCT/AU93/00127 [WO 93/20206]. The term "plant cell" includes a single plant cell or a group of plant cells such as in a callus, plantlet or plant or parts thereof including flowers and seeds.

Another aspect of the present invention provides a nucleic acid molecule comprising a sequence of nucleotides encoding or complementary to a sequence of nucleotides encoding a F3'H, wherein the translation of the said nucleic acid molecule comprises the amino acid sequence RPPNSGA (SEQ ID NO:43). Preferably, the translation of the said nucleic acid molecule comprises the amino acid sequence RPPNSGAXHXAYNYXDL (SEQ ID NO:44) and still more preferably the translation of the said nucleic acid molecule comprises the amino acid sequence RPPNSGAXHXAYNYXDL[X]$_n$GGEK (SEQ ID NO:45), where X represents any amino acid and [X]$_n$ represents an amino acid sequence of from 0 to 500 amino acids.

The present invention is further described by reference to the following non-limiting Figures and Examples.

BRIEF DESCRIPTION OF THE DRAWINGS

FIGS. 20(i)–(v) provide a multiple sequence alignment of the predicted amino acid sequences of petunia OGR-38 (A) (SEQ ID NO:2); carnation (B) (SEQ ID NO:4); snapdragon (C) (SEQ ID NO:6); arabidoposis Tt7 coding region (D) (SEQ ID NO:42); rose (E) (SEQ ID NO:15) chrysanthemum (F) SEQ ID NO:17; torenia (G) (SEQ ID NO:19); morning glory (H) (SEQ ID NO:21); pentian (partial sequence) (I) (SEQ ID NO:23); lisianthus (partial sequence) (J) (SEQ ID NO:25) and the petunia 651 cDNA (K) (SEQ ID NO:41). Conserved amino acids are shown in bolded capital letters and are boxed and shaded. Similar amino acids are shown in capital letters and are only lightly shaded, and dissimilar amino acids are shown in lower case letters.

Figure 1A:
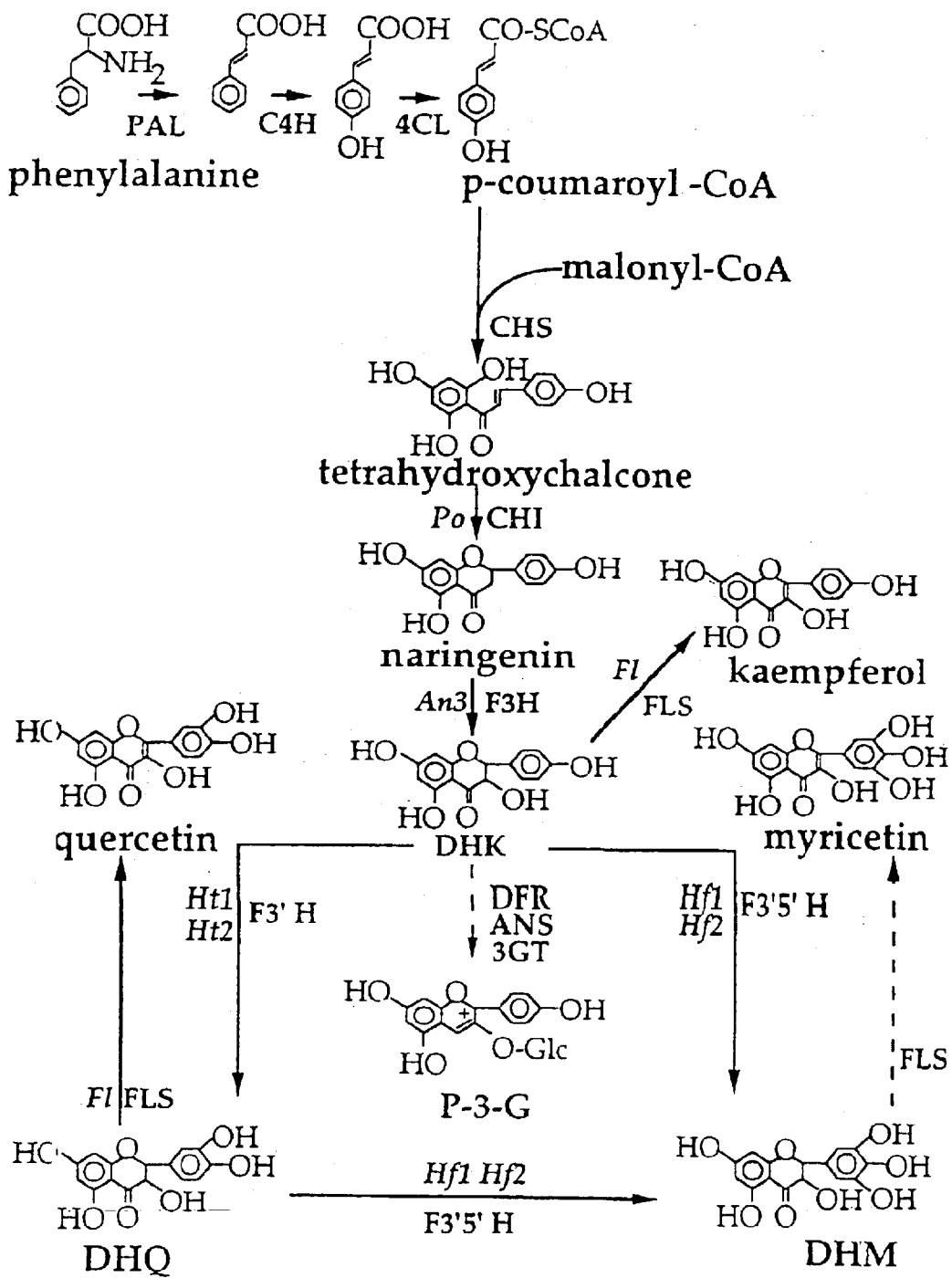
FIGS. 1A–1B are schematic representations of the flavonoid biosynthesis pathways in *P. hybrida* flowers showing the enzymes and genetic loci involved in the conversions. Enzymes involved in the pathway have been indicated as follows: PAL=phenylalanine ammonia-lyase; C4H= cinnamate 4-hydroxylase; 4CL=4coumarate: CoA ligase; CHS=chalcone synthase; CHI=chalcone isomerase; F3H= flavanone 3-hydroxylase; F3'H=flavonoid 3'-hydroxylase; F3'5'H=flavonoid 3'5' hydroxylase; FLS=flavonol synthase; DFR=dihydroflavonol-4-reductase; ANS=anthocyanin synthase; 3GT=UDP-glucose: anthocyanin-3-glucoside; 3RT= UDP-rhamnose: anthocyanidin-3-glucoside rhamnosyl-transferase; ACT=anthocyanidin-3-rutinoside acyltransferase; 5GT=UDP-glucose: anthocyanin 5-glucosyltransferase; 3' OMT=anthocyanin O-methyltransferase; 3',5' OMT=anthocyanin 3',5' O-methyltransferase. Three flavonoids in the pathway are indicated as: P-3-G=pelargonidin-3-glucoside; DHM= dihydomyricetin; DHQ=dihydroquercetin. The flavonol, myricetin, is only produced at low levels and the anthocyanin, pelargonidin, is rarely produced in *P. hybrida*.

Amino acid abbreviations used throughout the specification are shown in Table 2, below.

TABLE 2

Amino acid abbreviations

| Amino add | 3-letter | single-letter |
|---|---|---|
| L-alanine | Ala | A |
| L-arginine | Arg | R |
| L-asparagine | Asn | N |
| L-aspartic acid | Asp | D |
| L-cysteine | Cys | C |
| L-glutamine | Gln | Q |
| L-glutamic acid | Glu | E |
| L-glycine | Gly | G |
| L-histidine | His | H |
| L-isoleucine | Ile | I |
| L-leucine | Leu | L |
| L-lysine | Lys | K |
| L-methionine | Met | M |
| L-phenylalanine | Phe | F |
| L-proline | Pro | P |
| L-serine | Ser | S |
| L-threonine | Thr | T |
| L-tryptophan | Trp | W |
| L-tyrosine | Tyr | Y |
| L-valine | Val | V |

Table 3 provides a summary of the SEQ ID NO's assigned to the sequences referred to herein:

TABLE 3

| Sequence | Species | SEQ ID NO |
|---|---|---|
| cDNA insert of pCGP1805 | Petunia | SEQ ID NO: 1 |
| corresponding amino acid sequence | Petunia | SEQ ID NO: 2 |
| cDNA insert of pCGP1807 | Carnation | SEQ ID NO: 3 |
| corresponding amino acid sequence | Carnation | SEQ ID NO: 4 |
| cDNA insert of pCGP246 | Snapdragon | SEQ ID NO: 5 |
| corresponding amino acid sequence | Snapdragon | SEQ ID NO: 6 |
| cDNA partial sequence | Arabidopsis | SEQ ID NO: 7 |
| corresponding amino acid sequence | Arabidopsis | SEQ ID NO: 8 |
| genomic sequence | Arabidopsis | SEQ ID NO: 9 |
| corresponding amino acid sequence for exon I | Arabidopsis | SEQ ID NO: 10 |
| corresponding amino acid sequence for exon II | Arabidopsis | SEQ ID NO: 11 |
| corresponding amino acid sequence for exon III | Arabidopsis | SEQ ID NO: 12 |
| corresponding amino acid sequence for exon IV | Arabidopsis | SEQ ID NO: 13 |
| cDNA insert of pCGP2158 | Rose | SEQ ID NO: 14 |
| corresponding amino acid sequence | Rose | SEQ ID NO: 15 |

TABLE 3-continued

| Sequence | Species | SEQ ID NO |
|---|---|---|
| cDNA insert of pCHRM1 | Chrysanthemum | SEQ ID NO: 16 |
| corresponding amino acid sequence | Chrysanthemum | SEQ ID NO: 17 |
| THT cDNA sequence | Torenia | SEQ ID NO: 18 |
| corresponding amino acid sequence | Torenia | SEQ ID NO: 19 |
| MHT 8S cDNA sequence | Jap. Morning Glory | SEQ ID NO: 20 |
| corresponding amino acid sequence | Jap. Morning Glory | SEQ ID NO: 21 |
| GHT13 cDNA sequence | Gentian | SEQ ID NO: 22 |
| corresponding amino acid sequence | Gentian | SEQ ID NO: 23 |
| cDNA insert of pL3-6 | Lisianthus | SEQ ID NO: 24 |
| corresponding amino acid sequence | Lisianthus | SEQ ID NO: 25 |
| cDNA sequence from WO 93/20206 | Petunia | SEQ ID NO: 26 |
| oligonucleolide polyT-anchA | | SEQ ID NO: 27 |
| oligonucleotide polyT-anchC | | SEQ ID NO: 28 |
| oligonucleotide polyT-anchG | | SEQ ID NO: 29 |
| conserved amino acid primer region | | SEQ ID NO: 30 |
| corresponding oligonucleotide sequence | | SEQ ID NO: 31 |
| conserved amino acid primer region | | SEQ ID NO: 32 |
| corresponding oligonucleotide sequence | | SEQ ID NO: 33 |
| oligonucleotide primer Pet Haem-New | | SEQ ID NO: 34 |
| conserved amino acid primer region | | SEQ ID NO: 35 |
| corresponding oligonucleotide sequence | | SEQ ID NO: 36 |
| oligonucleotide Snapred Race A | | SEQ ID NO: 37 |
| oligonucleotide Snapred Race C | | SEQ ID NO: 38 |
| oligonucleotide poly-C Race | | SEQ ID NO: 39 |
| oligonucleotide primer Pet Haem | | SEQ ID NO: 40 |

The disarmed microorganism *Agrobacterium tumefaciens* strain AGL0 separately containing the plasmids pCGP1867, pCGP1810 and pCGP231 were deposited with the Australian Government Analytical Laboratories, 1 Suakin Street, Pymble, New South Wales, 2037. Australia on 23 Feb., 1996 and were given Accession Numbers 96/10967, 96/10968 and 96/10969, respectively.

ISOLATION OF FLAVONOID 3'-HYDROXYLASE AND RELATED NUCLEIC ACID SEQUENCES

EXAMPLE 1

Plant Material

Petunia

The *Petunia hybrida* varieties used are presented in Table 4.

TABLE 4

| Plant variety | Properties | Source/Reference |
|---|---|---|
| Old Glory Blue (OGB) | F$_1$ Hybrid | Ball Seed, USA |
| Old Glory Red (OGR) | F$_1$ Hybrid | Ball Seed, USA |
| V23 | An1, An2, An3, An4, An6, An8, An9, An10, ph1, Hf1, Hf2, hfI Rt, po, B1, F1 | Wallroth et al. (1986) Doodeman et al. (1984) |
| R51 | An1. An2, An3, an4, An6, An8, An9, An10, An11, Ph1, hf1, hf2, HtI, rt, Po. b1, f1 | Wallroth et al. (1986) Doodeman et al. (1984) |
| VR | V23 x 51 F$_1$ Hybrid | |
| SW63 | An1, An2, An3, an4, An6, An8, An9, An10, An11, Ph1, Ph2, Ph5, hf1, hf2, htI, ht2, po, mfI, f1 | I.N.R.A., Dijon, Cedex France |
| | An1, An2, An3, An4, An6, An11, | I.N.R.A., Dijon Cedex |

TABLE 4-continued

| Plant variety | Properties | Source/Reference |
|---|---|---|
| | hf1, hf2, htI, Ph1, Ph2, Ph5, rt, Po. Mf1, Mf2, f1 | France |
| Skr4 x SW63 | $F_1$ Hybrid | |

Plants were grown in specialised growth rooms with a 14 hour day length at a light intensity of 10,000 lux and a temperature of 22° C. to 26° C.

Carnation

Flowers of *Dianthus caryophyllus* cv. Korta Chanel were obtained from Van Wyk and Son Flower Supply, Victoria.

*Dianthus caryophyllus* flowers were harvested at developmental stages defined as follows:

Stage 1: Closed bud, petals not visible.

Stage 2: Flower buds opening: tips of petals visible.

Stage 3: Tips of nearly all petals exposed. "Paint-brush stage".

Stage 4: Outer petals at 45° angle to stem.

Stage 5: Flower fully open.

Snapdragon

The *Antirrhinum majus* lines used were derived from the parental lines K16 (eos⁻) and N8 (Eos⁺). A strict correlation exists between F3'H activity and the Eos gene which is known to control the 3'-hydroxylation of flavones, flavonols and anthocyanins (Forkmann and Stotz, 1981). K16 is a homozygous recessive mutant lacking F3'H activity while N8 is wild type for F3'H activity. These lines are similar, though not isogenic. Both parental lines and the seed from a selfed (K16×N8) $F_1$ plant were obtained from Dr C. Martin (John Innes Centre, Norwich, UK).

Arabidopsis

The *Arabidopsis thaliana* lines Columbia (Tt7), Landsberg erecta (Tt7) and NW88 (tt7) were obtained from the Nottingham Arabidopsis Stock Centre. Wild-type *A. thaliana* (Tt7) seeds have a characteristic brown colour. Seeds of tt7 mutants have pale brown seeds and the plants are characterized by a reduced anthocyanin content in leaves (Koornneef et al., 1982). Tt7 plants produce cyanidin while tt7 mutants accumulate pelargonidin, indicating that the Tt7 gene controls flavonoid 3'-hydroxylation.

Rose

Flowers of *Rosa hybrida* cv. Kardinal were obtained from Van Wyk and Son Flower Supply, Victoria.

Stages of *Rosa hybrida* flower development were defined as follows:

Stage 1: Unpigmented, tightly closed bud (10–12 mm high; 5 mm wide).

Stage 2: Pigmented, tightly closed bud (15 mm high; 9 mm wide).

Stage 3: Pigmented, closed bud; sepals just beginning to open (20–25 mm high; 13–15 mm wide)

Stage 4: Flower bud beginning to open; petals heavily pigmented; sepals have separated (bud is 25–30 mm high and 18 mm wide).

Stage 5: Sepals completely unfolded; some curling. Petals are heavily pigmented and unfolding (bud is 30–33 mm high and 20 mm wide).

Chrysanthemum

Stages of Chrysanthemum flower development were defined as follows:

Stage 0: No visible flower bud.

Stage 1: Flower bud visible: florets completely covered by the bracts.

Stage 2: Flower buds opening: tips of florets visible.

Stage 3: Florets tightly overlapped.

Stage 4: Tips of nearly all florets exposed; outer florets opening but none horizontal.

Stage 5: Outer florets horizontal.

Stage 6: Flower approaching maturity.

EXAMPLE 2

Bacterial Strains

The *Escherichia coli* strains used were:

DH5α supE44, Δ(lacZYA-ArgF)U169, ø80lacZΔM15, hsdR17 ($r_k-$, $m_k+$), recA1, endA1, gyrA96, thi-1, relA1, deoR (Hanahan, 1983 and BRL, 1986).

XL1-Blue MRF' Δ(mcr A)183, Δ(mcrCB-hsdSMR-mrr) 173, endA1, supE44, thi-1, recA1, gyrA96, relA1, lac[F' proAB, lacIqZΔM15, Tn10(Tet$^r$)]$^c$ (Stratagene)

XL1-Blue supE44, hsdR17 ($r_k-$, $m_k+$), recA1, endA1, gyrA96, thi-1, relA1, lac[F' proAB, lacIq, lacZΔM15, Tn10(tet$^r$)]

SOLR e14⁻ (mcrA), Δ(mcrCB-hsdSMR-mrr)171, sbcC, recB, recJ, umuC::Tn5(kan$^r$), uyrC,lac, gyrA96, thi-1, relA1, [F'proAB, lacIqZΔM15], Su⁻(non-suppressing) (Stratagene)

DH10 B(Zip) F⁻mcrA, Δ(mrr-hsdRMS-mcrBC), ø80d lacZΔM15, ΔlacX74, deoR, recA1, araD139, Δ(ara, leu)7697, galU, gal|K|λ, rspL, nupG Y1090r- ΔlacU169, (Δlon)?, araD139, strA, supF, mcrA, trpC22::Tn10Tet$^r$) [pMC9 Amp$^r$, Tet$^r$], mcrB, hsdR The disarmed *Agrobacterium tumefaciens* strain AGL0 (Lazo et al., 1991) was obtained from R. Ludwig (Department of Biology, University of California, Santa Cruz, USA).

The cloning vector pBluescript was obtained from Stratagene.

Transformation of the *E. coli* strain DH5α cells was performed according to the method of Inoue et al. (1990).

EXAMPLE 3

General Methods $^{32}$P-Labeling of DNA Probes

DNA fragments (50 to 100 ng) were radioactively labelled with 50 µCi of [α-$^{32}$P]-dCTP using an oligolabelling kit (Bresatec). Unincorporated [α-$^{32}$P]-dCTP was removed by chromatography on a Sephadex G-50 (Fine) column.

DNA Sequence Analysis

DNA sequencing was performed using the PRISM™Ready Reaction Dye Primer Cycle Sequencing Kits from Applied Biosystems. The protocols supplied by the manufacturer were followed. The cycle sequencing reactions were performed using a Perkin Elmer PCR machine (GeneAmp PCR System9600) and run on an automated 373A DNA sequencer (Applied Biosystems).

Homology searches against Genbank, SWISS-PROT and EMBL databases were performed using the FASTA and TFASTA programs (Pearson and Lipman, 1988) or BLAST programs (Altschul et al., 1990). Percentage sequence similarities were obtained using the LFASTA program (Pearson and Lipman, 1988). In all cases ktup values of 6 for nucleotide sequence comparisons and 2 for amino acid sequence comparisons were used, unless otherwise specified.

Multiple sequence alignments (ktp value of 2) were performed using the ClustalW program incorporated into the MaVector™6.0 application (Oxford Molecular Ltd.).

EXAMPLE 4

Isolation of a Flavonoid 3'-hydroxylase (F3'H) cDNA Done Corresponding to the Ht1 Locus from *P. hybrida* cv. Old Glory Red In order to isolate a cDNA clone that was linked to the Ht1 locus and that represented the flavonoid 3'-hydroxylase (F3'H) in the petunia flavonoid pathway, a petal cDNA library was prepared from RNA isolated from stages 1 to 3 of Old Glory Red (OGR) petunia flowers. OGR flowers contain cyanidin based pigments and have high levels of flavonoid 3'-hydroxylase activity. The OGR cDNA library was screened with a mixture of $^{32}$P-labelled fragments isolated from three cytochrome P450 cDNA clones known to be involved in the flavonoid pathway and from one cytochrome P450 cDNA clone (651) that had flavonoid 3'-hydroxylase activity in yeast. These included a petunia cDNA clone representing the cinnamtehydroxylase (C4H) and two petunia cDNA clones (coded by the Hf1 and Hf2 loci) representing flavonoid 3'5'-hydroxylase (F3'5'H) (Holton et al., 1993).

Construction of Petunia cv. OGR cDNA Library

Total RNA was isolated from the petal tissue of *P. hybrida* cv. OGR stage 1 to 3 flowers using the method of Turpen and Griffith (1986). Poly(A)$^+$ RNA was selected from the total RNA, using oligotex-dT™ (Qiagen).

A ZAP-cDNA Gigapack III Gold Cloning kit (Stratagene) was used to construct a directional petal cDNA library in λZAP using 5 μg of poly(A)+ RNA isolated from stages 1 to 3 of OGR as template. The total number of recombinants obtained was 2.46×10$^6$.

After transfecting XL1-Blue MRF' cells, the packaged cDNA mixture was plated at 50.000 pfu per 15 cm diameter plate. The plates were incubated at 37° C. for 8 hours;: and the phage were eluted in 100 mM NaCl, 8 mM MgSO$_4$, 50 mM Tris-HCl pH 8.0, 0.01% (w/v) gelatin (Phage Storage Buffer (PSB)) (Sambrook et al., 1989). Chloroform was added and the phage stored at 4° C. as an amplified library.

100,000 pfu of the amplified library were plated onto NZY plates (Sambrook et al., 1989) at a density of 10,000 pfu per 15 cm plate after transfecting XL1-Blue MRF' cells, and incubated at 37° C. for 8 hours. After incubation at 4° C. overnight, duplicate lifts were taken onto Colony/Plaque Screen™filters (DuPont) and treated as re amended by the manufacturer.

Isolation of Probes

F3'5'H Probes

The two flavonoid 3',5' hydroxylases corresponding to the Hf1 or Hf2 loci isolated as described in Holton et al. (1993) and U.S. Pat. No. 5,349,125, were used in the screening process.

C4H cDNA Clones from Petunia

Figure 2:
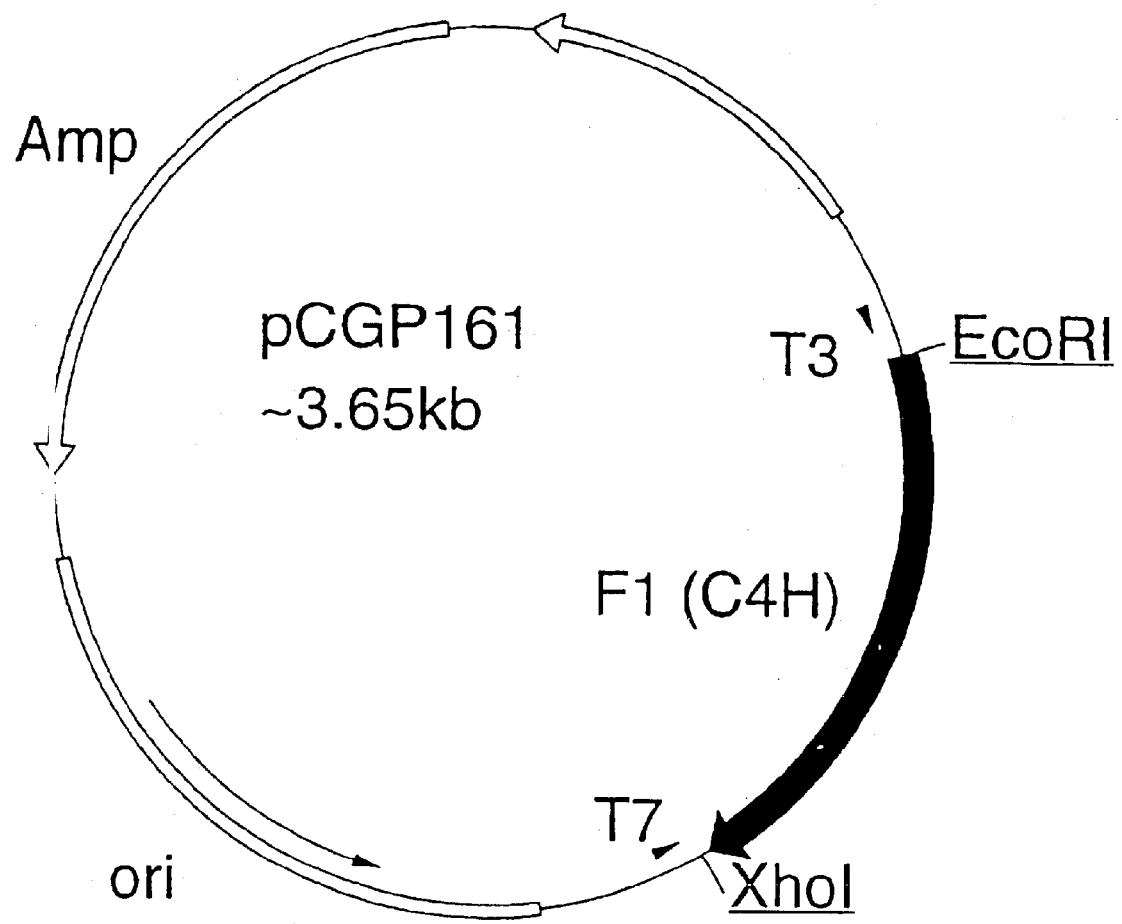
FIG. 2 is a diagrammatic representation of the plasmid pCGP161 containing a cDNA clone (F1) representing the cinnamate-4-hydroxylase from *P. hybrida*. $^{32}$P-labelled fragments of the 0.7 kb EcoRI/XhoI fragment were used to probe the Old Glory Red petal cDNA library. For details, refer to Example 4. Abbreviations are as follows: Amp=the ampicillin resistance gene; ori=origin of replication; T3=recognition sequence for T3 RNA polymerase; T7=recognition sequence for T7 RNA polymerase. Restriction enzyme sites are also marked.

A number of cytochrome P450 cDNA clones were isolated in the screening process used to isolate the two flavonoid 3',5' hydroxylase cDNA clones corresponding to the Hf1 or Hf2 loci (Holton et al., 1993; U.S. Pat. No. 5,349,125). One of these cDNA clones (F1) (contained in pCGP161) (FIG. 2) was identified as representing a cinnamate 4-hydroxylase (C4H), based on sequence identity with a previously-characterised C4H clone from mung bean (Mizutani et al., 1993). Sequence data was generated from 295 nucleotides at the 5' end of the petunia F1 cDNA clone. There was 83.1% similarity with the mung bean C4H clone over the 295 nucleotides sequenced and 93.9% similarity over the predicted amino acid sequence.

651 cDNA Clone

The isolation and identification of the 651 cDNA clone contained in pCGP619 (FIG. 5) was described in the International Patent Application, having publication number W093/20206. A protein extract of yeast containing the 651 cDNA clone udder the control of the yeast glyceraldehyde-3phosphate dehydrogenase promoter of pYE22m (Tanaka et al., 1988) exhibited F3'H activity.

Screening of OGR Library

Prior to hybridization, the duplicate plaque lifts were washed in prewashing solution (50 mM Tris-HCl pH7.5, 1 M NaCl, 1 mM EDTA, 0.1% (w/v) sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% (w/v) SDS at 65° C. for 30 minutes and finally rinsed in 2×SSC, 1.0% (w/v) SDS.

Figure 3:
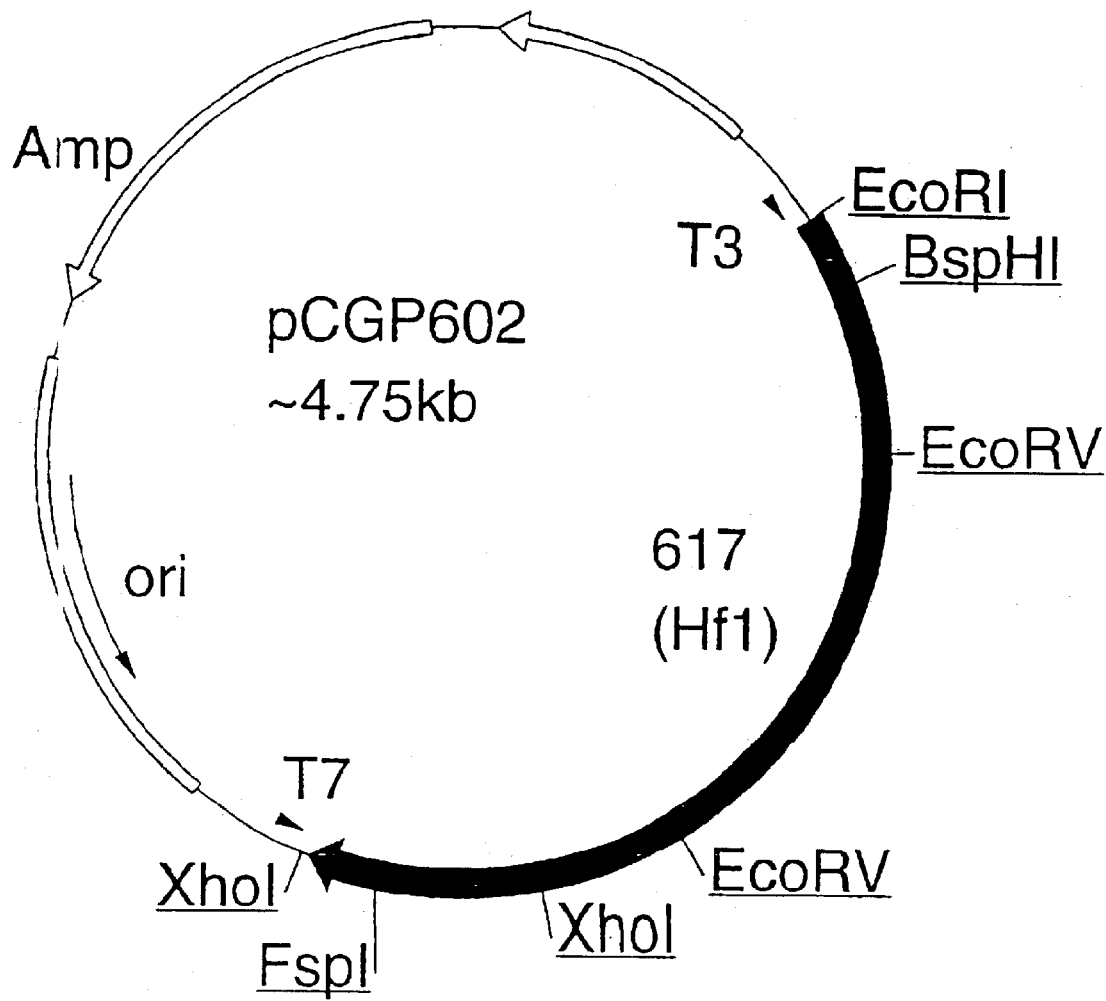
FIG. 3 is a diagrammatic representation of the plasmid pCGP602 containing a cDNA clone (617) representing a flavonoid 3'5' hydroxylase (Hf1) from *P. hybrida*. $^{32}$P-labelled fragments of the 1.6 kb BspI/EspI fragment containing the Hf1 coding region were used to probe the Old Glory Red petal cDNA library. For details, refer to Example 4. Abbreviations are as follows: Amp=the ampicillin resistance gene; ori=origin of replication; T3=recognition sequence for T3 RNA polymerase; T7=recognition sequence for T7 RNA polymerase. Restriction enzyme sites are also marked.
Figure 4:
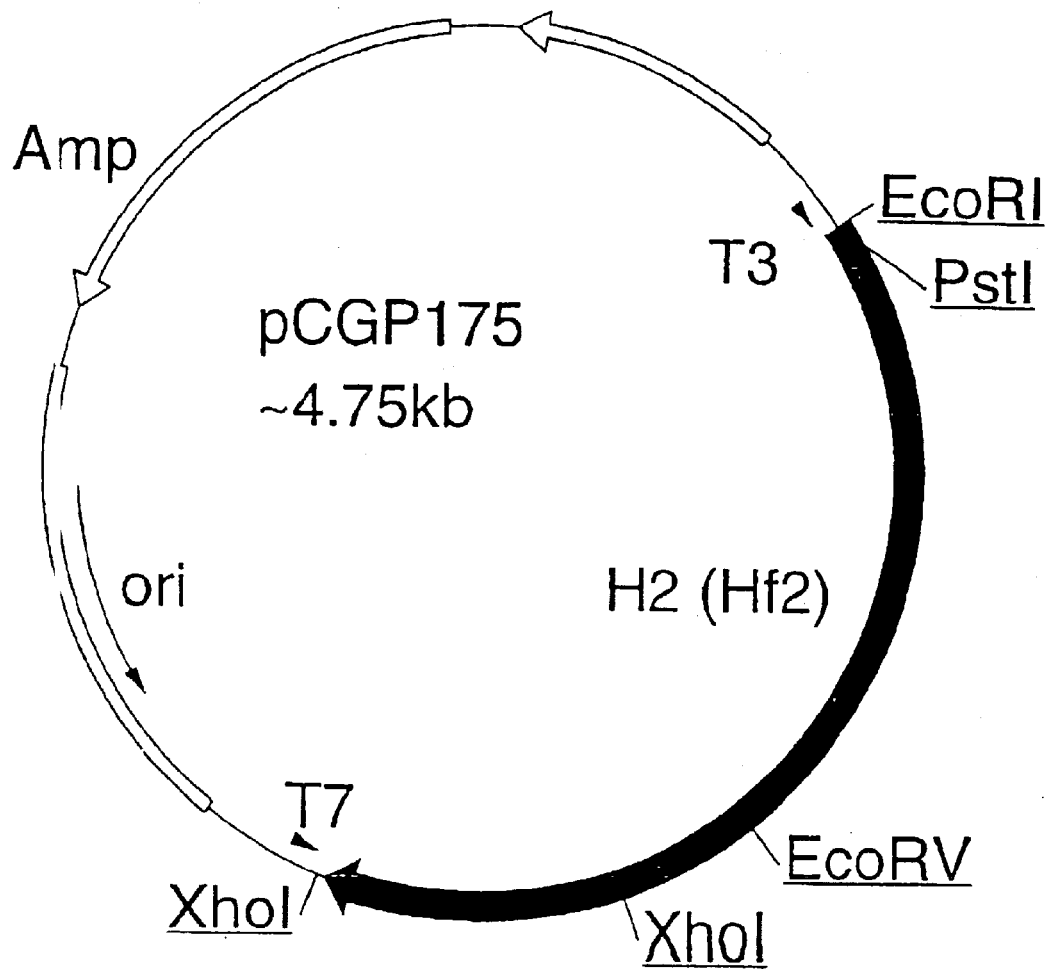
FIG. 4 is a diagrammatic representation of the plasmid pCGP175 containing a cDNA clone (H2) representing a flavonoid 3'5' hydroxylase (Hf2) from *P. hybrida*. $^{32}$P-labelled fragments of the 1.3 kb EcoI/XhoI and 0.5 kb XhoI fragments which together contain the coding region were used to probe the Old Glory Red petal cDNA library. For details, refer to Example 4. Abbreviations are as follows: Amp=the ampicillin resistance gene; ori=origin of replication; T3=recognition sequence for T3 RNA polymerase; T7=recognition sequence for T7 RNA polymerase. Restriction enzyme sites are also marked.
Figure 5:
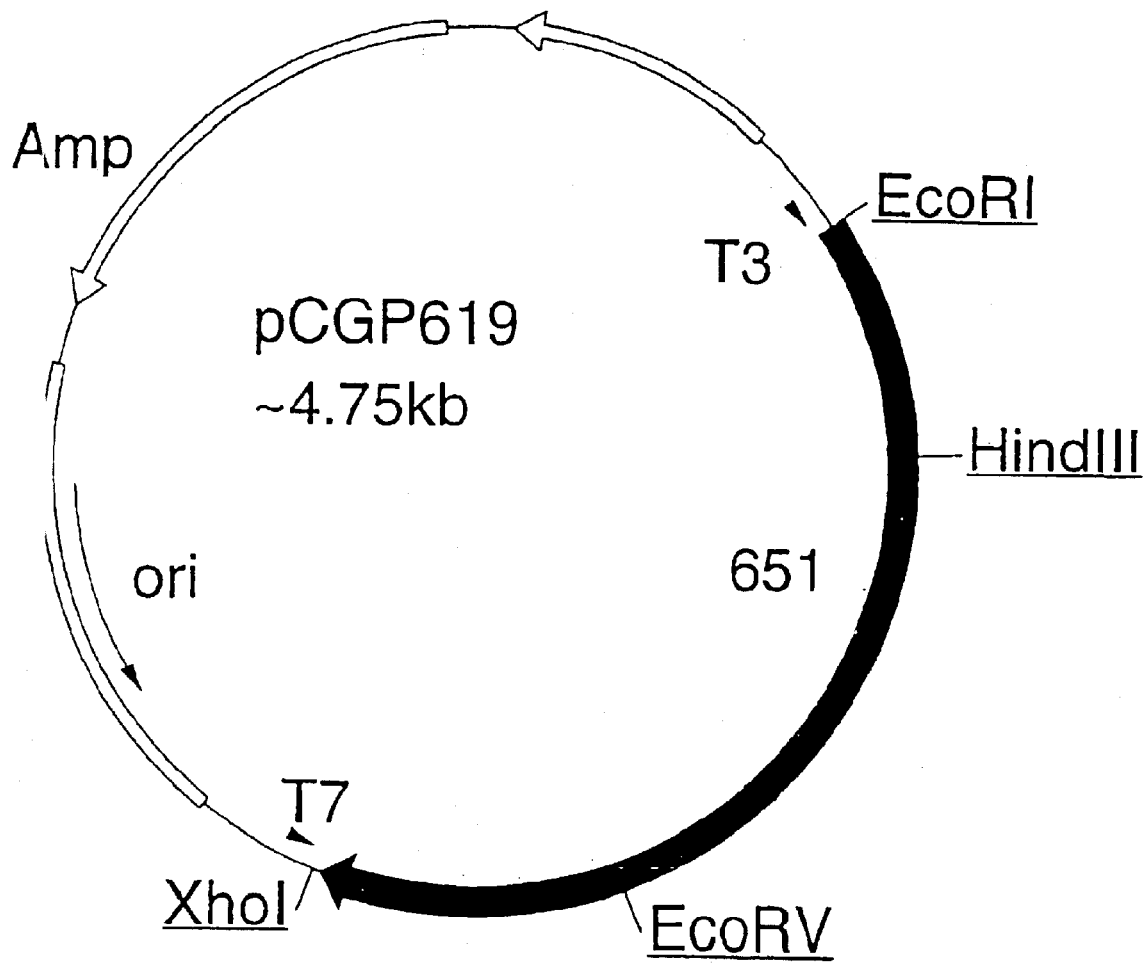
FIG. 5 is a diagrammatic representation of the plasmid pCGP619 containing the 651 cDNA clone representing a cytochrome P450 from *P. hybrida*. $^{32}$P-labelled fragments of the 1.8 kb EcoI/XhoI fragment were used to probe the Old Glory Red petal cDNA library. For details, refer to Example 4. Abbreviations are as follows: Amp=the ampicillin resistance gene; ori=origin of replication; T3=recognition sequence for T3 RNA polymerase; T7=recognition sequence for T7 RNA polymerase. Restriction enzyme sites are also marked.

The lifts from the OGR cDNA library were screened with $^{32}$P-labelled fragments of (1) a 0.7 kb EcoRI/XhoI fragment from pCGP161 containing the C4H cDNA clone (FIG. 2), (2) a 1.6 kb BspHI/FspI fragment from pCGP602 containing the Hf1 cDNA clone (FIG. 3), (3) a 1.3 kb EcoRI/XhoI fragment and a 0.5 kb XhoI fragment from pCGP175 containing the coding region of the Hf2 cDNA clone (FIG. 4) and (4) a 1.8 kb EcoRI/XhoI fragment pCGP619 containing the 651 cDNA clone (FIG. 5).

Hybridization conditions included a prehybridization step in 10% (v/v) formamide, 1 M NaCl, 10% (w/v) dextran sulphate, 1% (w/v) SDS at 42° C. for at least 1 hour. The $^{32}$P-labelled fragments (each at 1×10$^6$ cpm/mL) were then added to the hybridization solution and hybridization was continued at 42° C. for a further 16 hours. The filters were then washed in 2×SSC, 1% (w/v) SDS at 42° C. for 2×1 hour and exposed to Kodak XAR film with an intensifying screen at −70° C. for 16 hours.

Two hundred and thirty strongly hybridizing plaques were picked into PSB. Of these, 39 were rescreened to isolate purified plaques, using the hybridization conditions as described for the initial screening of the cDNA library. The plasmids contained in the λZAP bacteriophage vector were rescued and sequence data was generated from the 3' and 5' ends of the cDNA inserts. Based on sequence homology, 27 of the 39 were: identical to the petunia cinnamate 4-hydroxylase cDNA clone, 2 of the 39 were identical to the Hf1 cDNA ha clone and 7 of the 39 did not represent cytochrome P450s. The remaining 3 cDNA clones (designated as OGR-27, OGR-38, OGR-39) represented "new" cytochrome P450s, compared to the cytochrome P450 clones used in the screening procedure, and were further characterised.

EXAMPLE 5

Restriction Fragment Length Polymorphism (RFLP) Analysis

There are two genetic loci in *P. hybrida*, Ht1 and Ht2, that control flavonoid 3'-hydroxylase activity (Tabak et al., 1978;

Wiering and de Vlaming, 1984). Ht1 is expressed in both the limb and the tube of *P. hybrida* flowers and gives rise to higher levels of F3'H activity than does Ht2 which is only expressed in the tube. The F3'H is able to convert dihydrokaempferol and naringenin to dihydroquercetin and eriodictyol, respectively. In a flower producing delphinidin-based pigments, F3'H activity is masked by the F3'5'H activity. Therefore, the F3'H/F3'5'H assay (Stotz and Forkmann, 19182) is useless in determining the presence or absence of F3'H activity. The enzyme flavonol synthase is able to convert dihydrokaempferol to kaempferol and dihydroquercetin to quercetin (FIG. 1a). Myricetin, the 3',5' hydroxylated flavonol, is produced at low levels in petunia flowers.

Therefore, analysing the flowers for the 3' hydroxylated flavonol, quercetin, infers the presence of F3'H activity.

Restriction Fragment Length Polymorphism (RFLP) analysis of DNA isolated from individual plants in a VR (Ht1/ht1)×V23 (ht1/ht1) backcross was used to determine which, if any, of the cDNA clones representing P450s were linked to the Ht1 locus. Northern analysis of RNA isolated from these plants was also used to detect the presence or absence of a transcript in these lines.

Flowers from a VR (Ht1/ht1)×V23 (ht1/ht1) backcross population were analysed for the presence of the flavonols, kaempferol and quercetin. VR (Ht1/ht1) flowers accumulate quercetin and low levels of kaempferol while V23 (ht1/ht1) flowers accumulate kaempferol but little or no quercetin. Individual plants from the VR (Ht1/ht1)×V23 (ht1/ht1) backcross were designated as VR-like (Ht1/ht1), if a substantial level of quercetin was detected in the flower extracts, and V23-like (ht1/ht1), if little or no quercetin but substantial levels of kaempferol were detected in the flower extracts (see FIG. 6).

Isolation of Genomic DNA

DNA was isolated from leaf tissue essentially as described by Dellaporta et al., (1983). The DNA preparations were further purified by CsCl buoyant density centrifigation (Sambrook et al., 1989).

Southern Blots

The genomic DNA (10 μg) was digested for 16 hours with 60 units of EcoRI and electophoresed through a 0.7% (w/v) agarose gel in a running buffer of TAE (40 mM Tris-acetate, 50 mM EDTA). The DNA was then denatured in denaturing solution (1.5 M NaCl/0.5 M NaOH) for 1 to 1.5 hours, neutalized in 0.5 M Tris-HCl (pH 7.5)/1.5 M NaCl for 2 to 3 hours and then transferred to a Hybond N (Amersham) filter in 20×SSC.

RNA Blots

Total RNA was isolated from the petal tissue of *P. hybrida* cv OGR stage 1 to 3 flowers using the method of Turpen and Griffith (1986).

RNA samples were electrophoresed through 2.2 M formaldehyde/1.2% (w/v) agarose gels using running buffer containing 40 mM morpholinopropanesulphonic acid (pH 7.0), 5 mM sodium acetate, 0.1 mM EDTA (pH 8.0). The RNA was transferred to Hybond-N filters (Amersham) as described by the manufacturer.

Hybridization and Washing Conditions

Southern and RNA blots were probed with $^{32}$P-labelled cDNA fragment ($10^8$ cpm/μg, $2 \times 10^6$ cpm/mL). Prehybridizations (1 hour at 42° C.) and hybridizations (16 hours at 42° C.) were carried out in 50% (v/v) formamide, 1 M NaCl, 1% (w/v) SDS, 10% (w/v) dextran sulphate. Filters were wed in 2×SSC, 1% (w/v) SDS at 65° C. for 1 to 2 hours and then 0.2×SSC, 1% (w/v) SDS at 65° C. for 0.5 to 1 hour. Filters were exposed to Kodak XAR film with an intensifying screen at −70° C. for 16 hours.

RFLP and Northern Analysis of the Cytochrome P450 Fragments

RFLP analysis was used to investigate linkage of the genes corresponding to the OGR-27, OGR-38 and OGR-39 cDNA clones to the Ht1 locus.

Figure 6:
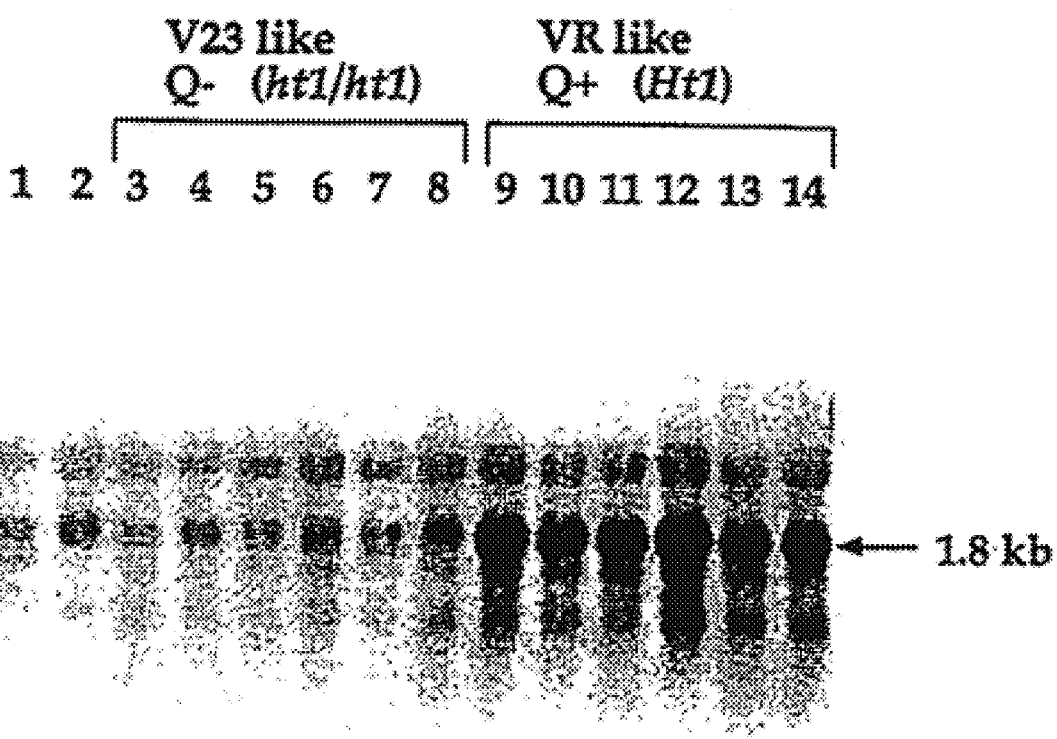
FIG. 6 is a representation of an autoradiograph of an RNA blot probed with $^{32}$P-labelled fragments of the OGR-38 cDNA clone contained in pCGP1805 (see Example 6). Each lane contained a 20 µg sample of total RNA isolated from the flowers or leaves of plants of a V23 (ht1/ht1)×VR (Ht1/ht1) backcross population. A 1.8 kb transcript was detected in the VR-like (Ht1/ht1) flowers that contained high levels of quercetin (Q+)(lanes 9–14). The same size transcript was detected at much lower levels in the V23-like (Ht1/ht1) flowers that contained little or no quercetin (Q–) (lanes 3–8). A reduced level of transcript was also detected in VR leaves (lane 1) and V23 petals (lane 2). This is described in Example 5.

$^{32}$P-labelled fragments of OGR-27, OGR-38 and OGR-39 cDNA clones were used to probe RNA blots and Southern blots of genomic DNA isolated from individual plants in the VR×V23 backcross population. Analysis of EcoRI digested genomic DNA isolated from a VR×V23 backcross population revealed a RFLP for the OGR-38 probe which was linked to Ht1. Furthermore, a much reduced level of transcript was detected in the V23-like lines, when compared with the high levels of transcript detected in VR-like lines (FIG. 6).

The data provided strong evidence that the OGR-38 cDNA clone, contained in plasmid pCGP1805, corresponded to the Ht1 locus and represented a F3'H.

RFLP Analysis of a V23×R51 $F_2$ Backcross

RFLP analysis was used to investigate linkage of the gene corresponding to the OGR-38 cDNA to known genetic loci.

The RFLP linkage analysis was performed using a Macintosh version 2.0 of the MapMaker mapping program (Du Pont) (Lander et at, 1987). A LOD score of 3.0 was used for the linkage threshold.

Analysis of EcoRI or XbaI digested genomic DNA isolated from a V23×R51 $F_2$ population revealed a RFLP for the OGR-38 probe which was linked to PAc4. PAc4, a petunia actin cDNA clone (Baird and Meagher, 1987), is a molecular marker for chromosome III and is linked to the Ht1 locus (McLean et al., 1990). There was co-segregation of the OGR-38 and PAc4 RFLPs for 36 out of 44 V23×R51 $F_2$ plants. This represents a recombination frequency of 8% which is similar to a reported recombination frequency of 16% between the Ht1 locus and PAc4 (Cornu et al., 1990).

Further Characterisation of OGR-38

The developmental expression profiles in OGR petals, as well as in other OGR tissues, were determined by using the $^{32}$P-labelled fragments of the OGR-38 cDNA insert as a probe against an RNA blot containing 20 μg of total RNA isolated from each of the five petunia OGR petal developmental stages as well as from leaves, sepals, roots, stems, peduncles, ovaries, anthers and styles. The OGR-38 probe hybridized with a 1.81 kb transcript that peaked at the younger stages of 1 to 3 of flower development. The OGR-38 hybridizing transcript was most abundant in the petals and ovaries and was also detected in the sepals, peduncles and anthers of the OGR plant. A low level of transcript was also" detected in the stems. Under the conditions used, no hybridizing transcript was detected by Northern analysis of total RNA isolated from leaf, style or roots.

EXAMPLE 6

Complete Sequence of OGR-38

The complete sequence of the OGR-38 cDNA clone (SEQ ID NO:1) was determined by compilation of sequence from different pUC18 subclones obtained using standard procedures for the generation of randomly-overlapping clones (Sambrook et al., 1989). The sequence contained an open reading frame of 1536 bases which encodes a putative polypeptide of 512 amino acids.

The nucleotide and predicted amino acid sequences of OGR-38 (SEQ ID NO:1 and SEQ ID NO:2) were compared with those of the cytochrome P450 probes used in the screening process and with other petunia cytochrome P450 sequences (U.S. Pat. No. 5,349,125) using an lfasta alignment (Pearson and Lipman, 1988). The nucleotide sequence of OGR-38 was most similar to the nucleic acid sequence of the flavonoid 3'5'-hydroxylases representing Hf1 and Hf2 loci from *P. hybrida* (Holton et al., 1993). The Hf1 clone showed 59.6% similarity to the OGR-38 cDNA clone, over 1471 nucleotides, and 49.9% similarity, over 513 amino acids, while the Hf2 clone showed 59.1% similarity to the OGR-38 cDNA clone, over 1481 nucleotides, and 49.0% similarity, over 511 amino acids.

EXAMPLE 7

The F3'H Assay of the Ht1 cDNA Clone (OGR-38) Expressed in Yeast Construction of pCGP1646

Figure 7:
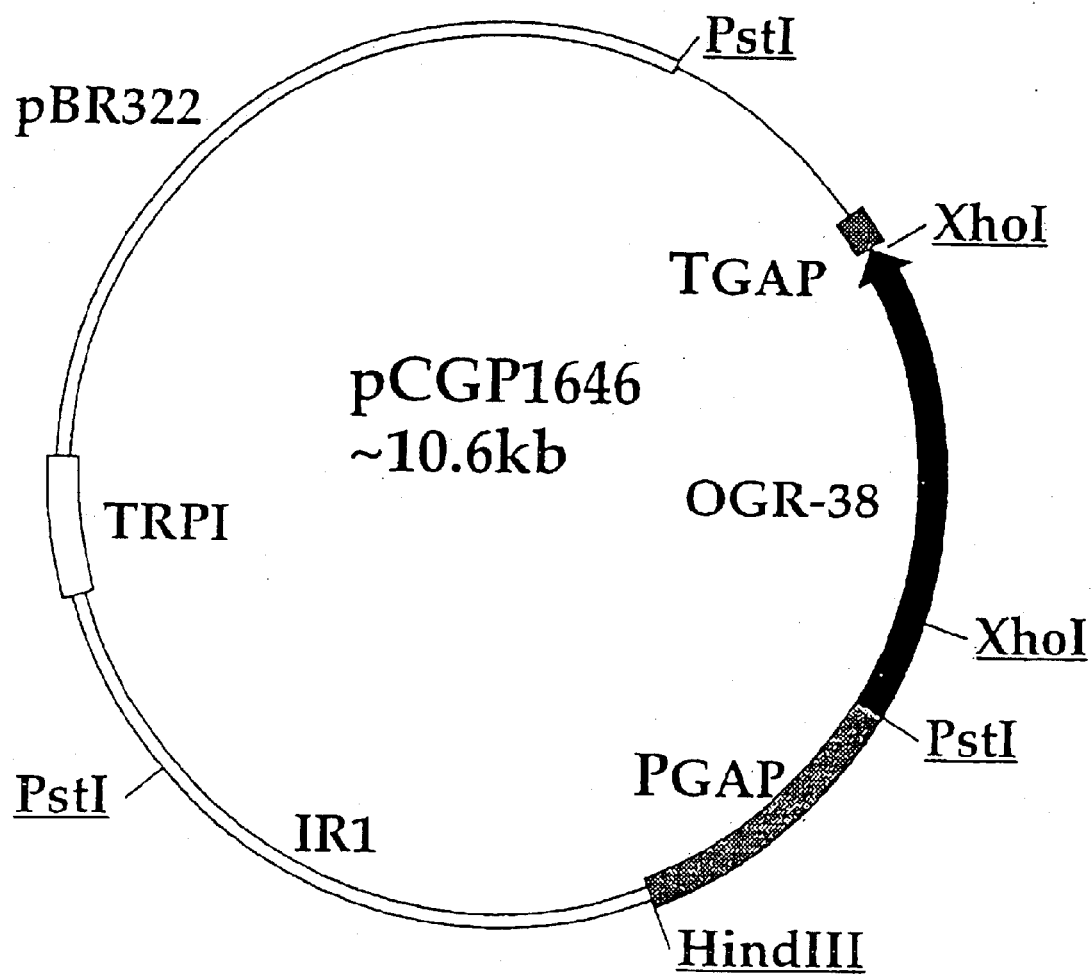
FIG. 7 is a diagrammatic representation of the yeast expression plasmid pCGP1646 (see Example 7). The OGR-38 cDNA insert from pCGP1805 was cloned in a "sense" orientation behind the yeast glyceraldehyde-3-phosphate dehydrogenase promoter (PGAP) in the expression vector pYE22m. TRP1=Trp1 gene, IR1=inverted repeat of, 2 µm plasmid, TGAP=terminator sequence from the yeast glyceraldehyde-3-phosphate dehydrogenase gene. Restriction enzyme sites are also marked.

The plasmid pCGP1646 (FIG. 7) was constructed by cloning the OGR-38 cDNA insert from pCGP1805 in a "sense" orientation behind the yeast glyceraldehyde-3-phosphate dehydrogenase promoter of pYE22m (Tanaka et al., 1988).

The plasmid pCGP1805 was linearised by digestion with Asp718. The overhanging 5' ends were "filled in" using DNA polymerase (Klenow fragment) according to standard protocols (Sambrook et al., 1989). The 1.8 kb OGR-38 cDNA fragment was released upon digestion with SmaI. The cDNA fragment was isolated and purified using the, Bresaclean kit (Bresatec) and ligated with blunted EcoRI ends of pYE22m. The plasmid pYE22m had been digested with EcoRI and the overhanging 5' ends were removed using DNA polymerase (Klenow fragment) according to standard protocols (Sambrook et al., 1989). The ligation was carried out with the Amersham Ligation kit using 100 ng of the 1.8 kb OGR-38; fragment and 150 ng of the prepared yeast vector, pYE22m. Correct insertion of the insert in pYE22m was established by XhoI/SalI restriction enzyme analysis of the plasmid DNA [1]isolated from ampicillin-resistant transformants.

Yeast Transformation

The yeast strain G-1315 (Mat α, trpl) (Ashikari et al., 1989) was transformed with pCGP1646 according to Ito et at. (1983). The transformants were selected by their ability to restore G-1315 to tryptophan prototrophy.

Preparation of Yeast Extracts for Assay of F3'H Activity

A single isolate of G-1315/pCGP1646 was used to inoculate 50 mL of Modified Burkholder's medium (20.0 g/L dextrose, 2.0 g/L L-asparagine, 1.5 g/L $KH_2PO_4$, 0.5 g/L $MgSO_4.7H_2O$, 0.33 g/L $CaCl_2$, 2 g/L $(NH_4)_2SO_4$, 0.1 mg/L KI, 0.92 g/L $(NH_4)_6Mo_7O_{24}.4H_2O$, 0.1 g/L nitrilotriacetic acid, 0.99 mg/L $FeSO_4.7H_2O$, 1.25 mg/L EDTA, 5.47 mg/L $ZuSO_4.7H_2O$, 2.5 mg/L $FeSO_4.7H_2O$, 0.77 mg/L $MSO_4.7H_2O$, 0.196 mg/L $CuSO_4.5H_2O$, 0.124 mg/L $Co(NH_4)_2(SO_4)_2.6H_2O$, 10.088 mg/L $Na_2B_4O_7.10H_2O$, 0.2 mg/L thiamine, 0.2 mg/L pyridoxine, 0.2 mg/L nicotinic acid, 0.2 mg/L pantothenate, 0.002 mg/L biotin, 10 mg/L inositol) which was subsequently incubated until the value at $OD_{600}$ was 1.8 at 30° C. Cells were collected by centrifugation and resuspened in Buffer 1 [10 mM Tris-HCl buffer (pH 7.5) containing 2 M sorbitol, 0.1 mM DTT, 0.1 mM EDTA, 0.4 mM phenylmethylsulfonyl fluoride (PMSF) and 5 mg yeast lytic enzyme/mL]. Following incubation for 1 hour at 30° C. with gentle shaking, the cells were pelleted by centrifugation and washed in ice cold Buffer 2 [10 mM Tris-HCl (pH7.5) containing 0.65 M sorbitol, 0.1 mM DTT, 0.1 mM EDTA, 0.4 mM PMSF]. The cells were then resuspended in Buffer 2 and sonicated using six 15-second bursts with a Branson Sonifier 250 at duty cycle 30% and output control 10%. The sonicated suspension was centrifiged at 10,000 rpm for 30 minutes and the supernatant was centrifuged at 13,000 rpm for 90 minutes. The microsomal pellet was resuspended in assay buffer (100 mM potassium phosphate (pH 8), 1 mM EDTA, 20 mM 2-mercaptoethanol) and 100 μL was assayed for activity.

F3'H Assay

F3'H enzyme activity was measured using a modified version of the method described by Stotz and Forkmann (1982). The assay reaction mixture typically contained 100 μL of yeast extract, 5 μL of 50 mM NADPH in assay buffer (100 mM potassium phosphate (pH8.0), 1 mM EDTA and 20 mM 2-mercaptoethanol) and 10 μCi of [$^3$H]-naringenin and was made up to a final volume of 210 μL with the assay buffer. Following incubation at 23° C. for 2–16 hours, the reaction mixture was extracted with 0.5 mL of ethylacetate. The ethylacetate phase was dried under vacuum and then resuspended in 10 μL of ethylacetate. The tritiated flavonoid molecules were separated on cellulose thin layer plates (Merck Art 5577, Germany) using a chloroform:acetic acid:water (10:9:1 v/v) solvent system. The reaction products were localised by autoradiography and identified by comparison to non-radioactive naringenin and eriodictyol standards which were run alongside the reaction products and visualised under UV light.

F3'H activity was detected in extracts of G1315/pCGP1646, but not in extracts of non-transgenic yeast. From this it was concluded that the cDNA insert from pCGP1805 (OGR-38), which was linked to the Ht1 locus, encoded a F3'H.

EXAMPLE 8

Transient Expression of the Ht1 cDNA Clone (OGR-38) in Plants Construction of pCGP1867

Figure 8:
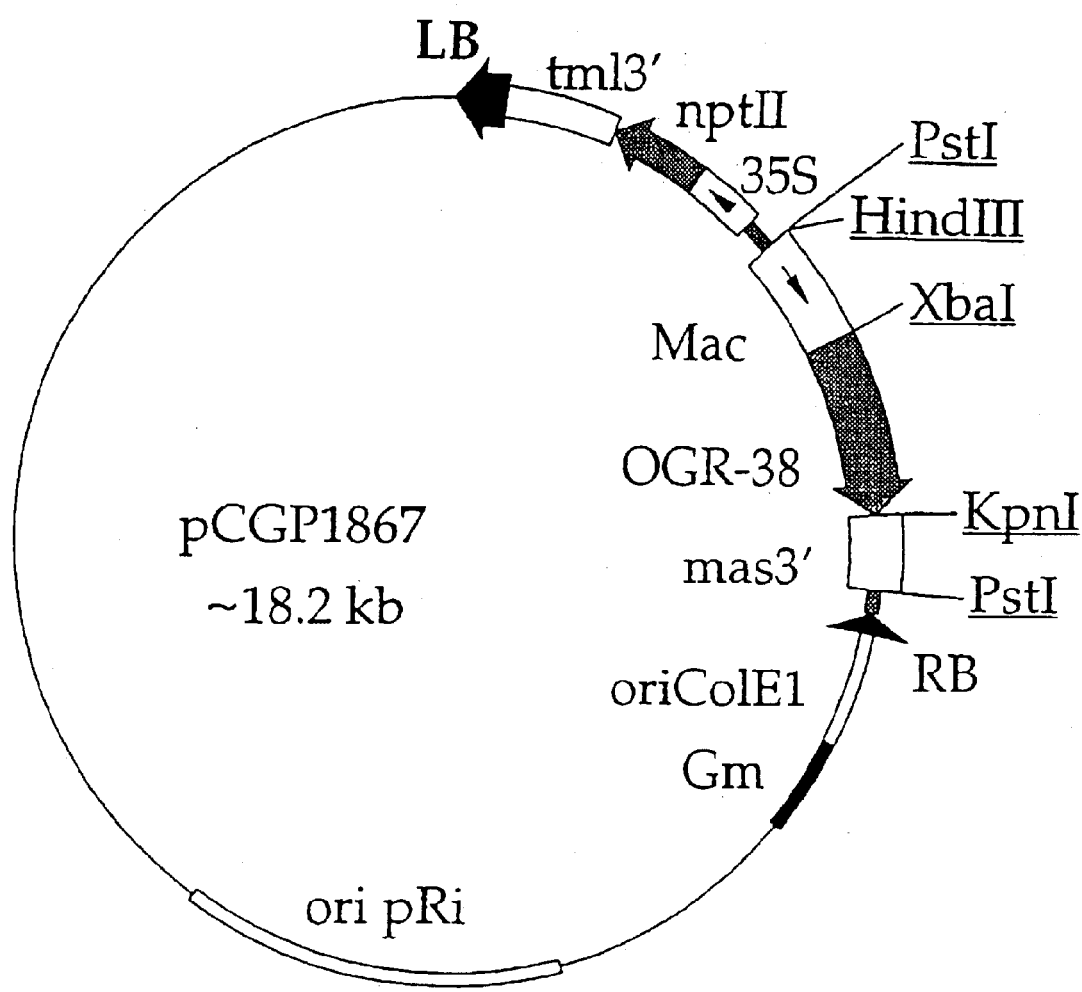
FIG. 8 is a diagrammatic representation of the binary plasmid pCGP1867 (described in Example 8). The Ht1 cDNA insert (OGR-38) from pCGP1805 was closed in a "sense" orientation behind the Mac promoter in the expression vector of pCGP293. Abbreviations are as follows: LB=left border; RB=right border; Gm=the gentamycin resistance gene; 35S=the promoter region from the Cauliflower Mosaic Virus 35S gene; nptII=the neomycin phosphotransferase II gene; tml3'=the terminator region from the tml gene of Agrobacterium; mas3'=the terminator region from the mannopine synthase gene of Agrobacterium; ori pRi=a broad host range origin of replication from an *Agrobacterium rhizogenes* plasmid; oriColE1=a high copy origin of replication from a Colcinin E1 plasmid. Restriction enzyme sites are also marked.

Plasmid pCGP1867 (FIG. 8) was constructed by cloning the cDNA insert from pCGP1805 in a "sense" orientation behind the Mac promoter (Comai et al., 1990) of pCGP293 (Brugliera et al., 1994). The plasmid pCGP1805 was digested with XbaI and KpnI to release the cDNA insert. The cDNA fragment was isolated and purified using the Bresaclean kit (Bresatec) and ligated with XhaI/KpnI ends of the pCGF293 binary vector. The ligation was carried out using the Amersham ligation kit. Correct insertion of the fragment in pCGP1867 was established by XbaI/KpnI restriction enzyme analysis of DNA isolated from gentamycin-resistant transformants.

Transient Expression of the Ht1 cDNA Clone (OGR-38) in Petunia Petals

In order to rapidly determine whether the OGR-38 cDNA fragment in pCGP1867 represented a functional F3'H in plants, a transient expression study was established. Petals of the mutant *P. hybrida* line Skr4×SW63 were bombarded with gold particles (1 μm diameter) coated with pCGP1867 DNA.

Gold microcarriers were prewashed 3 times in 100% ethanol and resuspended in sterile water. For each shot, 1 μg of pCGP1867 DNA, 0.5 mg of gold microcarriers, 10 μL of 2.5 M $CaCl_2$ and 2 μL of 100 mM spermidine (free base) were mixed by vortexing for 2 minutes. The DNA coated gold particles were pelleted by centrifugation, washed twice with 100% ethanol and finally resuspended in 10 μL of 100% ethanol. The suspension was placed directly on the centre of the macrocarrier and allowed to dry.

Stages 1 and 2 of Skr4×SW63 flowers were cut vertically into halves and partially embedded in MS solid media (3% (w/v) sucrose, 100 mg/L myo-inositol, 1×MS salts, 0.5 mg/L pyridoxine-HCl, 0.1 mg/L thiamine-HCl, 0.5 mg/L nicotinic acid and 2 mg/L glycine). The peals were placed so that the inside of the flower buds were facing upwards. A Biolistic PDS-1000/He System (Bio-Rad), using a Helium gas pressure of 900 psi and a chamber vacuum of 28 inches of mercury, was used to project the gold microcarriers into the petal tissue. After 6–12 hours under lights in a controlled plant growth room at 22° C., red anthocyanin spots were observed on the upper epidermal layer of the petal tissue bombarded with pCGP1867 ed particles. No coloured spots were observed in control petal bombarded with gold particles alone. These results indicated that the OGR-38 cDNA clone under the control of the Mac promoter was functional, at least transiently, in petal tissue.

EXAMPLE 9

Stable Expression of the Ht1 cDNA Clone (OGR-38) in Petunia Petals Complementation of a ht1/ht1 Petunia Cultivar A. *tumefaciens* Transformations The plasmid pCGP1867 (FIG. 8) was introduced into the *Agrobacterium tumefaciens* strain AGL0 by adding 5 µg of plasmid DNA to 100 µL of competent AGL0 cells prepared by inoculating a 50 mL MG/L (Garfinkel and Nester, 1980) culture and growing for 16 hours with shaking at 28° C. The cells were then pelleted and resuspended in 0.5 mL of 85% (v/v) 100 mM $CaCl_2$/15% (v/v) glycerol. The DNA-Agrobacterium mixture was frozen by incubation in liquid $N_2$ for 2 minutes and then allowed to thaw by incubation at 37° C. for 5 minutes. The DNA/bacterial mix was then placed on ice for a further 10 minutes. The cells were then mixed with 1 mL of LB (Sambrook et al., 1989) media and incubated with shaking for 16 hours at 28° C. Cells of A. *tumefaciens* carrying pCGP1867 were selected on LB agar plates containing 10 µg/mL gentamycin. The presence of pCGP1867 was confirmed by Southern analysis of DNA isolated from the gentamycin-resistant transformants.

Petunia Transformations (a) Plant Material

Leaf tissue from mature plants of *P. hybrida* cv Skr4×SW63 was treated in 1.25% (w/v) sodium hypochlorite for 2 minutes and then rinsed three times in sterile water. The leaf tissue was then cut into 25 $mm^2$ squares and precultured on MS media (Murashige and Skoog, 1962) supplemented with 0.05 mg/L kinetin and 1.0 mg/L 2,4-dichlorophenoxyacetic acid (2,4-D) for 24 hours.

(b) Co-cultivation of Agrobacterium and Petunia Tisue

A. *tumefaciens* strain AGL0 containing the binary vector pCGP1867 (FIG. 11) was maintained at 4° C. on MG/L agar plates with 100 mg/L gentamycin. A single colony was grown overnight in liquid medium containing 1% (w/v) Bacto-peptone, 0.5% (w/v) Bacto-yeast extract and 1% (w/v) NaCl. A final concentration of $5 \times 10^8$ cells/mL was prepared the next day by dilution in liquid MS medium containing B5 vitamins (Gamborg et al., 1968) and 3% (w/v) sucrose (BPM). The leaf discs were dipped for 2 minutes into BPM containing AGL0/pCGP1867. The leaf discs were then blotted dry and placed on co-cultivation media for 4 days. The co-cultivation medium consisted of SH medium (Schenk and Hildebrandt, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

(c) Recovery of Transgenic Petunia Plants

After co-cultivation, the leaf discs were transferred to selection medium (MS medium supplemented with 3% (w/v) sucrose, α-benzylaminopurine (BAP) 2 mg/L, 0.5 mg/L α-naphthalene acetic acid (NAA), kanamycin 300 mg/L, 350 mg/L cefotaxime and 0.3% (w/v) Gelrite Gellan Gum (Schweizerhall)). Regenerating explants were transferred to fresh selection medium after 4 weeks. Adventitious shoots which survived the kanamycin selection were isolated and transferred to BPM containing 100 mg/L kanamycin and 200 mg/L cefotaxime for root induction. All cultures were maintained under a 16 hour photoperiod (60 µmol. m-2, s-1 cool white fluorescent light) at 23±2° C. When roots reached 2–3 cm in length the transgenic petunia plantlets were transferred to autoclaved Debco 51410/2 potting mix in 8 cm tubes. After 4 weeks, plants were replanted into 15 cm pots, using the same potting mix, and maintained at 23° C. under a 14 hour photoperiod (300 mol. m-2, s-1 mercury halide light).

EXAMPLE 10

Transgenic Plant Phenotype Analysis pCGP1867 in Skr4×SW63

Table 5 shows the various petal and pollen colour phenotypes obtained with Skr4×SW63 plan transformed with the pCGP1867 plasmid. The transgenic plants #593A, 590A, 571A, 589A, 592A and 591A produced flowers with altered petal colour. Moreover, the anthers and pollen of the flowers from plants #593A, 590A, 589A, 592A and 5911A were pink, compared with those of the control Skr4×SW63 plant, which were white. The change in anther and pollen colour, observed on introduction of plasmid pCGP1867 into Skr4×SW63 petunia plants, was an unanticipated outcome. The colour codes are taken from the Royal Horticultural Society's Colour Chart (RHSCC). They provide an alternative means by which to describe the colour phenotypes observed. The designated numbers, however, should be taken only as a guide to the perceived colours and should not be regarded as limiting the possible colours which may be obtained.

TABLE 5

Summary of petal, anther and pollen colours obtained in Skr4 xSW63 uz,2/31 plants transformed with pCGP1867

| Accession Number | Petal Limb Colour | RHSCC Code (petal limb) | Anther & Pollen Colour |
|---|---|---|---|
| Skr4 x SW63 control (594A) | very pale lilac | 69B/73D | white |
| 593A | dark pink | 67B | pink |
| 590A | dark pink and pink sectors | sectored 67B and 73A | pink |
| 571A | pink | 68A and B | pink |
| 589A | dark pink | 68A | pink |
| 592A | pink and light pink sectors | 68A and 68B | light pink |
| 591A | dark pink | 68A | pink |
| 570A | very pale lilac | 69B/73D | white |

The expression of the introduced Ht1 cDNA in the Skr4×SW63 hybrid had a marked effect on flower colour. The stamen tissue of the non-transgenic control is white, whereas the same tissue in most of the transgenic plans was pink. In addition, expression of the Ht1 cDNA in the Skr4×SW63 hybrid conferred a dark pink hue to the corolla, which is normally very pale lilac.

EXAMPLE 11

Analysis of Products

The anthocyanidins and flavonols produced in the petals and stamens (included the pollen, anthers and filaments) of the Skr4×SW63 plants transformed with pCGP 1867 were analysed by TLC.

Extraction of Anthocyanins and Flavonols

Prior to TLC analysis, the anthocyanin and flavonol molecules present in petal and stamen extracts were acid hydrolysed to remove glycosyl moieties from the anthocyanidin or flavonol core. Anthocyanidin and flavonol standards were used to help identify the compounds present in the floral extracts.

Anthocyanins and flavonols were extracted and hydrolysed by boiling between 100 to 200 mg of petal limbs, or five stamens, in 1 mL of 2 M hydrochloric acid for 30 minutes. The hydrolysed anthocyanins and flavonols were excted with 200 µL of iso-amylalcohol. This mixture was then dried down under vacuum and resuspended in a smaller volume of methanol/1% (v/v) HCl. The volume of methanol/1% (v/v) HCl used was based on the initial fresh weight of the petal so that the relative levels of flavonoidsin the petals could be estimated. Extracts from the stamens were resuspended in 1 µL of methanol/1% (v/v) HCl. A 1 µL aliquot of the extracts from the pCGP1867 in Skr4×SW63 petals and stamens was spotted onto a TLC plate.

TLC Analysis of Floral Extracts

Acid-hydrolysed floral extracts were run in a Forestal solvent system (HOAc:water:HCl; 30:10:3) (Markham, 1982). Table 6 shows the results of the TLC analysis of the anthocyanidins and flavonols present in some of the flowers and stamens of the transgenic Skr4×SW63 petunia plants transformed with pCGP1867. Indicative relative amounts of the flavonols and anthocyanidins (designated with a "+" to "+++") were estimated by comparing the intensities of the spots observed on the TLC plate.

SW63/pCGP1867 plants correlated with the pink and dark pink colours observed in the petals, anthers and pollen of the same plants.

Co-suppression of F3'H Activity

The plasmid pCGP1867 was also introduced into *P. hybrida* cv. Old Glory: Red (Ht1) in order to reduce the level of F3'H activity.

Petunia transformations were carried out as described in Example 9, above.

Two out of 38 transgenic plants produced flowers with an altered phenotype. OGR normally produces deep red flowers (RHSCC#46B). The two transgenic plants with altered floral colour produced flowers with a light pink or light red hue (RHSCC#54B and #53C).

Northern analysis on RNA isolated from flowers produced by four transgenic plants (the two transgenics with an altered phenotype and two transgenics with the usual deep red flowers) was performed to examine the level of OGR-38 transcripts. Ten micrograms of total petal RNA was separated on a 1.2% (w/v) agarose/formaldehyde gel (Sambrook et al. 1989) and transferred to HybondN nylon membrane (Amersham), as described previously. Petal RNA from a non-transformed OGR flower was also included as a control. $^{32}$P-labelled fragments of the OGR-38 cDNA inserts were used to probe the RNA blot.

The OGR-38 probe detected transcripts of approximately 2.4 kb and 1.8 kb in the flowers of the transgenic plants. However, the level of both transcripts detected in the light pink and light red flowers was considerably lower than that detected in the deep red transgenic flowers. The endogenous 1.8 kb transcript was also detected in RNA from the non-transformed OGR flowers. In order to confirm that the 2.4 kb

TABLE 6

Relative levels of anthocyanidins and flavonols detected in the petal limbs and stamens of Skr4 x SW63 plants transformed with pCGP1867.

| Acc # | Petal Colour | Anthocyanidins | | | Flavonols | |
|---|---|---|---|---|---|---|
| | | Malvidin | Cyanidin | Peonidin | Kaempferol | Quercetin |
| Skr4 x SW63 control petal limb | pale lilac | +/− | − | − | + | − |
| 593A petal limb | dark pink | − | + | +++ | − | ++ |
| 571A petal limb | pink | − | + | + | − | + |
| 589A petal limb | dark pink | − | + | ++ | − | ++ |
| 570A petal limb | pale lilac | +/− | − | − | + | − |
| Skr4 x SW63 control stamens | white | − | − | − | +++ | + |
| 593A stamens | pink | − | − | ++ | − | +++ |

Figure 1B:
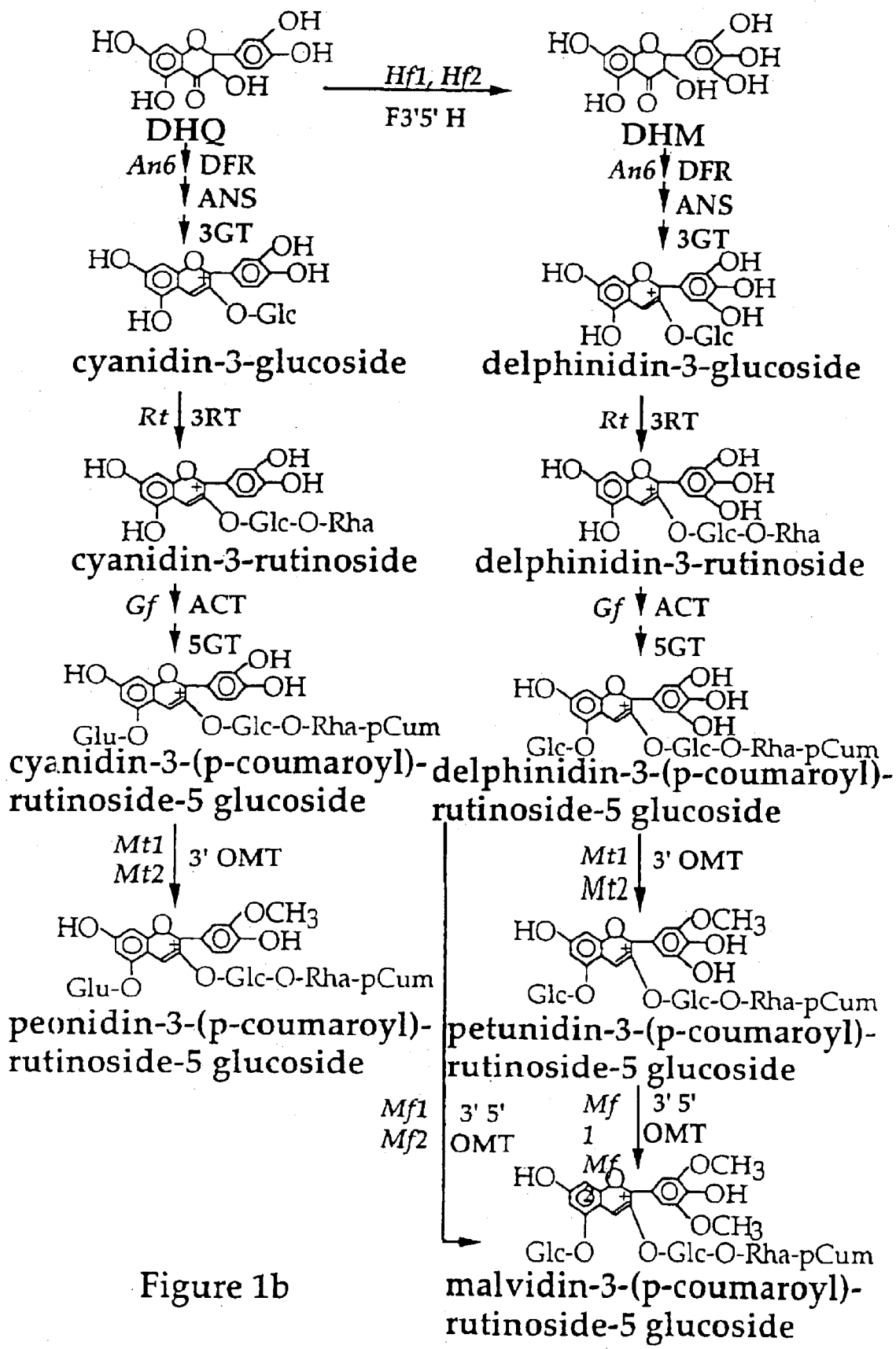

Introduction of the Ht1 cDNA clone into Skr4×SW63 led to production of the 3'-hydroxylated flavonoids, quercetin, peonidin and some cyanidin in the petals. Peonidin is the methylated derivative of cyanidin (FIGS. 1a and 1b). Only kaempferol and a small amount of malvidin were detected in the non-transgenic Skr4×SW63 control (Table 6). Although Skr4×SW63 is homozygous recessive for both the Hf1 and Hf2 genes, these mutations do not completely block production of F3'5'H (see U.S. Pat. No. 5,349,125) and low levels of malvidin are produced to give the petal limb a pale lilac colour.

The stamens with the pink pollen and anthers produced by the transgenic plant #593A contained peonidin and quercetin, while the non-transgenic Skr4×SW63 control with white pollen and anthers contained kaempferol and a low level of quercetin (Table 6).

The accumulation of the 3'-hydroxylated anthocyanidin, peonidin, in the petals and stamens of the transgenic Skr4× transcript was from the introduced OGR-38 transgene, $^{32}$P-labelled fragments of the mas terminator region were used to probe the same RNA blot. The mas probe detected the 2.4 kb transcript, suggesting that at least this transcript was derived from the introduced OGR-38 transgene.

Analysis of Anthocyanin Levels

The levels of anthocyanins in the control flowers and in the light pink transgenic flower were measured by spectrophotometric analysis.

Extraction of Anthocyanins and Flavonols

Anthocyanins and flavonols were extracted from petal limbs by incubating 200 to 300 mg of petal limb in 2 mL of methanol/1% (v/v) HCl for 16 hours at 4° C. Fifty µL of this solution was then added to 950 µL of methanol/1% (v/v) HCl and the absorbance of the diluted solution at 530 nm was determined. The anthocyanin level in nmoles per gram was determined using the formula: [(Abs (530 nm)/34,000)× volume of extraction buffer×dilution factor×$10^6$]/weight in grams.

The light pink flower was found to contain approximately 915 nmoles of anthocyanin per gram of petal limb tissue whilst the control flower contained around 4000 nmoles/ gram.

These data suggest that introduction of the petunia F3'H (OGR-38) cDNA clone in a sense orientation into OGR plants leads to "co-suppression" (i.e. reduction) of both the endogenous and the transgenic F3'H transcripts. A correlation was observed between lighter flower colours, reduced anthocyanin production and reduced F3'H transcript level.

EXAMPLE 12

Isolation of a F3'H cDNA Clone from *Dianthus caryophyllus*

In order to isolate a *Dianthus caryophylluss* (carnation) F3'H cDNA clone, the petunia Ht1-linked F3'H cDNA clone (OGR-38), contained in pCGP1805 (described above), was used to screen a Carnation cv. Kortina Chanel petal cDNA library, under low stringency conditions.

Construction of Carnation cv. Kortina Chanel cDNA Library

Twenty micrograms of total RNA isolated (as described previously) from stages 1, 2 and 3 of Kortina Chanel flowers was reverse transcribed in a 50 μL volume containing 1×Superscript™reaction buffer, 10 mM dithiothreitol (DTT) 500 μM dATP, 500 μM dGTP, 500 μM dTTP, 500 μM 5-methyl-dCTP, 2.8 μg Primer-Linker oligo from ZAP-cDNA Gigapack III Gold cloning kit (Stratagene) and 2 μL Superscript™ reverse transcriptase (BRL). The reaction mix was incubated at 37° C. for 60 minutes, then placed on ice. A ZAP-cDNA Gigapack III Gold Cloning kit (Stratagene) was used to complete the library construction. The total number of recombinants was 2.4×$10^6$.

A total of 200,000 pfu of the packaged cDNA was plated at 10,000 pfu per 15 cm diameter plate after transfecting XL1-Blue MRF' cells. The plates were incubated at 37° C. for 8 hours, then stored overnight at 4° C. Duplicate lifts were taken onto Colony/Plaque Screen™ filters (DuPont) and treated as recommended by the manufacturer.

Screening of Kortina Chanel Petal cDNA Library for a F3'H cDNA Clone

Prior to hybridization, the duplicate plaque lifts were treated as described previously. The duplicate lifts from the Kortina Chanel petal cDNA library were screened with $^{32}$P-labelled fragments of the 1.8 kb EcoRI/XhoI insert from pCGP1805. Low stringency conditions, as described for the screening of the petunia OGR cDNA library, were used.

One strongly-hybridizing plaque was picked into PSB and rescreened as detailed above to isolate purified plaques. The plasmid contained in the lZAP bacteriophage vector was rescued and named pCGP1807.

The KC-1 cDNA insert contained in pCGP1807 was released upon digestion with EcoRI/XhoI and is around 2 kb. The complete sequence of the KC-1 cDNA clone was determined by compilation of sequence from subclones of the KC-1 cDNA insert. (Partial sequence covering 458 nucleotides had previously been generated from a 800 bp KpnI fragment covering the 3' region of KC-1 which was subcloned into pBluesscript to give pCGP1808.) The complete sequence (SEQ ID NO:3) contained an open reading frame of 1508 bases which encodes a putative polypeptide of 500 amino acids (SEQ ID NO:4).

The nucleotide and predicted amino acid sequences of the carnation KC-1 cDNA clone were compared with those of the petunia OGR-38 F3'H cDNA clone (SEQ ID NO:1 and SEQ ID NO:2). The sequences of the carnation KC-1 cDNA clone (SEQ ID NO:3 and 4) showed 67.3% similarity, over 1555 nucleotides, and 71.5% similarity, over 488 amino acids, to that of the petunia OGR-38 F3'H cDNA clone.

Figure 20I:
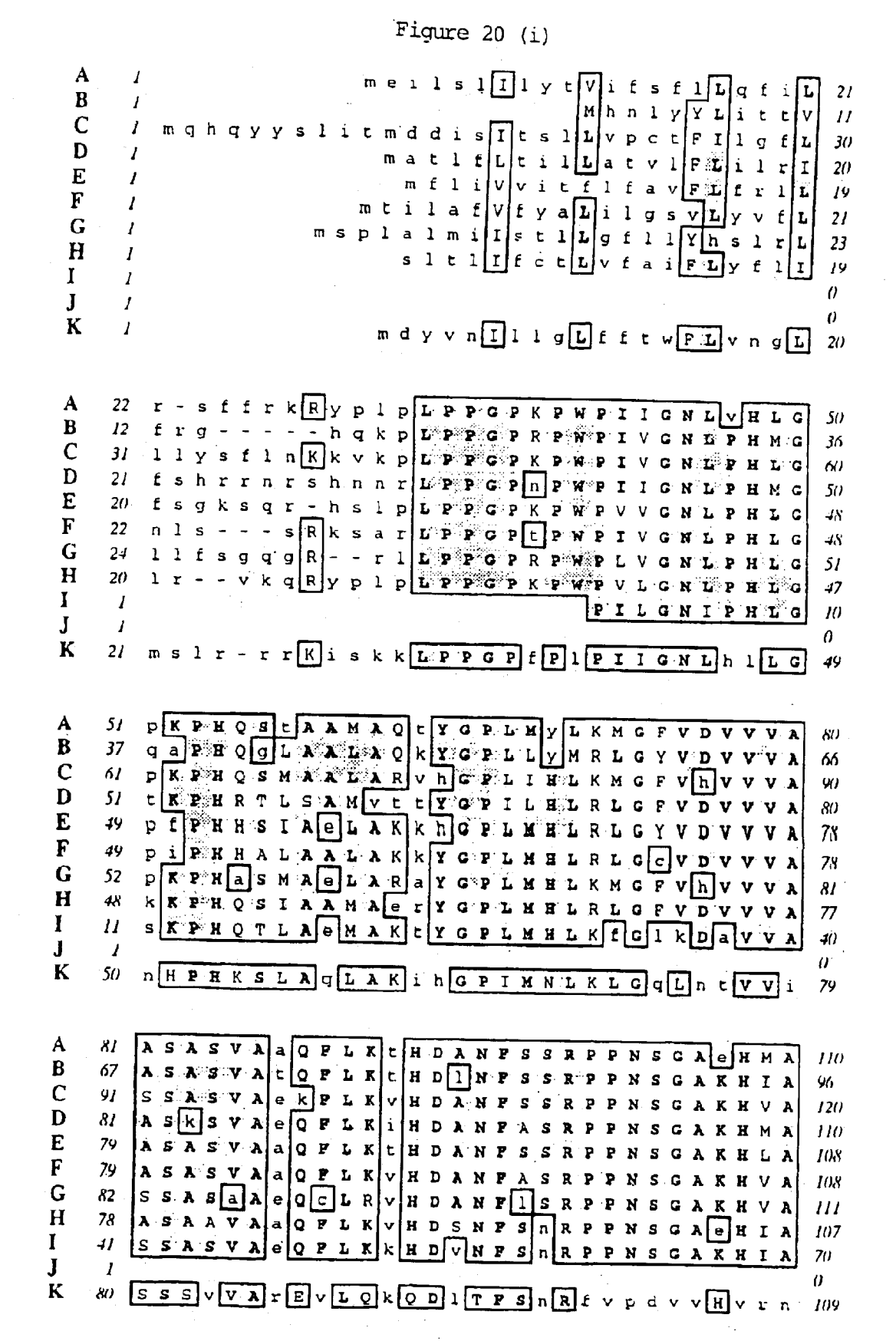
Figure 20II:
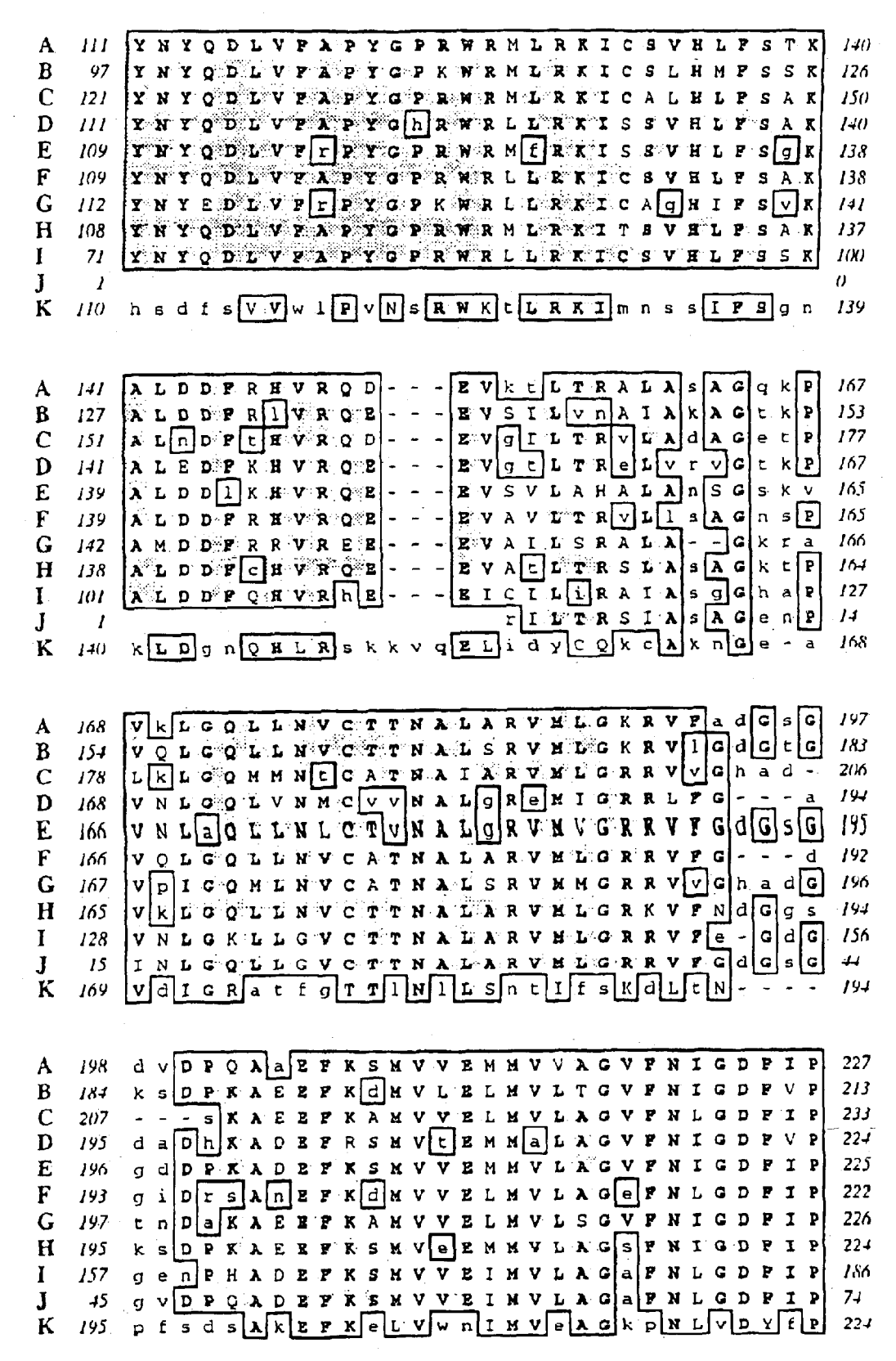
Figure 20V:
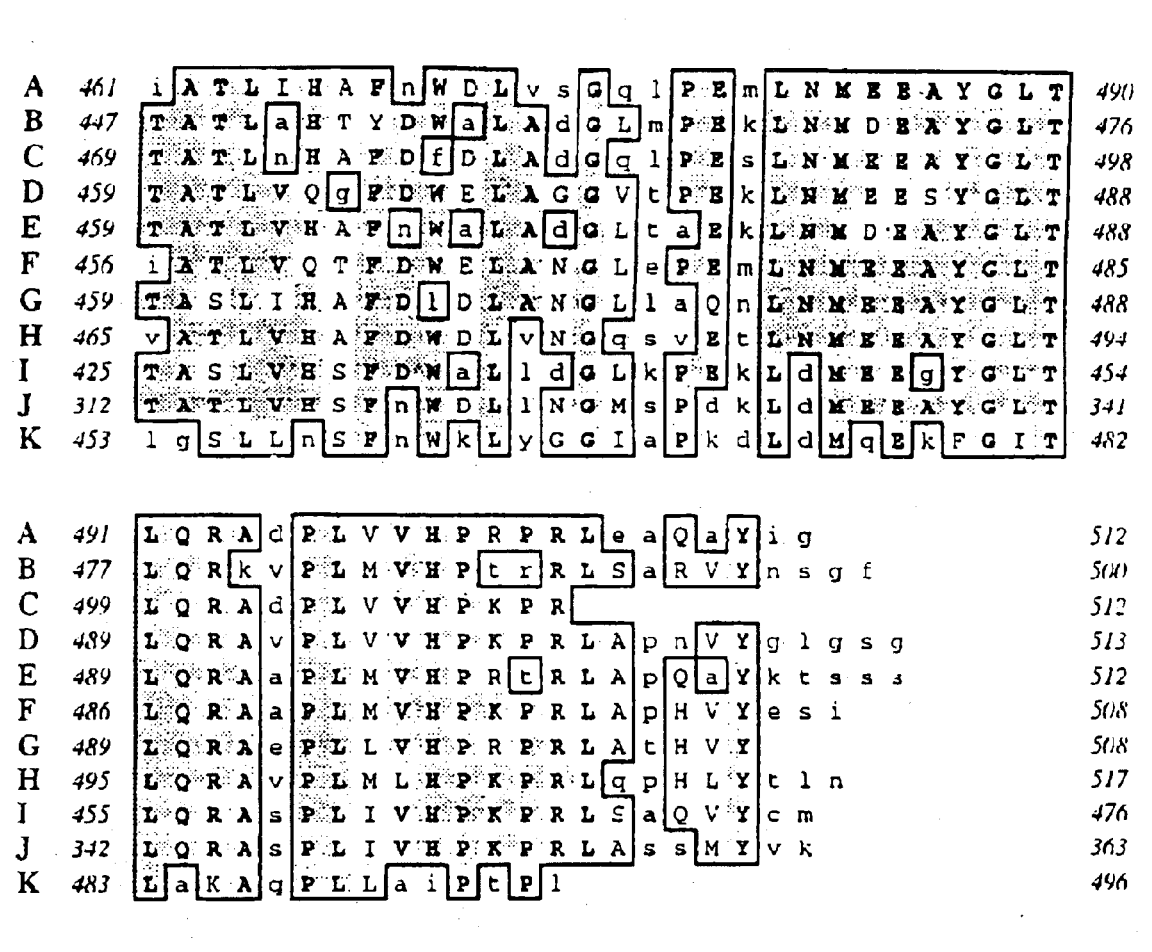

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

EXAMPLE 13

Stable Expression of the Carnation F3'H cDNA (KC-1) Clone in Petunia Petals—Complementation of a ht1/ht1 Petunia Cultivar Preparation of pCGP1810

Figure 9:
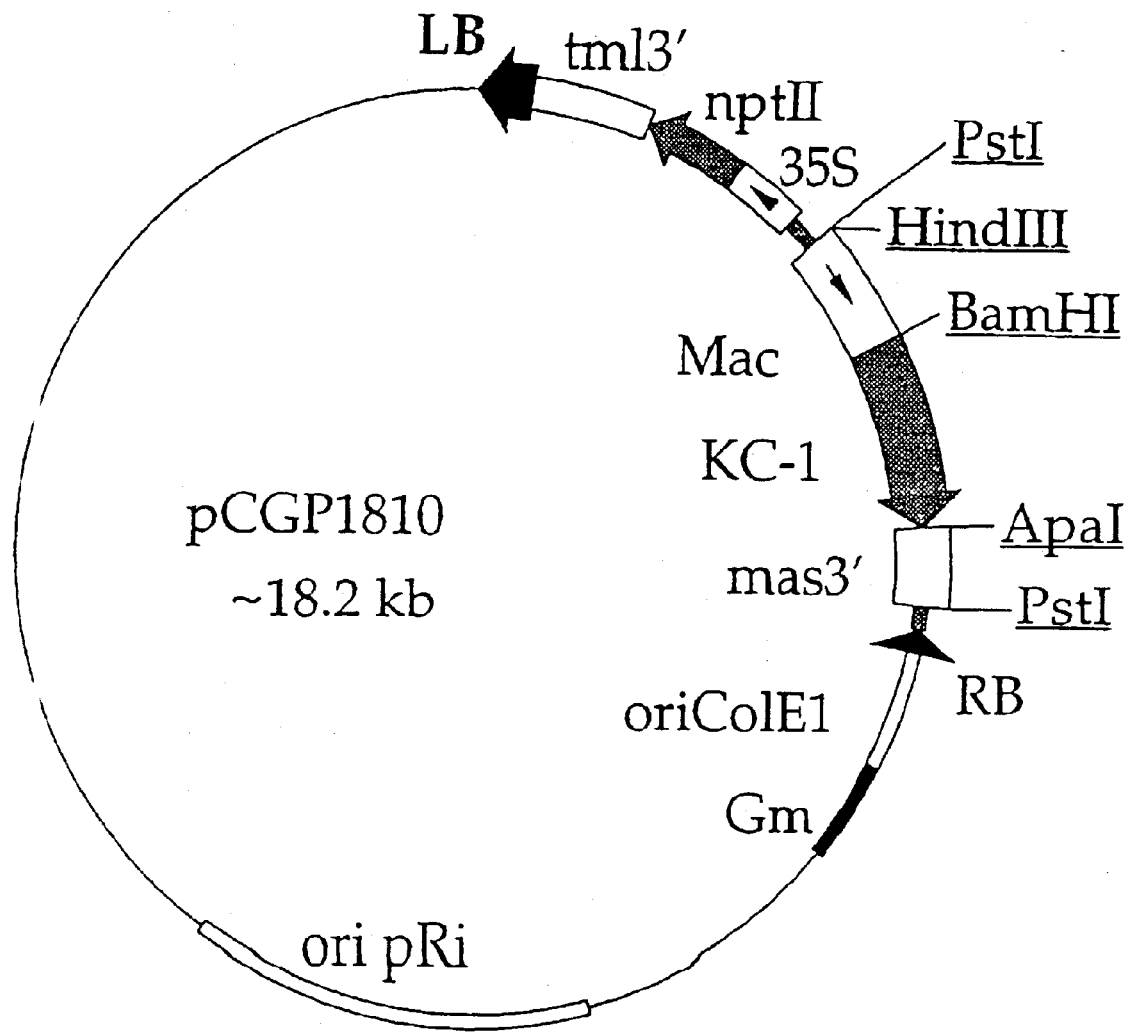
FIG. 9 is a diagrammatic representation of the binary plasmid pCGP1810, preparation of which is described in Example 13. The KC-1 cDNA insert from pCGP1807 (see Example 12) was cloned in a "sense" orientation behind the Mac promoter in the expression vector of pCGP293. Abbreviations are as follows: LB=left border; RB=right border; Gm=the gentamycin resistance gene; 35S=the promoter region from the Cauliflower Mosaic Virus 35S gene; nptII= the neomycin phosphotransferase II gene; tml3'=the terminator region from the tml gene of Agrobacterium; mas3'=the terminator region from the mannopine synthase gene of Agrobacterium; ori pRi=a broad host range origin of replication from a plasmid from *Agrobacterium rhizogenes*; oriColE1=a high copy origin of replication from a Colcinin E1 plasmid. Restriction enzyme sites are also marked.

Plasmid pCGP1810 (FIG. 9) was constructed by cloning the cDNA insert from pCGP1807 in a "sense" orientation behind the Mac promoter (Comai et al., 1990) of pCGP90 (U.S. Pat. No. 5,349,125), a pCGP293 based construct (Brugliera et al., 1994). The plasmid pCGP1807 was digested with BamHI and ApaI to release the KC-1 cDNA insert. The cDNA fragment was isolated and purified using the Bresaclean kit resatec). The pCGP90 binary vector was digested with BamHI and ApaI to release the linearised vector and the Hf1 cDNA insert. The linearised vector was isolated and purified using the Bresaclean kit (Bresatec) and ligated with BamHI/ApaI ends of the KC-1 cDNA clone. The ligation was carried out using the Amersham ligation. Correct insertion of the insert in pCGP1810 was established by BamHI/ApaI restriction enzyme analysis of DNA isolated from gentamycin-resistant transformants.

The binary vector pCGP1810 was introduced into *A. tumefaciens* strain AGL0 cells, as described in Example 9. The pCGP1810/AGL0 cells were subsequently used to transform Skr4×SW63 petunia plants (also described in Example 9), to test for stable expression and activity of the enzyme encoded by the gene corresponding to the KC-1 cDNA clone.

EXAMPLE 14

Transgenic Plant Phenotype Analysis pCGP1810 in Skr4×SW63

The expression of the introduced KC-1 cDNA n the Skr4×SW63 hybrid had a marked effect on flower colour. Ten of the twelve transgenic plants transformed with pCGP1810 produced flowers with an altered petal colour (RHSCC# 73A), compared with the Skr4×Sw63 control (RHSCC# 75C). Moreover the anthers and pollen of the transgenic flowers were pink, compared with those of the control Skr4×SW63 plant, which were white. In addition, expression of the KC-1 cDNA in the Skr4×SW63 hybrid conferred a dark pink hue to the corolla, which is normally pale lilac. The colour codes are taken from the Royal Horticultural Society's Colour Chart (RHSCC). They provide an alternative means by which to describe the colour phenotypes observed. The designated numbers, however, should be taken only as a guide to the perceived colours and should not be regarded as limiting the possible colours which may be obtained.

Acid-hydrolysed floral extracts (see Example 11) were run in a Forestal solvent system (HOAc:water:HCl; 30:10:3) (Markham, 1982). The 3' hydroxylated flavonoids, peonidin and quercetin, were readily detected in the petal limbs of the transgenic plants. Only kaempferol and a small amount of malvidin were detected in the non-transgenic Skr4×SW63 control.

The accumulation of the 3'-hydroxylated anthocyanidin, peonidin, in the petals of the transgenic Skr4×SW63/pCGP1810 plants correlated with the dark pink colours observed in the petals of the same plants.

Construction of pCGP1813

Plasmid pCGP1811 was constructed by cloning the cDNA insert from pCGP1807 in a "sense" orientation behind the Mac promoter (Comai et al., 1990) of pCGP1958. The plasmid pCGP1958 contains the Mac promoter and mannopine synthase (mas)(Comai et al., 1990) terminator in a pUC19 backbone. The plasmid pCGP1807 was digested with PstI and XhoI to release the cDNA insert. The overhanging 5' ends were filled in using DNA polymerase (Klenow fragment) (Sambrook et al., 1989). The cDNA fragment was isolated and purified using the Bresaclean kit (Bresatec) and ligated with SmaI ends of the pCGP1958 vector to produce pCGP1811.

Figure 10:
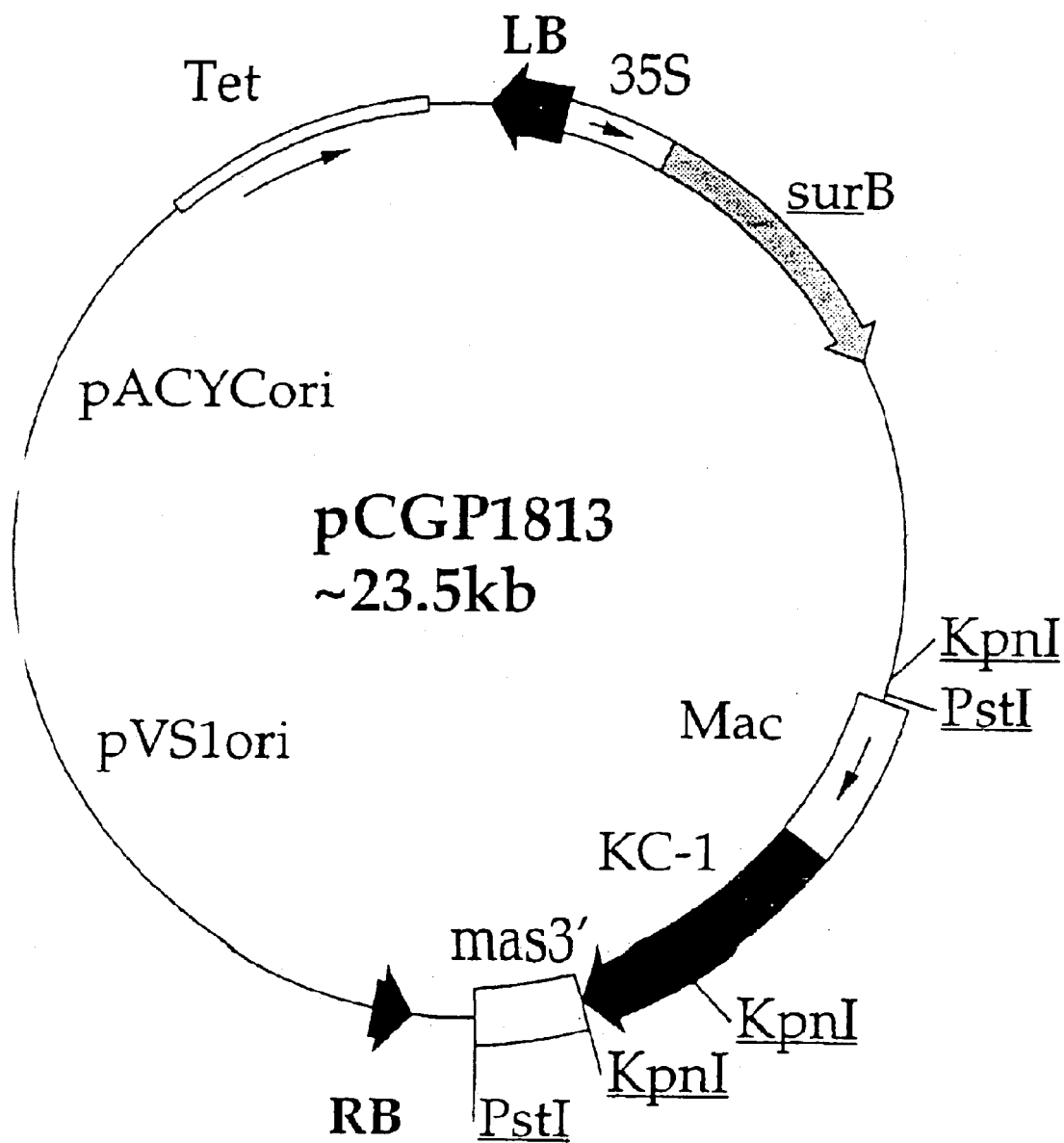
FIG. 10 is a diagrammatic representation of the binary plasmid pCGP1813, construction of which is described in Example 14. The KC-1 cDNA insert from pCGP1807 (see Example 12) was cloned in a "sense" orientation between the mac promoter and mas terminator. The Mac: KC-1: mas expression cassette was subsequently cloned into the binary vector pWTT2132. Abbreviations are as follows: Tet=the tetracycline resistance gene; LB=left border; RB=right border, surB=the coding region and terminator sequence from the acetolacate synthase gene; 35S=the promoter region from the cauliflower mosaic virus 35S gene, mas3'= the terminator region from the mannopine synthase gene of Agrobacterium pVS1=a broad host range origin of replication from a plasmid from *Pseodomonas aeruginosa*, pACYCori=modified replicon from pACYC184 from *E. coli*. Restriction enzyme sites are also marked.

The plasmid pCGP1811 was subsequently digested with PstI to release the expression cassette containing the Mac promoter driving the KC-1 cDNA with a mas terminator, all of which were contained on a 4 kb fragment. The expression cassette was isolated and ligated with PstI ends of the pWTT2132 binary vector (DNA Plant Technology, Corporation; Oakland, Calif.) to produce pCGP1813 (FIG. 10).

Transformation of *Dianthus caryophyllus* cv. Kortina Chanel with the Carnation F3'H cDNA Clone.

The binary vector pCGP1813 was introduced into *A. tumefaciens* strain AGL0 cells, as described in Example 9. The pCGP1813/AGL0 cells were used to transform carnation plants, to reduce the amount of 3'-hydroxylated flavonoids.

(a) Plant Material

*Dianthus caryophyllus* (cv. Kortina Chanel) cuttings were obtained from Van Wyk and Son Flower Supply, Victoria, Australia. The outer leaves were removed and the cuttings were sterilised briefly in 70% v/v ethanol followed by 1.25% w/v sodium hypochlorite (with Tween 20) for 6 min and rinsed three times with sterile water. All the visible leaves and axillary buds were removed under the dissecting microscope before co-cultivation.

(b) Co-cultivation of Agrobacterium and Dianthus Tissue

*Agrobacterium tumefaciens* strain AGL0 (Lazo et al., 1991), containing the binary vector pCGP1813, was maintained at 4° C. on LB agar plates with 50 mg/L tetracycline. A single colony was grown overnight in liquid LB broth containing 50 mg/L tetracycline and diluted to $5 \times 10^8$ cells/mL next day before inoculation. Dianthus stem tissue was co-cultivated with Agrobacterium for 5 days on MS medium supplemented with 3% w/v sucrose, 0.5 mg/L BAP, 0.5 mg/L 2,4-dichlorophenoxy-acetic acid (2,4-D), 100 mM acetosyringone and 0.25% w/v Gelrite (pH 5.7).

(c) Recovery of Transgenic Dianthus Plants

For selection of transformed stem tissue, the top 6–8 mm of each co-cultivated stem was cut into 3–4 mm segments, which were then transferred to MS medium (Murashige and Skoog, 1962) supplemented with 0.3% w/v sucrose, 0.5 mg/L BAP, 0.5 mg/L 2,4-D, 1 µg/L chlorsulfturon, 500 mg/L ticarcillin and 0.25% w/v Gelrite. After 2 weeks, explants were transferred to fresh MS medium containing 3% sucrose, 0.16 mg/L thidiazuron (TDZ), 0.5 mg/L indole-3-butyric acid (IBA), 2 µg/L chlorsulfturon, 500 mg/L ticarcillin and 0.25% w/v Gelrite and care was taken at this stage to remove axillary shoots from stem explants. After 3 weeks, healthy adventitious shoots were transferred to hormone free MS medium containing 3% w/v sucrose, 5 µg/L chlorsulfuron, 500 mg/L ticarcillin, 0.25% w/v Gelrite. Shoots which survived 5 µg/L chlorsulfuron were transferred to the same medium for shoot elongation.

Elongated shoots were transferred to hormone-free MS medium containing 5 µg/L chlorsulfuron, 500 mg/L ticarcillin and 0.4% w/v Gelrite, in glass jars, for normalisation and root production. All cultures were maintained under a 16 hour photoperiod (120 mE/m$^2$/s cool white fluorescent light) at 23±2° C. Normalised plantlets, approximately 1.5–2 cm tall, were transferred to soil (75% perlite/25% peat) for acclimation at 23° C. under a 14 hour photoperiod (200 mE/m$^2$/s mercury halide light) for 3–4 weeks. Plants were fertilised with a carnation mix containing 1 g/L CaNO$_3$ and 0.75 g/L of a mixture of microelements plus N:P:K in the ratio 4.7:3.5:29.2.

EXAMPLE 15

Isolation of a F3'H cDNA Clone from *Antirrhinum majus* (Snapdragon) Using a Differential Display Approach A novel approach was employed to isolate a cDNA sequence encoding P3'H from *Antirrhinum majus* (snapdragon). Modified methods based on the protocols for (i) isolation of plant cytochrome P450 sequences using redundant oligonucleotides (Holton et at. 1993) and (ii) differential display of eukaryotic messenger RNA (Liang and Pardee, 1992) were combined, to compare the petal cytochrome P450 transcript populations between wild type (Eos$^+$) and F3'H mutant (eos$^-$)snapdragon lines. Direct cloning of differentially expressed cDNA fragments allowed their further characterisation by Northern, RFLP and sequence analysis to identify putative F3'H encoding sequences. A full-length cDNA was obtained using the RACE protocol of Frohman et al. (1988) and the clone was shown to encode a functional F3'H following both transient and stable expression in petunia petal cells.

Plant Material

The *Antirrhinum majus* lines used were derived from the parental lines K16 (i) and N8 (Eos$^+$). K16 is a homozygous recessive mutant lacking F3'H activity, while N8 is wild type for F3'H activity. These lines are similar, though not isogenic. The seed of capsule E228$^2$ from the selfed K16× N8 F$_1$ plant (#E228) was germinated and the resultant plants (K16×N8 F$_2$ plants) were scored for the presence or absence of cyanidin, a product of F3'H activity (see FIGS. 1a and 1b). The presence of cyanidin could be scored visually, as the flowers were a crimson colour, unlike the mutant plants which were a pink colour (from pelargonidin-derived pigments). The accuracy of the visual scoring was confirmed by TLC analysis of the petal anthocyanins, carried out as described in Example 11.

Of 13 plants raised from the E228$^2$ seed, 9 (#3, #4, #5, #6, #7, #9, #10, #12, #15) produced flowers with cyanidin (Eos$^+$/Eos$^+$ and Eos$^+$/eos$^-$) while 4 (#8, #11, #13, #14) produced only pelargonidin-derived pigments (eos$^-$/eos$^-$).

Synthesis of cDNA

Total RNA was isolated from the leaves of plant #13 and petal tissue of plants #3, #5, and #12 of the *A. majus* K16×N8 F$_2$ segregating population (E228$^2$) using the method of Turpen and Griffith (1986). Contaminating DNA was removed by treating 50 µg total RNA with 1 unit RQ1 RNase-free DNase (Promega) in the presence of 40 units RNasin® ribonuclease inhibitor (Promega) for 3 hours at 37° C. in a buffer recommended by the manufacturers. The RNA was then further purified by extraction with phenol/chloroform/iso-amyl alcohol (25:24:1) and subsequent ethanol precipitation.

Anchored poly(T) oligonucleotides, complementary to the upstream region of the polyadenylation sequence, were used to prime cDNA synthesis from A. majus petal and leaf RNA. The oligonucleotide sequences synthesized were (5'-3'):

| polyT-anchA | TTTTTTTTTTTTTTTA | SEQ ID NO: 27 |
| polyT-anchC | TTTTTTTTTTTTTTTC | SEQ ID NO: 28 |
| polyT-anchG | TTTTTTTTTTTTTTTG | SEQ ID NO: 29 |

Two micrograms of total RNA and 100 pmol of the appropriate priming oligonucleotide were heated to 70° C. for 10 minutes, then chilled on ice. The RNA/primer hybrids were then added to a reaction containing 20 units RNasin® (Promega), 25 nM each DNTP 10 mM DTT and 1×Superscript buffer (BRL). This reaction was heated at 37° C. for 2 minutes, then 200 units of Superscript™reverse transcriptase (BRL) were added and the reaction allowed to proceed for 75 minutes, after which the reverse transcriptase was inactivated by heating the mixture at 95° C. for 20 minutes.

Amplification of Cytodirome P450 Sequences Using PCR

Cytodirome P450 sequences were amplified using redundant oligonucieotides (designed to be complementary to conserved regions near the 3' end of plant cytochrome P450 coding sequences) and polyT anchored oligonucleotides: A similar approach was previously used to generate cytochrome P450 sequences from Petunia hybrida and is described in U.S. Pat. No. 5,349,125.

Four oligonucleotides (referred to as upstream primers) were synthesized. These were derived from conserved amino acid regions in plant cytochrome P450 sequences. The oligonucleotides (written 5' to 3') were as follows:

```
WAIGRDP      TGG GCI ATI GGI (A/C)GI GA(T/C) CC
SEQ ID NO:30 SEQ ID NO:31

FRPERF       AGG AAT T(T/C)(A/C) GIC CIG A(A/G)(A/C) GIT T
SEQ ID NO:32 SEQ ID NO:33

Pet Haem-New CCI TT(T/C) GGI GCI GGI (A/C)GI (A/C)GI ATI TG(T/G)
             (C/G)CI GG
             SEQ ID NO:34

EFXPERF      GAI TT(T/C) III CCI GAI (A/C)GI TT
SEQ ID NO:35 SEQ ID NO:36
```

The upstream primers were used with each of the polyT anchored oligonucleotides to generate cytochrome P450 sequences in polymerase chain reactions using cDNA as a template. Fifty pmol of each oligonucleotide was combined with 2 µM of each dNTP, 1.5 mm $MgCl_2$, 1×PCR buffer (Perkin ELmer), 5 µCi α-[P] dATP (Bresatec, 1500 Ci/mmol), 2.5 units AmpliTaq® DNA polymerase (Perkin Elmer) and 1/10th of the polyT-anchor primed cDNA reaction (from above). Reaction mixes (50 µL) were cycled 40 times between 94° C. for 15 seconds, 42° C. for 15 seconds, and 70° C. for 45 seconds, following an initial 2 minute desaturation step at 94° C. Cycling reactions were performed using a Perkin Elmer 9600 Gene Amp Thermal Cycler.

DNA sequences were amplified using each upstream primer/anchored primer combination and the appropriately-primed cDNA template. Each primer combination was used with the cDNA from the petals of the $E228^2$ plants #3 and #5 (cyanidin-producing flowers) and #12 (non-cyanidin producing flowers). Reactions incorporating leaf cDNA from plant #13 (cyanidin-producing flowers) were also included, as negative controls, because F3'H activity is not present at a significant level in healthy, unstressed leaf tissues.

Differential Display of Cytochrome P450 Sequences $^{33}$P-labelled PCR fragments were visualised following separation on a 5% (w/v) polyacrylamide/urea denaturing gel (Sambrook et al. 1989). A $^{33}$P-labelled M13mp18 sequencing ladder was included on the gel to serve as a size marker. The sequencing gel was dried onto Whatman 3MM paper and exposed to Kodak XAR film at room temperature.

Comparison of bands between cyanidin-producing petal samples and the non-cyanidin petal sample revealed 11 bands which represent mRNAs exclusively present in the cyanidin-producing petals. Of these 11 bands, only two were also present (at a reduced intensity) in the leaf sample.

Isolation and Cloning of PCR Fragments from Sequencing Gel

PCR products were purified from the dried sequencing gel and reamplified by the method described by Liang et al. (1993). Amplified cDNAs were purified, following electrophoretic separation on a 1.2% (w/v) agarose/TAE gel, using a Bresaclean kit (Bresatec). The purified fragments were then directly ligated into either commercially-prepared pCR-Script™vector (Stratagene) or EcoRV-linearised pBluestript® (Stratagene) which had been T-tailed using the protocol of Marchuk et al. (1990).

Sequence of F3'H PCR Products

Each of the eleven cloned differential display PCR products (with inserts not exceeding 500 bp) was sequenced on both strands and compared to other known cytochrome P450 sequences involved in anthocyanin biosynthesis, using the FASTA algorithm of Pearson and Lipman (1988).

Of the eleven cDNAs cloned, two (Am1Gb and. Am3Ga) displayed strong homology with the petunia OGR-38 F3'H sequence (Examples 4 to 11) and the F3'5'H sequences (Holton et al., 1993). Conserved sequences between clones Am1Gb and Am3Ga suggested that they represented overlapping fragments of the same mRNA. Clone Am3Ga extends from the sequence encoding the haem-binding region of the molecule (as recognised by the "Pet Haem-New" oligonucleotide; SEQ ID NO:34) to the polyadenylation sequence. Clone Am1Gb extends from the cytochrome P450 sequence encoding the conserved "WAIGRDP" amino acid motif (complementary to primer 1; SEQ ID NO:30 and SEQ ID NO:31) to an area in the 3' untranslated region which was spuriously recognised by, the primer 1 ("WAIGRDP") oligonucleotide.

EXAMPLE 16

RFLP Analysis of Cytochrome P450 cDNAs

Figure 11:
FIG. 11 is a representation of an autoradiograph of a Southern blot probed with $^{32}$P-labelled fragments of the Am3Ga differential display PCR fragment (as described in Example 16). Each lane contained a 10 µg sample of EcoRV-digested genomic DNA isolated from N8 (Eos+), K16 (eos–) or plants of an K16×N8 F$_2$ population. Hybridizing bands were detected in the genomic DNA from cyanidin-producing plants (indicated with "+") (Lanes 1, 3, 4, 5, 6, 7, 9, 10, 12 and 15). No specific hybridization was observed in the genomic DNA samples from non-cyanidin-producing plants (indicated with "–") (Lanes 2, 8, 11, 13 and 14).

Restriction fragment length polymorphism (RFLP) analysis was again used to investigate linkage of the gene corresponding to cDNA clone Am3Ga to the presence, or absence, of cyanidin-producing activity in petals. A $^{32}$P-labelled insert of Am3Ga was used to probe Southern blots of genomic DNA isolated from K16×N8 $F_2$ segregating plants as well as the parental K16 and N8 lines. Analysis of EcoRV-digested genomic DNA from 13 plants of the K16× N8 $F_2$ segregating population revealed hybridization only to the sequences of N8 and the K16×N8 $F_2$ segregating lines which displayed floral cyanidin production (FIG. 11). The K16×N8 $F_2$ plants which produced only pelargonidin-derived pigments in their petals (including parental line, K16) showed no specific hybridization (FIG. 11, lanes 2, 8, 11, 13, 14). These data indicate a possible deletion of the genomic sequences corresponding to Am3Ga in the mutant K16 plant and, therefore, at least a partial deletion of the F3'H gene in this line.

EXAMPLE 17

Northern Analysis of Cytochrome P450 cDNAs

Northern analysis was used to confirm the expression profiles of the putative cytochrome P450 fragments as shown by differential display. Ten micrograms of total petal RNA from eight of the K16×N8 $F_2$ segregating population was separated on a 1.2% (w/v) agarose/formaldehyde gel (Sambrook et al. 1989) and transferred to HybondN nylon membrane (Amersham). Leaf RNA from the cyanidin-producing plant #13 was also included as a negative control in the Northern analysis. $^{32}$P-labelled fragments of the cDNA insert from clone Am3Ga was used to probe the RNA blot.

Figure 12:
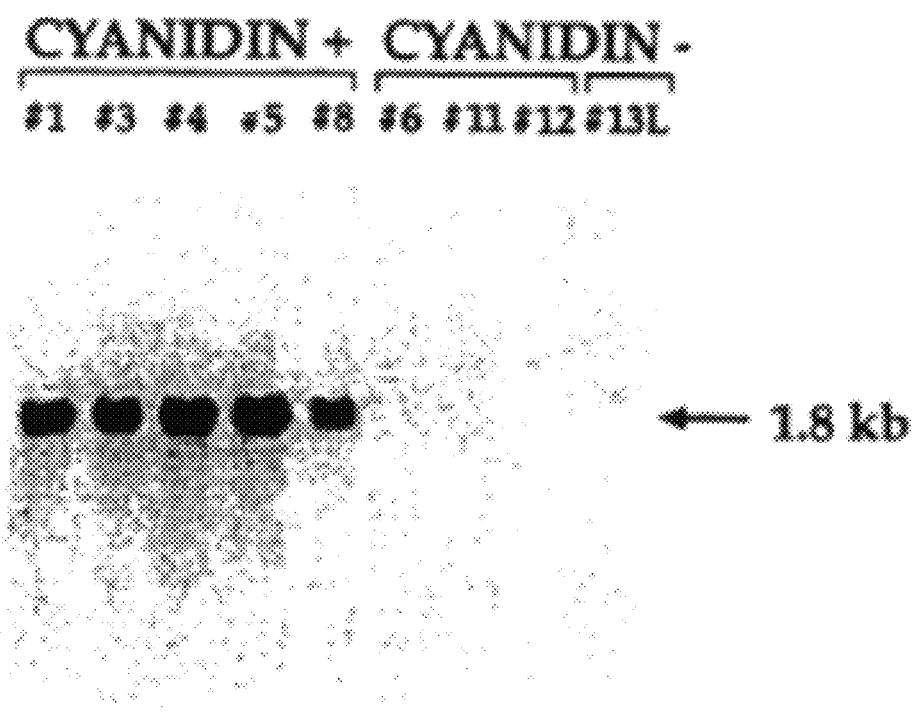
FIG. 12 is a representation of an autoradiograph of an RNA blot probed with $^{32}$P-labelled fragments of the Am3Ga differential display PCR fragment. Each lane contained a 10 μg sample of total RNA isolated from the flowers or leaves of plants of an N8 (Eos+)×K16 (eos-) $F_2$ population. A 1.8 kb transcript was detected in the K16×N8 $F_2$ flowers that produced cyanidin (cyanidin +) (plants #1, #3, #4, #5 and #8). No transcript was detected in the K16×N8 $F_2$ flowers that did not produce cyanidin (cyanidin -) (plants #6, #11, #12) or in a leaf sample (#13L) from an K16×N8 $F_2$ plant that produced cyanidin in the flowers. Details are provided in Example 17.

The Am3Ga probe recognised an approximately 1.8 kb transcript which was only detectable in the petals of cyanidin-producing plants (plants #1, #3, #4, #5, #8). No transcript was detectable in the pelargonidin-producing petals (plants #6, #11, #12) or in the leaf sample from plant #13 (FIG. 12).

These data, taken with those of the RFLP analysis, provide strong evidence that Am3Ga clone represents a cytochrome P450 gene which is responsible for F3'H activity in snapdragon. The total lack of a detectable transcript in the petals of non cyanidin-producing lines supports the findings of the RFLP analysis, that the loss of cyanidin-producing activity in the K16 line (and the homozygous recessive plants of the K16×N8 $F_2$ segregating population) is the result of a deletion in the F3'H structural gene.

EXAMPLE 18

Isolation of a Full-length Snapdragon F3'H cDNA

The Rapid Amplification of cDNA Ends (RACE) protocol of Frohman et al (1988) was employed to isolate a full-length F3'H cDNA clone using sequence knowledge of the partial Am3Ga clone. A gene-specific primer ("SnapredRace A"—complementary to Am3Ga sequences 361 to 334) was synthesized to allow reverse transcription from petal RNA. A 3' amplification primer ("SnapredRace C"—complementary to Am3Ga (3'UTR) sequences 283 to 259) was also synthesized to bind just upstream of "Snapre-dRace A". A "poly(C)" primer was used to amplify sequences from the 5' end of the cDNA molecule.

The sequences of the oligonucleotides used were (written 5'-3'):

| | | |
|---|---|---|
| Snapred Race A | CCA CAC GAG TAG TTT TGG CAT TTG ACC C | SEQ ID NO:37 |
| Snapred Race C | GTC TTG GAC ATC ACA CTT CAA TCT G | SEQ ID NO:38 |
| PolyC race | CCG AAT TCC CCC CCC CC | SEQ ID NO:39 |

"Snapred Race A-primed" petal cDNA was poly(G)-tailed and a 5' cDNA fragment amplified with primers "Snapred Race C" and "PolyC race" using the method of Frohman et al. (1988). Pfu DNA polymerase (0.15 unit) (Stratagene) was combined with 2.5 units AmpliTaq® DNA polymerase (Perkin Elmer) to increase the fidelity of the PCR reaction.

The resultant 1.71 kb DNA fragment (sdF3'H) was cloned directly into EcoRV-linearised pBluescript® (Stratagene) vector which had been T-tailed using the protocol of Marchuk et al. (1990). This plasmid was named pCGP246.

EXAMPLE 19

Complete Sequence of Snapdragon F3'H

Convenient restriction sites within the sdF3'H cDNA sequence of pCGP246 were exploited to generate a series of short overlapping subclones in the plasmid vectors pUC19. The sequence of each of these subclones was compiled to provide the sequence of the entire sdF3'H RACE cDNA. The sdF3'H cDNA sequence was coupled with that from clone Am3Ga to provide the entire sequence of a snapdragon F3'H cDNA (SEQ ID NO:5). It contains an open reading frame of 1711 bases which encodes a putative polypeptide of 512 amino acids (SEQ ID NO:6).

The nucleotide and predicted amino acid sequences of the snapdragon sdF3'H clone were compared with: those of the petunia OGR-38 cDNA clone (SEQ ID NO:1 and SEQ ID NO:2); the petunia F3'5'H cDNA clones Hf1 and Hf2; and other petunia cytochrome P450 sequences isolated previously (U.S. Pat. No. 5,349,125). The sequence of sdF3'H was most similar to that of the petunia F3'H cDNA clone (OGR-38) representing the Ht1 locus from P. hybrida, having 69% similarity at the nucleic acid level, over 1573 nucleotides, and 72.2% similarity at the amino acid level, over 507 amino acids.

The Hf1 clone showed 57.3% similarity, over 1563 nucleotides and 49.3% similarity, over 491 amino acids, to the snapdragon sdF3'H clone, while the Hf2 clone showed 57.7% similarity, over 1488 nucleotides, and 50.8% similarity, over 508 amino acids, to the snapdragon sdF3'H clone.

The snapdragon sdF3'H sequence contains two "in frame" ATG codons which could act to initiate translation. Initiation from the first of these codons (position 91 of SEQ ID NO:5) gives a protein with an additional 10 N-terminal amino acids and would be favoured according to the scanning model for translation (Kozak, 1989).

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

EXAMPLE 20

Transient Expression of sdF3'H in Plants
Constriction of pCGP250

Figure 13:
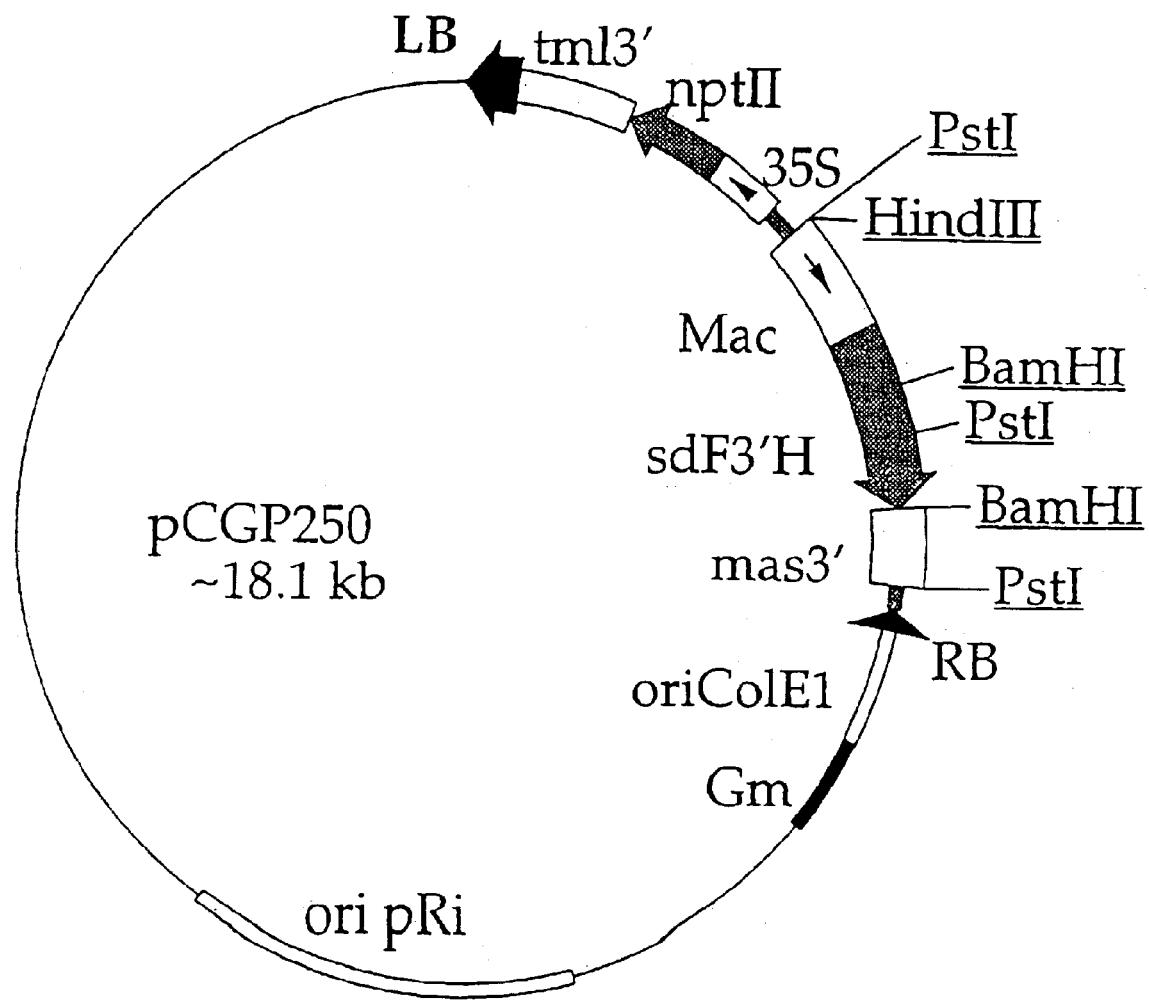
FIG. 13 is a diagrammatic representation of the binary plasmid pCGP250, construction of which is described in Example 20. The sdF3'H cDNA insert, containing the nucleotides 1 through to 1711 (SEQ ID NO:5) from pCGP246 (see Example 18), was cloned in a "sense" orientation behind the Mac promoter in the expression vector of pCGP293. Abbreviations are as follows: LB=left border; RB=right border; Gm=the gentamycin resistance gene; 35S=the promoter region from the Cauliflower Mosaic Virus 35S gene; nptII=the neomycin phosphotransferase II gene; tml3'=the terminator region from the tml gene of Agrobacterium; mas3'=the terminator region from the mannopine synthase gene of Agrobacterium; ori pRi=a broad host range origin of replication from a plasmid from *Agrobacterium rhizogenes*; oriColE1=a high copy origin of replication from a Colcinin E1 plasmid. Restriction enzyme sites are also marked.

Plasmid pCGP250 (FIG. 13) was created by cloning the entire sdF3'H RACE cDNA insert (from position 1 to 1711 (SEQ ID NO:5)) from pCGP246 in the "sense" orientation behind the Mac promoter (Comai et al., 1990) of pCGP293 (Brugliera et al., 1994). The plasmid pCGP246 was digested with EcoRI to release the cDNA insert. The cDNA fragment was blunt-ended by repairing the overhangs with the Klenow fragment of DNA polymerase I (Sambrook et al., 1989) and purified, following agarose gel electrophoresis, using a Bresaclean kit (Bresatec). The blunt cDNA fragment was then ligated into the binary vector pCGP293, which had been liearised with XbaI and blunt-ended using the Klenow fragment of DNA polymerase I. The ligation was carried out using the Amersham ligation kit. Correct insertion of the insert in pCGP250 was established by BamHI and PstI restriction enzyme analysis of DNA isolated from gentamycin-resistant transformants.
Construction of pCGP231

Figure 14:
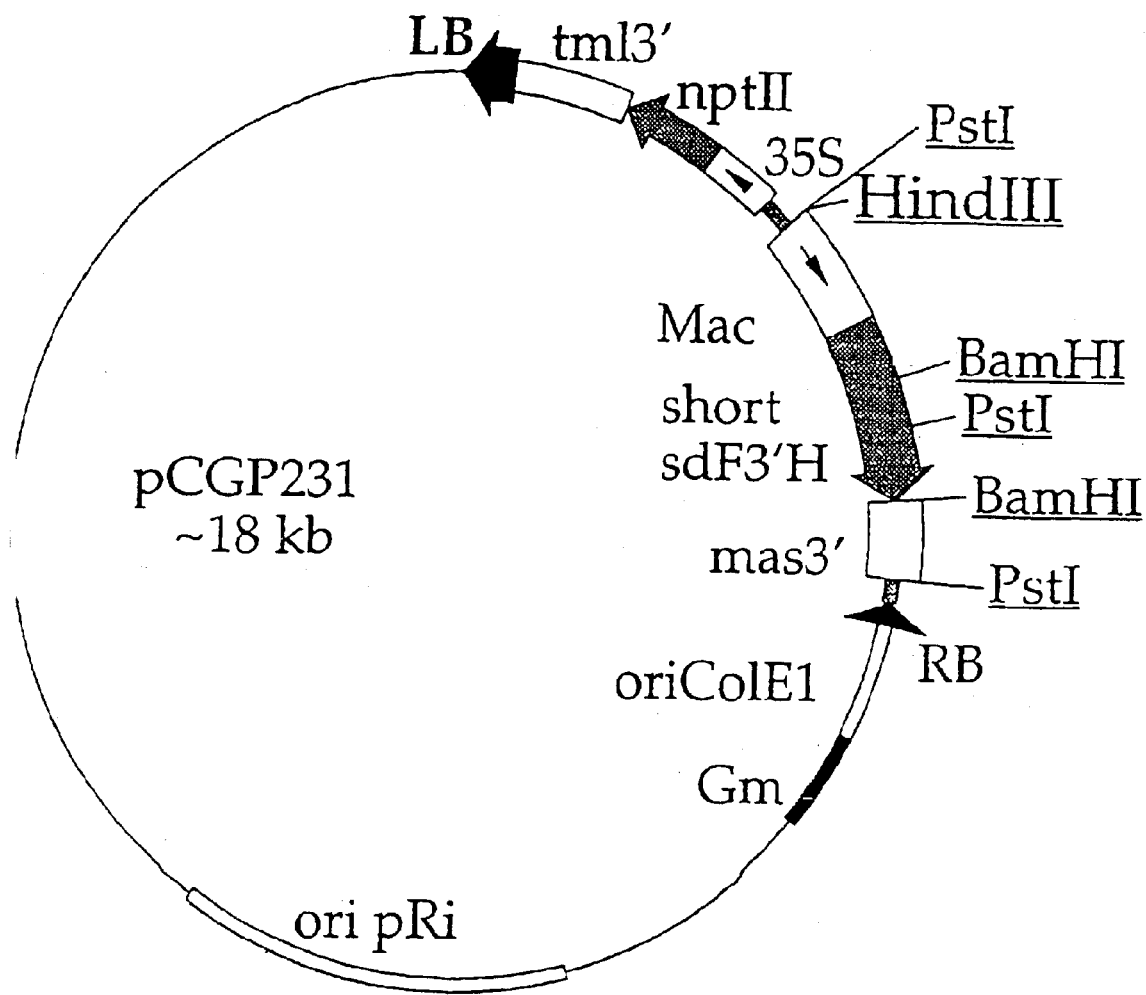
FIG. 14 is a diagrammatic representation of the binary plasmid pCGP231, construction of which is described in Example 20. The sdF3'H cDNA insert, containing the nucleotides 104 through to 1711 (SEQ ID NO:5) from pCGP246, was cloned in a "sense" orientation behind the Mac promoter in the expression vector of pCGP293. Abbreviations are as follows: LB=left border; RB=right border; Gm=the gentamycin resistance gene; 35S=the promoter region from the Cauliflower Mosaic Virus 35S gene; nptII=the neomycin phosphotransferase II gene; tml3'=the terminator region from the tml gene of Agrobacterium; mas3'=the terminator region from the mannopine synthase gene of Agrobacterium; ori pRi=a broad host range origin of replication from a plasmid from *Agrobacterium rhizogenes*; oriColE1=a high copy origin of replication from a Colcinin E1 plasmid. Restriction enzyme sites are also marked.

Plasmid pCGP231 (FIG. 14) was created by cloning the RACE cDNA insert from pCGP246, downstream of the first "in-frame" ATG codon (from position 104 to 1711 (SEQ ID NO:5), in the "sense" orientation behind the Mac promoter (Comai et al., 1990) of pCGP293 (Brugliera et al., 1994). The plasmid pCGP246 was digested with SspI (which recognises a site between the candidate ATG codons) and SmaI (with a site in the vector polylinker sequence) to release a blunt-ended cDNA fragment which includes the entire coding region downstream from the second putative initiation codon. The cDNA fragment was then ligated into the binary vector pCGP293, which had been linearised with XbaI and blunt-ended using the Klenow fragment of DNA polymerase I. The ligation was carried out using the Amersham ligation kit Correct insertion of the insert in pCGP231 was established by BamHI and PstI restriction enzyme analysis of DNA isolated from gentamycin-resistant transformants.
Transient Expression Studies To determine rapidly whether the pCGP246 sequences in pCGP231 and pCGP250 encoded active flavonoid 3'-hydroxylases in plants, a transient expression study was undertaken. Petals of the mutant P. hybrida line Skr4×SW63 were bombarded with gold particles (1 µm diameter) coated with either pCGP231 or pCGP250 plasmid DNA, using the method described in Example 8.

After 6–12 hours under lights in a controlled plant growth room at 22° C., red anthocyanin spots were observed on the surface of the petal tissue bombarded with pCGP231 coated particles. No coloured spots were observed in petals bombarded with pCGP250 or control petals bombarded with gold particles alone. These results indicated that the pCGP246 coding region (starting at the second ATG, position 121 of SEQ ID NO:5), under the control of the Mac promoter, was functional in petal tissue.

EXAMPLE 21

Stable Expression of the Snapdragon F3'H cDNA Clone in Petunia Petals—Complementation of a ht1/ht1 Petunia Cultivar The binary vectors pCGP250 and pCGP231 were introduced into A. tumefaciens strain AGL0 cells, as described in Example 9. The pCGP250/AGL0 and pCGP231/AGL0 cells were used to transform Skr4×SW63 petunia plants (also described in Example 9), to test for stable expression and activity of the enzyme encoded by the gene corresponding to the snapdragon sdF3'H cDNA clone.

Three of the nine transgenic plants transformed with pCGP250 produced flowers with a slightly-altered petal colour (RHSCC# 73A), compared with the Skr4×Sw63 control (RHSCC# 75C). Of the 11 transgenic plants transformed with pCGP231, one plant produced flowers with an altered petal colour (RHSCC# 73B). The anthers and pollen of the transgenic flowers were also white, as in the control. The codes are taken from the Royal Horticultural Society's Colour Chart (RHSCC). They provide an alternative means by which to describe the colour phenotypes observed. The designated numbers, however, should be taken only as a guide to the perceived colours and should not be regarded as limiting the possible colours which may be obtained.
TLC Analysis of Floral Extracts Acid-hydrolysed floral extracts (see Example 11) were run in a Forestal solvent system (HOAc:water:HCl; 30:10:3) (Markham, 1982). Introduction of the sdF3'H cDNA clone into Skr4×SW63 led to the production of increased levels of the 3'-hydroxylated flavonoid, peonidin, in the petals. Peonidin is the methylated derivative of cyanidin (FIGS. 1a and 1b).

EXAMPLE 22

Isolation of a F3'H cDNA Clone from *Arabidopsis thaliana* Using a PCR Approach

In order to isolate a cDNA clone representing flavonoid 3'-hydroxylase from *Arabidopsis thaliana*, PCR fragments were generated using primers from the conserved regions of cytochrome P450s. One PCR product (p58092.13) was found to have high sequence similarity with the petunia OGR-38 and snapdragon F3'H cDNA clones. The PCR fragment was then used, together with the Ht1 cDNA insert (OGR-38) from pCGP 805, to screen an A. thaliana cDNA library.
Design of Oligonucieotides Degenerate oligonucleotides for PCR DNA amplification were designed from the consensus amino acid sequence of *Petunia hybrida* cytochrome P450 partial sequences situated near the haem-binding domain. Primer degeneracy was established by the inclusion of deoxyinosine (designated as I below) in the third base of each codon (deoxyinosine base pairs with similar efficiency to A, T, G, and C), and the inclusion of alternate bases where the consensus sequences were non-specific. Thus, the amino-terminal directional primer "Pet Haem" (Petunia haem-binding domain), containing the cysteine residue codon crucial for haem binding, and the upstream primer "WAIGRDP" (See also Example 15) were designed.

```
WAIGRDP      TGG GCI ATI GGI (A/C)GI GA(T/C) CC
SEQ ID NO:30 SEQ ID NO:31

Pet Haem     CCI GG(A/G) CAI ATI C(G/T)(C/T) (C/T)TI CCI GCI CC(A/G) AAI GG
             SEQ ID NO:40
```

Generation of Cytochrome P450 Sequences Using PCR

Genomic DNA was isolated from *A. thaliana* ecotype Columbia, using the method described by Dellaporta et al. (1987). Polymerase chain reactions for amplification of cytochrome P450 homologues typically contained 100–200 ng of Columbia genomic DNA, 10 mM Tris-HCl (pH8.3), 50 mM KCl, 1.5 mM MgCl$_2$, 0.01% (w/v) gelatin, 0.2 mM each DNTP, 312 ng "WAIGRDP" and 484 ng "Pet Haem" and 1.25 units Taq polymerase (Cetus). Reaction mixes (50 µL) were cycled 40 times between 95° C. for 50 seconds, 45° C. for 50 seconds and 72° C. for 45 seconds.

The expected size of specific PCR amplification products, using the "WAIGRDP" and "Pet Haem" primers on a typical P450 gene template, without an intron, is approximately 150 base pairs. PCR fragments of approximately 140 to 155 base pairs were isolated and purified using the Mermaid® kit (BIO 101). The PCR fragments were re-amplified to obtain enough product for cloning and then end-repaired using Pfu DNA polymerase and finally cloned into pCR-Script™Direct SK(+) (Stratagene). The ligated DNA was then used to transform competent DH5α cells (Inoue et at., 1990).

Sequence of PCR Products

Plasmid DNA from 15 transformants was prepared (Del Sal et al., 1989). Sequencing data generated from these PCR fragments indicated that 11 out of the 15 represented unique clones. A distinct set of cytochrome P450 consensus amino acids was also found in the translated sequence encoded within the *A. thaliana* PCR inserts. The sequences of the PCR fragments were also compared with those of the petunia OGR-38 F3'H cDNA clone and the snapdragon F3'H cDNA clone. The PCR fragment, p58092.13, was most similar to the F3'H sequences from both petunia and snapdragon.

EXAMPLE 23

Screening of *A. thaliana* cDNA Library

To isolate a cDNA clone of the p58092.13 PCR product, an *A. thaliana* ecotype Columbia cDNA library (Newman et al., 1994; D'Alessio et al., 1992) was screened with a $^{32}$P-labelled fragment of p58092.13 together with a $^{32}$P-labelled fragment of the petunia Ht1 cDNA insert (OGR-38), contained in pCGP1805.

A total of 600,000 pfu was plated at a density of 50,000 pfus per 15 cm diameter plate, as described by D'Alessio et a (1992). After phage growth at 37° C. plates were stored at 4° C. overnight, duplicate lifts were taken onto Colony/Plaque Screen filters (DuPont) and treated as recommended by the manufacturer.

Prior to hybridization, the duplicate plaque lifts were washed in prewashing solution (50 mM Tris-HCl pH7.5, 1 M NaCl, 1 mM EDTA, 0.1% (w/v) sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% (w/v) SDS at 65° C. for 30 minutes and finally rinsed in 2×SSC, 1.0% (w/v) SDS.

Hybridization conditions included a prehybridization step in 50% (v/v) formamide, 1 M NaCl, 10% (w/v) dextran sulphate, 1% (w/v) SDS at 42° C. for at least 1 hour. The $^{32}$P-labelled fragment of p58092.13 (2×10$^6$ cpm/mL) was then added to the hybridization solution and hybridization was continued at 42° C. for a further 16 hours. The filters were then washed in 2×SSC, 1% (w/v) SDS at 42° C. for 2×1 hour and exposed to Kodak XAR film with an intensifying screen at −70° C. for 16 hours.

Eleven strongly-hybridizing plaques were picked into PSB and rescreened as detailed above, to isolate purified plaques. These filters were also probed with $^{32}$P-labelled fragment of the petunia Ht1 cDNA insert (OGR-38), contained in pCGP1805, under low stringency conditions. Low stringency conditions included prehybridization and hybridization at 42° C. in 20% (v/v) formamide, 1 M NaCl, 10% (w/v) dextran sulphate, 1% (w/v) SDS and washing in 6×SSC, 1% (w/v) SDS (w/v) at 65° C. for 1 hour.

The OGR-38 and p58092. 13 probes hybridized with identical plaques. The 11 pure plaques were picked into PSB and the plasmid vectors pZL1 containing the cDNA clones were rescued using the bacterial strain DH10B(Zip). Plasmid DNA was prepared (Del Sal et al., 1989) and the cDNA inserts were released upon digestion with BamHI and EcoRI. The 11 plasmids contained cDNA inserts of between 800 bp and 1 kb. Sequence data generated from the 5' region of the cDNA inserts suggested that nine of these clones were identical. Sequence data were generated from the 5' ends of all nine cDNA inserts and the 3' end of only one cDNA insert. The sequence data generated from all clones were compiled to produce the nucleotide and translated sequence shown as SEQ ID NO:7 and SEQ ID NO:8.

The *A. thaliana* putative F3'H sequences were compared with the sequences of the petunia OGR-38 F3'H cDNA clone (SEQ ID NO:1 and SEQ ID NO:2) and was 64.7% similar to the petunia F3'H cDNA clone, over 745 nucleotides, and 63.7% similar, over 248 amino An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

Isolation of a F3'H Genomic Clone from *Arabidopsis thaliana*

To isolate a genomic clone of the *A. thaliana* F3'H gene, a *A. thaliana* ecotype Landsberg erecta genomic DNA library was screened with $^{32}$P-labelled p60606.04 fragments. The library was created by cloning partial MboI-digested genomic DNA between BamHI-digested bacteriophage lambda EMBL4 arms. The primary library, which contained 30,000 clones, was amplified once before screening.

The p60606.04 clone, containing a 1 kb fragment of *A. thaliana* F3'H cDNA, was digested with BamHI/EcoRI to excise the insert which was purified using GeneClean (Bio 101). Probe was $^{32}$P-labelled using the nick-translation procedure (Sambrook let al., 1989). Approximately 20,000 plaques were probed at high stringency (50% formamide at 37° C.) and filters were washed in: 2×SSPE; 2×SSPE, 0.1% (w/v) SDS; 0.1×SSPE, all at 65° C. Re-screening was carried out under the same conditions.

DNA was purified from three positive plaques (λTT7-1, λTT7-5 and λTT7-6) and mapped by digestion with EcoRI and EcoRI/SalI. All three clones had an EcoRI fragment in common. λTT7-1 and λTT7-5 had overlapping but not identical restriction patterns. A Southern blot of these digests was probed as above and, for λTT7-1 and λTT7-5, a common 6.5 kb EcoRI/SalI fragment hybridized. A smaller EcoRI/SalI fragment in λTT7-6 also hybridized and was presumably at the insert boundary.

EcoRI/SalI fragments from lTT7-5 were cloned into pBlueScript SK+ and a clone containing the 6.5 kb fragment, designated E-5, was identified by hybridization (as above) and insert size. A restriction map was compiled for the fragment using EcoRI, SalI, KpnI, HindIII and BglII in various combinations, and by hybridization to Southern blots of these digests with the BamHI/EcoRI insert from the *A. thaliana* F3'H cDNA clone.

Complete Sequence of Tt7 Genonic Clone

A 6.4 kb BamHI fragment from pTt7-2, containing most of the Tt7 genomic fragment was purified, self-ligated, sonicated, end-repaired, size-fractionated (450 bp to 800 bp) and cloned into SmaI-cut pUC19 using standard techniques (Sambrook et al., 1989). Recombinant clones were isolated, and plasmid DNA was purified and sequenced using M13–21 or M13 reverse sequencing primers. The sequence from overlapping clones was combined into one contiguous fragment. The sequence of the ends of the Tt7 genomic fragment were also obtained by sequencing with the −21 and REV primers. All of the sequences were combined together to obtain the complete sequence of the 6.5 kb EcoRI/SalI fragment from E-5 (SEQ ID NO:9).

The sequences over the coding region of the arabidopsis Tt7 genomic clone (SEQ ID NO:10, 11, 12 and 13) were compared with those of the petunia OGR-38 F3'H cDNA clone (SEQ ID NO:1 and 2). The arabidopsis Tt7 coding region showed 65.4% similarity, over 1066 nucleotides, and 67.1% similarity, over 511 amino acids, to that of the petunia OGR-38 F3'H cDNA clone.

Transformation of a tt7 Arabidopsis Mutant

Preparation of Binary Vector

Figure 15:
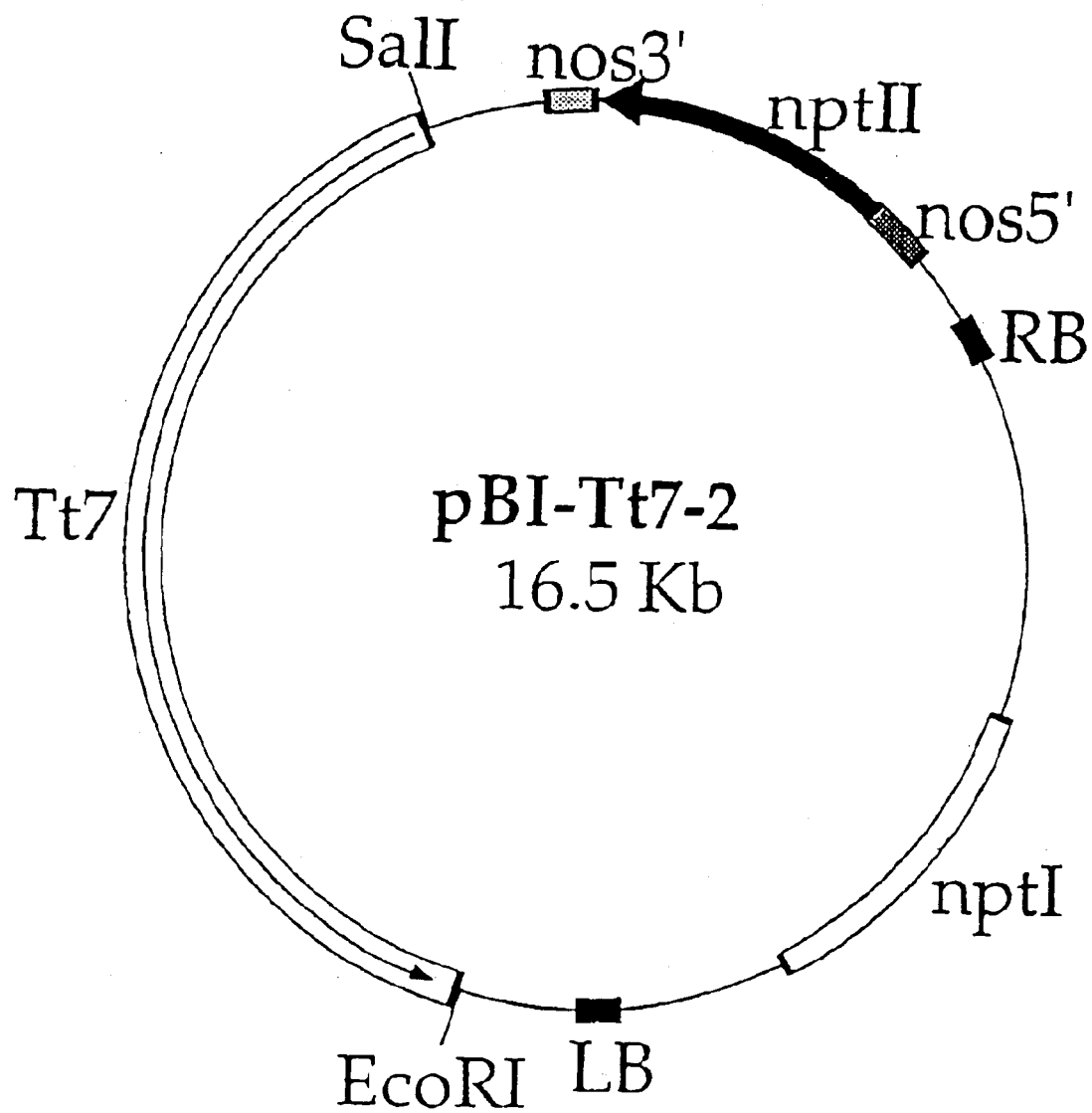
FIG. 15 is a diagrammatic representation of the binary plasmid pBI-Tt7-2. The 6.5 kb EcoRI/SalI Tt7 genomic fragment from E-5 was cloned into EcoRI/SalI-cut pBI101, replacing the resident GUS gene. The orientation of the Tt7 (F3'H) gene as indicated (5' to 3') was determined through DNA sequencing. Abbreviations are as follows: LB=left border; RB=right border; nos 5'=the promoter region from the nopaline synthase gene of Agrobacterium nptII=the coding region of the neomycin phosphotransferase II gene; nos 3'=the terminator region from the nopaline synthase gene of Agrobacterium; nptII=the coding region of the neomycin phosphotransferase I gene. Restriction enzyme sites are also marked.

The EcoRI/SalI fragment from E-5 was cloned into EcoRI/SalI-cut pBI101 (Jefferson et al., 1987). Two separate but identical clones were identified: pBI-Tt7-2 (FIG. 15) and pBI-Tt7-4. Both clones were used for transformation of *A. tumefaciens*.

Plant Transformation

Plasmids pBI-Tt7-2, pBI-Tt7-4 and pBI101 were transformed into Agrobacterium stain GV3101 pMP90 by electroporation. Transformants were selected on medium containing 50 µg/mL kanamycin (and 50 µg/mL gentamycin to select for the resident pMP90).

Plasmid DNA, from four transformant colonies for each clone, was isolated and digested with EcoRI/SalI, electrophoresed, Southern blotted, and probed with the Tt7 cDNA insert. For pBI-Tt7-2 and pBI-Tt7-4, the expected insert band was identified.

One transformant for each plasmid (i.e.: one control [PBI101 C4], one each of the two Tt7 clones [pBI-Tt7-2-3 and pBI Tt7-4-4]) was used to vacuum infiltrate the *A. thaliana* tt7 mutant line NW88 (4 pots of 10 plants each for each construct), using the a method essentially as described by Bechtold et al. (1993).

Seed from each pot was harvested. One hundred mg of seed (approximately 5,000) was plated on nutrient medium (described by Haughn and Somerville, 1986) containing 50 µg/mL kanamycin. Kanamycin-resistant transformants were visible after 7 to 10 days. In the case of pBI-Tt7-2-3 and pBI-Tt7-4-4, a total of 11 transformants were isolated from 5 different seed lots (i.e.: pots) and all kanamycin-resistant transformants were visibly Tt7 in phenotype and exhibited the characteristic red/purple anthocyanin pigments at the margins of the cotyledons and at the hypocotyl. A single kanamycin-resistant transformant was isolated from only one of the four pots of control transformants and it did not exhibit a "wild-type" Tt7 phenotype.

Complementation of tt7 Mutant

These transformants were planted out and grown to maturity and individually harvested for seed. In each case, for pBI-Tt7-2-3 and pBI-Tt7-4-4 transformants, the seeds were visibly more brown than the pale brown seed of the tt7 mutant plants. The seed from the control transformant was indistinguishable from the tt7 mutant parent. These seed were plated out on nutrient medium and nutrient medium with kanamycin added, and scored for the Tt7 phenotype (red/purple anthocyanin pigments at the margins of the cotyledons and at the hypocotyl) and kanamycin resistance. The progeny of at least one transformant for each seed lot was examined, since these were clearly independent transformation events.

Without exception, kanamycin-resistant seedlings exhibited the Tt7 phenotype while kanamycin-sensitive individuals were tt7. In some cases, kanamycin resistance was weak and variable among a family of seed and it was difficult to unequivocally determine whether individuals were kanamycin resistant or kanamycin sensitive.

EXAMPLE 24

Isolation of a F3'H cDNA Clone from *Rosa hybrids*

In order to isolate a Rose F3'H cDNA clone, a *Rosa hybrida* cv. Kardinal petal cDNA library was screened with $^{32}$P-labelled fragments of the petunia Ht1 cDNA clone (OGR-38), contained in pCGP1805, and snapdragon F3'H cDNA clone (sdF3'H), contained in pCGP246.

Construction of a Petal cDNA Library from Rose cv. Kardinal

Total RNA was prepared from the buds of *Rosa hybrida* cv. Kardinal stage 2. At this stage, the tightly closed buds were 1.5 cm high and approximately 0.9 cm wide with pale pink petals.

Frozen tissue (1–3 g) was ground in liquid nitrogen with a mortar and pestle, placed in 25 mL pre-chilled Buffer A [0.2 M boric acid, 10 mM EDTA (sodium salt) (pH 7.6)] and homogenized briefly. The extract was mixed on a rotary shaker until it reached room temperature and an equal volume of phenol/chloroform (1:1 v/v), equilibrated with Buffer A, was added. After mixing for a further 10 minutes, the RNA preparation was centrifuged at 10,000×g for 10 minutes at 20° C. The upper aqueous phase was retained and the phenol interface re-extracted as above. The aqueous phases were pooled and adjusted to 0.1 M sodium acetate (pH 6.0), 2.5 volumes 95% ethanol were added and the mixture was stored at −20° C. overnight.

The preparation was centrifuged at 10,000×g for 10 minutes at 4° C., the pellet dissolved gently in 20 mL Buffer B [25 mM boric acid, 1.25 mM EDTA (sodium salt), 0.1 M NaCl (pH 7.6)] and 0.4 volumes 2-butoxyethanol (2BE) were added. This solution was incubated on ice for 30 minutes. It was then centrifuged at 10,000×g for 10 minutes at 0° C. and the supernatant was carefully collected. After addition of 1.0 volume of 2BE and incubation on ice for a further 30 minutes, the supernatant was again centrifuged at 10,000×g for 10 minutes at 0° C. The resulting pellet was gently washed with Buffer A:2BE (1:1 v/v), then with 70% (v/v) ethanol, 0.1 M potassium acetate and finally with 95% ethanol. The pellet was air dried and dissolved in 1 mL diethyl pyrocarbonate (DEPC)-treated water. This was adjusted to 3 M lithium chloride, left on ice for 60 minutes and centrifuged at 10,000×g for 10 minutes at 0° C. The pellet was washed twice with 3 M LiCl and then with 70% ethanol, 0.1 M potassium acetate.

The resulting RNA pellet was dissolved in 400 µL DEPC-treated water and extracted with an equal volume phenol/chloroform. The RNA mix was then centrifuged at 10,000×g for 5 minutes at 20° C., the aqueous phase collected and made to 0.1 M sodium acetate, and a further 2.5 volumes of 95% ethanol were added. After 30 minutes incubation on ice, the mix was centrifuged at 13,000 rpm (5,000×g) for 20 minutes at 20° C. and the RNA pellet resuspended gently in 400 µL DEPC-treated water.

Poly (A)$^+$ RNA was selected from the total RNA by Oligotex dT-30 (Takara, Japan) following the manufacturer's protocol. The cDNA was synthesized according to the method in Brugliera et al. (1994) and used to construct a non-directional petal cDNA library in the EcoRI site of λZAPII (Stratagene). The total number of recombinants obtained was $3.5 \times 10^5$.

After transfecting XL1-Blue cells, the packaged cDNA mixture was plated at 50,000 pfu per 15 cm diameter plate. The plates were incubated at 37° C. for 8 hours, and the phage were eluted in 100 mM NaCl, 8 mM $MgSO_4$, 50 mM Tris-HCl pH 8.0, 0.01% (w/v) gelatin (Phage Storage Buffer (PSB)) (Sambrook et at., 1989). Chloroform was added and the phage stored at 4° C. as an amplified library.

200,000 pfus of the amplified library were plated onto NZY plates (Sambrook et al., 1989) at a density of 10,000 pfu per 15 cm plate after transfecting XL1-Blue MRF' cells, and incubated at 37° C. for 8 hours. After incubation at 4° C. overnight, duplicate lifts (labelled as group A and group B) were taken onto Colony/Plaque Screen filters (DuPont) and treated as recommended by the manufacturer.

Screening of Kardinal cDNA Library for a F3'H cDNA Clone

Prior to hybridization, The duplicate plaque lifts were washed in prewashing solution (50 mM Tris-HCl pH7.5, 1 M NaCl, 1 mM EDTA, 0.1% (w/v) sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% (w/v) SDS at 65° C. for 30 minutes and finally rinsed in 2×SSC, 1.0% (w/v) SDS.

The group A filters of the duplicate lifts from the Kardinal cDNA library were screened with $^{32}$P-labelled fragments of an NcoI fragment from pCGP1805 containing the petunia Ht1 (OGR-38) cDNA clone, while the group B filters were screened with $^{32}$P-labelled fragments of EcoRI/SspI fragment from pCGP246 containing the snapdragon F3'H clone.

Hybridization conditions included a prehybridization step in 10% (v/v) formamide, 1 M NaCl, 10% (w/v) dextran sulphate, 1% (w/v) SDS at 42° C. for at least 1 hour. The $^{32}$P-labelled fragment ($2 \times 10^6$ cpm/ml) was then added to the hybridization solution and hybridization was continued at 42° C. for a further 16 hours. The filters were then washed 42° C. in 2×SSC, 1% (w/v) SDS for 2 hours followed by 1×SSC, 1% (w/v) SDS for 1 hour and finally in 0.2×SSC/1% (w/v) SDS for 2 hours. The filters were exposed to Kodak XAR film with an intensifying screen at −70° C. for 16 hours.

Four strongly-hybridizing plaques (R1, R2, R3, R4) were picked into PSB and rescreened to isolate pure plaques. The plasmids contained in the λZAP bacteriophage vector were rescued and digested with EcoRI to release the cDNA inserts. Clone R1 contained a 1.0 kb insert while clones R2, R3 and R4 contained inserts of approximately 1.3 kb each. Sequence data were generated from the 3' and 5' ends of the R4 cDNA insert.

The rose R4 putative F3'H sequence was compared with that of the petunia OGR-38 F3'H sequence. At the nucleotide level, the R4 cDNA clone showed 63.2% and 62.1% similarity over 389 nucleotides at the 5' end and 330 nucleotides at the 3' end, respectively. At the amino acid level, the R4 clone showed 65.4% and 73.9% similarity over 130 amino acids at the 5' end and 69 amino acids at the 3' end, respectively. Based on the high sequence similarity of the Rose R4 cDNA clone to that of the petunia F3'H cDNA clone (OGR-38), a corresponding "full-length" cDNA clone was isolated, as described in Example 25, below.

EXAMPLE 25

Isolation of a Full-length Rose F3'H cDNA

In order to isolate a "full-length" F3'H cDNA clone from Rose, the *Rosa hybrida* cv Kardinal petal cDNA library described in Example 24 was screened with $^{32}$P-labelled fragments of the rose R4 cDNA clone, described above.

A total of $1.9 \times 10^6$ pfus of the amplified library were plated onto NZY plates at a density of 100,000 pfus per 15 cm diameter plate after transfecting XL1-Blue MRF' cells, and incubated at 37° C. for 8 hours. After incubation at 4° C. overnight, duplicate lifts were taken onto Colony/Plaque Screen™ filters (DuPont) and treated as recommended by the manufacturer.

Screening of Kardinal cDNA Library for Full-length F3'H cDNA Clones

Prior to hybridization, the duplicate plaque lifts were treated as described in Example 24.

The duplicate lifts from the Kardinal cDNA library were screened with $^{32}$P-labelled fragments of an EcoRI fragment from the rose R4 cDNA clone.

Hybridization conditions included a prehybridization step in 50% (v/v) formamide, 1 M NaCl, 10% (w/v) dextran sulphate, 1% (w/v) SDS at 42° C. for at least 1 hour. The $^{32}$P-labelled fragment of the rose R4 cDNA clone ($1 \times 10^6$ cpm/mL) was then added to the hybridization solution and hybridization was continued at 42° C. for a further 16 hours. The filters were then washed in 2×SSC, 1% (w/v) SDS at 42° C. for 2×1 hour and exposed to Kodak XAR film with an intensifying screen at −70° C. for 16 hours.

Seventy-three strongly-hybridizing plaques (1–73) were picked into 1 mL of PSB and stored at 4° C. overnight. 100 µL of each was then aliquoted into a microtitre tray as an ordered array.

XL1-Blue MRF' cells were added to 10 mL of molten NZY top agar, poured onto NZY plates (15 cm diameter) and allowed to set A replica plating device was used to transfer the 73 phage isolates in an ordered array onto the NZY plate previously inoculated with the XL1-Blue MRF' cells. After incubation at 37° C. for 6 hours followed by 4° C. overnight, triplicate lifts (arrays 1, 2 and 3) were taken onto Colony/Plaque Screen™filters (DuPont) and treated as recommended by the manufacturer.

Prior to hybridization, the duplicate plaque lifts were treated as described in Example 24.

The 3 arrays were screened with $^{32}$P-labelled fragments of a) an EcoRI/SalI fragment covering the 5' end of the rose R4 cDNA clone, b) an EcoRI/ClaI fragment covering the 5' end of the rose R4 cDNA clone or c) an EcoRI fragment of the entire rose R4 cDNA clone using the hybridisation and washing conditions described above, except that the final wash was in 0.1×SSC, 0.1% (w/v) SDS at 65° C. for 30 minutes. The filters were exposed to Kodak XAR film with an intensifying screen at −70° C. for 16 hours.

All 73 plaques hybridised with the full R4 cDNA clone (EcoRI fragment) whilst a total of only 17 hybridised with the 5' end of the R4 cDNA clone (either EcoRI/SalI or the EcoRI/ClaI fragments). The 17 phage isolates were rescreened as described above to isolate purified plaques. Pure plaques were Stained from 9 out of the 17 (2, 4, 26, 27, 34, 38, 43, 44, 56). The plasmids contained in the λZAP bacteriophage vector were rescued and the sizes of the cDNA inserts were determined using an EcoRI digestion. The cDNA inserts ranged from 0.9 kb to 1.9 kb. Of the nine, only #34 (named pCGP2158) and #38 (named pCGP2159) contained cDNA inserts of approximately 1.9 kb. Sequence data were generated from the 3' and 5' ends of the cDNA inserts and showed that clones #34 and #38 represented the same gene.

The complete sequence of the rose cDNA clone (#34) contained in the plasmid pCGP2158 was determined by compilation of sequence from different pUC18 subclones obtained using standard procedures for the generation of randomly-overlapping clones (Sambrook et al., 1989). The sequence (SEQ ID NO:14) contained an open reading frame of 1696 bases which encodes a putative polypeptide of 520 amino acids (SEQ ID NO:15).

The nucleotide and predicted amino acid sequences of the rose F3'H #34 cDNA clone (SEQ ID NO:14 and SEQ ID NO:15) were compared whit those of the petunia OGR-38 F3'H cDNA clones (SEQ ID NO:1 and SEQ ID NO:2) and the snapdragon sd F3'H clone (SEQ ID NO:5 and SEQ ID NO:6). The rose F3'H #34 cDNA clone showed 64.7% similarity, over 1651 nucleotides and 72.7% similarity, over 509 amino acids, to that of the petunia OGR-38 cDNA clone, and 67.2% similarity, over 1507 nucleotides, and 68.9 similarity, over 502 amino acids, to that of the snapdragon sdF3'H clone.

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

EXAMPLE 26

Stable Expression of the Rose F3'H cDNA Clone (#34) in Petunia Petals—Complementation of a ht1/ht1 Petunia Cultivar Preparation of pCGP2166

Figure 16:
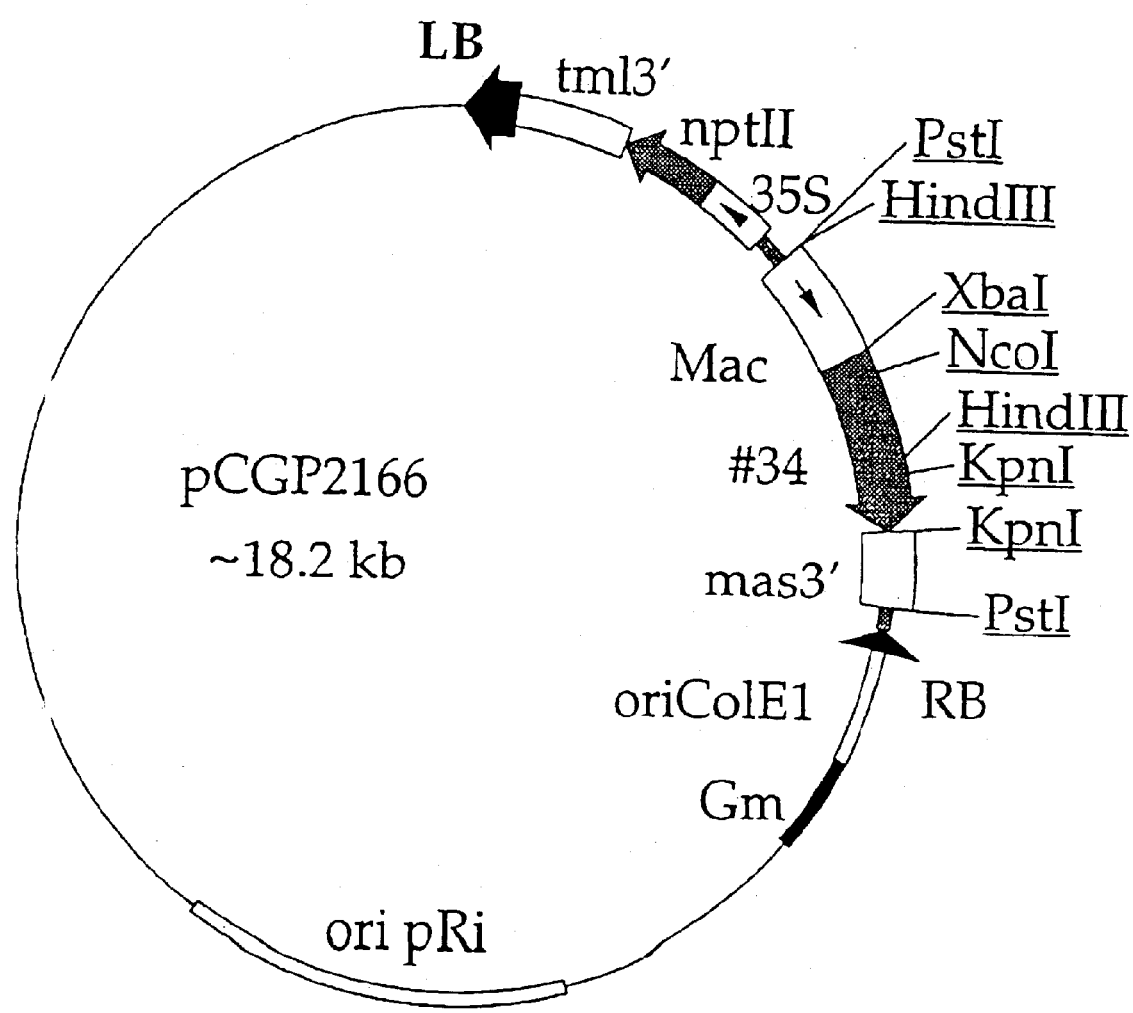
FIG. 16 is a diagrammatic representation of the binary plasmid pCGP2166, construction of which is described in Example 26. The rose #34 cDNA insert from pCGP2158 (see Example 25) was cloned in a "sense" orientation behind the Mac promoter in the expression vector of pCGP293. Abbreviations are as follows: LB=left border RB=right border; Gm=the gentamycin resistance gene; 35S=the promoter region from the Cauliflower Mosaic Virus 35S gene; nptII=the neomycin phosphotransferase II gene; tml3'=the terminator region from the tml gene of Agrobacterium; mas3'=the terminator region from the mannopine synthase gene of Agrobacterium; ori pRi=a broad host range origin of replication from a plasmid from Agrobacterium rhizogenes; oriColE1=a high copy origin of replication from a Colcinin E1 plasmid. Restriction enzyme sites are also marked.

Plasmid pCGP2166 (FIG. 16) was constructed by cloning the cDNA insert from pCGP2158 in a "sense" orientation behind the Mac promoter (Comai et al., 1990) of pCGP293 (Brugliera et al., 1994). The plasmid pCGP2158 was digested with EcoRI to release the cDNA insert. The overhanging 5' ends were filled in using DNA polymerase (Klenow fragment) (Sambrook et al., 1989). The cDNA fragment was isolated and ligated with filled in BamHI ends of the pCGP293 binary vector. Correct insertion of the fragment in pCGP2166 was established by restriction enzyme analysis of DNA isolated from gentamycin-resistant transformants.

The binary vector pCGP2166 was introduced into *A. tumefaciens* strain AGL0 cells, as described in Example 9.

The pCGP166/AGL0 cells were then used to transform Skr4×SW63 petunia plants (also described in Example 9), to test for stable expression and activity of the enzyme encoded by the gene corresponding to the rose #34 cDNA clone.

EXAMPLE 27

Transgenic Plant Phenotype Analysis
pCGP2166 in Skr4×SW63

The expression of the introduced rose F3'H cDNA in the Skr4×SW63 hybrid had a marked effect on flower colour. The stamen tissue of the non-transgenic control is white, whereas the same tissue in most of the transgenic plants was pink. In addition, expression of the rose F3'H cDNA in the Skr4×SW63 hybrid conferred a dark pink hue (RHSCC# 64° C. and 74° C.) to the corolla, which is normally pale lilac (RHSCC# 75C). The colour codes are taken from the Royal Horticultural Society's Colour Chart (RHSCC). They provide an alternative means by which to describe the colour phenotypes observed. The designated numbers, however, should be taken only as a guide to the perceived colours and should not be regarded as limiting the possible colours which may be obtained.

Acid-hydrolysed floral extracts (see Example 11) were run in a Forestal solvent system (HOAc:water:HCl; 30:10:3) (Markham, 1982). The 3' hydroxylated flavonoids, peonidin and quercetin, were readily detected in the petal limbs of the transgenic plants. Only kaempferol and a small amount of malvidin were detected in the non-transgenic Skr4×SW63 control.

The accumulation of the 3'-hydroxylated anthocyanidin, peonidin and the flavonol, quercetin, in the petals of the transgenic Skr4×SW63/pCGP2166 plants correlated with the pink and dark pink colours observed in the petals of the same plants.

Preparation of pCGP2169

Figure 17:
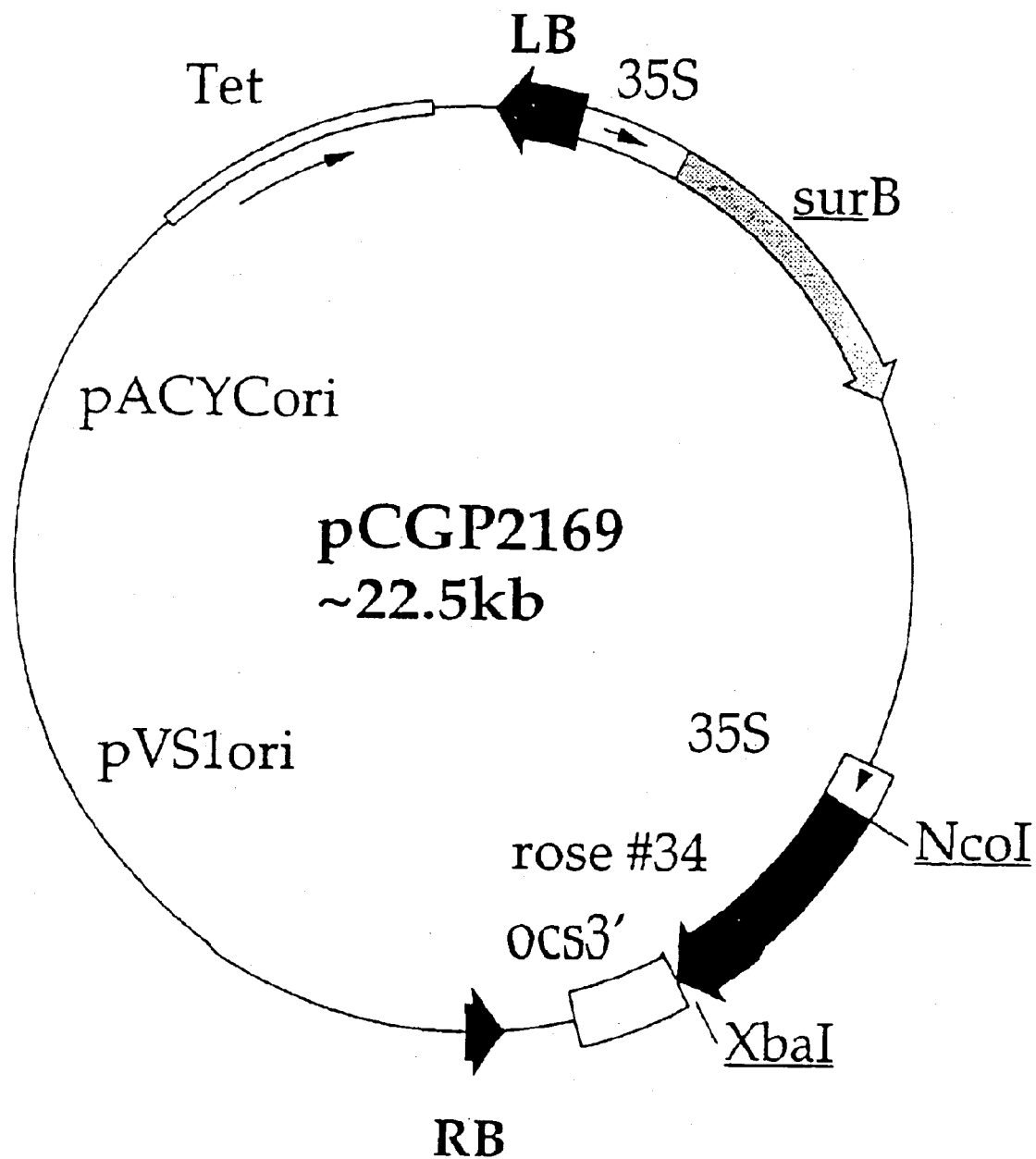
FIG. 17 is a diagrammatic representation of the binary plasmid pCGP2169 construction of which is described in Example 27. The rose #34 cDNA insert from pCGP2158 was cloned in a "sense" orientation between the CaMV35S promoter and the ocs terminator. The 35S: rose #34: ocs expression cassette was subsequently cloned into the binary vector pWTT2132. Abbreviations are as follows: Tet=the tetracycline resistance gene; LB=left border; RB=right border; surB=the boding region and terminator sequence from the acetolactate synthase gene; 35S=the promoter region from the cauliflowe mosaic virus 35S gene, ocs=terminator region from the octopine synthase gene from Agrobacterium; pVS1=a broad host range origin of replication from a plasmid from *Pseodomous aeruginosa*, pACYCori= modified replicon from pACYC184 from *E. coli*. Restriction enzyme sites are also marked.

The binary construct pCGP2169 (FIG. 17) was prepared by cloning the cDNA insert from pCGP2158 in a "sense" orientation between the CaMV35S promoter (Franck et al., 1980; Guilley et al., 1982) and ocs terminator (De Greve et al., 1982). The plasmid pCGP1634 contained a CaMV35S promoter, β-glucuronidase (GUS) reporter gene encoded by the *E. coli* uidA locus (Jefferson et al., 1987) and ocs terminator region in a pUC19 vector. The plasmid pCGP2158 was digested with NcoI/XbaI to release the cDNA insert. The plasmid pCGP1634 was also digested with NcoI/XbaI to release the backbone vector containing the CaMV35S promoter and the ocs terminator. The fragments were isolated and ligated together to produce pCGP2167. The plasmid pCGP2167 was subsequently digested with PyuII to release the expression cassette containing the CaMV35S promoter, the rose F3'H cDNA clone and the ocs termintor. This expression cassette fragment was isolated and ligated with SmaI ends of pWTT2132 binary vector (DNA Plant Technology Corporation; Oakland, Calif.) to produce pCGP2169 (FIG. 17).

The binary vector pCGP2169 was introduced into *A. tumefaciens* strain AGL0 cells, as described in Example 9. The pCGP2169/AGL0 cells are used to transform rose plants, to reduce the amount of 3'-hydroxylated flavonoids.

EXAMPLE 28

Isolation of a Putative F3'H cDNA Clone from Chrysanthemum

In order to isolate a chrysanthemum F3'H cDNA clone, a chrysanthemum cv. Red Minstral petal cDNA library was screened with $^{32}$P-labelled fragments of the petunia Ht1 cDNA clone (OGR-38), contained in pCGP1805.

Construction of a Petal cDNA Library from Chrysanthemum cv. Red Minstral

Total RNA was prepared from the petals (stages 3 to 5) of chrysanthemum cv. Red Minstral using Trizol™ reagent (Life Technologies) (Chomczynski and Sacchi, 1987) according to the manufacturer's recommendations. Poly(A)$^+$ RNA was enriched from the total RNA, using a mRNA isolation kit (Pharmacia) which relies on oligo-(dT) affinity spun-column chromatography.

A Superscript™ cDNA synthesis kit (Life Technologies) was used to construct a petal cDNA library in ZipLox using 5 µg of poly(A)+ RNA isolated from stages 3 to 5 of Red Minstral as template.

30,000 pfus of the library were plated onto LB plates (Sambrook et al., 1989) at a density of 3,000 pfus per 15 cm plate after transfecting Y1090r-, and incubated at 37° C. for 16 hours. After incubation at 4° C. for one hour, duplicate lifts were taken onto Hybond N+™ filters (Amersham) and treated as recommended by the manufacturer.

Screening of the Red Minstral DNA Library

The duplicate lifts from the Red Minstral petal cDNA library were screened with $^{32}$P-labelled fragments of the 1.8 kb Asp718/BamHI insert from pCGP1805.

Hybridization conditions included a prehybridization step in 1 mM EDTA (pH8.0), 0.5MNa$_2$HPO$_4$ (pH7.2), 7% (w/v) SDS (Church and Gilbert, 1984) at 65° C. for at least 1 hour. The $^{32}$P-labelled fragments (1×10$^6$ cpm/mL) were then added to the hybridization solution and hybridization was continued at 65° C. for a further 16 hours. The filters were then washed in 2×SSC, 0.1% (w/v) SDS at 65° C. for 2×1 hour and exposed to Kodak BioMax™ film with an intensifying screen at −70° C. for 48 hours.

Eight strongly-hybridizing plaques were picked into PSB (Sambrook et al., 1989). Of these, 2 (RM6i and RM6ii) were rescreened to isolate purified plaques, using the hybridization conditions as described for the initial screening of the cDNA library. The plasmids contained in the λZipLox bacteriophage vector were rescued according to the manufacturer's protocol and sequence data was generated from the 3' and 5' ends of the cDNA inserts. The partial sequences of the RM6i and RM6ii cDNA inserts were compared with the complete sequence of the petunia OGR-38 F3'H cDNA clone. The RM6i cDNA clone showed relatively high sequence similarity with that of the petunia OGR-38 cDNA clone, and was further characterised.

The RM6i cDNA insert contained in pCHRM1 was released upon digestion with EcoRI and was approximately 1.68 kb. The complete sequence of RM6i cDNA clone (SEQ ID NO:16) contained in the plasmid pCHRM1 was determined by compilation of sequence from subclones of the RM6i cDNA insert.

The nucleotide and predicted amino acid sequences of the chrysanthemum RM6i cDNA insert (SEQ ID NO:16 and SEQ ID NO:17) were compared with those of the petunia OGR-38 F3'H cDNA clone (SEQ ID NO:1 and SEQ ID NO:2). The sequence of the chrysanthemum RM6i cDNA insert showed 68.5% similarity, over 1532 nucleotides, and 73.6% similarity, over 511 amino acids, to that of the petunia OGR-38 F3'H$_1$ cDNA clone.

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

Conduction of pLN85 (Antisense Binary)

Figure 18:
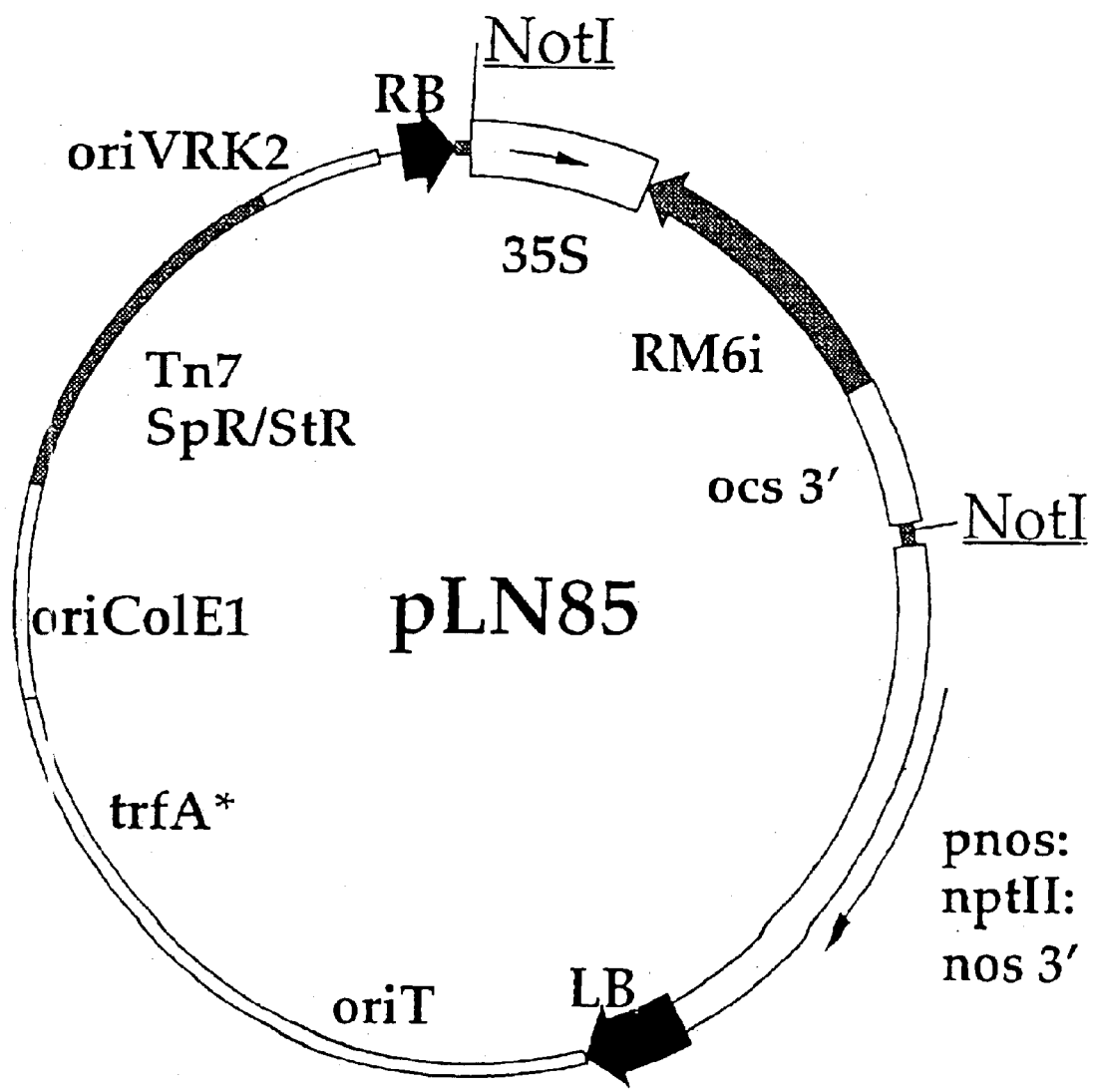
FIG. 18 is a diagrammatic representation of the binary plasmid pLN85, construction of which is described in Example 28. The chrysanthemum RM6i cDNA insert from pCHRM1 was cloned in "anti-sense" orientation behind the promoter from the Cauliflower Mosaic Virus 35S gene (35S). Other abbreviations are as follows: LB=left border; RB=right border; ocs3'=the terminator region from the octopine synthase gene of Agrobacterium; pnos:nptII:nos 3'=the expression cassette containing the promoter region from the nopaline synthase gene of Agrobacterium; the coding region of the neomycin phosphotransferase II gene and the terminator region from the nopaline synthase gene of Agrobacterium; oriT=origin of transfer of replication; trfA*=a trans-acting replication function; oriColE1=a high copy origin of replication from a Colcinin E1 plasmid; Tn7SpR/StR=the spectinomycin and streptomycin resistance genes from transposon Tn7; oriVRK2=a broad host range origin of replication from plasmid RK2. Restriction enzyme sites are also marked.

A plasmid designated pLN84 was constructed by cloning the RM6i cDNA insert from pCHRM1 in the "antisense" orientation behind the complete CaMV35S promoter contained in pART7 (Gleave 1992). The plasmid pCHRM1 was digested with NotI to release the cDNA insert. The RM6i cDNA fragment was blunt-ended using T4 DNA polymerase (Sambrook et al., 1989) and purified, following agarose gel electrophoresis and GELase (Epicentre Technologies). The purified fragment was ligated with SmaI ends of the pART7 shuttle vector to produce pLN84. The plasmid pLN84 was subsequently digested with NotI to release the expression cassette containing CaMV35S: RM6i cDNA: ocs. The expression cassette was isolated as a single fragment and ligated with NotI ends of the pART727 binary vector (Gleave, 1992) to produce pLN85 (FIG. 18). Correct insertion of the fragment was established by restriction enzyme analysis of DNA isolated from streptomycin-resistant E.coli transformants.

The binary vector pLN85 is introduced into chrysanthemum plants via Agrobacterium-mediated transformation, as described in Ledger et al, 1991), to reduce the amount of 3'-hydroxylated flavonoids.

EXAMPLE 29

Isolation of a Putative F3'H cDNA Clone from *Torenia fournieri*

In order to isolate a torenia F3'H cDNA clone, the petunia Ht1-linked F3'H cDNA clone (OGR-38), contained in pCGP1805, was used to screen a *Torenia fournieri* cv. Summer Wave petal cDNA library, under low stringency conditions.

Construction of *Torenia fournieri* cv. Summer Wave Petal cDNA Library

A directional petal cDNA library was prepared from Summer Wave flowers, essentially as described in Example 4.

Screening of Summer Wave Petal cDNA Library

Lifts of a total of 200,000 of the amplified Summer Wave petal cDNA library were screened with DIG-labelled fragments of the 1.8 kb OGR-38 cDNA insert from pCGP1805. A DIG DNA labelling and detection kit from Boehringer-Mannheim was used according to the manufacturer's recommendations.

Hybridizations were carried out in 30% (v/v) formamide, 5×SSC, 1% (w/v) SDS at 37° C. for 16 hours. The filters were then washed in 5×SSC, 1% (w/v) SDS at 65° C. for 1 hour.

The signals were visualized following the protocol of the DIG DNA labelling and detection kit.

Twelve strongly-hybridizing plaques were picked into PSB and rescreened to isolate pure plaques. The plasmids contained in the λZAPII bacteriophage vector were rescued and digested with EcoRI/XhoI to release the cDNA inserts. Most of the twelve clones contained cDNA inserts of approximately 1.8 kb. One clone, THT52, contained the longest 5' non-coding-region sequence. The complete sequence of the torenia cDNA clone (THT52), contained in the plasmid pTHT52, was determined by compilation of sequence from different pUC18 subclones obtained using standard procedures for the generation of randomly-overlapping clones (Sambrook et al., 1989). The sequence (SEQ ID NO:18) contained an open reading frame of 1524 bases which encodes a putative polypeptide of 508 amino acids (SEQ ID NO:19).

The nucleotide and predicted amino acid sequences of the torenia TH$_1$T2 cDNA clone (SEQ ID NO:18 and SEQ ID NO:19) were compared with those of the petunia OGR-38 F3'H cDNA clone (SEQ ID NO:1 and SEQ ID NO:2). The torenia THT52 cDNA clone showed 63.6% similarity, over 1694 nucleotides, and 67.4% similarity, over 515 amino acids, to that of the petunia OGR-38 cDNA clone.

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in Table 7 and in Tables 8, 9, 10, 11 and 12, respectively. These Tables are in Example 34, at the end of the specification.

EXAMPLE 30

The 3'H Assay of the Torenia THT cDNA Clone Expressed in Yeast Construction of pYTMT6

Figure 19:
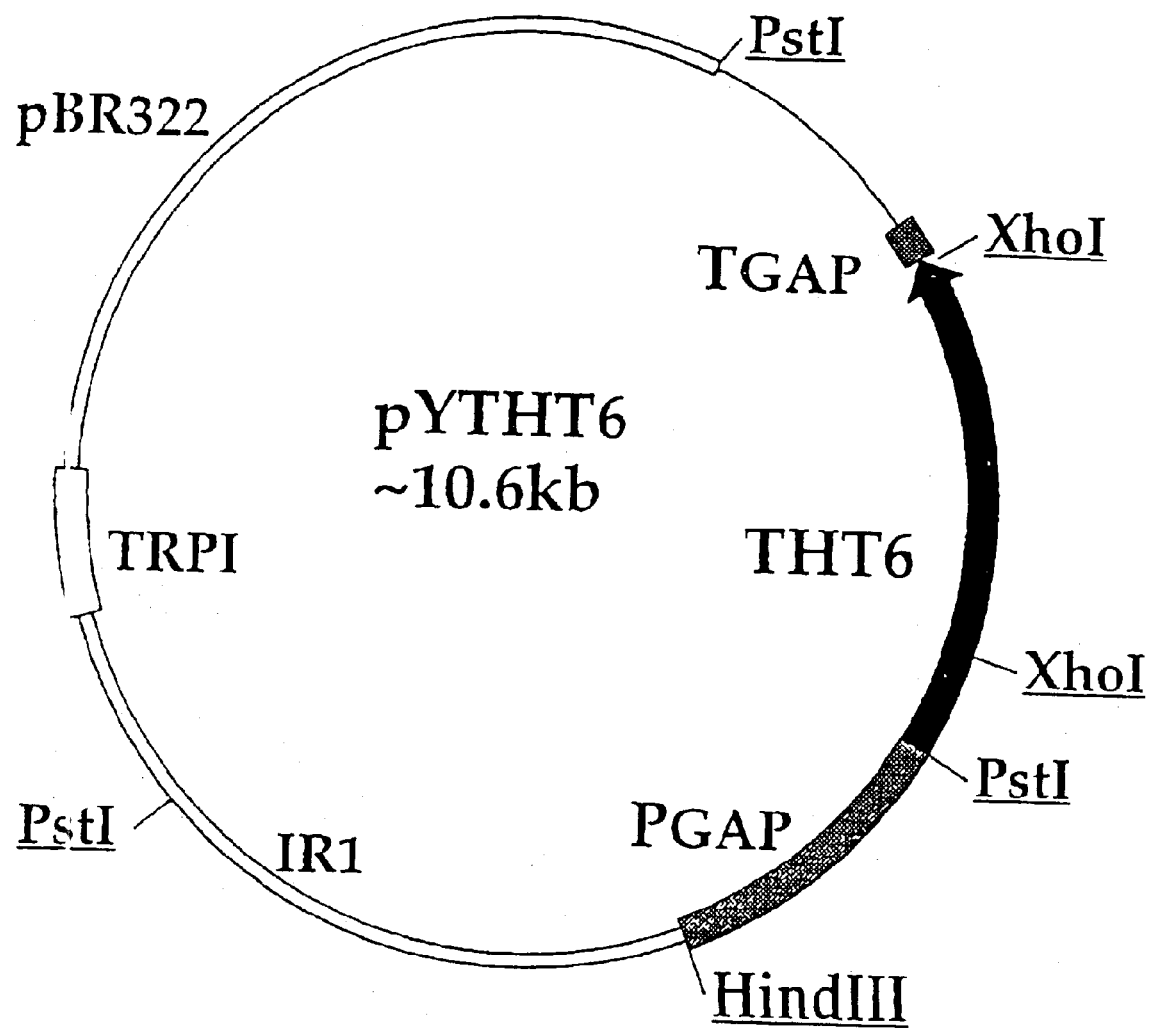
FIG. 19 is a diagrammatic representation of the yeast expression plasmid pYTHT6, construction of which is described in Example 30. The THT6 cDNA insert from pTHT6 was cloned in a "sense" orientation behind the yeast glyceraldehyde-3-phosphate dehydrogenase promoter (PGAP) in the expression vector pYE22m. Abbreviations are as follows: TRP1=Trp1 gene; IR1=inverted repeat of 2 μm plasmid; TGAP=the terminator sequence from the yeast glyceraldehyde-3phosphate dehydrogenase gene. Restriction enzyme sites are also marked.

The plasmid pYTHT6 (FIG. 19) was constructed by cloning the cDNA insert from pTHT6 in a "sense" orientation behind the yeast glyceraldebyde-3-phosphate dehydrogenase promoter of pYE22m (Tanaka et al., 1988). The plasmid pTHT6 contained the THT6 cDNA clone. THT6 is identical to THT52, except that its 5' non-coding region is 75 bp shorter.

The 1.7 kb THT6 cDNA insert was released from the plasmid pTHT6 upon digestion with EcoI/XhoI. The THT6 cDNA fragment was isolated, purified and ligated with EcoRI/SalI ends of pYE22m to produce pYTHT6.

Yeast transformation, preparation of yeast extracts and the F3'H assay are described in Example 6.

F3'H activity was detected in extracts of G1315/pYTHT6, but not in extracts of non-transgenic yeast. From this it was concluded that the THT6 cDNA insert contained in pYTHT6, encoded a F3'H.

EXAMPLE 31

Isolation of a Putative F3'H cDNA Clone from *Pharbitis nil* (Japanese Morning Glory)

In order to isolate a morning glory F3'H cDNA clone, the petunia Ht1-linked F3'H cDNA clone (OGR-38), contained in pCGP1805, was used to screen a Japanese morning glory petal cDNA library, under low stringency conditions.
Construction of Japanese Morning Glory Petal cDNA Library The petal cDNA library from young petals of *Pharbitis nil* (Japanese morning glory) was obtained from Dr Iida (National Institute of Basic Biology, Japan).
Screening of Japanese Morning Glory Petal cDNA Library Lifts or a total of 200,000 of the amplified Japanese morning glory petal cDNA library were screened with DIG-labelled fragments of the 1.8 kb OGR-38 cDNA insert from pCGP1805. A DIG DNA labelling and detection kit from Boehringer-Mannheim was used according to the manufacturer's recommendations.

Hybridizations were carried out in 30% (v/v) formamide, 5×SSC, 1% (w/v) SDS at 37° C. for 16 hours. The filters were then washed in 5×SSC, 1% (w/v) SDS at 65° C. for 1 hour. The signals were visualized following the protocol of the DIG DNA labelling and detection kit.

Twenty strongly-hybridizing plaques were picked into PSB and rescreened to isolate pure plaques. The plasmids contained in the λZAPII bacteriophage vector were rescued and digested with EcoRI/XhoI to release the cDNA inserts. One clone (MHT85) contained a 1.8 kb insert. The complete sequence of the Japanese morning glory cDNA clone (MHT85) (SEQ ID NO:20), contained in the plasmid pMHT85, was determined by compilation of sequence from different pUC18 subclones obtained using standard procedures for the generation of randomly-overlapping clones (Sambrook et al., 1989). The MHT85 sequence appears to be 5 bases short of "full-lent".

The nucleotide and predicted amino acid sequences of the Japanese morning glory MHT85 cDNA clone (SEQ ID NO:20 and SEQ ID NO:21) were compared with those of the petunia OGR-38 F3'H cDNA clone (SEQ ID NO:1 and SEQ ID NO:2). The Japanese morning glory MHT85 cDNA clone showed 69.6% similarity, over 869 nucleotides, and 74.8% similarity, over 515 amino acids, to that of the petunia OGR-38 cDNA clone.

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

EXAMPLE 32

Isolation of a Putative F3'H cDNA Clone from *Gentiana triflora*

In order to isolate a gentian F3'H cDNA clone, the petunia Ht1-link F3'4 cDNA clone (OGR-38), contained in pCGP1805, was used to screen a *Gentiana triflora* Pall. var japonica Hara petal cDNA library, under low stringency conditions.
Construction of Gentian Petal cDNA Library A petal cDNA library was prepared from *Gentiana triflora* Pall. var japonica Hara flowers, as described by Tanaka et al., 1996.
Screening of Gentian Petal cDNA Library Lifts of a total of 200,000 of the amplified gentian petal cDNA library were screened with DIG-labelled fragments of the 1.8 kb OGR-38 cDNA insert from pCGP1805. A DIG DNA labelling and detection kit from Boehringer-Mannheim was used according to the manufacturer's recommendations.

Hybridizations were carried out in 30% (v/v) formamide, 5×SSC, 1% (w/v) SDS at 37° C. for 16 hours. The filters were then washed in 5×SSC, 1% (w/v) SDS at 65° C. for 1 hour. The signals were visualized following the protocol of the DIG DNA labelling land detection kit.

Fifteen strongly-hybridizing plaques were picked into PSB and rescreened to isolate pure plaques. The plasmids contained in the λZAPII bacteriophage vector were rescued and digested with EcoRI/XboI to release the cDNA inserts. One clone (GHT13) contained a 1.8 kb insert The sequence of the partial gentian cDNA clone (GHT13) (SEQ ID NO:22), contained in the plasmid pGHT13, was determined by compilation of sequence from different pUC18 subclones obtained using standard procedures for the generation of randomly-overlapping clones (Sambrook et al 1989).

The nucleotide and predicted amino acid sequences of the gentian GHT13 cDNA clone (SEQ ID NO:22 and SEQ ID NO:23) were compared with those of the petunia OGR-38 F3'H cDNA clone. The gentian GHT13 cDNA clone showed 68.3% similarity, over 1519 nucleotides, and 71.8% similarity, over 475 amino acids, to that of the petunia OGR-38 cDNA clone.

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

EXAMPLE 33

Isolation of Putative F3'H cDNA Clone from Lisianthus

In order to isolate a lisianthus F3'H cDNA clone, the petunia Ht1-linked F3'H cDNA clone EA (OGR-38), contained in pCGP1805, was used to screen a lisianthus petal cDNA library, under low stringency conditions.

Construction and Screening of Lisianthus Petal cDNA Library 10,000 pfus of a lisianthus petal cDNA library described by Davies et al. (1993) and Markham and Offman (1993) were plated onto LB plates (Sambrook et al., 1989) at a density of 3,000 pfus per 15 cm plate after transfecting Y1090r-, and incubated at 37° C. for 16 hours. After incubation at 4° C. for one hour, duplicate lifts were taken onto Hybond N+™ filters (Amersham) and treated as recommended by the manufacturer.

The duplicate lifts from the lisianthus line #54 petal cDNA library were screened with $^{32}$P-labelled fragments of the 1.8 kb AsP718/BAmHI insert from pCGP1805.

Hybridization conditions included a prehybridization step in 1 mM EDTA (pH8.0), 0.5MNa$_2$HPO$_4$ (pH7.2), 7% (w/v) SDS (Church and Gilbert, 1984) at 55° C. for at least 1 hour. The $^{32}$P-labelled fragments (1×10$^6$ cpm/mL) were then added to the hybridization solution and hybridization was continued at 55° C. for a further 16 hours. The filters were then washed in 2×SSC, 0.1% (w/v) SDS at 55° C. for 2×15 minutes, and exposed to Kodak BioMax™ film with an intensifying screen at –70° C. for 18 hours.

Twelve strongly-hybridizing plaques were picked into PSB (Sambrook et al., 1989) and rescreened to isolate purified plaques, using the hybridization conditions as described for the initial screening of the cDNA library. Sequence data were generated from the 3' and 5' ends of the cDNA inserts of four clones.

Based on sequence comparisons, pL3-6 showed similarity with the petunia OGR-38 F3'H cDNA clone and was further characterised.

The 2.2 kb cDNA insert, contained in pL3-6, was subsequently found to contain 3 truncated cDNA clones, the longest (L3-6) having high sequence similarity to the petunia OGR-38 cDNA sequence. The sequence of this L3-6 partial cDNA clone contained in the plasmid pL3-6 was determined by compilation of sequence from subclones of the L3-6 cDNA insert (SEQ ID NO:24).

The nucleotide and predicted amino acid sequences of the lisianthus L3-6 cDNA clone (SEQ ID NO:24 and SEQ ID NO:25) were compared with those of the petunia OGR-38 F3'H cDNA clone (SEQ ID NO:1 and SEQ ID NO:2). The sequence of the lisianthus L3-6 cDNA clone showed 71.4% similarity, over 1087 nucleotides, and 74.6% similarity, over 362 amino acids, to that of the petunia OGR-38 F3'H cDNA clone.

An alignment of the petunia, carnation, snapdragon, arabidopsis, rose, chrysanthemum and torenia sequences, all of which are disclosed in this specification, and various summaries of comparisons of sequence similarities among the nucleotide and corresponding amino acid sequences, can be found in FIGS. 20(i)–(v) and in Tables 7, 8, 9, 10, and 11 respectively. Tables 7–11 are in Example 34, at the end of the specification.

Further investigation of the remaining clones isolated from the screening of the lisianthus library identified another putative F3'H cDNA clone (L3-10), contained in the plasmid pL3-10. The L3–10 cDNA insert is approximately 1.8 kb and appears to represent a "full-length" clone.

EXAMPLE 34

Alignments and Comparisons Among Nucleotide and Amino Acid Sequences Disclosed Herein Multiple sequence alignments were performed using the ClustalW program as described in Example 3. FIG. 20(i)–(v) provide a multiple sequence alignment of the predicted amino acid sequences of petunia OGR-38 (A) (SEQ ID NO:2); carnation (B) (SEQ ID NO:4); snapdragon (C) (SEQ ID NO:6); arabidopsis Tt7 coding region (D) (SEQ ID NO:42); rose (E) (SEQ ID NO:15) chrysanthemum (F) (SEQ ID NO:17); torenia (G) (SEQ ID NO:19); morning glory (H) (SEQ ID NO:21); gentian (partial sequence) (I) (SEQ ID NO:23); lisianthus (partial sequence) (J) (SEQ ID NO:25) and the petunia 651 cDNA (K) (SEQ ID NO:41). Conserved amino acids are shown in bolded capital letters and are boxed and shaded. Similar amino acids are shown in capital letters and are only lightly shaded, and dissimilar amino acids are shown in lower case letters.

The nucleotide and predicted amino acid sequences of the rose F3'H; #34 cDNA clone (SEQ ID NO:14 and SEQ ID NO:15) were compared with those of the petunia OGR-38 F3'H cDNA clone (SEQ ID NO:1 and SEQ ID NO:2) and the snapdragon sd F3'H clone (SEQ ID NO:5 and SEQ ID NO:6). The rose F3'H #34 cDNA clone showed 64.7% similarity, over 1651 nucleotides and 72.7% similarity, over 509 amino acids, to that of the petunia OGR-38 cDNA clone, and 67.2% similarity, over 1507 nucleotides, and 68.9 similarity, over 502 amino acids, to that of the snapdragon sdF3'H clone.

Nucleotide and amino acid sequences of the F3'H cDNA clones from the above mentioned species and the coding region of the genomic clone from arabidopsis were compared using the LFASTA program, as described in Example 3. Summaries of similarity comparisons are presented in Tables 8 to 12, below.

TABLE 7

Percentage of sequence similarity between F3'H sequence of petunia OGR-38 and F3'H sequences from other species and other P450 molecules

| Species/Clone | Number of nucleotides (nt) | Number of amino acids (aa) | % similarity to OGR-38/ no. nt (area of similarity) | % similarity to OGR-38/ no. aa (area of similarity) |
|---|---|---|---|---|
| Petunia OGR-38 | 1789nt | 512aa | | |
| Snapdragon F3'H cDNA | 1711nt | 512aa | 69.0%/1573nt (19–1578) | 72.2%/507aa (1–504) |
| Arabidopsis partial F3'H cDNA | 971nt | 270aa | 64.7%/745nt (854–1853) | 63.7%/248aa (269–510) |
| Arabidopsis Tt7 coding region | 1774nt | 513aa | 65.4%/1066nt | 67.1%/511aa |
| Carnation F3'H cDNA | 1745nt | 496aa | 67.3%/1555nt (28–1571) | 71.5%/488aa (17–503) |
| Rose F3'H cDNA | 1748nt | 513aa | 64.7%/165nt (56–1699) | 72.7%/509aa (7–510) |
| Gentian partial F3'H cDNA | 1667nt | 476aa | 68.3%/1519nt (170–1673) | 71.8%/475aa (40–510) |
| Morning Glory F3'H cDNA | 1824nt | 517aa | 69.6%/869nt (60–1000) | 74.8%/515aa (3–503) |
| Chrysanthemum F3'H cDNA | 1660nt | 508aa | 68.5%/1532nt (50–1580) | 73.6%/511aa (1–510) |
| Lisianthus partial F3'H cDNA | 1214nt | 363aa | 71.4%/1087nt (520–1590) | 74.6%/362aa (160–510) |
| Torenia F3'H cDNA | 1815nt | 508aa | 63.6%/1694nt (90–1780) | 67.4%/515aa (1–510) |
| Petunia Hf1 cDNA | 1812nt | 508aa | 58.9%/1471nt (29–1474) | 49.9%/513aa (1–511) |
| Petunia Hf2 cDNA | 1741nt | 508aa | 58.9%/1481nt (37–1498) | 49.1%/511aa (3–510) |
| Petunia 651 cDNA | 1716nt | 496aa | 53.5%/1284nt (50–1309) | 38.0%/502aa (7–503) |
| Mung Bean C4H cDNA | 1766nt | 505aa | 56.0%/725nt (703–1406) | 29.2%/511aa (1–503) |

TABLE 8

Percentage of sequence similarity between F3'H sequence of Snapdragon and F3'H sequences from other species and other P450 molecules

| Species/Clone | Number of nucleotides (nt) | Number of amino acids (aa) | % similarity to snapdragon/no. nt | % similarity to snapdragon/no. aa |
|---|---|---|---|---|
| Snapdragon | 1711nt | 512aa | | |
| Petunia OGR-38 F3'H cDNA | 1789nt | 512aa | 69.0%/1573nt | 72.2%/507aa |
| Arabidopsis partial F3'H cDNA | 971nt | 270aa | 64.5%/740nt | 60.4%/240aa |
| Carnation F3'H cDNA | 1745nt | 496aa | 66.7%/1455nt | 68.4%/487aa |
| Torenia F3'H cDNA | 1815nt | 508aa | 67.6%/1603nt | 70.3%/505aa |
| Rose F3'H cDNA | 1748nt | 513aa | 67.2%/1507nt | 68.9%/502aa |
| Petunia Hf1 cDNA | 1812nt | 508aa | 57.3%/1563nt | 49.3%/491aa |
| Petunia Hf2 cDNA | 1741nt | 508aa | 57.7%/1488nt | 47.8%/508aa |
| Petunia 651 cDNA | 1716nt | 496aa | 54.4%/1527nt | 39.0%/493aa |
| Mung Bean C4H cDNA | 1766nt | 505aa | 50.6%/1344nt | 32.0%/490aa |

TABLE 9

Percentage of sequence similarity between F3'H sequence of Arabidopsis and F3'H sequences from other species and other P450 molecules

| Species/Clone | Number of nucleotides (nt) | Number of amino acids (aa) | % similarity to Arabidopsis/no. nt | % similarity to Arabidopsis/no. aa |
|---|---|---|---|---|
| Arabidopsis | 971nt | 270aa | | |
| Petunia OGR-38 F3'H cDNA | 1789nt | 512aa | 64.7%/745nt | 63.7%/245% |
| Snapdragon F3'H CDNA | 1711nt | 512aa | 64.5%/740nt | 60.4%/240aa |
| Carnation F3'H cDNA | 1745nt | 496aa | 64.7%/782nt | 60.6%/241aa |
| Rose F3'H cDNA | 1748nt | 513aa | 68.5%/739nt | 63.7%/248aa |
| Petunia 651 cDNA | 1716nt | 496aa | 57.0%/521nt | 40.5%/227aa |
| Petunia Hf1 cDNA | 1812nt | 508aa | 58.2%/632nt | 46.5%/243aa |
| Petunia Hf2 cDNA | 1741nt | 508aa | 57.4%/632nt | 46.1%/243aa |

TABLE 10

Percentage of sequence similarity between F3'H sequence of Rose and F3'H sequences from other species and other P450 molecules

| Species/clone | Number of nucleo-tides (nt) | Number of amino acids (aa) | % similarity to Rose/ no. nt | % similarity to Rose/ no. aa |
|---|---|---|---|---|
| Rose | 1748bp | 513aa | | |
| Petunia OGR-38 Fe'H cDNA | 1789bp | 5123aa | 64.7%/1651nt | 72.7%/509aa |
| Snapdragon Fe'H cDNA | 1711bp | 512aa | 67.2%/1507 | 68.9%/502aa |
| Carnation Fe'H cDNA | 1745bp | 496aa | 67.4%/1517nt | 72.6%/486aa |
| Arabidopsis partial F3'H cDNA | 971bp | 270aa | 68.5%/739nt | 63.7%/248aa |
| Petunia 651 cDNA | 1716bp | 496aa | 53.1%/1182nt | 37.8%/502aa |
| Petunia Hf1 cDNA | 1812bp | 506aa | 57%/1366nt | 49.9%/503aa |
| Petunia Hf2 cDNA | 1741bp | 508aa | 57.3%/1331nt | 49.1%/505aa |
| Mung Bean C4H cDNA | 1766bp | 505aa | 52.4%/1502nt | 32.0%/510aa |

TABLE 11

Percentage of sequence similarity between coding region of Arabidopsis tt7 genomic sequence and F3'H cDNA sequences from other species and other P450 molecules

| Species/Clone | Number of nucleo-tides (nt) | Number of amino acids (aa) | % similarity to Arabidopsis tt7/no. nt | % similarity to Arabidopsis tt7/no. aa |
|---|---|---|---|---|
| Arabidopsis Tt7 coding region | 1774nt | 513aa | | |
| Petunia OGR-38 F3'H cDNA | 1789nt | 512aa | 65.4%/1066nt | 67.1%/511aa |
| Snapdragon F3'H cDNA | 1711nt | 512aa | 62.7%/990nt | 64.9%/504aa |
| Carnation F3'H cDNA | 1745nt | 496aa | 63.2%/1050nt | 65.9%/495aa |
| Rose F3'H cDNA | 1748nt | 513aa | 65.5%/1076nt | 68%/512aa |
| Petunia 651 cDNA | 1716nt | 496aa | 56.5%/990nt | 36.5%/502aa |
| Petunia Hf1 F3'H cDNA | 1812nt | 506aa | 56.8%/995nt | 47.5%/509aa |
| Petunia Hf2 F3'H cDNA | 1741nt | 508aa | 55.2%/1063nt | 46.8%/509aa |

Those skilled in the art, will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Altschul, S. F., Gish, W., Miller, W., Myers, E. W. and Lipman, D. J. *J. Mol. Biol.* 215: 403410, 1990.

Ashikari, T., Kiuchi-Goto, N., Tanaka, Y., Shibano, Y., Amachi, T., and Yoshizumi, H. *Appl. Microbiol. Biotechnol.* 30: 515–520, 1989.

Baird, W. V. and Meagher, R. B. *EMBO J.* 6, 3223–3231, 1987.

Bechtold, N., Ellis, J. and Pelletier, G. C. R. Acad. Sci. Paris, Sciences de la vie 316: 1194–1199, 1993.

Bethesda Research Laboratories. BRL pUC host: *E. coli* DH5α™ competent cells. *Bethesda Res. Lab. Focus.* 8(2): 9, 1986.

Brugliera, F., Holton, T. A., Stevenson, T. W., Farcy, E., Lu, C-Y and Cornish, E. C. *Plan J.* 5(1): 81–92, 1994.

Church, G. M. and Gilbert, W. *PNAS USA*, 81: 1991–1995.

Chomczynski, P. and Sacchi, N. *Anal Biochem*. 162: 156–159.

Comai, L., Moran, P. and Maslyar, D., *Plant Mol. Biol*. 15: 373–381, 1990.

Cornu, A., Farcy, E., Maizonnier, D., Haring, M., Veerman, W. and Gerats, A. G. M., In: *Genetic maps—Locus maps of complex genomes*. 5th edition, Stephen J. O'Brien (ed.), Cola Spring Harbor Laboratory Press, USA, 1990.

Davies et al., *Plant Science*, 95: 67–77, 1993.

D'Alessio et al., *Focus*, 14: 76–79, 1992

De Greve, H., Dhaese, P., Seurinck, J., Lemmers, M., Van Montagu, M and Schell, J. *J. Mol Appl Genet*. 1: 499–511.

Dellaporta, S. J., Wood, J. and Hick, J. B., *Plant Mol. Biol. Rep*. 1: 19–21, 1983.

Del Sal, G., Manfioletti, G. and Schneider, C. *Biotechniques*, 7(S): 514–519, 1989.

Doodeman, M., Gerats, A. G. M., Schram, A. W., De Vlaming, P. and Bianchi, F., *Theor. Appl. Genet*. 67: 357–366, 1984.

Dooner, H. K., Robbins, T. R. and Jorgensen, R. A. *Ann. Rev. Genet*. 25: 173–199, 1991.

Ebel, J. and Hahlbrock, K., In: *The Flavonoids: Advances in Research Since 1980*. Harbounie, J. B. (ed.), Academic Press, New York, USA, 641679, 1988.

Forkmann, G. and Stotz, G. Z. *Naturforsch*. 36c:411–416, 1981.

Forkmann, G. *Plant Breeding* 106: 1–26, 1991.

Franck, A., Guilley, H., Jonard, G. Richards, K. and Hirth, L. *Cell*, 21, 285–294, 1980.

Frohman, M. A., Dush, M. K., Martin, G. R. *Proc. Natl. Acad. Sci. USA* 85: 8998–9002, 1988.

Gamborg, O. L., Miller, R. A. and Ojira, K., *Exp. Cell Res*. 50: 151–158, 1968.

Garfinkel, D. J. and Nester, E. W. *J. Bacteriol*. 144:732–743, 1980.

Gleave, A. P. *Plant Molecular Biology* 20: 1203–1207, 1992.

Guilley, H., Dudley, R. K., Jonard, G., Balazs, E. and Richards, K. E. *Cell*, 30, 763–773, 1982.

Hahlbrock, K. and Grisebach, H., *Annu. Rev. Plant Physiol*. 30: 105–130, 1979.

Hanahan, D., *J. Mol. Biol*. 166: 557, 1983.

Haughn, G. W. and Somerville, C. *Molecular and General Genetics* 204: 430–434, 1986.

Holton, T. A., Brugliera, F. Lester, D. R., Tanaka, Y., Hyland, C. D., Menting, J. G. T., Lu, C., Farcy, E., Stevenson, T. W. and Cornish, E. C., *Nature*, 366, 276–279, 1993.

Holton, T. A. and Cornish, E. C. *Plant Cell*, 7: 1071–1083, 1995.

Inoue, H., Nojima, H. and Okayama, H. *Gene*, 96: 23–28, 1990.

Ito, H., Fukuda, Y., Murata, K. and Kimura, A. *J. Bacteriol*. 153: 163–168, 1983.

Jefferson, R. A. *Plant Mol. Biol. Rep*. 5: 387–405, 1987.

Jefferson, R. A., Kavanagh, T. A., and Bevan, M. W. *EMBO J*. 6: 3901–3907, 1987.

Koorrneef, M, Luiten, W., de Vlaming, P. and Schram, A. W. *Arabidopsis Information Service* 19: 113–115, 1982.

Kozak, M. *J. Cell. Biol*. 108: 229, 1989.

Lander, E. S., Green, P., Abrahamson, J., Barlow, A., Day, M. J., Lincoln, S. E. and Newberg, L. *Genomics*, 121, 185–199, 1987.

Lazo, G. R., Pascal, A. S. and Ludwig, R. A., *Bio/technology*, 9: 963–967, 1.991.

Ledger, S. E., Delores, S. C. and Given, N. K. *Plant Cell Reports*, 10: 195–199, 1991.

Liang, P. and Pardee, A. B. *Science*, 257: 967–971, 1992.

Liang, P., Averboukh, L. and Pardee, A. B. *Nucl. Acids Res*. 21: 3269–3275, 1993.

Marchuk, D., Drumm, M., Saulino, A., Collins, F. S. *Nucl. Acids Res*. 19: 1154, 1990.

Markham, K. R., *Techniques of flavonoid identification*, London: Academic Press, 1982.

Markham, K. R and Offman, D. J. *Phytochem*., 34: 679–685.

Martin, C. and Gerats, T. In: *The molecular biology of flowering*. (Jordan, B. R. ed), UK, CAB International, 219–255, 1993.

McLean, M., Gerats, A. G. M., Baird, W. V. and Meagher, R. B. *J. Heredity* 81: 341–346, 1990.

Merrifield, *J. Am. Chem. Soc*. 85: 2149, 1964.

Mizutani, M., Ward, E., DiMaio, J., Ohta, D., Ryals, J. and Sato, R. *Biochem. Biophys. Res. Commun*. 190: 875–880, 1993.

Murashige, T. and Skoog, F., *Physiol. Plant*, 15: 73–97, 1962.

Newman, T., de Bruijn, F. J., Green, P., Keegstra, K., Kende, H., McIntosh, L., Ohlrogge, J., Raikhel, N., Somerville, S., Thomashow, M. *Plant Physiol*. 106: 1241–1255, 1994.

Pearson, W. R. and Lipman, D. J., *Proc. Natl. Acad. Sci. USA* 85: 2444–2448, 1988.

Sambrook, J., Fritsch, E. F. and Maniatis, T. *Molecular Cloning: A Laboratory Manual* (2nd edition). Cold Spring Harbor Laboratory Press, USA, 1989.

Schenk, R. U. and Hilderbrandt, A. C., *Can. J. Bot*. 50: 199–204, 1972.

Schram, A. W., Jonsson, L. M. V. and Bennink, G. J. H., Biochemistry of flavonoid synthesis in *Petunia hybrida*. In: *Petunia* Sink, K. C. (ed.), Springer-Verlag, Berlin, Germany, pp 68–75, 1984.

Stafford, H. A., *Flavonoid Metabolism*. CRC Press, Inc. Boca Raton, Fla., USA, 1990.

Stotz, G. and Forkmann, G. Z. *Naturforsch* 37c: 19–23, 1982.

Tabak, A. J. H., Meyer, H. and Bennink, G. J. H., *Planta* 139, 67–71, 1978.

Tanaka, Y., Ashikari, T., Shibano, Y., Amachi, T., Yoshizumi, H. and Maltsubara, H. *J. Biochem*. 103: 954–961, 1988.

Tanaka, Y., Yonekura, K., Fukuchi-Mizutani, M., Fukui, Y., Fujiwara, H., Ashikari, T. and Kusumi, T. *Plant Cell Physiol*. 37(5): 711–716, 1996.

Turpen, T. H. and Griffith, O. M. *Biotechniques*, 4: 11–15, 1986.

van Tunen A. J. and Mol J. N. M. In: *Plant Biotechnology* (Grierson, D. ed.) Glasgow: Blackie, 2: 9–31, 1990.

Wiering, H. and de Vlaming, P., Inheritance and Biochemistry of Pigments. In: *Petunia* Sink, K. C. (ed.), Springer-Verlag, Berlin, Germany, pp 49–65, 1984.

Wallroth, M., Gerats, A. G. M., Rogers, S. G., Fraley, R. T. and Horsch, R. B., *Mol. Gen. Genet*. 202: 6–15, 1986.

What is claimed is:

1. An isolated nucleic acid molecule comprising the nucleotide sequence as set forth in SEQ ID NO:1.
2. An isolated nucleic acid molecule comprising the nucleotide sequence as set forth in SEQ ID NO: 3.
3. An isolated nucleic acid molecule comprising the nucleotide sequence as set forth in SEQ ID NO: 5.
4. An isolated nucleic acid molecule consisting of the nucleotide sequence as set forth in SEQ ID NO: 7.
5. An isolated nucleic acid molecule comprising the nucleotide sequence as set forth in SEQ ID NO: 9.
6. An isolated nucleic acid molecule comprising the nucleotide sequence as set forth in SEQ ID NO: 14.
7. An isolated nucleic acid molecule comprising the nucleotide sequence as set forth in SEQ ID NO: 16.
8. An isolated nucleic acid molecule comprising the nucleotide sequence as set forth in SEQ ID NO: 18.
9. An isolated nucleic acid molecule consisting of the nucleotide sequence as set forth in SEQ ID NO: 20.
10. An isolated nucleic acid molecule consisting of the nucleotide sequence as set forth in SEQ ID NO: 22.
11. An isolated nucleic acid molecule consisting of the nucleotide sequence as set forth in SEQ ID NO: 24.
12. An isolated nucleic acid molecule encoding the amino acid sequence as set forth in SEQ ID NO: 2, or the complement of said nucleic acid molecule.
13. An isolated nucleic acid molecule encoding the amino acid sequence as set forth in SEQ ID NO: 4, or the complement of said nucleic acid molecule.
14. An isolated nucleic acid molecule encoding the amino acid sequence as set fort in SEQ ID NO: 6, or the complement of said nucleic acid molecule.
15. An isolated nucleic acid molecule encoding the amino acid sequence as set forth in SEQ ID NO: 8, or the complement of said nucleic acid molecule.
16. An isolated nucleic acid molecule encoding the amino acid sequence as set forth in SEQ ID NO: 10 or SEQ ID NO:11 or SEQ D NO:12 or SEQ ID NO:13, or the complement of said nucleic acid molecule.
17. An isolated nucleic acid molecule encoding the amino acid sequence as set fort in SEQ ID NO: 15, or the complement of said nucleic acid molecule.
18. An isolated nucleic acid molecule encoding the amino acid sequence as set forth in SEQ ID NO: 17, or the complement of said nucleic acid molecule.
19. An isolated nucleic acid molecule encoding the amino acid sequence as set forth in SEQ ID NO: 19, or the complement of said nucleic acid molecule.
20. An isolated nucleic acid molecule encoding the amino acid sequence as set forth in SEQ ID NO: 21, or the complement of said nucleic acid molecule.
21. An isolated nucleic acid molecule encoding the amino acid sequence as set forth in SEQ ID NO: 23, or the complement of said nucleic acid molecule.
22. An isolated nucleic acid molecule encoding the amino acid sequence as set forth in SEQ ID NO: 25, or the complement of said nucleic acid molecule.
23. A DNA construct capable of reducing expression of an endogenous gene encoding a flavonoid 3'-hydroxylase in a plant, said DNA construct comprising a nucleotide sequence selected from the group consisting of:
   (i) a nucleotide sequence encoding an amino acid sequence selected from the group consisting of SEQ ID NO:2, SEQ ID NO: 4, SEQ ID NO: 6, SEQ ID NO: 15, SEQ ID NO: 17, and SEQ ID NO: 19; and
   (ii) a nucleotide sequence selected from the group consisting of SEQ ID NO: 1, SEQ ID NO: 3, SEQ ID NO: 5, SEQ ID NO: 14, SEQ ID NO: 16, SEQ ID NO: 18, and nucleotides 1478 to 3897 of SEQ ID NO: 9.
24. A method for producing a transgenic plant which synthesizes a flavonoid 3'-hydroxylase, said method comprising stably transforming a cell of a plant with the nucleic acid molecule according to any one of claims 1–3, 5–8 and 13–19 to produce a transformed cell, regenerating a transgenic plant from the transformed cell, and growing said transgenic plant wherein the nucleic acid molecule is expressed.
25. The method according to claim 24 wherein said plant is selected from the group consisting of petunia, carnation, chrysanthemum, rose, snapdragon, tobacco, cornflower, pelargonium, lisianthus, gerbera, apple, iris, lily, African violet and morning glory.
26. A transgenic plant having tissue exhibiting altered colour, said transgenic plant comprising a nucleic acid molecule selected from the group consisting of:
   (i) a nucleotide sequence encoding an amino acid sequence selected from the group consisting of SEQ ID NO:2, SEQ ID NO: 4, SEQ ID NO: 6, SEQ ID NO: 15, SEQ ID NO: 17, and SEQ ID NO: 19; and
   (ii) a nucleotide sequence selected from the group consisting of SEQ ID NO: 1, SEQ ID NO: 3, SEQ ID NO: 5, SEQ ID NO: 14, SEQ ID NO: 16, SEQ ID NO: 18, and nucleotides 1478 to 3897 of SEQ ID NO: 9.
27. A transgenic cut flower from the transgenic plant according to claim 26.
28. A transgenic seed from the transgenic plant according to claim 26.
29. A transgenic fruit from the transgenic plant according to claim 26.
30. A transgenic leaf from the transgenic plant according to claim 26.

* * * * *

UNITED STATES PATENT AND TRADEMARK OFFICE
CERTIFICATE OF CORRECTION

PATENT NO. : 6,774,285 B1
DATED : December 21, 2004
INVENTOR(S) : F. Brugliera et al.

It is certified that error appears in the above-identified patent and that said Letters Patent is hereby corrected as shown below:

Title page,
Item [73], Assignee, "Florigene Limited" should read -- International Flower Developments Pty Ltd. --

Signed and Sealed this

Twenty-second Day of February, 2005

JON W. DUDAS
*Director of the United States Patent and Trademark Office*

SEQUENCE LISTING

<160> NUMBER OF SEQ ID NOS: 45

<210> SEQ ID NO 1
<211> LENGTH: 1789
<212> TYPE: DNA
<213> ORGANISM: Petunia x hybrida
<220> FEATURE:
<221> NAME/KEY: CDS
<222> LOCATION: (50)..(1588)

<400> SEQUENCE: 1

```
gcaggaattg gtgaacccca tagaagtaaa atactcctat ctttatttc atg gaa atc      58
                                                    Met Glu Ile
                                                      1 tta agc cta att ctg tac acc gtc att ttc tca ttt ctt cta caa ttc     106
Leu Ser Leu Ile Leu Tyr Thr Val Ile Phe Ser Phe Leu Leu Gln Phe
      5              10                  15 att ctt aga tca ttt ttc cgt aaa cgt tac cct tta cca tta cca cca     154
Ile Leu Arg Ser Phe Phe Arg Lys Arg Tyr Pro Leu Pro Leu Pro Pro
 20              25                  30                  35 ggt cca aaa cca tgg cca att ata gga aac cta gtc cat ctt gga ccc     202
Gly Pro Lys Pro Trp Pro Ile Ile Gly Asn Leu Val His Leu Gly Pro
             40                  45                  50 aaa cca cat caa tca act gca gcc atg gct caa act tat gga cca ctc     250
Lys Pro His Gln Ser Thr Ala Ala Met Ala Gln Thr Tyr Gly Pro Leu
         55                  60                  65 atg tat ctt aag atg ggg ttc gta gac gtg gtg gtt gca gcc tcg gca     298
Met Tyr Leu Lys Met Gly Phe Val Asp Val Val Val Ala Ala Ser Ala
     70                  75                  80 tcg gtt gca gct cag ttc ttg aaa act cat gat gct aat ttc tcg agc     346
Ser Val Ala Ala Gln Phe Leu Lys Thr His Asp Ala Asn Phe Ser Ser
 85                  90                  95 cgt cca cca aat tct ggt gca gaa cat atg gct tat aat tat cag gat     394
Arg Pro Pro Asn Ser Gly Ala Glu His Met Ala Tyr Asn Tyr Gln Asp
100                 105                 110                 115 ctt gtt ttt gca cct tat gga cct aga tgg cgt atg ctt agg aaa att     442
Leu Val Phe Ala Pro Tyr Gly Pro Arg Trp Arg Met Leu Arg Lys Ile
                120                 125                 130 tgc tca gtt cac ctt ttc tct acc aag gct tta gat gac ttc cgc cat     490
Cys Ser Val His Leu Phe Ser Thr Lys Ala Leu Asp Asp Phe Arg His
            135                 140                 145 gtc cgc cag gat gaa gtg aaa aca ctg acg cgc gca cta gca agt gca     538
Val Arg Gln Asp Glu Val Lys Thr Leu Thr Arg Ala Leu Ala Ser Ala
        150                 155                 160 ggc caa aag cca gtc aaa tta ggt cag tta ttg aac gtg tgc acg acg     586
Gly Gln Lys Pro Val Lys Leu Gly Gln Leu Leu Asn Val Cys Thr Thr
    165                 170                 175 aac gca ctc gcg cga gta atg cta ggt aag cga gta ttt gcc gac gga     634
Asn Ala Leu Ala Arg Val Met Leu Gly Lys Arg Val Phe Ala Asp Gly
180                 185                 190                 195 agt ggc gat gtt gat cca caa gcg gcg gag ttc aag tca atg gtg gtg     682
Ser Gly Asp Val Asp Pro Gln Ala Ala Glu Phe Lys Ser Met Val Val
                200                 205                 210 gaa atg atg gta gtc gcc ggt gtt ttt aac att ggt gat ttt att ccg     730
Glu Met Met Val Val Ala Gly Val Phe Asn Ile Gly Asp Phe Ile Pro
            215                 220                 225 caa ctt aat tgg tta gat att caa ggt gta gcc gct aaa atg aag aag     778
Gln Leu Asn Trp Leu Asp Ile Gln Gly Val Ala Ala Lys Met Lys Lys
        230                 235                 240
```

```
                                                       -continued ctc cac gcg cgt ttc gac gcg ttc ttg act gat ata ctt gaa gag cat         826
Leu His Ala Arg Phe Asp Ala Phe Leu Thr Asp Ile Leu Glu Glu His
    245                 250                 255 aag ggt aaa att ttt gga gaa atg aaa gat ttg ttg agt act ttg atc         874
Lys Gly Lys Ile Phe Gly Glu Met Lys Asp Leu Leu Ser Thr Leu Ile
260                 265                 270                 275 tct ctt aaa aat gat gat gcg gat aat gat gga ggg aaa ctc act gat         922
Ser Leu Lys Asn Asp Asp Ala Asp Asn Asp Gly Gly Lys Leu Thr Asp
                    280                 285                 290 aca gaa att aaa gca tta ctt ttg aac ttg ttt gta gct gga aca gac         970
Thr Glu Ile Lys Ala Leu Leu Leu Asn Leu Phe Val Ala Gly Thr Asp
                295                 300                 305 aca tct tct agt aca gtt gaa tgg gcc att gct gag ctt att cgt aat         1018
Thr Ser Ser Ser Thr Val Glu Trp Ala Ile Ala Glu Leu Ile Arg Asn
310                 315                 320 cca aaa ata cta gcc caa gcc cag caa gag atc gac aaa gtc gtt gga         1066
Pro Lys Ile Leu Ala Gln Ala Gln Gln Glu Ile Asp Lys Val Val Gly
    325                 330                 335 agg gac cgg cta gtt ggc gaa ttg gac cta gcc caa ttg aca tac ttg         1114
Arg Asp Arg Leu Val Gly Glu Leu Asp Leu Ala Gln Leu Thr Tyr Leu
340                 345                 350                 355 gaa gct ata gtc aag gaa acc ttt cgg ctt cat cca tca acc cct ctt         1162
Glu Ala Ile Val Lys Glu Thr Phe Arg Leu His Pro Ser Thr Pro Leu
                    360                 365                 370 tca ctt cct aga att gca tct gag agt tgt gag atc aat ggc tat ttc         1210
Ser Leu Pro Arg Ile Ala Ser Glu Ser Cys Glu Ile Asn Gly Tyr Phe
                375                 380                 385 att cca aaa ggc tca acg ctt ctc ctt aat gtt tgg gcc att gct cgt         1258
Ile Pro Lys Gly Ser Thr Leu Leu Leu Asn Val Trp Ala Ile Ala Arg
390                 395                 400 gat cca aat gca tgg gct gat cca ttg gag ttt agg cct gaa agg ttt         1306
Asp Pro Asn Ala Trp Ala Asp Pro Leu Glu Phe Arg Pro Glu Arg Phe
    405                 410                 415 ttg cca gga ggt gag aag ccc aaa gtt gat gtc cgt ggg aat gac ttt         1354
Leu Pro Gly Gly Glu Lys Pro Lys Val Asp Val Arg Gly Asn Asp Phe
420                 425                 430                 435 gaa gtc ata cca ttt gga gct gga cgt agg att tgt gct gga atg aat         1402
Glu Val Ile Pro Phe Gly Ala Gly Arg Arg Ile Cys Ala Gly Met Asn
                    440                 445                 450 ttg ggt ata cgt atg gtc cag ttg atg att gca act tta ata cat gca         1450
Leu Gly Ile Arg Met Val Gln Leu Met Ile Ala Thr Leu Ile His Ala
                455                 460                 465 ttt aac tgg gat ttg gtc agt gga caa ttg ccg gag atg ttg aat atg         1498
Phe Asn Trp Asp Leu Val Ser Gly Gln Leu Pro Glu Met Leu Asn Met
470                 475                 480 gaa gaa gca tat ggg ctg acc tta caa cgg gct gat cca ttg gtt gtg         1546
Glu Glu Ala Tyr Gly Leu Thr Leu Gln Arg Ala Asp Pro Leu Val Val
    485                 490                 495 cac cca agg cct cgc tta gaa gcc caa gcg tac att ggg tga                 1588
His Pro Arg Pro Arg Leu Glu Ala Gln Ala Tyr Ile Gly
500                 505                 510 gcagcaacag cccatggaga taacatgagt gttaaatgta tgagtctcca tatcttgttt       1648
agtttgttta tgctttggat ttagtagttt ttatattgat agatcaatgt ttgcattgtc       1708
agtaagaata tccgttgctt gtttcattaa ctccaggtgg acaataaaag aagtaatttg       1768
tatgaaaaaa aaaaaaaaaa a                                                 1789

<210> SEQ ID NO 2
<211> LENGTH: 512
```

```
<212> TYPE: PRT
<213> ORGANISM: Petunia x hybrida

<400> SEQUENCE: 2

Met Glu Ile Leu Ser Leu Ile Leu Tyr Thr Val Ile Phe Ser Phe Leu
 1               5                  10                  15

Leu Gln Phe Ile Leu Arg Ser Phe Arg Lys Arg Tyr Pro Leu Pro
                20                  25                  30

Leu Pro Pro Gly Pro Lys Pro Trp Pro Ile Ile Gly Asn Leu Val His
            35                  40                  45

Leu Gly Pro Lys Pro His Gln Ser Thr Ala Ala Met Ala Gln Thr Tyr
 50                  55                  60

Gly Pro Leu Met Tyr Leu Lys Met Gly Phe Val Asp Val Val Ala
 65                  70                  75                  80

Ala Ser Ala Ser Val Ala Ala Gln Phe Leu Lys Thr His Asp Ala Asn
                85                  90                  95

Phe Ser Ser Arg Pro Pro Asn Ser Gly Ala Glu His Met Ala Tyr Asn
               100                 105                 110

Tyr Gln Asp Leu Val Phe Ala Pro Tyr Gly Pro Arg Trp Arg Met Leu
           115                 120                 125

Arg Lys Ile Cys Ser Val His Leu Phe Ser Thr Lys Ala Leu Asp Asp
130                 135                 140

Phe Arg His Val Arg Gln Asp Glu Val Lys Thr Leu Thr Arg Ala Leu
145                 150                 155                 160

Ala Ser Ala Gly Gln Lys Pro Val Lys Leu Gly Gln Leu Leu Asn Val
                165                 170                 175

Cys Thr Thr Asn Ala Leu Ala Arg Val Met Leu Gly Lys Arg Val Phe
                180                 185                 190

Ala Asp Gly Ser Gly Asp Val Asp Pro Gln Ala Ala Glu Phe Lys Ser
            195                 200                 205

Met Val Val Glu Met Met Val Val Ala Gly Val Phe Asn Ile Gly Asp
            210                 215                 220

Phe Ile Pro Gln Leu Asn Trp Leu Asp Ile Gln Gly Val Ala Ala Lys
225                 230                 235                 240

Met Lys Lys Leu His Ala Arg Phe Asp Ala Phe Leu Thr Asp Ile Leu
                245                 250                 255

Glu Glu His Lys Gly Lys Ile Phe Gly Glu Met Lys Asp Leu Leu Ser
                260                 265                 270

Thr Leu Ile Ser Leu Lys Asn Asp Asp Ala Asp Asn Asp Gly Gly Lys
            275                 280                 285

Leu Thr Asp Thr Glu Ile Lys Ala Leu Leu Leu Asn Leu Phe Val Ala
            290                 295                 300

Gly Thr Asp Thr Ser Ser Ser Thr Val Glu Trp Ala Ile Ala Glu Leu
305                 310                 315                 320

Ile Arg Asn Pro Lys Ile Leu Ala Gln Ala Gln Glu Ile Asp Lys
                325                 330                 335

Val Val Gly Arg Asp Arg Leu Val Gly Glu Leu Asp Leu Ala Gln Leu
                340                 345                 350

Thr Tyr Leu Glu Ala Ile Val Lys Glu Thr Phe Arg Leu His Pro Ser
            355                 360                 365

Thr Pro Leu Ser Leu Pro Arg Ile Ala Ser Glu Ser Cys Glu Ile Asn
            370                 375                 380

Gly Tyr Phe Ile Pro Lys Gly Ser Thr Leu Leu Leu Asn Val Trp Ala
385                 390                 395                 400
```

-continued

```
Ile Ala Arg Asp Pro Asn Ala Trp Ala Asp Pro Leu Glu Phe Arg Pro
                405                 410                 415
Glu Arg Phe Leu Pro Gly Gly Glu Lys Pro Lys Val Asp Val Arg Gly
            420                 425                 430
Asn Asp Phe Glu Val Ile Pro Phe Gly Ala Gly Arg Arg Ile Cys Ala
        435                 440                 445
Gly Met Asn Leu Gly Ile Arg Met Val Gln Leu Met Ile Ala Thr Leu
    450                 455                 460
Ile His Ala Phe Asn Trp Asp Leu Val Ser Gly Gln Leu Pro Glu Met
465                 470                 475                 480
Leu Asn Met Glu Glu Ala Tyr Gly Leu Thr Leu Gln Arg Ala Asp Pro
                485                 490                 495
Leu Val Val His Pro Arg Pro Arg Leu Glu Ala Gln Ala Tyr Ile Gly
                500                 505                 510
```

<210> SEQ ID NO 3
<211> LENGTH: 1737
<212> TYPE: DNA
<213> ORGANISM: Dianthus caryophyllus
<220> FEATURE:
<221> NAME/KEY: CDS
<222> LOCATION: (172)..(1674)

<400> SEQUENCE: 3

```
aagttcggca cgagcgtcac attcacaccg tcacattact attcaaacca ctcatttct    60 acctctcttt tctacccacc aaacaaaac aaaacaaaaa aaaacacata aaaaaactca   120
aaaaaaaatt ataatgtcac ccttagaggt aactttctac accatagtcc t atg cac   177
                                                         Met His
                                                           1
aat ctc tac tac ctc atc acc acc gtc ttc cgc ggc cac caa aaa ccg   225
Asn Leu Tyr Tyr Leu Ile Thr Thr Val Phe Arg Gly His Gln Lys Pro
        5                   10                  15
ctt cct cca ggg cca cga cca tgg ccc atc gtg gga aac ctc cca cat   273
Leu Pro Pro Gly Pro Arg Pro Trp Pro Ile Val Gly Asn Leu Pro His
 20                  25                  30
atg ggc cag gca ccg cac cag ggc tta gca gcc ctg gcg caa aag tat   321
Met Gly Gln Ala Pro His Gln Gly Leu Ala Ala Leu Ala Gln Lys Tyr
 35                  40                  45                  50
ggc cct cta ttg tat atg aga ctg ggg tac gtg gac gtt gtt gtg gcc   369
Gly Pro Leu Leu Tyr Met Arg Leu Gly Tyr Val Asp Val Val Val Ala
             55                  60                  65
gcc tca gcg tct gta gcg acc cag ttt ctt aag aca cat gac cta aat   417
Ala Ser Ala Ser Val Ala Thr Gln Phe Leu Lys Thr His Asp Leu Asn
         70                  75                  80
ttt tcg agt agg cca ccg aat tcg ggg gct aaa cac att gct tat aac   465
Phe Ser Ser Arg Pro Pro Asn Ser Gly Ala Lys His Ile Ala Tyr Asn
     85                  90                  95
tat caa gac ctt gtt ttt gca cct tat gga cct aaa tgg cgc atg ctt   513
Tyr Gln Asp Leu Val Phe Ala Pro Tyr Gly Pro Lys Trp Arg Met Leu
    100                 105                 110
agg aaa att tgt tcc tta cac atg ttt tct tct aag gct ttg gac gat   561
Arg Lys Ile Cys Ser Leu His Met Phe Ser Ser Lys Ala Leu Asp Asp
115                 120                 125                 130
ttt aga ctt gtc cgt cag gaa gaa gta tct ata ctg gta aat gcg ata   609
Phe Arg Leu Val Arg Gln Glu Glu Val Ser Ile Leu Val Asn Ala Ile
                135                 140                 145
gca aaa gca gga aca aag cca gta caa cta gga caa cta ctc aac gtg   657
Ala Lys Ala Gly Thr Lys Pro Val Gln Leu Gly Gln Leu Leu Asn Val
```

-continued

```
                150                 155                 160
tgc aca aca aat gcc tta tcg agg gtg atg cta ggg aag cga gtt ctc      705
Cys Thr Thr Asn Ala Leu Ser Arg Val Met Leu Gly Lys Arg Val Leu
        165                 170                 175 ggt gat ggc aca ggg aaa agc gac cca aaa gcc gag gaa ttt aag gac      753
Gly Asp Gly Thr Gly Lys Ser Asp Pro Lys Ala Glu Glu Phe Lys Asp
    180                 185                 190 atg gtg ctg gag tta atg gtt ctc acc gga gtt ttt aac att ggc gat      801
Met Val Leu Glu Leu Met Val Leu Thr Gly Val Phe Asn Ile Gly Asp
195                 200                 205                 210 ttt gta ccg gca ttg gaa tgt cta gac tta caa ggt gtt gca tct aaa      849
Phe Val Pro Ala Leu Glu Cys Leu Asp Leu Gln Gly Val Ala Ser Lys
                215                 220                 225 atg aag aaa tta cat aaa aga ctt gat aat ttt atg agt aac att ttg      897
Met Lys Lys Leu His Lys Arg Leu Asp Asn Phe Met Ser Asn Ile Leu
            230                 235                 240 gag gaa cac aag agt gtt gca cat caa caa aat ggt gga gat ttg cta      945
Glu Glu His Lys Ser Val Ala His Gln Gln Asn Gly Gly Asp Leu Leu
        245                 250                 255 agc att ttg ata tct ttg aag gat aat tgt gat ggt gaa ggt ggc aag      993
Ser Ile Leu Ile Ser Leu Lys Asp Asn Cys Asp Gly Glu Gly Gly Lys
    260                 265                 270 ttt agt gcc aca gaa att aag gcc ttg cta ttg gat tta ttt aca gct     1041
Phe Ser Ala Thr Glu Ile Lys Ala Leu Leu Leu Asp Leu Phe Thr Ala
275                 280                 285                 290 gga aca gac aca tca tct agt aca act gaa tgg gcc ata gcc gaa cta     1089
Gly Thr Asp Thr Ser Ser Ser Thr Thr Glu Trp Ala Ile Ala Glu Leu
                295                 300                 305 att cgc cat cca aaa atc tta gcc caa gtt caa caa gaa atg gac tca     1137
Ile Arg His Pro Lys Ile Leu Ala Gln Val Gln Gln Glu Met Asp Ser
            310                 315                 320 gtc gtg ggc cga gac cga ctc ata gcc gaa gct gac ata ccg aac cta     1185
Val Val Gly Arg Asp Arg Leu Ile Ala Glu Ala Asp Ile Pro Asn Leu
        325                 330                 335 acc tac ttc caa gcc gta atc aaa gag gtt ttc cga ctt cac ccg tcc     1233
Thr Tyr Phe Gln Ala Val Ile Lys Glu Val Phe Arg Leu His Pro Ser
    340                 345                 350 acc ccg ctt tcc cta cca cgg gtc gca aac gaa tcg tgc gaa ata aac     1281
Thr Pro Leu Ser Leu Pro Arg Val Ala Asn Glu Ser Cys Glu Ile Asn
355                 360                 365                 370 ggg tac cac att ccc aaa aac acc act tta ttg gta aat gtg tgg gcc     1329
Gly Tyr His Ile Pro Lys Asn Thr Thr Leu Leu Val Asn Val Trp Ala
                375                 380                 385 atc gca cgc gac cct gag gtt tgg gcc gac ccg tta gag ttt aaa ccc     1377
Ile Ala Arg Asp Pro Glu Val Trp Ala Asp Pro Leu Glu Phe Lys Pro
            390                 395                 400 gaa aga ttt ttg ccg ggc ggc gaa aag ccc aat gtg gat gtg aaa gga     1425
Glu Arg Phe Leu Pro Gly Gly Glu Lys Pro Asn Val Asp Val Lys Gly
        405                 410                 415 aac gat ttt gag ctg att ccg ttc ggg gcg ggc cga cgg att tgt gct     1473
Asn Asp Phe Glu Leu Ile Pro Phe Gly Ala Gly Arg Arg Ile Cys Ala
    420                 425                 430 ggg ctg agt ttg ggc ctg cgt atg gtc cag ttg atg aca gcc act ttg     1521
Gly Leu Ser Leu Gly Leu Arg Met Val Gln Leu Met Thr Ala Thr Leu
435                 440                 445                 450 gcc cat act tat gat tgg gcc tta gct gat ggg ctt atg ccc gaa aag     1569
Ala His Thr Tyr Asp Trp Ala Leu Ala Asp Gly Leu Met Pro Glu Lys
                455                 460                 465 ctt aac atg gat gag gct tat ggg ctt acc tta cag cgt aag gtg cca     1617
```

-continued

```
            Leu Asn Met Asp Glu Ala Tyr Gly Leu Thr Leu Gln Arg Lys Val Pro
                        470                 475                 480 cta atg gtc cac ccg acc cgt cgg ctc tcg gcc cgc gtt tat aat tcg       1665
Leu Met Val His Pro Thr Arg Arg Leu Ser Ala Arg Val Tyr Asn Ser
        485                 490                 495 ggg ttt taa agcgggtact tttgttatgt attattccgt actagtttga               1714
Gly Phe * aaaataatgt attagagaaa atg                                             1737

<210> SEQ ID NO 4
<211> LENGTH: 500
<212> TYPE: PRT
<213> ORGANISM: Dianthus caryophyllus

<400> SEQUENCE: 4

Met His Asn Leu Tyr Tyr Leu Ile Thr Thr Val Phe Arg Gly His Gln
 1               5                   10                  15

Lys Pro Leu Pro Pro Gly Pro Arg Pro Trp Pro Ile Val Gly Asn Leu
            20                  25                  30

Pro His Met Gly Gln Ala Pro His Gln Gly Leu Ala Ala Leu Ala Gln
        35                  40                  45

Lys Tyr Gly Pro Leu Leu Tyr Met Arg Leu Gly Tyr Val Asp Val Val
    50                  55                  60

Val Ala Ala Ser Ala Ser Val Ala Thr Gln Phe Leu Lys Thr His Asp
65                  70                  75                  80

Leu Asn Phe Ser Ser Arg Pro Pro Asn Ser Gly Ala Lys His Ile Ala
                85                  90                  95

Tyr Asn Tyr Gln Asp Leu Val Phe Ala Pro Tyr Gly Pro Lys Trp Arg
            100                 105                 110

Met Leu Arg Lys Ile Cys Ser Leu His Met Phe Ser Ser Lys Ala Leu
        115                 120                 125

Asp Asp Phe Arg Leu Val Arg Gln Glu Glu Val Ser Ile Leu Val Asn
    130                 135                 140

Ala Ile Ala Lys Ala Gly Thr Lys Pro Val Gln Leu Gly Gln Leu Leu
145                 150                 155                 160

Asn Val Cys Thr Thr Asn Ala Leu Ser Arg Val Met Leu Gly Lys Arg
                165                 170                 175

Val Leu Gly Asp Gly Thr Gly Lys Ser Asp Pro Lys Ala Glu Glu Phe
            180                 185                 190

Lys Asp Met Val Leu Glu Leu Met Val Leu Thr Gly Val Phe Asn Ile
        195                 200                 205

Gly Asp Phe Val Pro Ala Leu Glu Cys Leu Asp Leu Gln Gly Val Ala
    210                 215                 220

Ser Lys Met Lys Lys Leu His Lys Arg Leu Asp Asn Phe Met Ser Asn
225                 230                 235                 240

Ile Leu Glu Glu His Lys Ser Val Ala His Gln Asn Gly Gly Asp
                245                 250                 255

Leu Leu Ser Ile Leu Ile Ser Leu Lys Asp Asn Cys Asp Gly Glu Gly
            260                 265                 270

Gly Lys Phe Ser Ala Thr Glu Ile Lys Ala Leu Leu Leu Asp Leu Phe
        275                 280                 285

Thr Ala Gly Thr Asp Thr Ser Ser Ser Thr Thr Glu Trp Ala Ile Ala
    290                 295                 300

Glu Leu Ile Arg His Pro Lys Ile Leu Ala Gln Val Gln Gln Glu Met
305                 310                 315                 320
```

```
Asp Ser Val Val Gly Arg Asp Arg Leu Ile Ala Glu Ala Asp Ile Pro
            325                 330                 335
Asn Leu Thr Tyr Phe Gln Ala Val Ile Lys Glu Val Phe Arg Leu His
            340                 345                 350
Pro Ser Thr Pro Leu Ser Leu Pro Arg Val Ala Asn Glu Ser Cys Glu
            355                 360                 365
Ile Asn Gly Tyr His Ile Pro Lys Asn Thr Thr Leu Leu Val Asn Val
            370                 375             380
Trp Ala Ile Ala Arg Asp Pro Glu Val Trp Ala Asp Pro Leu Glu Phe
385                 390                 395                 400
Lys Pro Glu Arg Phe Leu Pro Gly Glu Lys Pro Asn Val Asp Val
                405                 410                 415
Lys Gly Asn Asp Phe Glu Leu Ile Pro Phe Gly Ala Gly Arg Arg Ile
            420                 425                 430
Cys Ala Gly Leu Ser Leu Gly Leu Arg Met Val Gln Leu Met Thr Ala
            435                 440                 445
Thr Leu Ala His Thr Tyr Asp Trp Ala Leu Ala Asp Gly Leu Met Pro
450                 455                 460
Glu Lys Leu Asn Met Asp Glu Ala Tyr Gly Leu Thr Leu Gln Arg Lys
465                 470                 475                 480
Val Pro Leu Met Val His Pro Thr Arg Arg Leu Ser Ala Arg Val Tyr
                485                 490                 495
Asn Ser Gly Phe
            500

<210> SEQ ID NO 5
<211> LENGTH: 1711
<212> TYPE: DNA
<213> ORGANISM: Antirrhinum majus
<220> FEATURE:
<221> NAME/KEY: CDS
<222> LOCATION: (91)..(1629)

<400> SEQUENCE: 5
cgaattcccc cccccccaca ccattcaatg cctaagtcct ccatttgccg gcctaataac      60
taaaagccca ctctttccga ccatctatac atg caa cac caa tat tat tct tta     114
                                  Met Gln His Gln Tyr Tyr Ser Leu
                                    1               5 att acg atg gat gat att agc ata acc agc tta ttg gtg cca tgt act     162
Ile Thr Met Asp Asp Ile Ser Ile Thr Ser Leu Leu Val Pro Cys Thr
    10              15                  20 ttt ata tta ggg ttc ttg ctt cta tat tcc ttc ctc aac aaa aaa gta     210
Phe Ile Leu Gly Phe Leu Leu Leu Tyr Ser Phe Leu Asn Lys Lys Val
25              30                  35                  40 aag cca ctg cca cct gga ccg aag cca tgg ccc atc gtc gga aat ctg     258
Lys Pro Leu Pro Pro Gly Pro Lys Pro Trp Pro Ile Val Gly Asn Leu
                45                  50                  55 cca cat ctt ggg ccg aag ccc cac cag tcg atg gcg gcg ctg gca cgg     306
Pro His Leu Gly Pro Lys Pro His Gln Ser Met Ala Ala Leu Ala Arg
            60                  65                  70 gtg cac ggc cca tta att cat ctg aag atg ggc ttt gtg cat gtg gtt     354
Val His Gly Pro Leu Ile His Leu Lys Met Gly Phe Val His Val Val
        75                  80                  85 gtg gcc tcc tca gca tcc gtt gcg gag aaa ttt ctg aag gtg cat gac     402
Val Ala Ser Ser Ala Ser Val Ala Glu Lys Phe Leu Lys Val His Asp
    90                  95                 100 gca aac ttc tcg agc agg cct ccc aat tcg ggt gca aaa cac gtg gcc     450
```

```
Ala Asn Phe Ser Ser Arg Pro Pro Asn Ser Gly Ala Lys His Val Ala
105                 110                 115                 120 tac aac tat cag gac ttg gtc ttt gct cct tat ggc cca cgc tgg cgg        498
Tyr Asn Tyr Gln Asp Leu Val Phe Ala Pro Tyr Gly Pro Arg Trp Arg
                125                 130                 135 atg ctc agg aaa atc tgt gca ctc cac ctc ttc tcc gcc aaa gcc ttg        546
Met Leu Arg Lys Ile Cys Ala Leu His Leu Phe Ser Ala Lys Ala Leu
            140                 145                 150 aac gac ttc aca cac gtc aga cag gat gag gtg ggg atc ctc act cgc        594
Asn Asp Phe Thr His Val Arg Gln Asp Glu Val Gly Ile Leu Thr Arg
            155                 160                 165 gtt cta gca gat gca gga gaa acg ccg ttg aaa tta ggg cag atg atg        642
Val Leu Ala Asp Ala Gly Glu Thr Pro Leu Lys Leu Gly Gln Met Met
        170                 175                 180 aac aca tgc gcc acc aat gca ata gcg cgt gtt atg ttg ggt cga cgc        690
Asn Thr Cys Ala Thr Asn Ala Ile Ala Arg Val Met Leu Gly Arg Arg
185                 190                 195                 200 gtg gtt gga cac gca gac tca aag gcg gag gag ttt aag gca atg gta        738
Val Val Gly His Ala Asp Ser Lys Ala Glu Glu Phe Lys Ala Met Val
                205                 210                 215 gtg gag ttg atg gta tta gct ggt gtg ttc aac tta ggt gat ttt atc        786
Val Glu Leu Met Val Leu Ala Gly Val Phe Asn Leu Gly Asp Phe Ile
            220                 225                 230 cca cct ctt gaa aaa ttg gat ctt caa ggt gtc att gct aag atg aag        834
Pro Pro Leu Glu Lys Leu Asp Leu Gln Gly Val Ile Ala Lys Met Lys
            235                 240                 245 aag ctt cac ttg cgt ttc gac tcg ttc ttg agt aag atc ctt gga gac        882
Lys Leu His Leu Arg Phe Asp Ser Phe Leu Ser Lys Ile Leu Gly Asp
        250                 255                 260 cac aag atc aac agc tca gat gaa acc aaa ggc cat tcg gat ttg ttg        930
His Lys Ile Asn Ser Ser Asp Glu Thr Lys Gly His Ser Asp Leu Leu
265                 270                 275                 280 aac atg tta att tct ttg aag gac gct gat gat gcc gaa gga ggg agg        978
Asn Met Leu Ile Ser Leu Lys Asp Ala Asp Asp Ala Glu Gly Gly Arg
                285                 290                 295 ctc acc gac gta gaa att aaa gcg ttg ctc ttg aac ttg ttt gct gca       1026
Leu Thr Asp Val Glu Ile Lys Ala Leu Leu Leu Asn Leu Phe Ala Ala
            300                 305                 310 gga act gac aca aca tca agc act gtg gaa tgg tgc ata gct gag tta       1074
Gly Thr Asp Thr Thr Ser Ser Thr Val Glu Trp Cys Ile Ala Glu Leu
            315                 320                 325 gta cga cat cct gaa atc ctt gcc caa gtc caa aaa gaa ctc gac tct       1122
Val Arg His Pro Glu Ile Leu Ala Gln Val Gln Lys Glu Leu Asp Ser
        330                 335                 340 gtt gtt ggt aag aat cgg gtg gtg aag gag gct gat ctg gcc gga tta       1170
Val Val Gly Lys Asn Arg Val Val Lys Glu Ala Asp Leu Ala Gly Leu
345                 350                 355                 360 cca ttc ctc caa gcg gtc gtc aag gaa aat ttc cga ctc cat ccc tcc       1218
Pro Phe Leu Gln Ala Val Val Lys Glu Asn Phe Arg Leu His Pro Ser
                365                 370                 375 acc ccg ctc tcc cta ccg agg atc gca cat gag agt tgt gaa gtg aat       1266
Thr Pro Leu Ser Leu Pro Arg Ile Ala His Glu Ser Cys Glu Val Asn
            380                 385                 390 gga tac ttg att cca aag ggt tcg aca ctt ctt gtc aat gtt tgg gca       1314
Gly Tyr Leu Ile Pro Lys Gly Ser Thr Leu Leu Val Asn Val Trp Ala
            395                 400                 405 att gct cgc gat cca aat gtg tgg gat gaa cca cta gag ttc cgg cct       1362
Ile Ala Arg Asp Pro Asn Val Trp Asp Glu Pro Leu Glu Phe Arg Pro
    410                 415                 420
```

-continued

| | | | | | | | | | | | | | | | | |
|---|---|---|---|---|---|---|---|---|---|---|---|---|---|---|---|---|
| gaa | cga | ttc | ttg | aag | ggc | ggg | gaa | aag | cct | aat | gtc | gat | gtt | aga | ggg | 1410 |
| Glu | Arg | Phe | Leu | Lys | Gly | Gly | Glu | Lys | Pro | Asn | Val | Asp | Val | Arg | Gly | |
| 425 | | | | 430 | | | | | 435 | | | | | 440 | | |
| aat | gat | ttc | gaa | ttg | ata | ccg | ttc | gga | gcg | ggc | cga | aga | att | tgt | gca | 1458 |
| Asn | Asp | Phe | Glu | Leu | Ile | Pro | Phe | Gly | Ala | Gly | Arg | Arg | Ile | Cys | Ala | |
| | | | | 445 | | | | | 450 | | | | | 455 | | |
| gga | atg | agc | tta | gga | ata | cgt | atg | gtc | cag | ttg | ttg | aca | gca | act | ttg | 1506 |
| Gly | Met | Ser | Leu | Gly | Ile | Arg | Met | Val | Gln | Leu | Leu | Thr | Ala | Thr | Leu | |
| | | | 460 | | | | | 465 | | | | | 470 | | | |
| aac | cat | gcg | ttt | gac | ttt | gat | ttg | gcg | gat | gga | cag | ttg | cct | gaa | agc | 1554 |
| Asn | His | Ala | Phe | Asp | Phe | Asp | Leu | Ala | Asp | Gly | Gln | Leu | Pro | Glu | Ser | |
| | | 475 | | | | | 480 | | | | | 485 | | | | |
| tta | aac | atg | gag | gaa | gct | tat | ggg | ctg | acc | ttg | caa | cga | gct | gac | cct | 1602 |
| Leu | Asn | Met | Glu | Glu | Ala | Tyr | Gly | Leu | Thr | Leu | Gln | Arg | Ala | Asp | Pro | |
| | 490 | | | | | 495 | | | | | 500 | | | | | |

| | | | | | | | |
|---|---|---|---|---|---|---|---|
| ttg | gta | gtg | cac | ccg | aag | cct | agg | tag gcacctcatg tttatcaaac | 1649 |
| Leu | Val | Val | His | Pro | Lys | Pro | Arg | |
| 505 | | | | 510 | | | | | ttaggactca tgtttagaga acctcttgtt gttttatcag attgaagtgt gatgtccaag    1709 ac                                                                    1711

<210> SEQ ID NO 6
<211> LENGTH: 512
<212> TYPE: PRT
<213> ORGANISM: Antirrhinum majus

<400> SEQUENCE: 6

Met Gln His Gln Tyr Tyr Ser Leu Ile Thr Met Asp Asp Ile Ser Ile
 1               5                  10                  15

Thr Ser Leu Leu Val Pro Cys Thr Phe Ile Leu Gly Phe Leu Leu
             20                  25                  30

Tyr Ser Phe Leu Asn Lys Lys Val Lys Pro Leu Pro Pro Gly Pro Lys
         35                  40                  45

Pro Trp Pro Ile Val Gly Asn Leu Pro His Leu Gly Pro Lys Pro His
     50                  55                  60

Gln Ser Met Ala Ala Leu Ala Arg Val His Gly Pro Leu Ile His Leu
 65                  70                  75                  80

Lys Met Gly Phe Val His Val Val Ala Ser Ser Ala Ser Val Ala
                 85                  90                  95

Glu Lys Phe Leu Lys Val His Asp Ala Asn Phe Ser Ser Arg Pro Pro
            100                 105                 110

Asn Ser Gly Ala Lys His Val Ala Tyr Asn Tyr Gln Asp Leu Val Phe
        115                 120                 125

Ala Pro Tyr Gly Pro Arg Trp Arg Met Leu Arg Lys Ile Cys Ala Leu
    130                 135                 140

His Leu Phe Ser Ala Lys Ala Leu Asn Asp Phe Thr His Val Arg Gln
145                 150                 155                 160

Asp Glu Val Gly Ile Leu Thr Arg Val Leu Ala Asp Ala Gly Glu Thr
                165                 170                 175

Pro Leu Lys Leu Gly Gln Met Met Asn Thr Cys Ala Thr Asn Ala Ile
            180                 185                 190

Ala Arg Val Met Leu Gly Arg Arg Val Gly His Ala Asp Ser Lys
        195                 200                 205

Ala Glu Glu Phe Lys Ala Met Val Val Glu Leu Met Val Leu Ala Gly
    210                 215                 220

Val Phe Asn Leu Gly Asp Phe Ile Pro Pro Leu Glu Lys Leu Asp Leu

```
                225                 230                 235                 240
Gln Gly Val Ile Ala Lys Met Lys Lys Leu His Leu Arg Phe Asp Ser
                245                 250                 255
Phe Leu Ser Lys Ile Leu Gly Asp His Lys Ile Asn Ser Ser Asp Glu
                260                 265                 270
Thr Lys Gly His Ser Asp Leu Leu Asn Met Leu Ile Ser Leu Lys Asp
                275                 280                 285
Ala Asp Asp Ala Glu Gly Gly Arg Leu Thr Asp Val Glu Ile Lys Ala
                290                 295                 300
Leu Leu Leu Asn Leu Phe Ala Ala Gly Thr Asp Thr Thr Ser Ser Thr
305                 310                 315                 320
Val Glu Trp Cys Ile Ala Glu Leu Val Arg His Pro Glu Ile Leu Ala
                325                 330                 335
Gln Val Gln Lys Glu Leu Asp Ser Val Val Gly Lys Asn Arg Val Val
                340                 345                 350
Lys Glu Ala Asp Leu Ala Gly Leu Pro Phe Leu Gln Ala Val Val Lys
                355                 360                 365
Glu Asn Phe Arg Leu His Pro Ser Thr Pro Leu Ser Leu Pro Arg Ile
                370                 375                 380
Ala His Glu Ser Cys Glu Val Asn Gly Tyr Leu Ile Pro Lys Gly Ser
385                 390                 395                 400
Thr Leu Leu Val Asn Val Trp Ala Ile Ala Arg Asp Pro Asn Val Trp
                405                 410                 415
Asp Glu Pro Leu Glu Phe Arg Pro Glu Arg Phe Leu Lys Gly Gly Glu
                420                 425                 430
Lys Pro Asn Val Asp Val Arg Gly Asn Asp Phe Glu Leu Ile Pro Phe
                435                 440                 445
Gly Ala Gly Arg Arg Ile Cys Ala Gly Met Ser Leu Gly Ile Arg Met
                450                 455                 460
Val Gln Leu Leu Thr Ala Thr Leu Asn His Ala Phe Asp Phe Asp Leu
465                 470                 475                 480
Ala Asp Gly Gln Leu Pro Glu Ser Leu Asn Met Glu Glu Ala Tyr Gly
                485                 490                 495
Leu Thr Leu Gln Arg Ala Asp Pro Leu Val Val His Pro Lys Pro Arg
                500                 505                 510

<210> SEQ ID NO 7
<211> LENGTH: 971
<212> TYPE: DNA
<213> ORGANISM: Arabidopsis thaliana
<220> FEATURE:
<221> NAME/KEY: CDS
<222> LOCATION: (1)..(813)

<400> SEQUENCE: 7 gat atg ctt agc act tta atc tcc ctt aaa gga act gat ctt gac ggt      48
Asp Met Leu Ser Thr Leu Ile Ser Leu Lys Gly Thr Asp Leu Asp Gly
  1               5                  10                  15 gac gga gga agc tta acg gat act gag att aaa gcc ttg cta ttg aac      96
Asp Gly Gly Ser Leu Thr Asp Thr Glu Ile Lys Ala Leu Leu Leu Asn
             20                  25                  30 atg ttc aca gct gga act gac acg tca gca agt acg gtg gac tgg gct     144
Met Phe Thr Ala Gly Thr Asp Thr Ser Ala Ser Thr Val Asp Trp Ala
         35                  40                  45 ata gct gaa ctt atc cgt cac ccg gat ata atg gtt aaa gcc caa gaa     192
Ile Ala Glu Leu Ile Arg His Pro Asp Ile Met Val Lys Ala Gln Glu
     50                  55                  60
```

```
gaa ctt gat att gtt gtg ggc cgt gac agg cct gtt aat gaa tca gac        240
Glu Leu Asp Ile Val Val Gly Arg Asp Arg Pro Val Asn Glu Ser Asp
 65                  70                  75                  80 atc gct cag ctt cct tac ctt cag gcg gtt atc aaa gag aat ttc agg        288
Ile Ala Gln Leu Pro Tyr Leu Gln Ala Val Ile Lys Glu Asn Phe Arg
                 85                  90                  95 ctt cat cca cca aca cca ctc tcg tta cca cac atc gcg tca gag agc        336
Leu His Pro Pro Thr Pro Leu Ser Leu Pro His Ile Ala Ser Glu Ser
            100                 105                 110 tgt gag atc aac ggc tac cat atc ccg aaa gga tcg act cta ttt gac        384
Cys Glu Ile Asn Gly Tyr His Ile Pro Lys Gly Ser Thr Leu Phe Asp
        115                 120                 125 gga cat atg ggc cta ggc cgt gac ccg gat caa tgg tcc gac ccg tta        432
Gly His Met Gly Leu Gly Arg Asp Pro Asp Gln Trp Ser Asp Pro Leu
    130                 135                 140 gca ttt aaa ccc gag aga ttc tta ccc ggt ggt gaa aaa tcc ggc gtt        480
Ala Phe Lys Pro Glu Arg Phe Leu Pro Gly Gly Glu Lys Ser Gly Val
145                 150                 155                 160 gat gtg aaa gga agc gat ttc gag cta ata ccg ttc ggg gct ggg agg        528
Asp Val Lys Gly Ser Asp Phe Glu Leu Ile Pro Phe Gly Ala Gly Arg
                165                 170                 175 cca atc tgt gca ggt tta agt tta ggg cta cgt aca gat tta agt tgc        576
Pro Ile Cys Ala Gly Leu Ser Leu Gly Leu Arg Thr Asp Leu Ser Cys
            180                 185                 190 ctt cac gcc aac gtt gct cac aag cat ttg att ggg aac ttc agc tgg        624
Leu His Ala Asn Val Ala His Lys His Leu Ile Gly Asn Phe Ser Trp
        195                 200                 205 aga agt tac gcc gga caa cct gaa tat cgc agg aaa agt tta ctg ggc        672
Arg Ser Tyr Ala Gly Gln Pro Glu Tyr Arg Arg Lys Ser Leu Leu Gly
    210                 215                 220 ttt aca ctg caa aga gcg gtt cct tcg gtg gta cac cct aag cca agg        720
Phe Thr Leu Gln Arg Ala Val Pro Ser Val Val His Pro Lys Pro Arg
225                 230                 235                 240 ttg gcc ccg aac gtt tat gga ccc cgg gtc ggc tta aaa ttt aac ttt        768
Leu Ala Pro Asn Val Tyr Gly Pro Arg Val Gly Leu Lys Phe Asn Phe
                245                 250                 255 gct tct tgg aca agg tat atg gct tgc acg aaa cta acg ttt taa            813
Ala Ser Trp Thr Arg Tyr Met Ala Cys Thr Lys Leu Thr Phe
            260                 265                 270 cacaccgtag tttgatccgg agttagcttt atgtaagaac gtgtaacgcc aaatcaagcc      873
attatcaact accgtgagct gtttgtaccc tatctataaa tcttgaagag gaacatttca      933
gaactcttga ctatgtttca ggaacaaaaa aaaaaaaa                              971

<210> SEQ ID NO 8
<211> LENGTH: 270
<212> TYPE: PRT
<213> ORGANISM: Arabidopsis thaliana

<400> SEQUENCE: 8

Asp Met Leu Ser Thr Leu Ile Ser Leu Lys Gly Thr Asp Leu Asp Gly
 1               5                  10                  15

Asp Gly Gly Ser Leu Thr Asp Thr Glu Ile Lys Ala Leu Leu Leu Asn
                20                  25                  30

Met Phe Thr Ala Gly Thr Asp Thr Ser Ala Ser Thr Val Asp Trp Ala
            35                  40                  45

Ile Ala Glu Leu Ile Arg His Pro Asp Ile Met Val Lys Ala Gln Glu
        50                  55                  60
```

-continued

```
Glu Leu Asp Ile Val Val Gly Arg Asp Arg Pro Val Asn Glu Ser Asp
 65                  70                  75                  80

Ile Ala Gln Leu Pro Tyr Leu Gln Ala Val Ile Lys Glu Asn Phe Arg
                 85                  90                  95

Leu His Pro Pro Thr Pro Leu Ser Leu Pro His Ile Ala Ser Glu Ser
            100                 105                 110

Cys Glu Ile Asn Gly Tyr His Ile Pro Lys Gly Ser Thr Leu Phe Asp
        115                 120                 125

Gly His Met Gly Leu Gly Arg Asp Pro Asp Gln Trp Ser Asp Pro Leu
    130                 135                 140

Ala Phe Lys Pro Glu Arg Phe Leu Pro Gly Gly Glu Lys Ser Gly Val
145                 150                 155                 160

Asp Val Lys Gly Ser Asp Phe Glu Leu Ile Pro Phe Gly Ala Gly Arg
                165                 170                 175

Pro Ile Cys Ala Gly Leu Ser Leu Gly Leu Arg Thr Asp Leu Ser Cys
            180                 185                 190

Leu His Ala Asn Val Ala His Lys His Leu Ile Gly Asn Phe Ser Trp
        195                 200                 205

Arg Ser Tyr Ala Gly Gln Pro Glu Tyr Arg Arg Lys Ser Leu Leu Gly
    210                 215                 220

Phe Thr Leu Gln Arg Ala Val Pro Ser Val His Pro Lys Pro Arg
225                 230                 235                 240

Leu Ala Pro Asn Val Tyr Gly Pro Arg Val Gly Leu Lys Phe Asn Phe
                245                 250                 255

Ala Ser Trp Thr Arg Tyr Met Ala Cys Thr Lys Leu Thr Phe
            260                 265                 270
```

```
<210> SEQ ID NO 9
<211> LENGTH: 6595
<212> TYPE: DNA
<213> ORGANISM: Arabidopsis thaliana
<220> FEATURE:
<221> NAME/KEY: CDS
<222> LOCATION: (1478)..(1927)
<220> FEATURE:
<221> NAME/KEY: CDS
<222> LOCATION: (2651)..(3091)
<220> FEATURE:
<221> NAME/KEY: CDS
<222> LOCATION: (3170)..(3340)
<220> FEATURE:
<221> NAME/KEY: CDS
<222> LOCATION: (3421)..(3897)

<400> SEQUENCE: 9
gtcgactctc tcccttttcgc ttgctacttt ttctacataa ataaatgcaa tgataaattt      60
gtgcacacat tcgtatgttt gaaacatggt aggatccaca atttatactt tatagactca     120
aaatggaaaa gaaacgtaca ttataaattt atctgcaatt tgttttctct tgctaaacta     180
gactgtataa taacctctgt atatgctatt actcgattgt aaacgtaccc cgcaagtcgc     240
aagcaaggta aataaagtat aattatattt tcacacacga aactttaatt attatttta      300 tcacttgcag attaacagta aaaaaaaaaa aaatgtgact ttaacggcga caaaaactac     360
tgatctttct ccaatatta aataatataa ttaataaacg tcttttcata cttgtatttt      420
ccgacccgag ttctgaaagt gaaaacatat ggtactagat attctcgatt tgttttgtag     480
ccactagact ctaaacagaa aaagaagcc aaaaggacaa cgttaaaaaa gagacactgt     540
tattaaaagt tagaaaccaa acggtgaaaa tccagctaca tacataaaat aaagccaagg     600
```

-continued

```
taccaaacta atgaactgta aacctctttt tcttttcttt tttgttaaag gatttatgaa    660
ctgtaactta gaatgcttgg tttgtgggca gtgtaatata tgacacacat gcatttttt     720 tgtttgtcaa ataggaagac ttcttttttc tttatcaact tccttatttt cataaaacaa    780
aacactgaaa aaagtacaga tgttctcacg tacgtcacgt gtacatacat atatattaga    840
ccactatata ataagatatg aagtgttagg tttaaatcaa ttaacgaatc ccatccaaat    900
gatgaaacag ttaacaagaa atcaaaatag tttattaggg ttacaatgat tttatacttt    960
taagaaatct tagaacctat cacttacaaa tgagtaaatg accattactc ctcgagaatc   1020
taaggcgctt aaggaagcat tgcgaatcgg gtgtgaaaaa gatctatttt ttgaattatt   1080
tcacacaatt tcttaatgtc aattttcgat gctcccatat tctccacggt ttaaagcaag   1140
attggtggga aagggatatt ctcgcatcga ttacaatgaa atatgggttg aaaaaaaaaa   1200
aaaaaaatta ctcaatgttg caccaaaaac cagaaaactc taagttgcgc taataaaaaa   1260
aaaagttata aacccaacat caaaccaaaa ccgtactaaa ctgtcccata tgagatttag   1320
ctttaaataa attagtactt ctcataacga taactaaatt aaatttccct agccaagaca   1380
tacatatagt tttgattgac aaaaaaaaaa aaaactcctc tatttatagc ttgtgttttg   1440
tttcctcatt tttcacttac cattcaaacc caacact atg gca act cta ttt ctc   1495
                                        Met Ala Thr Leu Phe Leu
                                          1               5 aca atc ctc cta gcc act gtc ctc ttc ctc atc ctc cgt atc ttc tct   1543
Thr Ile Leu Leu Ala Thr Val Leu Phe Leu Ile Leu Arg Ile Phe Ser
             10                  15                  20 cac cgt cgc aac cgc agc cac aac aac cgt ctt cca ccg ggg cca aac   1591
His Arg Arg Asn Arg Ser His Asn Asn Arg Leu Pro Pro Gly Pro Asn
         25                  30                  35 cca tgg ccc atc atc gga aac ctc cct cac atg ggc act aag cct cat   1639
Pro Trp Pro Ile Ile Gly Asn Leu Pro His Met Gly Thr Lys Pro His
     40                  45                  50 cga acc ctt tcc gcc atg gtt act act tac ggc cct atc ctc cac ctc   1687
Arg Thr Leu Ser Ala Met Val Thr Thr Tyr Gly Pro Ile Leu His Leu
 55                  60                  65                  70 cga cta ggg ttc gta gac gtc gtg gtc gcc gct tct aaa tcc gtg gcc   1735
Arg Leu Gly Phe Val Asp Val Val Val Ala Ala Ser Lys Ser Val Ala
             75                  80                  85 gag cag ttc ttg aaa ata cac gac gcc aat ttc gct agc cga cca cca   1783
Glu Gln Phe Leu Lys Ile His Asp Ala Asn Phe Ala Ser Arg Pro Pro
         90                  95                 100 aac tca gga gcc aaa cac atg gca tat aac tat caa gat ctt gtc ttt   1831
Asn Ser Gly Ala Lys His Met Ala Tyr Asn Tyr Gln Asp Leu Val Phe
    105                 110                 115 gca cct tac gga cac cga tgg aga ctg ttg aga aag att agt tct gtt   1879
Ala Pro Tyr Gly His Arg Trp Arg Leu Leu Arg Lys Ile Ser Ser Val
120                 125                 130 cat cta ttt tca gct aaa gct ctc gaa gat ttc aaa cat gtt cga cag   1927
His Leu Phe Ser Ala Lys Ala Leu Glu Asp Phe Lys His Val Arg Gln
135                 140                 145                 150 gtaaaacaat tataaacggt attctcattt tctaacgcta tagctcactg gcctgtaatc   1987
atgtcatttc aatgttttga cttttctctt tatatacat aattataatt tataattggg   2047
atttcaaacc ctatctctca ctatttcaag actagaccgg attggaattt gaacttttgt   2107
aatgaatatt agtatctgca cataaatttt atgttaaagt tgggttttct taaagtgaat   2167
ttatatatta aaaatatata aacgattggg ttttactcaa atgaatttac ataagagcta   2227
ggtataagtg caaatatgca atactgtcat tgtcgtggat gtataaaagt atgatctaac   2287
```

```
tttgatgatg ccatggaaaa attggaaagt tcagatccag aggaaacatt gcttgaatta      2347
taaaatgtat ggaccacatt gtttccttaa atggaaggtc tcacgagttt ctcaatttca      2407
gactactgat aatatatgct attatagatt ttattttctg attatttttt ttggtttaat      2467
ttaattagag taaatttttta aaaagaaata tatggttttg ttaaccgtgt tttaaaattt      2527
gatagagctt ttagatcata atcataattt tttcgtatta attgtgatta tgttggacga      2587
aaatacttaa ttagtattca agaaaactct tattctaaaa acagaaataa atgaatttta      2647 cag gaa gag gtt gga acg cta acg cgg gag cta gtg cgt gtt ggc acg        2695
    Glu Glu Val Gly Thr Leu Thr Arg Glu Leu Val Arg Val Gly Thr
      1               5                  10                  15 aaa ccc gtg aat tta ggc cag ttg gtg aac atg tgt gta gtc aac gct        2743
Lys Pro Val Asn Leu Gly Gln Leu Val Asn Met Cys Val Val Asn Ala
                 20                  25                  30 cta gga cga gag atg atc gga cgg cga ctg ttc ggc gcc gac gcc gat        2791
Leu Gly Arg Glu Met Ile Gly Arg Arg Leu Phe Gly Ala Asp Ala Asp
             35                  40                  45 cat aaa gct gac gag ttt cga tcg atg gtg acg gaa atg atg gct ctc        2839
His Lys Ala Asp Glu Phe Arg Ser Met Val Thr Glu Met Met Ala Leu
         50                  55                  60 gcc gga gta ttt aac atc gga gat ttc gtg ccg tca ctt gat tgg tta        2887
Ala Gly Val Phe Asn Ile Gly Asp Phe Val Pro Ser Leu Asp Trp Leu
     65                  70                  75 gat tta caa ggc gtc gct ggt aaa atg aaa cgg ctt cac aaa aga ttc        2935
Asp Leu Gln Gly Val Ala Gly Lys Met Lys Arg Leu His Lys Arg Phe
 80                  85                  90                  95 gac gct ttt cta tcg tcg att ttg aaa gag cac gaa atg aac ggt caa        2983
Asp Ala Phe Leu Ser Ser Ile Leu Lys Glu His Glu Met Asn Gly Gln
                100                 105                 110 gat caa aag cat aca gat atg ctt agc act tta atc tcc ctt aaa gga        3031
Asp Gln Lys His Thr Asp Met Leu Ser Thr Leu Ile Ser Leu Lys Gly
            115                 120                 125 act gat ctt gac ggt gac gga gga agc tta acg gat act gag att aaa        3079
Thr Asp Leu Asp Gly Asp Gly Gly Ser Leu Thr Asp Thr Glu Ile Lys
        130                 135                 140 gcc ttg cta ttg gtcagttttt tgacaattaa tttccttaaa aatcgtatat            3131
Ala Leu Leu Leu
    145 aatgaaagtt agattgtttt ttttggttgt aaatacag aac atg ttc aca gct          3184
                                            Asn Met Phe Thr Ala
                                              1               5 gga act gac acg tca gca agt acg gtg gac tgg gct ata gct gaa ctt        3232
Gly Thr Asp Thr Ser Ala Ser Thr Val Asp Trp Ala Ile Ala Glu Leu
             10                  15                  20 atc cgt cac ccg gat ata atg gtt aaa gcc caa gaa gaa ctt gat att        3280
Ile Arg His Pro Asp Ile Met Val Lys Ala Gln Glu Glu Leu Asp Ile
         25                  30                  35 gtt gtg ggc cgt gac agg cct gtt aat gaa tca gac atc gct cag ctt        3328
Val Val Gly Arg Asp Arg Pro Val Asn Glu Ser Asp Ile Ala Gln Leu
     40                  45                  50 cct tac ctt cag gtaccgttaa cccaaaccgg aatttggaat tgttttggtt            3380
Pro Tyr Leu Gln
     55 agcgagctat tgttgttaat ccggttttgg tttaaaacag gcg gtt atc aaa gag        3435
                                            Ala Val Ile Lys Glu
                                              1               5 aat ttc agg ctt cat cca cca aca cca ctc tcg tta cca cac atc gcg        3483
Asn Phe Arg Leu His Pro Pro Thr Pro Leu Ser Leu Pro His Ile Ala
```

```
                     10                   15                   20
tca gag agc tgt gag atc aac ggc tac cat atc ccg aaa gga tcg act     3531
Ser Glu Ser Cys Glu Ile Asn Gly Tyr His Ile Pro Lys Gly Ser Thr
                25                   30                   35 cta ttg acg aac ata tgg gcc ata gcc cgt gac ccg gat caa tgg tcc     3579
Leu Leu Thr Asn Ile Trp Ala Ile Ala Arg Asp Pro Asp Gln Trp Ser
            40                   45                   50 gac ccg tta gca ttt aaa ccc gag aga ttc tta ccc ggt ggt gaa aaa     3627
Asp Pro Leu Ala Phe Lys Pro Glu Arg Phe Leu Pro Gly Gly Glu Lys
        55                   60                   65 tcc ggc gtt gat gtg aaa gga agc gat ttc gag cta ata ccg ttc gga     3675
Ser Gly Val Asp Val Lys Gly Ser Asp Phe Glu Leu Ile Pro Phe Gly
    70                   75                   80                   85 gct ggg agg aga atc tgt gcc ggt tta agt tta ggg tta cgt acg att     3723
Ala Gly Arg Arg Ile Cys Ala Gly Leu Ser Leu Gly Leu Arg Thr Ile
                 90                   95                  100 cag ttt ctt acg gcg acg ttg gtt caa gga ttt gat tgg gaa tta gct     3771
Gln Phe Leu Thr Ala Thr Leu Val Gln Gly Phe Asp Trp Glu Leu Ala
            105                  110                  115 gga gga gtt acg ccg gag aag ctg aat atg gag gag agt tat ggg ctt     3819
Gly Gly Val Thr Pro Glu Lys Leu Asn Met Glu Glu Ser Tyr Gly Leu
        120                  125                  130 aca ctg caa aga gcg gtt cct ttg gtg gta cat cct aag cca agg ttg     3867
Thr Leu Gln Arg Ala Val Pro Leu Val Val His Pro Lys Pro Arg Leu
    135                  140                  145 gct ccg aac gtt tat gga ctc ggg tcg ggt taaaatttaa ctttgcttct       3917
Ala Pro Asn Val Tyr Gly Leu Gly Ser Gly
150                  155 tggacaaggt atatggcttg cacgaaaata aagttttaaa acagcgtagt ttgatccgga   3977
gttagcttta tgtaagaacg tgtaacgcca aatcaagtca ttattaaata ttgtgagttg   4037
tttgtaacct atatataaat cttgaagagg aagatttcag aaatcttgaa tatgttttag   4097
gaaaaacatt gttttttta cagtagcgca agttgaatta aaacctattc cttacagaac    4157
caaatgcatt aataattcta gatatttttg gccaagacaa tcagattttt caatatttca   4217
tatatactag gtggaacacc accacctgca actctgcaac acatgttacg ttacacaatc   4277
acttttggcg gttttcaatt atttatataa aattgtaaat gtttgtacac agtagaaaat   4337
tagtaatagt gaattttgtt tctccgaata tgtatagcaa tatatatggc atggatcaaa   4397
ctagccgaca tcctaacttg ttcacagctt cctttttac ttatctagtc gattaagcat    4457
cagaaagtat gttttaattt ttaaatttga aaaaggtgta cttacaagtt cgggtgttca   4517 cacgaggag agctacaata atgaaaaagc tgactcaaga agggctatag aagaaacaag    4577
agtcacggaa caagttgtca ctctcaatct ccagtacact agcttccata actctctctc   4637
tttctctctt tcttctctct ctaaaagtta tcagaataga aatctctctc tctcaacaag   4697
tctaacagtg ccatttgtat ctctgaactc caacatggcc cctctggttc tctaccttct   4757
cactctcctc atggctggcc attccagtaa gaactctcac tgatcttctt caccttgtt    4817 tatggatttg gtctctcagt ctcactctcg cttacccttt cacattcagc tctggctctc   4877
tggtttaaga aacccttaat ctacaaagct tgctttcctc gcaaatgaac taccttactt   4937
atctcttatg caactcttgt tgatgatttg caaacatctt aacctctcga aacaagattt   4997
acaaatctta ctggcttcac ttacaatttt gttcccattt ttttcttctt tggtaggtgc   5057
ctcatggtgt gtgtgcaaaa cagggctgag tgactcagtg ctacaaaaga cattagacta   5117
tgcttgtgga aatggagctg actgtaaccc aactcaccca aaaggctctt gcttcaatcc   5177
```

-continued

```
tgacaatgtt agggctcatt gcaactatgc agtcaatagc ttcttccaaa agaaaggtca   5237
agcttctgag tcttgtaact tcactggtac tgccactctt accaccaccg atcccagtaa   5297
gttttcagaa tgttaacact cttgtgatct ttagaaccct acaaaatttt gagtctcaga   5357
aagttcaagt tcaaggtctt ttggttagag tactaaagat tcaagtagag actaggcgtg   5417 agatatttt tctctgatgt gtgattttt ggcacaggct atacaggatg tgcattccct   5477
tctagtgcta ggtacggctc tttgcttctc tacacattta ttttcttaat ggctttatct   5537
agaactttga aggataccat tttattttt ttggacaaag aaggatagcc atttaatact   5597
acactttaat gttggattaa ctaacttatt atgcctattt aatggcctac actttaagtg   5657
gacacaagct tgatttggtt ataaaaaaag tgcactataa tcttatttta ctgaacccctt   5717 ttttctatga tttttttact aaactttaga taacatctac aacaattcaa ttgccttttt   5777
ttggggattg tataagtttg aacctatggt tagtgtattg acttgcgcgt ctcttattgc   5837
aacggttctt tgaaaacaca ttaatgataa ataaattgaa aagtatagag atggcaattg   5897
tttcaaaagc taatctttct gcttgctaat actttacata aaaaacaaaa aattaagaag   5957
attttcaaac aatacaactt ttttaccttg tcctaacaaa ttcaactcaa atgacatgtg   6017
tttgctttaa aatagtaaca actgtaaatt catttgctct tgagacataa gtgcaagcta   6077
aagataaacg caagcaatac aattaggcct aattaagatt acgaatattg ttgtttgttt   6137
atagtggttc tagtggaagc ggtagcacca ccgtgacgcc aggcaaaaac agtccaaaag   6197
gaagcaacag catcaccaca tttcccggcg gaaacagtcc atacactggc acaccatcca   6257
ccggattatt aggaggcaat atcactgatg caactggaac cgggttgaac ccggattact   6317
caaccgaaag cagtggattt gcgctctatt actccaacaa ccttctgtta accggcttt   6377 gttctctcgt gatgatgctc tgaagaagaa tcaccgtctt cttttagttt atgcttagtc   6437 aaaaaatat gttatttata tgttcttgtt gttttagaga taatttaatc tggatttcgg   6497 ttcttttta ctttccggtt ttaagaaaac aattatcaat gtaaaccaa atctactatc   6557 gatcggttg gtacgaattc ctgcagcccg ggggatcc   6595
```

<210> SEQ ID NO 10
<211> LENGTH: 150
<212> TYPE: PRT
<213> ORGANISM: Arabidopsis thaliana

<400> SEQUENCE: 10

```
Met Ala Thr Leu Phe Leu Thr Ile Leu Leu Ala Thr Val Leu Phe Leu
 1               5                  10                  15

Ile Leu Arg Ile Phe Ser His Arg Arg Asn Arg Ser His Asn Asn Arg
                20                  25                  30

Leu Pro Pro Gly Pro Asn Pro Trp Pro Ile Ile Gly Asn Leu Pro His
            35                  40                  45

Met Gly Thr Lys Pro His Arg Thr Leu Ser Ala Met Val Thr Thr Tyr
        50                  55                  60

Gly Pro Ile Leu His Leu Arg Leu Gly Phe Val Asp Val Val Val Ala
 65                  70                  75                  80

Ala Ser Lys Ser Val Ala Glu Gln Phe Leu Lys Ile His Asp Ala Asn
                85                  90                  95

Phe Ala Ser Arg Pro Pro Asn Ser Gly Ala Lys His Met Ala Tyr Asn
               100                 105                 110

Tyr Gln Asp Leu Val Phe Ala Pro Tyr Gly His Arg Trp Arg Leu Leu
```

```
                115                 120                 125
Arg Lys Ile Ser Ser Val His Leu Phe Ser Ala Lys Ala Leu Glu Asp
        130                 135                 140

Phe Lys His Val Arg Gln
145                 150

<210> SEQ ID NO 11
<211> LENGTH: 147
<212> TYPE: PRT
<213> ORGANISM: Arabidopsis thaliana

<400> SEQUENCE: 11

Glu Glu Val Gly Thr Leu Thr Arg Glu Leu Val Arg Val Gly Thr Lys
  1               5                  10                  15

Pro Val Asn Leu Gly Gln Leu Val Asn Met Cys Val Val Asn Ala Leu
             20                  25                  30

Gly Arg Glu Met Ile Gly Arg Leu Phe Gly Ala Asp Ala Asp His
         35                  40                  45

Lys Ala Asp Glu Phe Arg Ser Met Val Thr Glu Met Met Ala Leu Ala
     50                  55                  60

Gly Val Phe Asn Ile Gly Asp Phe Val Pro Ser Leu Asp Trp Leu Asp
 65                  70                  75                  80

Leu Gln Gly Val Ala Gly Lys Met Lys Arg Leu His Lys Arg Phe Asp
                 85                  90                  95

Ala Phe Leu Ser Ser Ile Leu Lys Glu His Glu Met Asn Gly Gln Asp
            100                 105                 110

Gln Lys His Thr Asp Met Leu Ser Thr Leu Ile Ser Leu Lys Gly Thr
        115                 120                 125

Asp Leu Asp Gly Asp Gly Gly Ser Leu Thr Asp Thr Glu Ile Lys Ala
    130                 135                 140

Leu Leu Leu
145

<210> SEQ ID NO 12
<211> LENGTH: 57
<212> TYPE: PRT
<213> ORGANISM: Arabidopsis thaliana

<400> SEQUENCE: 12

Asn Met Phe Thr Ala Gly Thr Asp Thr Ser Ala Ser Thr Val Asp Trp
  1               5                  10                  15

Ala Ile Ala Glu Leu Ile Arg His Pro Asp Ile Met Val Lys Ala Gln
             20                  25                  30

Glu Glu Leu Asp Ile Val Val Gly Arg Asp Arg Pro Val Asn Glu Ser
         35                  40                  45

Asp Ile Ala Gln Leu Pro Tyr Leu Gln
     50                  55

<210> SEQ ID NO 13
<211> LENGTH: 159
<212> TYPE: PRT
<213> ORGANISM: Arabidopsis thaliana

<400> SEQUENCE: 13

Ala Val Ile Lys Glu Asn Phe Arg Leu His Pro Pro Thr Pro Leu Ser
  1               5                  10                  15

Leu Pro His Ile Ala Ser Glu Ser Cys Glu Ile Asn Gly Tyr His Ile
             20                  25                  30
```

```
Pro Lys Gly Ser Thr Leu Leu Thr Asn Ile Trp Ala Ile Ala Arg Asp
         35                  40                  45

Pro Asp Gln Trp Ser Asp Pro Leu Ala Phe Lys Pro Glu Arg Phe Leu
 50                  55                  60

Pro Gly Gly Glu Lys Ser Gly Val Asp Val Lys Gly Ser Asp Phe Glu
 65                  70                  75                  80

Leu Ile Pro Phe Gly Ala Gly Arg Arg Ile Cys Ala Gly Leu Ser Leu
                 85                  90                  95

Gly Leu Arg Thr Ile Gln Phe Leu Thr Ala Thr Leu Val Gln Gly Phe
             100                 105                 110

Asp Trp Glu Leu Ala Gly Gly Val Thr Pro Glu Lys Leu Asn Met Glu
         115                 120                 125

Glu Ser Tyr Gly Leu Thr Leu Gln Arg Ala Val Pro Leu Val Val His
130                 135                 140

Pro Lys Pro Arg Leu Ala Pro Asn Val Tyr Gly Leu Gly Ser Gly
145                 150                 155
```

<210> SEQ ID NO 14
<211> LENGTH: 1748
<212> TYPE: DNA
<213> ORGANISM: Rosa hybrida
<220> FEATURE:
<221> NAME/KEY: CDS
<222> LOCATION: (22)..(1563)

<400> SEQUENCE: 14

```
tgtcgagaaa gaagaacagc c atg ttt ctc ata gta gtg atc acc ttc ctc        51
                        Met Phe Leu Ile Val Val Ile Thr Phe Leu
                          1               5                  10 ttc gcc gtg ttt ttg ttc cgg ctt ctt ttc tcc ggc aaa tcc caa cgc        99
Phe Ala Val Phe Leu Phe Arg Leu Leu Phe Ser Gly Lys Ser Gln Arg
             15                  20                  25 cac tcg ctc cct ctc cct cct ggc ccc aaa cca tgg ccg gtg gtt ggc       147
His Ser Leu Pro Leu Pro Pro Gly Pro Lys Pro Trp Pro Val Val Gly
         30                  35                  40 aac tta cct cac ttg ggc ccc ttc ccg cac cac tcc atc gcg gag ttg       195
Asn Leu Pro His Leu Gly Pro Phe Pro His His Ser Ile Ala Glu Leu
     45                  50                  55 gcg aag aaa cac ggg ccg ctc atg cac ctc cgc ctc ggc tac gtt gac       243
Ala Lys Lys His Gly Pro Leu Met His Leu Arg Leu Gly Tyr Val Asp
 60                  65                  70 gta gtc gtg gcg gca tca gca tcc gta gcg gcc cag ttc ttg aag act       291
Val Val Val Ala Ala Ser Ala Ser Val Ala Ala Gln Phe Leu Lys Thr
 75                  80                  85                  90 cac gac gcc aat ttc tcc agc cga ccg ccc aac tcc ggc gcc aag cac       339
His Asp Ala Asn Phe Ser Ser Arg Pro Pro Asn Ser Gly Ala Lys His
                 95                 100                 105 ctc gcc tat aac tac cag gac ctc gtg ttc agg ccg tac ggt cca cgg       387
Leu Ala Tyr Asn Tyr Gln Asp Leu Val Phe Arg Pro Tyr Gly Pro Arg
             110                 115                 120 tgg cgc atg ttc cgg aag atc agc tcc gtc cat ctg ttc tcc ggc aaa       435
Trp Arg Met Phe Arg Lys Ile Ser Ser Val His Leu Phe Ser Gly Lys
         125                 130                 135 gcc ttg gat gat ctt aaa cac gtc cgg cag gag gag gta agt gtg cta       483
Ala Leu Asp Asp Leu Lys His Val Arg Gln Glu Glu Val Ser Val Leu
     140                 145                 150 gcg cat gcc ttg gca aat tca ggg tca aag gta gtg aac ctg gcg caa       531
Ala His Ala Leu Ala Asn Ser Gly Ser Lys Val Val Asn Leu Ala Gln
155                 160                 165                 170
```

-continued

| | | |
|---|---|---|
| ctg ctg aac ctg tgc acg gtc aat gct cta gga agg gtg atg gta ggg<br>Leu Leu Asn Leu Cys Thr Val Asn Ala Leu Gly Arg Val Met Val Gly<br>                175                        180                        185 | 579 |
| cgg agg gtt ttc ggc gac ggc agc gga ggc gac gat ccg aag gcg gac<br>Arg Arg Val Phe Gly Asp Gly Ser Gly Gly Asp Asp Pro Lys Ala Asp<br>                190                        195                        200 | 627 |
| gag ttc aaa tcg atg gtg gtg gag atg atg gtg ttg gca gga gtg ttc<br>Glu Phe Lys Ser Met Val Val Glu Met Met Val Leu Ala Gly Val Phe<br>                205                        210                        215 | 675 |
| aac ata ggt gac ttc atc ccc tct ctc gaa tgg ctt gac ttg caa ggc<br>Asn Ile Gly Asp Phe Ile Pro Ser Leu Glu Trp Leu Asp Leu Gln Gly<br>220                        225                        230 | 723 |
| gtg gcg tcc aag atg aag aag ctc cac aag aga ttc gac gac ttc ttg<br>Val Ala Ser Lys Met Lys Lys Leu His Lys Arg Phe Asp Asp Phe Leu<br>235                        240                        245                        250 | 771 |
| aca gcc att gtc gag gac cac aag aag ggc tcc ggc acg gcg ggg cac<br>Thr Ala Ile Val Glu Asp His Lys Lys Gly Ser Gly Thr Ala Gly His<br>                    255                        260                        265 | 819 |
| gtc gac atg ttg acc act ctg ctc tcg ctc aag gaa gac gcc gac ggc<br>Val Asp Met Leu Thr Thr Leu Leu Ser Leu Lys Glu Asp Ala Asp Gly<br>                270                        275                        280 | 867 |
| gaa gga ggc aag ctc acc gat act gaa atc aaa gct ttg ctt ttg aac<br>Glu Gly Gly Lys Leu Thr Asp Thr Glu Ile Lys Ala Leu Leu Leu Asn<br>              285                        290                        295 | 915 |
| atg ttc acg gct ggc act gat acg tca tcg agc acg gtg gaa tgg gca<br>Met Phe Thr Ala Gly Thr Asp Thr Ser Ser Ser Thr Val Glu Trp Ala<br>300                        305                        310 | 963 |
| ata gct gaa ctc att cgg cac cct cat atg cta gcg cga gtt cag aaa<br>Ile Ala Glu Leu Ile Arg His Pro His Met Leu Ala Arg Val Gln Lys<br>315                        320                        325                        330 | 1011 |
| gag ctt gac gat ttt gtt ggc cat gac cga ctt gtg acc gaa tcc gac<br>Glu Leu Asp Asp Phe Val Gly His Asp Arg Leu Val Thr Glu Ser Asp<br>                    335                        340                        345 | 1059 |
| ata ccc aac ctc cct tac ctc caa gcc gtg atc aag gaa acg ttc cga<br>Ile Pro Asn Leu Pro Tyr Leu Gln Ala Val Ile Lys Glu Thr Phe Arg<br>                    350                        355                        360 | 1107 |
| ctc cac cca tcc act cct ctc tcg ttg cct cgt atg gca gcc gag agt<br>Leu His Pro Ser Thr Pro Leu Ser Leu Pro Arg Met Ala Ala Glu Ser<br>                365                        370                        375 | 1155 |
| tgc gaa atc aac ggg tac cac atc ccg aaa ggc tcc aca ctc ttg gtc<br>Cys Glu Ile Asn Gly Tyr His Ile Pro Lys Gly Ser Thr Leu Leu Val<br>380                        385                        390 | 1203 |
| aat gta tgg gcc ata tcg cgt gac ccg gct gaa tgg gcc gac cca ctg<br>Asn Val Trp Ala Ile Ser Arg Asp Pro Ala Glu Trp Ala Asp Pro Leu<br>395                        400                        405                        410 | 1251 |
| gag ttc aag ccc gag agg ttc ctg ccg ggg ggc gaa aag cct aat gtt<br>Glu Phe Lys Pro Glu Arg Phe Leu Pro Gly Gly Glu Lys Pro Asn Val<br>                    415                        420                        425 | 1299 |
| gat att aga gga aac gat ttt gaa gtc ata ccc ttc ggt gcc ggg cga<br>Asp Ile Arg Gly Asn Asp Phe Glu Val Ile Pro Phe Gly Ala Gly Arg<br>                    430                        435                        440 | 1347 |
| aga ata tgt gcc ggg atg agc ttg ggc ctg cgt atg gtc cat tta atg<br>Arg Ile Cys Ala Gly Met Ser Leu Gly Leu Arg Met Val His Leu Met<br>                445                        450                        455 | 1395 |
| act gca aca ttg gtc cac gca ttt aat tgg gcc ttg gct gat ggg ctg<br>Thr Ala Thr Leu Val His Ala Phe Asn Trp Ala Leu Ala Asp Gly Leu<br>460                        465                        470 | 1443 |
| acc gct gag aag tta aac atg gat gaa gca tat ggg ctc act cta caa<br>Thr Ala Glu Lys Leu Asn Met Asp Glu Ala Tyr Gly Leu Thr Leu Gln | 1491 |

```
                   475                 480                 485                 490
cga gct gca ccg tta atg gtg cac ccg cgc acc agg ctg gcc cca cag             1539
Arg Ala Ala Pro Leu Met Val His Pro Arg Thr Arg Leu Ala Pro Gln
                495                 500                 505 gca tat aaa act tca tca tct taa ttagagagct atgttctggg tgtgcccggt            1593
Ala Tyr Lys Thr Ser Ser Ser
            510 ttgatgtctc catgttttct atttaggttt aaatctgtaa gataaggtga ttctatgctg           1653 aatcacaaaa gttgctatct aaattccatg tccaatgaaa acgttcttct tcccttctta           1713 taatttatga atacttatga tataggcgac agcaa                                      1748

<210> SEQ ID NO 15
<211> LENGTH: 513
<212> TYPE: PRT
<213> ORGANISM: Rosa hybrida

<400> SEQUENCE: 15

Met Phe Leu Ile Val Val Ile Thr Phe Leu Phe Ala Val Phe Leu Phe
 1               5                  10                  15

Arg Leu Leu Phe Ser Gly Lys Ser Gln Arg His Ser Leu Pro Leu Pro
                20                  25                  30

Pro Gly Pro Lys Pro Trp Pro Val Gly Asn Leu Pro His Leu Gly
            35                  40                  45

Pro Phe Pro His His Ser Ile Ala Glu Leu Ala Lys Lys His Gly Pro
         50                  55                  60

Leu Met His Leu Arg Leu Gly Tyr Val Asp Val Val Ala Ala Ser
 65                  70                  75                  80

Ala Ser Val Ala Ala Gln Phe Leu Lys Thr His Asp Ala Asn Phe Ser
                85                  90                  95

Ser Arg Pro Pro Asn Ser Gly Ala Lys His Leu Ala Tyr Asn Tyr Gln
            100                 105                 110

Asp Leu Val Phe Arg Pro Tyr Gly Pro Arg Trp Arg Met Phe Arg Lys
        115                 120                 125

Ile Ser Ser Val His Leu Phe Ser Gly Lys Ala Leu Asp Asp Leu Lys
130                 135                 140

His Val Arg Gln Glu Glu Val Ser Val Leu Ala His Ala Leu Ala Asn
145                 150                 155                 160

Ser Gly Ser Lys Val Val Asn Leu Ala Gln Leu Leu Asn Leu Cys Thr
                165                 170                 175

Val Asn Ala Leu Gly Arg Val Met Val Gly Arg Arg Val Phe Gly Asp
            180                 185                 190

Gly Ser Gly Gly Asp Asp Pro Lys Ala Asp Glu Phe Lys Ser Met Val
        195                 200                 205

Val Glu Met Met Val Leu Ala Gly Val Phe Asn Ile Gly Asp Phe Ile
    210                 215                 220

Pro Ser Leu Glu Trp Leu Asp Leu Gln Gly Val Ala Ser Lys Met Lys
225                 230                 235                 240

Lys Leu His Lys Arg Phe Asp Asp Phe Leu Thr Ala Ile Val Glu Asp
                245                 250                 255

His Lys Lys Gly Ser Gly Thr Ala Gly His Val Asp Met Leu Thr Thr
            260                 265                 270

Leu Leu Ser Leu Lys Glu Asp Ala Asp Gly Glu Gly Gly Lys Leu Thr
        275                 280                 285

Asp Thr Glu Ile Lys Ala Leu Leu Leu Asn Met Phe Thr Ala Gly Thr
```

```
                    290                 295                 300
Asp Thr Ser Ser Thr Val Glu Trp Ala Ile Ala Glu Leu Ile Arg
305                 310                 315                 320

His Pro His Met Leu Ala Arg Val Gln Lys Glu Leu Asp Asp Phe Val
                325                 330                 335

Gly His Asp Arg Leu Val Thr Glu Ser Asp Ile Pro Asn Leu Pro Tyr
                340                 345                 350

Leu Gln Ala Val Ile Lys Glu Thr Phe Arg Leu His Pro Ser Thr Pro
                355                 360                 365

Leu Ser Leu Pro Arg Met Ala Ala Glu Ser Cys Glu Ile Asn Gly Tyr
370                 375                 380

His Ile Pro Lys Gly Ser Thr Leu Leu Val Asn Val Trp Ala Ile Ser
385                 390                 395                 400

Arg Asp Pro Ala Glu Trp Ala Asp Pro Leu Glu Phe Lys Pro Glu Arg
                405                 410                 415

Phe Leu Pro Gly Gly Glu Lys Pro Asn Val Asp Ile Arg Gly Asn Asp
                420                 425                 430

Phe Glu Val Ile Pro Phe Gly Ala Gly Arg Arg Ile Cys Ala Gly Met
                435                 440                 445

Ser Leu Gly Leu Arg Met Val His Leu Met Thr Ala Thr Leu Val His
450                 455                 460

Ala Phe Asn Trp Ala Leu Ala Asp Gly Leu Thr Ala Glu Lys Leu Asn
465                 470                 475                 480

Met Asp Glu Ala Tyr Gly Leu Thr Leu Gln Arg Ala Ala Pro Leu Met
                485                 490                 495

Val His Pro Arg Thr Arg Leu Ala Pro Gln Ala Tyr Lys Thr Ser Ser
                500                 505                 510

Ser
```

<210> SEQ ID NO 16
<211> LENGTH: 1660
<212> TYPE: DNA
<213> ORGANISM: Chrysanthemum
<220> FEATURE:
<221> NAME/KEY: CDS
<222> LOCATION: (4)..(1530)

<400> SEQUENCE: 16

```
aaa atg acc att tta gct ttc gta ttt tac gcc ctc atc ctc ggg tca      48
    Met Thr Ile Leu Ala Phe Val Phe Tyr Ala Leu Ile Leu Gly Ser
    1               5                   10                  15 gta ctc tat gta ttt ctt aac tta agt tca cgt aaa tcc gcc aga ctc      96
Val Leu Tyr Val Phe Leu Asn Leu Ser Ser Arg Lys Ser Ala Arg Leu
                20                  25                  30 cca ccc ggg cca aca cca tgg cct ata gtc ggg aac tta cca cac ctt     144
Pro Pro Gly Pro Thr Pro Trp Pro Ile Val Gly Asn Leu Pro His Leu
            35                  40                  45 ggc cca atc cca cac cac gca ctc gcg gcc tta gcc aag aag tac ggg     192
Gly Pro Ile Pro His His Ala Leu Ala Ala Leu Ala Lys Lys Tyr Gly
        50                  55                  60 cca ttg atg cac ctg cgg ctc ggg tgt gtg gac gtg gtt gtg gcc gcg     240
Pro Leu Met His Leu Arg Leu Gly Cys Val Asp Val Val Val Ala Ala
65                  70                  75 tct gct tcc gta gct gca cag ttt tta aaa gtt cac gac gca aat ttt     288
Ser Ala Ser Val Ala Ala Gln Phe Leu Lys Val His Asp Ala Asn Phe
80                  85                  90                  95 gct agt agg ccg cca aat tct ggc gcg aaa cat gtg gcg tat aat tat     336
```

```
                Ala Ser Arg Pro Pro Asn Ser Gly Ala Lys His Val Ala Tyr Asn Tyr
                            100                 105                 110 cag gat ctt gtg ttt gca cct tat ggt cca agg tgg cgt ttg tta agg          384
Gln Asp Leu Val Phe Ala Pro Tyr Gly Pro Arg Trp Arg Leu Leu Arg
                115                 120                 125 aag att tgt tcg gtc cat ttg ttt tct gct aaa gca ctt gat gat ttt          432
Lys Ile Cys Ser Val His Leu Phe Ser Ala Lys Ala Leu Asp Asp Phe
            130                 135                 140 cgt cat gtt cga cag gag gag gta gca gtc cta acc cgc gta cta ctg          480
Arg His Val Arg Gln Glu Glu Val Ala Val Leu Thr Arg Val Leu Leu
        145                 150                 155 agt gct gga aac tca ccg gta cag ctt ggc caa cta ctt aac gtg tgt          528
Ser Ala Gly Asn Ser Pro Val Gln Leu Gly Gln Leu Leu Asn Val Cys
160                 165                 170                 175 gcc aca aac gcc tta gca cgg gta atg tta ggt agg aga gtt ttc gga          576
Ala Thr Asn Ala Leu Ala Arg Val Met Leu Gly Arg Arg Val Phe Gly
                180                 185                 190 gac gga att gac agg tca gcc aat gag ttc aaa gat atg gta gta gag          624
Asp Gly Ile Asp Arg Ser Ala Asn Glu Phe Lys Asp Met Val Val Glu
                195                 200                 205 tta atg gta tta gca gga gaa ttt aac ctt ggt gac ttt att cct gta          672
Leu Met Val Leu Ala Gly Glu Phe Asn Leu Gly Asp Phe Ile Pro Val
            210                 215                 220 ctt gac cta ttc gac cta caa ggc att act aaa aaa atg aag aag ctt          720
Leu Asp Leu Phe Asp Leu Gln Gly Ile Thr Lys Lys Met Lys Lys Leu
        225                 230                 235 cat gtt cgg ttc gat tca ttt ctt agt aag atc gtt gag gag cat aaa          768
His Val Arg Phe Asp Ser Phe Leu Ser Lys Ile Val Glu Glu His Lys
240                 245                 250                 255 acg gca cct ggt ggg ttg ggt cat act gat ttg ctg agc acg ttg att          816
Thr Ala Pro Gly Gly Leu Gly His Thr Asp Leu Leu Ser Thr Leu Ile
                260                 265                 270 tca ctt aaa gat gat gct gat att gaa ggt ggg aag ctt aca gat act          864
Ser Leu Lys Asp Asp Ala Asp Ile Glu Gly Gly Lys Leu Thr Asp Thr
                275                 280                 285 gaa atc aaa gct ttg ctt ctg aat tta ttc gct gcg gga aca gac aca          912
Glu Ile Lys Ala Leu Leu Leu Asn Leu Phe Ala Ala Gly Thr Asp Thr
            290                 295                 300 tcc tct agt aca gta gaa tgg gca ata gcc gaa ctc att cgt cat cca          960
Ser Ser Ser Thr Val Glu Trp Ala Ile Ala Glu Leu Ile Arg His Pro
305                 310                 315 caa ata tta aaa caa gcc cga gaa gag ata gac gct gta gtt ggt caa         1008
Gln Ile Leu Lys Gln Ala Arg Glu Glu Ile Asp Ala Val Val Gly Gln
320                 325                 330                 335 gac cgg ctt gta aca gaa ttg gac ttg agc caa cta aca tac ctc cag         1056
Asp Arg Leu Val Thr Glu Leu Asp Leu Ser Gln Leu Thr Tyr Leu Gln
                340                 345                 350 gct ctt gtg aaa gag gtg ttt agg ctc cac cct tca acg cca ctc tcc         1104
Ala Leu Val Lys Glu Val Phe Arg Leu His Pro Ser Thr Pro Leu Ser
            355                 360                 365 tta cca aga ata tca tcc gag agt tgt gag gtc gat ggg tat tat atc         1152
Leu Pro Arg Ile Ser Ser Glu Ser Cys Glu Val Asp Gly Tyr Tyr Ile
        370                 375                 380 cct aag gga tcc aca ctc ctc gtt aac gtg tgg gcc att gcg cga gac         1200
Pro Lys Gly Ser Thr Leu Leu Val Asn Val Trp Ala Ile Ala Arg Asp
385                 390                 395 cca aaa atg tgg gcg gat cct ctt gaa ttt agg cct tct cgg ttt tta         1248
Pro Lys Met Trp Ala Asp Pro Leu Glu Phe Arg Pro Ser Arg Phe Leu
400                 405                 410                 415
```

```
ccc ggg gga gaa aag ccc ggt gct gat gtt agg gga aat gat ttt gaa    1296
Pro Gly Gly Glu Lys Pro Gly Ala Asp Val Arg Gly Asn Asp Phe Glu
                420                 425                 430 gtt ata cca ttt ggg gca gga cga agg att tgt gcg ggt atg agc cta    1344
Val Ile Pro Phe Gly Ala Gly Arg Arg Ile Cys Ala Gly Met Ser Leu
                435                 440                 445 ggc ttg aga atg gtc cag ttg ctc att gca aca ttg gtc caa act ttt    1392
Gly Leu Arg Met Val Gln Leu Leu Ile Ala Thr Leu Val Gln Thr Phe
            450                 455                 460 gat tgg gaa ctg gct aac ggg tta gag ccg gag atg ctc aac atg gaa    1440
Asp Trp Glu Leu Ala Asn Gly Leu Glu Pro Glu Met Leu Asn Met Glu
        465                 470                 475 gaa gcg tat gga ttg acc ctt caa cgg gct gca ccc ttg atg gtt cac    1488
Glu Ala Tyr Gly Leu Thr Leu Gln Arg Ala Ala Pro Leu Met Val His
480                 485                 490                 495 ccg aag ccg agg tta gct ccc cac gta tat gaa agt att taa            1530
Pro Lys Pro Arg Leu Ala Pro His Val Tyr Glu Ser Ile
                500                 505 ggactagttt ctcttttgcc tttttgtttc gcaaaggtta atgaataaac gatttcatga   1590
ctcagatagt tatgtaaaca attgtgtttg ctgtttatat atttatctat ttttctagaa   1650
caaaaaaaaa                                                         1660

<210> SEQ ID NO 17
<211> LENGTH: 508
<212> TYPE: PRT
<213> ORGANISM: Chrysanthemum

<400> SEQUENCE: 17

Met Thr Ile Leu Ala Phe Val Phe Tyr Ala Leu Ile Leu Gly Ser Val
 1               5                  10                  15

Leu Tyr Val Phe Leu Asn Leu Ser Ser Arg Lys Ser Ala Arg Leu Pro
                20                  25                  30

Pro Gly Pro Thr Pro Trp Pro Ile Val Gly Asn Leu Pro His Leu Gly
            35                  40                  45

Pro Ile Pro His His Ala Leu Ala Ala Leu Ala Lys Lys Tyr Gly Pro
        50                  55                  60

Leu Met His Leu Arg Leu Gly Cys Val Asp Val Val Ala Ala Ser
65                  70                  75              80

Ala Ser Val Ala Ala Gln Phe Leu Lys Val His Asp Ala Asn Phe Ala
                85                  90                  95

Ser Arg Pro Pro Asn Ser Gly Ala Lys His Val Ala Tyr Asn Tyr Gln
                100                 105                 110

Asp Leu Val Phe Ala Pro Tyr Gly Pro Arg Trp Arg Leu Leu Arg Lys
            115                 120                 125

Ile Cys Ser Val His Leu Phe Ser Ala Lys Ala Leu Asp Asp Phe Arg
        130                 135                 140

His Val Arg Gln Glu Glu Val Ala Val Leu Thr Arg Val Leu Leu Ser
145                 150                 155                 160

Ala Gly Asn Ser Pro Val Gln Leu Gly Gln Leu Leu Asn Val Cys Ala
                165                 170                 175

Thr Asn Ala Leu Ala Arg Val Met Leu Gly Arg Arg Val Phe Gly Asp
                180                 185                 190

Gly Ile Asp Arg Ser Ala Asn Glu Phe Lys Asp Met Val Val Glu Leu
            195                 200                 205

Met Val Leu Ala Gly Glu Phe Asn Leu Gly Asp Phe Ile Pro Val Leu
        210                 215                 220
```

-continued

```
Asp Leu Phe Asp Leu Gln Gly Ile Thr Lys Lys Met Lys Lys Leu His
225                 230                 235                 240

Val Arg Phe Asp Ser Phe Leu Ser Lys Ile Val Glu His Lys Thr
                245                 250                 255

Ala Pro Gly Gly Leu Gly His Thr Asp Leu Leu Ser Thr Leu Ile Ser
                260                 265                 270

Leu Lys Asp Asp Ala Asp Ile Glu Gly Gly Lys Leu Thr Asp Thr Glu
            275                 280                 285

Ile Lys Ala Leu Leu Leu Asn Leu Phe Ala Ala Gly Thr Asp Thr Ser
290                 295                 300

Ser Ser Thr Val Glu Trp Ala Ile Ala Glu Leu Ile Arg His Pro Gln
305                 310                 315                 320

Ile Leu Lys Gln Ala Arg Glu Glu Ile Asp Ala Val Val Gly Gln Asp
                325                 330                 335

Arg Leu Val Thr Glu Leu Asp Leu Ser Gln Leu Thr Tyr Leu Gln Ala
                340                 345                 350

Leu Val Lys Glu Val Phe Arg Leu His Pro Ser Thr Pro Leu Ser Leu
            355                 360                 365

Pro Arg Ile Ser Ser Glu Ser Cys Glu Val Asp Gly Tyr Tyr Ile Pro
370                 375                 380

Lys Gly Ser Thr Leu Leu Val Asn Val Trp Ala Ile Ala Arg Asp Pro
385                 390                 395                 400

Lys Met Trp Ala Asp Pro Leu Glu Phe Arg Pro Ser Arg Phe Leu Pro
                405                 410                 415

Gly Gly Glu Lys Pro Gly Ala Asp Val Arg Gly Asn Asp Phe Glu Val
                420                 425                 430

Ile Pro Phe Gly Ala Gly Arg Arg Ile Cys Ala Gly Met Ser Leu Gly
            435                 440                 445

Leu Arg Met Val Gln Leu Leu Ile Ala Thr Leu Val Gln Thr Phe Asp
450                 455                 460

Trp Glu Leu Ala Asn Gly Leu Glu Pro Glu Met Leu Asn Met Glu Glu
465                 470                 475                 480

Ala Tyr Gly Leu Thr Leu Gln Arg Ala Ala Pro Leu Met Val His Pro
                485                 490                 495

Lys Pro Arg Leu Ala Pro His Val Tyr Glu Ser Ile
            500                 505
```

<210> SEQ ID NO 18
<211> LENGTH: 1815
<212> TYPE: DNA
<213> ORGANISM: Torenia
<220> FEATURE:
<221> NAME/KEY: CDS
<222> LOCATION: (107)..(1633)

<400> SEQUENCE: 18

```
ctaaattaat taataaatac acacgacg agatgtatgt aatgtaatgt aatattatta      60
catacatcat caccgaatac gcacgctact accactgcga ttagcc atg agt ccc     115
                                                  Met Ser Pro
                                                    1 tta gcc ttg atg atc ata agt acc tta tta ggg ttt ctc cta tac cac   163
Leu Ala Leu Met Ile Ile Ser Thr Leu Leu Gly Phe Leu Leu Tyr His
    5                   10                  15 tct ctt cgc tta cta ctc ttc tcc ggc caa ggt cgc cga cta cta cca   211
Ser Leu Arg Leu Leu Leu Phe Ser Gly Gln Gly Arg Arg Leu Leu Pro
 20                  25                  30                  35
```

-continued

```
cca ggt cca cgc ccg tgg ccg ctg gtg gga aat ctc ccg cac tta ggc      259
Pro Gly Pro Arg Pro Trp Pro Leu Val Gly Asn Leu Pro His Leu Gly
             40                  45                  50 ccg aag cca cac gcc tcc atg gcc gag ctc gcg cga gcc tac gga ccc      307
Pro Lys Pro His Ala Ser Met Ala Glu Leu Ala Arg Ala Tyr Gly Pro
         55                  60                  65 ctc atg cac cta aag atg ggg ttc gtc cac gtc gtg gtg gct tcg tcg      355
Leu Met His Leu Lys Met Gly Phe Val His Val Val Val Ala Ser Ser
         70                  75                  80 gcg agc gcg gcg gag cag tgc ctg agg gtt cac gac gcg aat ttc ttg      403
Ala Ser Ala Ala Glu Gln Cys Leu Arg Val His Asp Ala Asn Phe Leu
 85                  90                  95 agc agg cca ccc aac tcc ggc gcc aag cac gtc gct tac aac tac gag      451
Ser Arg Pro Pro Asn Ser Gly Ala Lys His Val Ala Tyr Asn Tyr Glu
100                 105                 110                 115 gac ttg gtt ttc aga ccg tac ggt ccc aag tgg agg ctg ttg agg aag      499
Asp Leu Val Phe Arg Pro Tyr Gly Pro Lys Trp Arg Leu Leu Arg Lys
                120                 125                 130 ata tgc gct cag cat att ttc tcc gtc aag gct atg gat gac ttc agg      547
Ile Cys Ala Gln His Ile Phe Ser Val Lys Ala Met Asp Asp Phe Arg
            135                 140                 145 cgc gtc aga gag gaa gag gtg gcc atc ctg agt cgc gct cta gca ggc      595
Arg Val Arg Glu Glu Glu Val Ala Ile Leu Ser Arg Ala Leu Ala Gly
            150                 155                 160 aaa agg gcc gta ccc ata ggc caa atg ctc aac gtg tgc gcc aca aac      643
Lys Arg Ala Val Pro Ile Gly Gln Met Leu Asn Val Cys Ala Thr Asn
165                 170                 175 gcc cta tct cgc gtc atg atg ggg cgg cgc gtg gtg ggc cac gcg gat      691
Ala Leu Ser Arg Val Met Met Gly Arg Arg Val Val Gly His Ala Asp
180                 185                 190                 195 gga acc aac gac gcc aag gcg gag gag ttc aaa gcc atg gtc gtc gag      739
Gly Thr Asn Asp Ala Lys Ala Glu Glu Phe Lys Ala Met Val Val Glu
                200                 205                 210 ctc atg gtc ctc tcc ggc gtc ttc aac atc ggt gat ttc atc ccc ttc      787
Leu Met Val Leu Ser Gly Val Phe Asn Ile Gly Asp Phe Ile Pro Phe
            215                 220                 225 ctc gag cct ctc gac ttg cag gga gtg gct tcc aag atg aag aaa ctc      835
Leu Glu Pro Leu Asp Leu Gln Gly Val Ala Ser Lys Met Lys Lys Leu
            230                 235                 240 cac gcg cgg ttc gat gca ttc ttg acc gag att gta cga gag cgt tgt      883
His Ala Arg Phe Asp Ala Phe Leu Thr Glu Ile Val Arg Glu Arg Cys
245                 250                 255 cat ggg cag atc aac aac agt ggt gct cat cag gat gat ttg ctt agc      931
His Gly Gln Ile Asn Asn Ser Gly Ala His Gln Asp Asp Leu Leu Ser
260                 265                 270                 275 acg ttg att tcg ttc aaa ggg ctt gac gat ggc gat ggt tcc agg ctc      979
Thr Leu Ile Ser Phe Lys Gly Leu Asp Asp Gly Asp Gly Ser Arg Leu
                280                 285                 290 act gac aca gaa atc aag gcg ctg ctc ttg aac ctt ttg gac acg acg     1027
Thr Asp Thr Glu Ile Lys Ala Leu Leu Leu Asn Leu Leu Asp Thr Thr
            295                 300                 305 tcg agc acg gtg gaa tgg gcc gta gcc gaa ctc cta cgc cac cct aag     1075
Ser Ser Thr Val Glu Trp Ala Val Ala Glu Leu Leu Arg His Pro Lys
            310                 315                 320 aca tta gcc caa gtc cgg caa gag ctc gac tcg gtc gtg ggt aag aac     1123
Thr Leu Ala Gln Val Arg Gln Glu Leu Asp Ser Val Val Gly Lys Asn
325                 330                 335 agg ctc gtg tcc gag acc gat ctg aat cag ctg ccc tat cta caa gct     1171
Arg Leu Val Ser Glu Thr Asp Leu Asn Gln Leu Pro Tyr Leu Gln Ala
```

```
                340             345             350             355
gtc gtc aaa gaa act ttc cgc ctc cat cct ccg acg ccg ctc tct cta    1219
Val Val Lys Glu Thr Phe Arg Leu His Pro Pro Thr Pro Leu Ser Leu
                360             365             370 ccg aga ctc gcg gaa gat gat tgc gag atc gac gga tac ctc atc ccc    1267
Pro Arg Leu Ala Glu Asp Asp Cys Glu Ile Asp Gly Tyr Leu Ile Pro
            375             380             385 aag ggc tcg acc ctt ctg gtg aac gtt tgg gcc ata gcc cgc gat ccc    1315
Lys Gly Ser Thr Leu Leu Val Asn Val Trp Ala Ile Ala Arg Asp Pro
            390             395             400 aag gtt tgg gcc gat ccg ttg gag ttt agg ccc gaa cga ttc ttg acg    1363
Lys Val Trp Ala Asp Pro Leu Glu Phe Arg Pro Glu Arg Phe Leu Thr
            405             410             415 ggc gga gaa aag gcc gac gtc gat gtc aag ggg aac gat ttc gaa gtg    1411
Gly Gly Glu Lys Ala Asp Val Asp Val Lys Gly Asn Asp Phe Glu Val
420             425             430             435 ata ccg ttc ggg gcg ggt cgt agg atc tgc gct ggc gtt ggc ttg gga    1459
Ile Pro Phe Gly Ala Gly Arg Arg Ile Cys Ala Gly Val Gly Leu Gly
                440             445             450 ata cgt atg gtc caa ctg ttg acg gcg agt ttg atc cat gca ttc gat    1507
Ile Arg Met Val Gln Leu Leu Thr Ala Ser Leu Ile His Ala Phe Asp
                455             460             465 ctg gac ctt gct aat ggg ctt ttg gcc caa aat ctg aac atg gaa gaa    1555
Leu Asp Leu Ala Asn Gly Leu Leu Ala Gln Asn Leu Asn Met Glu Glu
            470             475             480 gca tat ggg ctt acg cta caa cgg gct gag cct ttg ttg gtc cac cct    1603
Ala Tyr Gly Leu Thr Leu Gln Arg Ala Glu Pro Leu Leu Val His Pro
            485             490             495 agg ccg cgg ttg gcc act cat gtc tat taa ttaaattagg cctaaactac      1653
Arg Pro Arg Leu Ala Thr His Val Tyr
500             505 gatgaatgac ccatttaacg ttaataagag ttttcaattt atgtgagttt gcatggtatg  1713
gtatggtatg gtgcttgtaa taaattgtat ctgttaggtg tgttcattga tgataaatct  1773
agtttgtact gctgctcaaa aaaaaaaaaa aaaaaaaaaa aa                     1815

<210> SEQ ID NO 19
<211> LENGTH: 508
<212> TYPE: PRT
<213> ORGANISM: Torenia

<400> SEQUENCE: 19

Met Ser Pro Leu Ala Leu Met Ile Ile Ser Thr Leu Leu Gly Phe Leu
  1               5                  10                  15

Leu Tyr His Ser Leu Arg Leu Leu Phe Ser Gly Gln Gly Arg Arg
                 20                  25                  30

Leu Leu Pro Pro Gly Pro Arg Pro Trp Pro Leu Val Gly Asn Leu Pro
             35                  40                  45

His Leu Gly Pro Lys Pro His Ala Ser Met Ala Glu Leu Ala Arg Ala
         50                  55                  60

Tyr Gly Pro Leu Met His Leu Lys Met Gly Phe Val His Val Val
 65                  70                  75                  80

Ala Ser Ser Ala Ser Ala Ala Glu Gln Cys Leu Arg Val His Asp Ala
                 85                  90                  95

Asn Phe Leu Ser Arg Pro Pro Asn Ser Gly Ala Lys His Val Ala Tyr
            100                 105                 110

Asn Tyr Glu Asp Leu Val Phe Arg Pro Tyr Gly Pro Lys Trp Arg Leu
        115                 120                 125
```

```
Leu Arg Lys Ile Cys Ala Gln His Ile Phe Ser Val Lys Ala Met Asp
    130                 135                 140

Asp Phe Arg Arg Val Arg Glu Glu Val Ala Ile Leu Ser Arg Ala
145                 150                 155                 160

Leu Ala Gly Lys Arg Ala Val Pro Ile Gly Gln Met Leu Asn Val Cys
                165                 170                 175

Ala Thr Asn Ala Leu Ser Arg Val Met Met Gly Arg Arg Val Val Gly
            180                 185                 190

His Ala Asp Gly Thr Asn Asp Ala Lys Ala Glu Glu Phe Lys Ala Met
        195                 200                 205

Val Val Glu Leu Met Val Leu Ser Gly Val Phe Asn Ile Gly Asp Phe
    210                 215                 220

Ile Pro Phe Leu Glu Pro Leu Asp Leu Gln Gly Val Ala Ser Lys Met
225                 230                 235                 240

Lys Lys Leu His Ala Arg Phe Asp Ala Phe Leu Thr Glu Ile Val Arg
                245                 250                 255

Glu Arg Cys His Gly Gln Ile Asn Asn Ser Gly Ala His Gln Asp Asp
            260                 265                 270

Leu Leu Ser Thr Leu Ile Ser Phe Lys Gly Leu Asp Asp Gly Asp Gly
        275                 280                 285

Ser Arg Leu Thr Asp Thr Glu Ile Lys Ala Leu Leu Asn Leu Leu
    290                 295                 300

Asp Thr Thr Ser Ser Thr Val Glu Trp Ala Val Ala Glu Leu Leu Arg
305                 310                 315                 320

His Pro Lys Thr Leu Ala Gln Val Arg Gln Glu Leu Asp Ser Val Val
                325                 330                 335

Gly Lys Asn Arg Leu Val Ser Glu Thr Asp Leu Asn Gln Leu Pro Tyr
            340                 345                 350

Leu Gln Ala Val Val Lys Glu Thr Phe Arg Leu His Pro Pro Thr Pro
        355                 360                 365

Leu Ser Leu Pro Arg Leu Ala Glu Asp Asp Cys Glu Ile Asp Gly Tyr
    370                 375                 380

Leu Ile Pro Lys Gly Ser Thr Leu Leu Val Asn Val Trp Ala Ile Ala
385                 390                 395                 400

Arg Asp Pro Lys Val Trp Ala Asp Pro Leu Glu Phe Arg Pro Glu Arg
                405                 410                 415

Phe Leu Thr Gly Gly Glu Lys Ala Asp Val Asp Val Lys Gly Asn Asp
            420                 425                 430

Phe Glu Val Ile Pro Phe Gly Ala Gly Arg Arg Ile Cys Ala Gly Val
        435                 440                 445

Gly Leu Gly Ile Arg Met Val Gln Leu Leu Thr Ala Ser Leu Ile His
    450                 455                 460

Ala Phe Asp Leu Asp Leu Ala Asn Gly Leu Leu Ala Gln Asn Leu Asn
465                 470                 475                 480

Met Glu Glu Ala Tyr Gly Leu Thr Leu Gln Arg Ala Glu Pro Leu Leu
                485                 490                 495

Val His Pro Arg Pro Arg Leu Ala Thr His Val Tyr
            500                 505

<210> SEQ ID NO 20
<211> LENGTH: 1824
<212> TYPE: DNA
<213> ORGANISM: Jap. Morning Glory
<220> FEATURE:
```

-continued

```
<221> NAME/KEY: CDS
<222> LOCATION: (2)..(1555)

<400> SEQUENCE: 20 g agc tta acc tta att ttc tgc act tta gtt ttt gca atc ttt cta tat      49
  Ser Leu Thr Leu Ile Phe Cys Thr Leu Val Phe Ala Ile Phe Leu Tyr
   1               5                  10                  15 ttt ctt att ctc agg gtg aaa cag cgt tac cct tta cct ctc cca ccc        97
Phe Leu Ile Leu Arg Val Lys Gln Arg Tyr Pro Leu Pro Leu Pro Pro
             20                  25                  30 gga cca aaa cca tgg ccg gtg tta gga aac ctt ccc cac ctg ggc aag       145
Gly Pro Lys Pro Trp Pro Val Leu Gly Asn Leu Pro His Leu Gly Lys
         35                  40                  45 aag cct cac cag tcg att gcg gcc atg gct gag agg tac ggc ccc ctc       193
Lys Pro His Gln Ser Ile Ala Ala Met Ala Glu Arg Tyr Gly Pro Leu
     50                  55                  60 atg cac ctc cgc cta gga ttc gtg gac gtg gtt gtg gcc gcc tcc gcc       241
Met His Leu Arg Leu Gly Phe Val Asp Val Val Val Ala Ala Ser Ala
 65                  70                  75                  80 gcc gtg gcc gct cag ttc ttg aaa gtt cac gac tcg aac ttc tcc aac       289
Ala Val Ala Ala Gln Phe Leu Lys Val His Asp Ser Asn Phe Ser Asn
                 85                  90                  95 cgg ccg ccg aac tcc ggc gcg gaa cac att gct tat aac tat caa gac       337
Arg Pro Pro Asn Ser Gly Ala Glu His Ile Ala Tyr Asn Tyr Gln Asp
            100                 105                 110 ctc gtc ttc gcg ccc tac ggc ccg cgg tgg cgc atg ctt agg aag atc       385
Leu Val Phe Ala Pro Tyr Gly Pro Arg Trp Arg Met Leu Arg Lys Ile
        115                 120                 125 acc tcc gtg cat ctc ttc tcg gcc aag gcg ttg gat gac ttc tgc cat       433
Thr Ser Val His Leu Phe Ser Ala Lys Ala Leu Asp Asp Phe Cys His
    130                 135                 140 gtt cgc cag gaa gag gtt gca act ctg aca cgc agt cta gca agt gca       481
Val Arg Gln Glu Glu Val Ala Thr Leu Thr Arg Ser Leu Ala Ser Ala
145                 150                 155                 160 ggc aaa act cca gta aaa cta ggg cag tta cta aac gtg tgc acc acg       529
Gly Lys Thr Pro Val Lys Leu Gly Gln Leu Leu Asn Val Cys Thr Thr
                165                 170                 175 aac gcc cta gct cgt gta atg cta ggg cgg aag gtc ttt aat gac gga       577
Asn Ala Leu Ala Arg Val Met Leu Gly Arg Lys Val Phe Asn Asp Gly
            180                 185                 190 ggt agc aag agc gac cca aag gcg gag gag ttc aag tcg atg gtg gag       625
Gly Ser Lys Ser Asp Pro Lys Ala Glu Glu Phe Lys Ser Met Val Glu
        195                 200                 205 gag atg atg gtg ttg gcc gga agt ttt aac atc ggc gat ttc att ccg       673
Glu Met Met Val Leu Ala Gly Ser Phe Asn Ile Gly Asp Phe Ile Pro
    210                 215                 220 gtc ttg ggt tgg ttt gac gtt cag ggt atc gta ggg aag atg aag aaa       721
Val Leu Gly Trp Phe Asp Val Gln Gly Ile Val Gly Lys Met Lys Lys
225                 230                 235                 240 cta cac gcg cgt ttt gat gcg ttc ttg aac acc att cta gag gaa cac       769
Leu His Ala Arg Phe Asp Ala Phe Leu Asn Thr Ile Leu Glu Glu His
                245                 250                 255 aaa tgt gtc aac aat caa cac acg acg ttg tcg aaa gat gtg gac ttc       817
Lys Cys Val Asn Asn Gln His Thr Thr Leu Ser Lys Asp Val Asp Phe
            260                 265                 270 ttg agc acc cta att agg ctc aaa gat aat ggg gct gat atg gat tgt       865
Leu Ser Thr Leu Ile Arg Leu Lys Asp Asn Gly Ala Asp Met Asp Cys
        275                 280                 285 gaa gag gga aaa ctc acc gac act gaa att aag gct ttg ctc ttg aac       913
Glu Glu Gly Lys Leu Thr Asp Thr Glu Ile Lys Ala Leu Leu Leu Asn
```

```
                    290                 295                 300
ctg ttc aca gct ggg act gat aca tca tct agc act gtg gag tgg gca    961
Leu Phe Thr Ala Gly Thr Asp Thr Ser Ser Ser Thr Val Glu Trp Ala
305                 310                 315                 320 atc gca gaa cta cta cgc aac cca aaa atc tta aac caa gca caa caa   1009
Ile Ala Glu Leu Leu Arg Asn Pro Lys Ile Leu Asn Gln Ala Gln Gln
                325                 330                 335 gag ctt gac tta gtg gtg ggt caa aat cag cta gtc aca gaa tct gac   1057
Glu Leu Asp Leu Val Val Gly Gln Asn Gln Leu Val Thr Glu Ser Asp
            340                 345                 350 tta acc gat cta cct ttc ctg caa gca ata gtg aag gag acc ttc agg   1105
Leu Thr Asp Leu Pro Phe Leu Gln Ala Ile Val Lys Glu Thr Phe Arg
        355                 360                 365 cta cac cca tcc acc cca ctc tct ctt cca aga atg gga gct cag ggt   1153
Leu His Pro Ser Thr Pro Leu Ser Leu Pro Arg Met Gly Ala Gln Gly
    370                 375                 380 tgc gag atc aat ggc tac ttc atc ccc aaa ggc gca acg ctt ttg gtc   1201
Cys Glu Ile Asn Gly Tyr Phe Ile Pro Lys Gly Ala Thr Leu Leu Val
385                 390                 395                 400 aac gtt tgg gcc ata gct cgt gat ccc aat gtg tgg aca aat cct ctt   1249
Asn Val Trp Ala Ile Ala Arg Asp Pro Asn Val Trp Thr Asn Pro Leu
                405                 410                 415 gag ttc aac cca cac cga ttc ttg cct ggt gga gaa aag ccc aac gtg   1297
Glu Phe Asn Pro His Arg Phe Leu Pro Gly Gly Glu Lys Pro Asn Val
            420                 425                 430 gat att aaa ggg aat gac ttt gaa gtg att cct ttt gga gcc ggg cgt   1345
Asp Ile Lys Gly Asn Asp Phe Glu Val Ile Pro Phe Gly Ala Gly Arg
        435                 440                 445 aga ata tgc tct ggg atg agt ttg ggg ata agg atg gtt cac ctg ttg   1393
Arg Ile Cys Ser Gly Met Ser Leu Gly Ile Arg Met Val His Leu Leu
    450                 455                 460 gtt gca act ttg gtg cat gct ttt gat tgg gat ttg gtg aat gga caa   1441
Val Ala Thr Leu Val His Ala Phe Asp Trp Asp Leu Val Asn Gly Gln
465                 470                 475                 480 tct gta gag acg ctc aat atg gag gaa gct tat ggt ctc acc ctt caa   1489
Ser Val Glu Thr Leu Asn Met Glu Glu Ala Tyr Gly Leu Thr Leu Gln
                485                 490                 495 cga gct gtt cct ttg atg ttg cat cca aag ccc aga tta caa cca cat   1537
Arg Ala Val Pro Leu Met Leu His Pro Lys Pro Arg Leu Gln Pro His
            500                 505                 510 ctc tat act ctc aat taa attgcaattt gattttggtg attatacaat         1585
Leu Tyr Thr Leu Asn
        515 tataatcgag ggacatagga tccccattta tttatattca gttataagag acttccaaca  1645 aaggtctagc tttcgacctt aaaagttgta aaagaggtcc tacatatgta aaagcccgcc  1705 aaaggaaaac tggttgtatt caattccgct aggccttgtc cgaaagacct catgaagact  1765 acaaggtca tatataatgg taaacccagt gtatttgttg taaaaaaaaa aaaaaaaa    1824
```

<210> SEQ ID NO 21
<211> LENGTH: 517
<212> TYPE: PRT
<213> ORGANISM: Jap. Morning Glory

<400> SEQUENCE: 21

```
Ser Leu Thr Leu Ile Phe Cys Thr Leu Val Phe Ala Ile Phe Leu Tyr
 1               5                  10                  15

Phe Leu Ile Leu Arg Val Lys Gln Arg Tyr Pro Leu Pro Leu Pro Pro
            20                  25                  30
```

```
Gly Pro Lys Pro Trp Pro Val Leu Gly Asn Leu Pro His Leu Gly Lys
         35                  40                  45

Lys Pro His Gln Ser Ile Ala Ala Met Ala Glu Arg Tyr Gly Pro Leu
     50                  55                  60

Met His Leu Arg Leu Gly Phe Val Asp Val Val Ala Ala Ser Ala
 65                  70                  75                  80

Ala Val Ala Ala Gln Phe Leu Lys Val His Asp Ser Asn Phe Ser Asn
                 85                  90                  95

Arg Pro Pro Asn Ser Gly Ala Glu His Ile Ala Tyr Asn Tyr Gln Asp
                100                 105                 110

Leu Val Phe Ala Pro Tyr Gly Pro Arg Trp Arg Met Leu Arg Lys Ile
             115                 120                 125

Thr Ser Val His Leu Phe Ser Ala Lys Ala Leu Asp Asp Phe Cys His
             130                 135                 140

Val Arg Gln Glu Glu Val Ala Thr Leu Thr Arg Ser Leu Ala Ser Ala
145                 150                 155                 160

Gly Lys Thr Pro Val Lys Leu Gly Gln Leu Leu Asn Val Cys Thr Thr
                165                 170                 175

Asn Ala Leu Ala Arg Val Met Leu Gly Arg Lys Val Phe Asn Asp Gly
             180                 185                 190

Gly Ser Lys Ser Asp Pro Lys Ala Glu Glu Phe Lys Ser Met Val Glu
         195                 200                 205

Glu Met Met Val Leu Ala Gly Ser Phe Asn Ile Gly Asp Phe Ile Pro
     210                 215                 220

Val Leu Gly Trp Phe Asp Val Gln Gly Ile Val Gly Lys Met Lys Lys
225                 230                 235                 240

Leu His Ala Arg Phe Asp Ala Phe Leu Asn Thr Ile Leu Glu Glu His
                245                 250                 255

Lys Cys Val Asn Asn Gln His Thr Thr Leu Ser Lys Asp Val Asp Phe
             260                 265                 270

Leu Ser Thr Leu Ile Arg Leu Lys Asp Asn Gly Ala Asp Met Asp Cys
         275                 280                 285

Glu Glu Gly Lys Leu Thr Asp Thr Glu Ile Lys Ala Leu Leu Leu Asn
 290                 295                 300

Leu Phe Thr Ala Gly Thr Asp Thr Ser Ser Thr Val Glu Trp Ala
305                 310                 315                 320

Ile Ala Glu Leu Leu Arg Asn Pro Lys Ile Leu Asn Gln Ala Gln Gln
                325                 330                 335

Glu Leu Asp Leu Val Val Gly Gln Asn Gln Leu Val Thr Glu Ser Asp
             340                 345                 350

Leu Thr Asp Leu Pro Phe Leu Gln Ala Ile Val Lys Glu Thr Phe Arg
         355                 360                 365

Leu His Pro Ser Thr Pro Leu Ser Leu Pro Arg Met Gly Ala Gln Gly
     370                 375                 380

Cys Glu Ile Asn Gly Tyr Phe Ile Pro Lys Gly Ala Thr Leu Leu Val
385                 390                 395                 400

Asn Val Trp Ala Ile Ala Arg Asp Pro Asn Val Trp Thr Asn Pro Leu
                405                 410                 415

Glu Phe Asn Pro His Arg Phe Leu Pro Gly Gly Glu Lys Pro Asn Val
             420                 425                 430

Asp Ile Lys Gly Asn Asp Phe Glu Val Ile Pro Phe Gly Ala Gly Arg
         435                 440                 445
```

-continued

```
Arg Ile Cys Ser Gly Met Ser Leu Gly Ile Arg Met Val His Leu Leu
    450                 455                 460

Val Ala Thr Leu Val His Ala Phe Asp Trp Asp Leu Val Asn Gly Gln
465                 470                 475                 480

Ser Val Glu Thr Leu Asn Met Glu Glu Ala Tyr Gly Leu Thr Leu Gln
                485                 490                 495

Arg Ala Val Pro Leu Met Leu His Pro Lys Pro Arg Leu Gln Pro His
                500                 505                 510

Leu Tyr Thr Leu Asn
        515

<210> SEQ ID NO 22
<211> LENGTH: 1667
<212> TYPE: DNA
<213> ORGANISM: Gentian
<220> FEATURE:
<221> NAME/KEY: CDS
<222> LOCATION: (1)..(1431)

<400> SEQUENCE: 22 ccc atc ctc gga aac atc ccc cat ctc ggc tcc aaa ccg cac caa aca      48
Pro Ile Leu Gly Asn Ile Pro His Leu Gly Ser Lys Pro His Gln Thr
  1               5                  10                  15 ctc gcg gaa atg gcg aaa acc tac ggt ccg ctc atg cac ttg aag ttc      96
Leu Ala Glu Met Ala Lys Thr Tyr Gly Pro Leu Met His Leu Lys Phe
             20                  25                  30 ggg ctt aag gac gcg gtg gtg gcg tcg tct gcg tcg gtg gca gag cag     144
Gly Leu Lys Asp Ala Val Val Ala Ser Ser Ala Ser Val Ala Glu Gln
         35                  40                  45 ttt ctg aag aaa cac gac gtg aat ttc tcg aac cgg ccg cca aac tcc     192
Phe Leu Lys Lys His Asp Val Asn Phe Ser Asn Arg Pro Pro Asn Ser
     50                  55                  60 ggg gcc aaa cat ata gct tat aac tat cag gac ctg gta ttc gct ccc     240
Gly Ala Lys His Ile Ala Tyr Asn Tyr Gln Asp Leu Val Phe Ala Pro
 65                  70                  75                  80 tat gga ccc cgg tgg cgg ttg ctt agg aaa atc tgt tcc gtc cat ctt     288
Tyr Gly Pro Arg Trp Arg Leu Leu Arg Lys Ile Cys Ser Val His Leu
                 85                  90                  95 ttc tcg tct aag gcc ttg gat gac ttt cag cat gtt cga cat gag gag     336
Phe Ser Ser Lys Ala Leu Asp Asp Phe Gln His Val Arg His Glu Glu
            100                 105                 110 ata tgc atc ctt ata cga gca ata gcg agt ggc ggt cat gct ccg gtg     384
Ile Cys Ile Leu Ile Arg Ala Ile Ala Ser Gly Gly His Ala Pro Val
        115                 120                 125 aat tta ggc aag tta tta gga gtg tgc aca acc aat gcc ctg gca aga     432
Asn Leu Gly Lys Leu Leu Gly Val Cys Thr Thr Asn Ala Leu Ala Arg
    130                 135                 140 gtg atg ctt gga aga aga gta ttc gaa ggc gac ggc ggc gag aat ccg     480
Val Met Leu Gly Arg Arg Val Phe Glu Gly Asp Gly Gly Glu Asn Pro
145                 150                 155                 160 cat gcc gac gag ttt aaa tca atg gtg gtg gag att atg gta tta gcc     528
His Ala Asp Glu Phe Lys Ser Met Val Val Glu Ile Met Val Leu Ala
                165                 170                 175 ggt gca ttc aac ttg ggt gat ttc atc ccg gtt cta gat tgg ttc gat     576
Gly Ala Phe Asn Leu Gly Asp Phe Ile Pro Val Leu Asp Trp Phe Asp
            180                 185                 190 ttg caa gga att gct ggt aaa atg aag aaa ctt cat gcc cgt ttc gac     624
Leu Gln Gly Ile Ala Gly Lys Met Lys Lys Leu His Ala Arg Phe Asp
        195                 200                 205 aag ttt tta aat ggg atc cta gaa gat cgt aaa tct aac ggc tct aat     672
```

-continued

```
                    Lys Phe Leu Asn Gly Ile Leu Glu Asp Arg Lys Ser Asn Gly Ser Asn
                        210                 215                 220 gga gct gaa caa tac gtg gac ttg ctc agt gtg ttg atc tct ctt caa         720
Gly Ala Glu Gln Tyr Val Asp Leu Leu Ser Val Leu Ile Ser Leu Gln
225                 230                 235                 240 gat agt aat atc gac ggt ggt gac gaa gga acc aaa ctc aca gat act         768
Asp Ser Asn Ile Asp Gly Gly Asp Glu Gly Thr Lys Leu Thr Asp Thr
                245                 250                 255 gaa atc aaa gct ctc ctt ttg aac ttg ttc ata gcc gga aca gac act         816
Glu Ile Lys Ala Leu Leu Leu Asn Leu Phe Ile Ala Gly Thr Asp Thr
            260                 265                 270 tca agt agt act gta gaa tgg gcc atg gca gaa cta atc cga aac cca         864
Ser Ser Ser Thr Val Glu Trp Ala Met Ala Glu Leu Ile Arg Asn Pro
        275                 280                 285 aag tta cta gtc caa gcc caa gaa gag cta gac aga gta gtc ggg ccg         912
Lys Leu Leu Val Gln Ala Gln Glu Glu Leu Asp Arg Val Val Gly Pro
    290                 295                 300 aac cga ttc gta acc gaa tct gat ctt cct caa ctg aca ttc ctt caa         960
Asn Arg Phe Val Thr Glu Ser Asp Leu Pro Gln Leu Thr Phe Leu Gln
305                 310                 315                 320 gcc gtc atc aaa gag act ttc agg ctt cat cca tcc acc cca ctc tct        1008
Ala Val Ile Lys Glu Thr Phe Arg Leu His Pro Ser Thr Pro Leu Ser
                325                 330                 335 ctt cca cga atg gcg gcg gag gac tgt gag atc aat ggg tat tat gtc        1056
Leu Pro Arg Met Ala Ala Glu Asp Cys Glu Ile Asn Gly Tyr Tyr Val
            340                 345                 350 tca gaa ggt tcg aca ttg ctc gtc aat gtg tgg gcc ata gct cgt gat        1104
Ser Glu Gly Ser Thr Leu Leu Val Asn Val Trp Ala Ile Ala Arg Asp
        355                 360                 365 cca aat gcg tgg gcc aat cca cta gat ttc aac ccg act cgt ttc ttg        1152
Pro Asn Ala Trp Ala Asn Pro Leu Asp Phe Asn Pro Thr Arg Phe Leu
    370                 375                 380 gcc ggt gga gag aag cct aat gtt gat gtt aaa ggg aat gat ttt gaa        1200
Ala Gly Gly Glu Lys Pro Asn Val Asp Val Lys Gly Asn Asp Phe Glu
385                 390                 395                 400 gtg ata cct ttc ggt gct ggg cgc agg ata tgt gcc gga atg agc tta        1248
Val Ile Pro Phe Gly Ala Gly Arg Arg Ile Cys Ala Gly Met Ser Leu
                405                 410                 415 ggt ata cgg atg gtt caa cta gta acg gct tcg tta gtt cat tcg ttt        1296
Gly Ile Arg Met Val Gln Leu Val Thr Ala Ser Leu Val His Ser Phe
            420                 425                 430 gat tgg gct ttg ttg gat gga ctt aaa ccc gag aag ctt gac atg gag        1344
Asp Trp Ala Leu Leu Asp Gly Leu Lys Pro Glu Lys Leu Asp Met Glu
        435                 440                 445 gaa ggt tat gga cta acg ctt caa cga gct tca cct tta atc gtc cat        1392
Glu Gly Tyr Gly Leu Thr Leu Gln Arg Ala Ser Pro Leu Ile Val His
    450                 455                 460 cca aag ccg agg ctc tcg gct caa gtt tat tgt atg taa caagtttgtg        1441
Pro Lys Pro Arg Leu Ser Ala Gln Val Tyr Cys Met
465                 470                 475 aagccagtct gatttcagtt ggatttgtag ttattttatg atcatttggt attttatttt     1501
gtatttcggt tgaatacaat aaagggaagg tggatcgtct gctgtataat agcgacgttt     1561
taacgtgttg tgatagtacc gtgttttact aaaacgatgt cgtttgattt tttatagtat     1621
taaaaaaata aacagctgga ttttgaacca aaaaaaaaaa aaaaaa                    1667

<210> SEQ ID NO 23
<211> LENGTH: 476
<212> TYPE: PRT
```

<213> ORGANISM: Gentian

<400> SEQUENCE: 23

```
Pro Ile Leu Gly Asn Ile Pro His Leu Gly Ser Lys Pro His Gln Thr
  1               5                  10                  15

Leu Ala Glu Met Ala Lys Thr Tyr Gly Pro Leu Met His Leu Lys Phe
             20                  25                  30

Gly Leu Lys Asp Ala Val Val Ala Ser Ser Ala Ser Val Ala Glu Gln
         35                  40                  45

Phe Leu Lys Lys His Asp Val Asn Phe Ser Asn Arg Pro Pro Asn Ser
     50                  55                  60

Gly Ala Lys His Ile Ala Tyr Asn Tyr Gln Asp Leu Val Phe Ala Pro
 65                  70                  75                  80

Tyr Gly Pro Arg Trp Arg Leu Leu Arg Lys Ile Cys Ser Val His Leu
                 85                  90                  95

Phe Ser Ser Lys Ala Leu Asp Asp Phe Gln His Val Arg His Glu Glu
                100                 105                 110

Ile Cys Ile Leu Ile Arg Ala Ile Ala Ser Gly Gly His Ala Pro Val
            115                 120                 125

Asn Leu Gly Lys Leu Leu Gly Val Cys Thr Thr Asn Ala Leu Ala Arg
        130                 135                 140

Val Met Leu Gly Arg Arg Val Phe Glu Gly Asp Gly Glu Asn Pro
145                 150                 155                 160

His Ala Asp Glu Phe Lys Ser Met Val Val Glu Ile Met Val Leu Ala
                165                 170                 175

Gly Ala Phe Asn Leu Gly Asp Phe Ile Pro Val Leu Asp Trp Phe Asp
            180                 185                 190

Leu Gln Gly Ile Ala Gly Lys Met Lys Lys Leu His Ala Arg Phe Asp
        195                 200                 205

Lys Phe Leu Asn Gly Ile Leu Glu Asp Arg Lys Ser Asn Gly Ser Asn
    210                 215                 220

Gly Ala Glu Gln Tyr Val Asp Leu Leu Ser Val Leu Ile Ser Leu Gln
225                 230                 235                 240

Asp Ser Asn Ile Asp Gly Gly Asp Glu Gly Thr Lys Leu Thr Asp Thr
                245                 250                 255

Glu Ile Lys Ala Leu Leu Leu Asn Leu Phe Ile Ala Gly Thr Asp Thr
            260                 265                 270

Ser Ser Ser Thr Val Glu Trp Ala Met Ala Glu Leu Ile Arg Asn Pro
        275                 280                 285

Lys Leu Leu Val Gln Ala Gln Glu Glu Leu Asp Arg Val Val Gly Pro
    290                 295                 300

Asn Arg Phe Val Thr Glu Ser Asp Leu Pro Gln Leu Thr Phe Leu Gln
305                 310                 315                 320

Ala Val Ile Lys Glu Thr Phe Arg Leu His Pro Ser Thr Pro Leu Ser
                325                 330                 335

Leu Pro Arg Met Ala Ala Glu Asp Cys Glu Ile Asn Gly Tyr Tyr Val
            340                 345                 350

Ser Glu Gly Ser Thr Leu Leu Val Asn Val Trp Ala Ile Ala Arg Asp
        355                 360                 365

Pro Asn Ala Trp Ala Asn Pro Leu Asp Phe Asn Pro Thr Arg Phe Leu
    370                 375                 380

Ala Gly Gly Glu Lys Pro Asn Val Asp Val Lys Gly Asn Asp Phe Glu
385                 390                 395                 400
```

-continued

```
Val Ile Pro Phe Gly Ala Gly Arg Arg Ile Cys Ala Gly Met Ser Leu
                405                 410                 415

Gly Ile Arg Met Val Gln Leu Val Thr Ala Ser Leu Val His Ser Phe
            420                 425                 430

Asp Trp Ala Leu Leu Asp Gly Leu Lys Pro Glu Lys Leu Asp Met Glu
        435                 440                 445

Glu Gly Tyr Gly Leu Thr Leu Gln Arg Ala Ser Pro Leu Ile Val His
    450                 455                 460

Pro Lys Pro Arg Leu Ser Ala Gln Val Tyr Cys Met
465                 470                 475

<210> SEQ ID NO 24
<211> LENGTH: 1214
<212> TYPE: DNA
<213> ORGANISM: Lisianthus
<220> FEATURE:
<221> NAME/KEY: CDS
<222> LOCATION: (2)..(1093)

<400> SEQUENCE: 24 t cgc atc ctc acg cga tct ata gcg agt gct ggg gaa aat ccg att aac        49
  Arg Ile Leu Thr Arg Ser Ile Ala Ser Ala Gly Glu Asn Pro Ile Asn
  1               5                   10                  15 tta ggt caa tta ctc ggg gtg tgt acc aca aat gct ctg gcg aga gtg          97
Leu Gly Gln Leu Leu Gly Val Cys Thr Thr Asn Ala Leu Ala Arg Val
            20                  25                  30 atg ctt gga agg agg gta ttc ggc gat ggg agc ggc ggc gta gat cct         145
Met Leu Gly Arg Arg Val Phe Gly Asp Gly Ser Gly Gly Val Asp Pro
        35                  40                  45 cag gcg gac gag ttc aaa tcc atg gtg gtg gaa atc atg gtg ttg gcc         193
Gln Ala Asp Glu Phe Lys Ser Met Val Val Glu Ile Met Val Leu Ala
    50                  55                  60 ggc gcg ttt aat cta ggt gat ttt att ccc gct ctt gat tgg ttc gat         241
Gly Ala Phe Asn Leu Gly Asp Phe Ile Pro Ala Leu Asp Trp Phe Asp
65                  70                  75                  80 ctg cag gga att acg gca aaa atg aag aaa gtt cac gct cgt ttc gat         289
Leu Gln Gly Ile Thr Ala Lys Met Lys Lys Val His Ala Arg Phe Asp
                85                  90                  95 gcg ttc tta gac gcg atc ctt gag gag cac aaa tcc aac ggc tct cgc         337
Ala Phe Leu Asp Ala Ile Leu Glu Glu His Lys Ser Asn Gly Ser Arg
            100                 105                 110 gga gct aag caa cac gtt gac ttg ctg agt atg ttg atc tcc ctt caa         385
Gly Ala Lys Gln His Val Asp Leu Leu Ser Met Leu Ile Ser Leu Gln
        115                 120                 125 gat aat aac att gat ggt gaa agt ggc gcc aaa ctc act gat aca gaa         433
Asp Asn Asn Ile Asp Gly Glu Ser Gly Ala Lys Leu Thr Asp Thr Glu
    130                 135                 140 atc aaa gct ttg ctt ctg aac ttg ttc acg gct gga aca gac acg tca         481
Ile Lys Ala Leu Leu Leu Asn Leu Phe Thr Ala Gly Thr Asp Thr Ser
145                 150                 155                 160 tca agt act gtg gag tgg gca atc gca gag cta atc cga aac cca gaa         529
Ser Ser Thr Val Glu Trp Ala Ile Ala Glu Leu Ile Arg Asn Pro Glu
                165                 170                 175 gta ttg gtt caa gcc caa caa gag ctc gat aga gta gtt ggg cca agt         577
Val Leu Val Gln Ala Gln Gln Glu Leu Asp Arg Val Val Gly Pro Ser
            180                 185                 190 cgt ctt gtg acc gaa tct gat ctg cct caa ttg gca ttc ctt caa gct         625
Arg Leu Val Thr Glu Ser Asp Leu Pro Gln Leu Ala Phe Leu Gln Ala
        195                 200                 205 gtc atc aaa gag act ttc aga ctt cat cca tcc act cca ctc tct ctt         673
```

```
                Val Ile Lys Glu Thr Phe Arg Leu His Pro Ser Thr Pro Leu Ser Leu
                    210                 215                 220 cca cga atg gct tca gag ggt tgt gaa atc aat gga tac tcc atc cca        721
Pro Arg Met Ala Ser Glu Gly Cys Glu Ile Asn Gly Tyr Ser Ile Pro
225                 230                 235                 240 aag ggt tcg aca ttg ctc gtt aac gta tgg tcc ata gcc cgt gat cct        769
Lys Gly Ser Thr Leu Leu Val Asn Val Trp Ser Ile Ala Arg Asp Pro
                245                 250                 255 agt ata tgg gcc gac cca tta gaa ttt agg ccg gca cgt ttc ttg ccc        817
Ser Ile Trp Ala Asp Pro Leu Glu Phe Arg Pro Ala Arg Phe Leu Pro
            260                 265                 270 ggc gga gaa aag ccc aat gtt gat gtg aga ggc aat gat ttt gag gtc        865
Gly Gly Glu Lys Pro Asn Val Asp Val Arg Gly Asn Asp Phe Glu Val
        275                 280                 285 ata cca ttt ggt gct gga cgt agg ata tgt gct gga atg agc ttg ggt        913
Ile Pro Phe Gly Ala Gly Arg Arg Ile Cys Ala Gly Met Ser Leu Gly
    290                 295                 300 tta aga atg gtt caa ctt tcg aca gct act ttg gtt cat tcg ttt aat        961
Leu Arg Met Val Gln Leu Ser Thr Ala Thr Leu Val His Ser Phe Asn
305                 310                 315                 320 tgg gat ttg ctg aat ggg atg agc cca gat aaa ctt gac atg gaa gaa       1009
Trp Asp Leu Leu Asn Gly Met Ser Pro Asp Lys Leu Asp Met Glu Glu
                325                 330                 335 gct tat ggg ctt aca ttg caa cgg gct tca cct ttg att gtc cac cca       1057
Ala Tyr Gly Leu Thr Leu Gln Arg Ala Ser Pro Leu Ile Val His Pro
            340                 345                 350 aag ccc agg ctt gct agc tct atg tat gtt aaa tga aattatgctg            1103
Lys Pro Arg Leu Ala Ser Ser Met Tyr Val Lys
        355                 360 tgcgaataat tccttattta tagcaggaaa tgtcatcttg aattatgtgt aatgttcttc      1163
taactttcga tggaagtgca aaacaagttt tattaaaaaa aaaaaaaaaa a               1214

<210> SEQ ID NO 25
<211> LENGTH: 363
<212> TYPE: PRT
<213> ORGANISM: Lisianthus

<400> SEQUENCE: 25

Arg Ile Leu Thr Arg Ser Ile Ala Ser Ala Gly Glu Asn Pro Ile Asn
 1               5                  10                  15

Leu Gly Gln Leu Leu Gly Val Cys Thr Thr Asn Ala Leu Ala Arg Val
            20                  25                  30

Met Leu Gly Arg Arg Val Phe Gly Asp Gly Ser Gly Val Asp Pro
        35                  40                  45

Gln Ala Asp Glu Phe Lys Ser Met Val Val Glu Ile Met Val Leu Ala
    50                  55                  60

Gly Ala Phe Asn Leu Gly Asp Phe Ile Pro Ala Leu Asp Trp Phe Asp
65                  70                  75                  80

Leu Gln Gly Ile Thr Ala Lys Met Lys Lys Val His Ala Arg Phe Asp
                85                  90                  95

Ala Phe Leu Asp Ala Ile Leu Glu Glu His Lys Ser Asn Gly Ser Arg
            100                 105                 110

Gly Ala Lys Gln His Val Asp Leu Leu Ser Met Leu Ile Ser Leu Gln
        115                 120                 125

Asp Asn Asn Ile Asp Gly Glu Ser Gly Ala Lys Leu Thr Asp Thr Glu
    130                 135                 140

Ile Lys Ala Leu Leu Leu Asn Leu Phe Thr Ala Gly Thr Asp Thr Ser
```

```
145                 150                 155                 160
Ser Ser Thr Val Glu Trp Ala Ile Ala Glu Leu Ile Arg Asn Pro Glu
                165                 170                 175

Val Leu Val Gln Ala Gln Gln Glu Leu Asp Arg Val Val Gly Pro Ser
                180                 185                 190

Arg Leu Val Thr Glu Ser Asp Leu Pro Gln Leu Ala Phe Leu Gln Ala
                195                 200                 205

Val Ile Lys Glu Thr Phe Arg Leu His Pro Ser Thr Pro Leu Ser Leu
    210                 215                 220

Pro Arg Met Ala Ser Glu Gly Cys Glu Ile Asn Gly Tyr Ser Ile Pro
225                 230                 235                 240

Lys Gly Ser Thr Leu Leu Val Asn Val Trp Ser Ile Ala Arg Asp Pro
                245                 250                 255

Ser Ile Trp Ala Asp Pro Leu Glu Phe Arg Pro Ala Arg Phe Leu Pro
                260                 265                 270

Gly Gly Glu Lys Pro Asn Val Asp Val Arg Gly Asn Asp Phe Glu Val
                275                 280                 285

Ile Pro Phe Gly Ala Gly Arg Arg Ile Cys Ala Gly Met Ser Leu Gly
                290                 295                 300

Leu Arg Met Val Gln Leu Ser Thr Ala Thr Leu Val His Ser Phe Asn
305                 310                 315                 320

Trp Asp Leu Leu Asn Gly Met Ser Pro Asp Lys Leu Asp Met Glu Glu
                325                 330                 335

Ala Tyr Gly Leu Thr Leu Gln Arg Ala Ser Pro Leu Ile Val His Pro
                340                 345                 350

Lys Pro Arg Leu Ala Ser Ser Met Tyr Val Lys
                355                 360

<210> SEQ ID NO 26
<211> LENGTH: 1757
<212> TYPE: DNA
<213> ORGANISM: Petunia sp.
<220> FEATURE:
<221> NAME/KEY: CDS
<222> LOCATION: (35)..(1525)

<400> SEQUENCE: 26
ccgttgctgt cgagaaaaca gaaagaagag aaaa atg gac tac gtg aat att ttg        55
                                    Met Asp Tyr Val Asn Ile Leu
                                     1               5 ctg gga ctg ttt ttc act tgg ttc ttg gtg aat gga ctc atg tca ctt       103
Leu Gly Leu Phe Phe Thr Trp Phe Leu Val Asn Gly Leu Met Ser Leu
        10                  15                  20 cga aga aga aaa atc tct aag aaa ctt cca cca ggt cca ttt cct ttg       151
Arg Arg Arg Lys Ile Ser Lys Lys Leu Pro Pro Gly Pro Phe Pro Leu
    25                  30                  35 cct atc atc gga aat ctt cac tta ctt ggt aat cat cct cac aaa tca       199
Pro Ile Ile Gly Asn Leu His Leu Leu Gly Asn His Pro His Lys Ser
 40                  45                  50                  55 ctt gct caa ctt gca aaa att cat ggt cct att atg aat ctc aaa tta       247
Leu Ala Gln Leu Ala Lys Ile His Gly Pro Ile Met Asn Leu Lys Leu
                 60                  65                  70 ggc caa cta aac aca gtg gtc att tca tca tca gtc gtg gca aga gaa       295
Gly Gln Leu Asn Thr Val Val Ile Ser Ser Ser Val Val Ala Arg Glu
        75                  80                  85 gtc ttg caa aaa caa gac tta aca ttt tcc aat agg ttt gtc ccg gac       343
Val Leu Gln Lys Gln Asp Leu Thr Phe Ser Asn Arg Phe Val Pro Asp
        90                  95                 100
```

-continued

| | |
|---|---|
| gta gtc cat gtc cga aat cac tcc gat ttt tct gtt gtt tgg tta cca<br>Val Val His Val Arg Asn His Ser Asp Phe Ser Val Val Trp Leu Pro<br>105                            110                             115 | 391 |
| gtc aat tct cga tgg aaa acg ctt cgc aaa atc atg aac tct agc atc<br>Val Asn Ser Arg Trp Lys Thr Leu Arg Lys Ile Met Asn Ser Ser Ile<br>120                          125                            130                            135 | 439 |
| ttt tct ggt aac aag ctt gat ggt aat caa cat ctg agg tct aaa aag<br>Phe Ser Gly Asn Lys Leu Asp Gly Asn Gln His Leu Arg Ser Lys Lys<br>140                            145                            150 | 487 |
| gtc caa gag tta att gat tat tgt caa aag tgt gcc aag aat ggc gaa<br>Val Gln Glu Leu Ile Asp Tyr Cys Gln Lys Cys Ala Lys Asn Gly Glu<br>           155                            160                            165 | 535 |
| gca gtg gat ata gga aga gca act ttt gga act act ttg aat ttg cta<br>Ala Val Asp Ile Gly Arg Ala Thr Phe Gly Thr Thr Leu Asn Leu Leu<br>           170                            175                            180 | 583 |
| tcc aac acc att ttc tct aaa gat ttg act aat ccg ttt tct gat tct<br>Ser Asn Thr Ile Phe Ser Lys Asp Leu Thr Asn Pro Phe Ser Asp Ser<br>185                            190                             195 | 631 |
| gct aaa gag ttt aag gaa ttg gtt tgg aac att atg gtt gag gct gga<br>Ala Lys Glu Phe Lys Glu Leu Val Trp Asn Ile Met Val Glu Ala Gly<br>200                            205                            210                            215 | 679 |
| aaa ccc aat ttg gtg gac tac ttt cct ttc ctt gag aaa att gat ccg<br>Lys Pro Asn Leu Val Asp Tyr Phe Pro Phe Leu Glu Lys Ile Asp Pro<br>                       220                            225                            230 | 727 |
| caa ggt ata aag cga cgc atg act aat aat ttt act aag ttt ctt ggc<br>Gln Gly Ile Lys Arg Arg Met Thr Asn Asn Phe Thr Lys Phe Leu Gly<br>                 235                            240                            245 | 775 |
| ctt atc agc ggt ttg att gat gac cgg tta aag gaa agg aat cta agg<br>Leu Ile Ser Gly Leu Ile Asp Asp Arg Leu Lys Glu Arg Asn Leu Arg<br>250                            255                            260 | 823 |
| gac aat gca aat att gat gtt tta gac gcc ctt ctc aac att agc caa<br>Asp Asn Ala Asn Ile Asp Val Leu Asp Ala Leu Leu Asn Ile Ser Gln<br>           265                            270                            275 | 871 |
| gag aac cca gaa gag att gac agg aat caa atc gag cag ttg tgt ctg<br>Glu Asn Pro Glu Glu Ile Asp Arg Asn Gln Ile Glu Gln Leu Cys Leu<br>280                            285                            290                            295 | 919 |
| gac ttg ttt gca gca ggg act gat act aca tcg aat acc ttg gag tgg<br>Asp Leu Phe Ala Ala Gly Thr Asp Thr Thr Ser Asn Thr Leu Glu Trp<br>                       300                            305                            310 | 967 |
| gca atg gca gaa cta ctt cag aat cca cac aca ttg cag aaa gca caa<br>Ala Met Ala Glu Leu Leu Gln Asn Pro His Thr Leu Gln Lys Ala Gln<br>                 315                            320                            325 | 1015 |
| gaa gaa ctt gca caa gtc att ggt aaa ggc aaa caa gta gaa gaa gca<br>Glu Glu Leu Ala Gln Val Ile Gly Lys Gly Lys Gln Val Glu Glu Ala<br>330                            335                            340 | 1063 |
| gat gtt gga cga cta cct tac ttg cga tgc ata gtg aaa gaa acc tta<br>Asp Val Gly Arg Leu Pro Tyr Leu Arg Cys Ile Val Lys Glu Thr Leu<br>345                            350                            355 | 1111 |
| cga ata cac cca gcg gct cct ctc tta att cca cgt aaa gtg gag gaa<br>Arg Ile His Pro Ala Ala Pro Leu Leu Ile Pro Arg Lys Val Glu Glu<br>360                            365                            370                            375 | 1159 |
| gac gtt gag ttg tct acc tat att att cca aag gat tca caa gtt cta<br>Asp Val Glu Leu Ser Thr Tyr Ile Ile Pro Lys Asp Ser Gln Val Leu<br>                       380                            385                            390 | 1207 |
| gtg aac gta tgg gca att gga cgc aac tct gat cta tgg gaa aat cct<br>Val Asn Val Trp Ala Ile Gly Arg Asn Ser Asp Leu Trp Glu Asn Pro<br>                 395                            400                            405 | 1255 |
| ttg gtc ttt aag cca gaa agg ttt tgg gag tca gaa ata gat atc cga<br>Leu Val Phe Lys Pro Glu Arg Phe Trp Glu Ser Glu Ile Asp Ile Arg | 1303 |

-continued

```
                410                 415                 420
ggt cga gat ttt gaa ctc att cca ttt ggt gct ggt cga aga att tgc    1351
Gly Arg Asp Phe Glu Leu Ile Pro Phe Gly Ala Gly Arg Arg Ile Cys
        425                 430                 435 cct gga ttg cct ttg gct atg agg atg att cca gta gca cta ggt tca    1399
Pro Gly Leu Pro Leu Ala Met Arg Met Ile Pro Val Ala Leu Gly Ser
440                 445                 450                 455 ttg cta aac tca ttt aat tgg aaa cta tat ggt gga att gca cct aaa    1447
Leu Leu Asn Ser Phe Asn Trp Lys Leu Tyr Gly Gly Ile Ala Pro Lys
                460                 465                 470 gat ttg gac atg cag gaa aag ttt ggc att acc ttg gcg aaa gcc caa    1495
Asp Leu Asp Met Gln Glu Lys Phe Gly Ile Thr Leu Ala Lys Ala Gln
            475                 480                 485 cct ctg cta gct atc cca act ccc ctg tag ctatagggat aaattaagtt      1545
Pro Leu Leu Ala Ile Pro Thr Pro Leu
            490                 495 gaggttttaa gttactagta gattctattg cagctatagg atttctttca ccatcacgta  1605
tgctttaccg ttggatgatg gaaagaaata tctatagctt tgggtttgtt tagtttgcac  1665
ataaaaattg aatgaatgga ataccatgga gttataagaa ataataagac tatgattctt  1725
accctacttg aacaatgaca tggctatttc ac                                1757
```

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
tttttttttt tttttta                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tttttttttt ttttttc                                                 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
tttttttttt ttttttg                                                 18

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide representing a conserved region in plant cytochrome p450
      sequences.

```
<400> SEQUENCE: 30

Trp Ala Ile Gly Arg Asp Pro
  1               5

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: Modified Base
<222> LOCATION: (6)
<223> OTHER INFORMATION: n is inosine
<220> FEATURE:
<221> NAME/KEY: Modified Base
<222> LOCATION: (9)
<223> OTHER INFORMATION: n is inosine
<220> FEATURE:
<221> NAME/KEY: Modified Base
<222> LOCATION: (12)
<223> OTHER INFORMATION: n is inosine
<220> FEATURE:
<221> NAME/KEY: Modified Base
<222> LOCATION: (15)
<223> OTHER INFORMATION: n is inosine

<400> SEQUENCE: 31
tgggcnatng gnmgngaycc                                            20

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide representing a conserved region in plant cytochrome p450
      sequences.

<400> SEQUENCE: 32

Phe Arg Pro Glu Arg Phe
  1               5

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: Modified base
<222> LOCATION: (11)
<223> OTHER INFORMATION: n is inosine
<220> FEATURE:
<221> NAME/KEY: Modified base
<222> LOCATION: (14)
<223> OTHER INFORMATION: n is inosine
<220> FEATURE:
<221> NAME/KEY: Modified base
<222> LOCATION: (20)
<223> OTHER INFORMATION: n is inosine

<400> SEQUENCE: 33
aggaattymg nccngarmgn tt                                         22

<210> SEQ ID NO 34
<211> LENGTH: 32
<212> TYPE: DNA
<213> ORGANISM: Artificial Sequence
```

```
<220> FEATURE:
<223> OTHER INFORMATION: Description of Artificial Sequence:
      oligonucleotide
<220> FEATURE:
<221> NAME/KEY: Modified base
<222> LOCATION: (3)
<223> OTHER INFORMATION: 2853:<223) n is inosine
<220> FEATURE:
<221> NAME/KEY: Modified base
<222> LOCATION: (9)
<223> OTHER INFORMATION: 2858:<223) n is inosine
<220> FEATURE:
<221> NAME/KEY: Modified base
<222> LOCATION: (12)
<223> OTHER INFORMATION: 2863:<223) n is inosine
<220> FEATURE:
<221> NAME/KEY: Modified base
<222> LOCATION: (15)
<223> OTHER INFORMATION: 2868:<223) n is inosine
<220> FEATURE:
<221> NAME/KEY: Modified base
<222> LOCATION: (18)
<223> OTHER INFORMATION: 2874:<223) n is inosine
<220> FEATURE:
<221> NAME/KEY: Modified base
<222> LOCATION: (21)
<223> OTHER INFORMATION: 2879:<223) n is inosine
<220> FEATURE:
<221> NAME/KEY: Modified base
<222> LOCATION: (24)
<223> OTHER INFORMATION: 2884:<223) n is inosine
<220> FEATURE:
<221> NAME/KEY: Modified base
<222> LOCATION: (30)
<223> OTHER INFORMATION: 2889:<223) n is inosine

<400> SEQUENCE: 34
ccnttyggng cnggnmgnmg natntgkscn gg                                32

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide representing a conserved region in plant cytochrome p450
      sequences.
<220> FEATURE:
<221> NAME/KEY: UNSURE
<222> LOCATION: (3)
<223> OTHER INFORMATION: Xaa can be any amino acid.

<400> SEQUENCE: 35

Glu Phe Xaa Pro Glu Arg Phe
 1               5

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: Modified base
<222> LOCATION: (3)
<223> OTHER INFORMATION: n is inosine
<220> FEATURE:
<221> NAME/KEY: Modified base
<222> LOCATION: (7)
<223> OTHER INFORMATION: n is inosine
<220> FEATURE:
<221> NAME/KEY: Modified base
<222> LOCATION: (8)
<223> OTHER INFORMATION: n is inosine
```

```
<220> FEATURE:
<221> NAME/KEY: Modified base
<222> LOCATION: (9)
<223> OTHER INFORMATION: n is inosine
<220> FEATURE:
<221> NAME/KEY: Modified base
<222> LOCATION: (12)
<223> OTHER INFORMATION: n is inosine
<220> FEATURE:
<221> NAME/KEY: Modified base
<222> LOCATION: (15)
<223> OTHER INFORMATION: n is inosine
<220> FEATURE:
<221> NAME/KEY: Modified base
<222> LOCATION: (18)
<223> OTHER INFORMATION: n is inosine

<400> SEQUENCE: 36
ganttynnnc nganmgntt                                            20

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
ccacacgagt agttttggca tttgaccc                                  28

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
gtcttggaca tcacacttca atctg                                     25

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
ccgaattccc cccccc                                               17

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: Modified base
<222> LOCATION: (3)
<223> OTHER INFORMATION: n is inosine
<220> FEATURE:
<221> NAME/KEY: Modified base
<222> LOCATION: (9)
<223> OTHER INFORMATION: n is inosine
<220> FEATURE:
<221> NAME/KEY: Modified base
<222> LOCATION: (12)
```

```
<223> OTHER INFORMATION: n is inosine
<220> FEATURE:
<221> NAME/KEY: Modified base
<222> LOCATION: (18)
<223> OTHER INFORMATION: n is inosine
<220> FEATURE:
<221> NAME/KEY: Modified base
<222> LOCATION: (21)
<223> OTHER INFORMATION: n is inosine
<220> FEATURE:
<221> NAME/KEY: Modified base
<222> LOCATION: (24)
<223> OTHER INFORMATION: n is inosine
<220> FEATURE:
<221> NAME/KEY: Modified base
<222> LOCATION: (30)
<223> OTHER INFORMATION: n is inosine

<400> SEQUENCE: 40
ccnggrcana tnckyytncc ngcnccraan gg                                   32

<210> SEQ ID NO 41
<211> LENGTH: 496
<212> TYPE: PRT
<213> ORGANISM: Petunia sp.

<400> SEQUENCE: 41
```

Met Asp Tyr Val Asn Ile Leu Leu Gly Leu Phe Phe Thr Trp Phe Leu
 1               5                  10                  15

Val Asn Gly Leu Met Ser Leu Arg Arg Arg Lys Ile Ser Lys Lys Leu
            20                  25                  30

Pro Pro Gly Pro Phe Pro Leu Pro Ile Ile Gly Asn Leu His Leu Leu
        35                  40                  45

Gly Asn His Pro His Lys Ser Leu Ala Gln Leu Ala Lys Ile His Gly
    50                  55                  60

Pro Ile Met Asn Leu Lys Leu Gly Gln Leu Asn Thr Val Val Ile Ser
65                  70                  75                  80

Ser Ser Val Val Ala Arg Glu Val Leu Gln Lys Gln Asp Leu Thr Phe
                85                  90                  95

Ser Asn Arg Phe Val Pro Asp Val Val His Val Arg Asn His Ser Asp
            100                 105                 110

Phe Ser Val Val Trp Leu Pro Val Asn Ser Arg Trp Lys Thr Leu Arg
        115                 120                 125

Lys Ile Met Asn Ser Ser Ile Phe Ser Gly Asn Lys Leu Asp Gly Asn
130                 135                 140

Gln His Leu Arg Ser Lys Lys Val Gln Glu Leu Ile Asp Tyr Cys Gln
145                 150                 155                 160

Lys Cys Ala Lys Asn Gly Glu Ala Val Asp Ile Gly Arg Ala Thr Phe
                165                 170                 175

Gly Thr Thr Leu Asn Leu Leu Ser Asn Thr Ile Phe Ser Lys Asp Leu
            180                 185                 190

Thr Asn Pro Phe Ser Asp Ser Ala Lys Glu Phe Lys Glu Leu Val Trp
        195                 200                 205

Asn Ile Met Val Glu Ala Gly Lys Pro Asn Leu Val Asp Tyr Phe Pro
    210                 215                 220

Phe Leu Glu Lys Ile Asp Pro Gln Gly Ile Lys Arg Arg Met Thr Asn
225                 230                 235                 240

Asn Phe Thr Lys Phe Leu Gly Leu Ile Ser Gly Leu Ile Asp Asp Arg
                245                 250                 255

Leu Lys Glu Arg Asn Leu Arg Asp Asn Ala Asn Ile Asp Val Leu Asp

```
                    260                 265                 270
Ala Leu Leu Asn Ile Ser Gln Glu Asn Pro Glu Glu Ile Asp Arg Asn
                275                 280                 285
Gln Ile Glu Gln Leu Cys Leu Asp Leu Phe Ala Ala Gly Thr Asp Thr
    290                 295                 300
Thr Ser Asn Thr Leu Glu Trp Ala Met Ala Glu Leu Leu Gln Asn Pro
305                 310                 315                 320
His Thr Leu Gln Lys Ala Gln Glu Glu Leu Ala Gln Val Ile Gly Lys
                325                 330                 335
Gly Lys Gln Val Glu Glu Ala Asp Val Gly Arg Leu Pro Tyr Leu Arg
                340                 345                 350
Cys Ile Val Lys Glu Thr Leu Arg Ile His Pro Ala Ala Pro Leu Leu
                355                 360                 365
Ile Pro Arg Lys Val Glu Glu Asp Val Glu Leu Ser Thr Tyr Ile Ile
            370                 375                 380
Pro Lys Asp Ser Gln Val Leu Val Asn Val Trp Ala Ile Gly Arg Asn
385                 390                 395                 400
Ser Asp Leu Trp Glu Asn Pro Leu Val Phe Lys Pro Glu Arg Phe Trp
                405                 410                 415
Glu Ser Glu Ile Asp Ile Arg Gly Arg Asp Phe Glu Leu Ile Pro Phe
                420                 425                 430
Gly Ala Gly Arg Arg Ile Cys Pro Gly Leu Pro Leu Ala Met Arg Met
435                 440                 445
Ile Pro Val Ala Leu Gly Ser Leu Leu Asn Ser Phe Asn Trp Lys Leu
    450                 455                 460
Tyr Gly Gly Ile Ala Pro Lys Asp Leu Asp Met Gln Glu Lys Phe Gly
465                 470                 475                 480
Ile Thr Leu Ala Lys Ala Gln Pro Leu Leu Ala Ile Pro Thr Pro Leu
                485                 490                 495

<210> SEQ ID NO 42
<211> LENGTH: 513
<212> TYPE: PRT
<213> ORGANISM: Arabidopsis thaliana

<400> SEQUENCE: 42

Met Ala Thr Leu Phe Leu Thr Ile Leu Leu Ala Thr Val Leu Phe Leu
  1               5                  10                  15
Ile Leu Arg Ile Phe Ser His Arg Arg Asn Arg Ser His Asn Asn Arg
                 20                  25                  30
Leu Pro Pro Gly Pro Asn Pro Trp Pro Ile Ile Gly Asn Leu Pro His
             35                  40                  45
Met Gly Thr Lys Pro His Arg Thr Leu Ser Ala Met Val Thr Thr Tyr
         50                  55                  60
Gly Pro Ile Leu His Leu Arg Leu Gly Phe Val Asp Val Val Val Ala
 65                  70                  75                  80
Ala Ser Lys Ser Val Ala Glu Gln Phe Leu Lys Ile His Asp Ala Asn
                 85                  90                  95
Phe Ala Ser Arg Pro Pro Asn Ser Gly Ala Lys His Met Ala Tyr Asn
                100                 105                 110
Tyr Gln Asp Leu Val Phe Ala Pro Tyr Gly His Arg Trp Arg Leu Leu
            115                 120                 125
Arg Lys Ile Ser Ser Val His Leu Phe Ser Ala Lys Ala Leu Glu Asp
    130                 135                 140
```

-continued

```
Phe Lys His Val Arg Gln Glu Val Gly Thr Leu Thr Arg Glu Leu
145                 150                 155                 160

Val Arg Val Gly Thr Lys Pro Val Asn Leu Gly Gln Leu Val Asn Met
                165                 170                 175

Cys Val Val Asn Ala Leu Gly Arg Glu Met Ile Gly Arg Arg Leu Phe
            180                 185                 190

Gly Ala Asp Ala Asp His Lys Ala Asp Glu Phe Arg Ser Met Val Thr
        195                 200                 205

Glu Met Met Ala Leu Ala Gly Val Phe Asn Ile Gly Asp Phe Val Pro
    210                 215                 220

Ser Leu Asp Trp Leu Asp Leu Gln Gly Val Ala Gly Lys Met Lys Arg
225                 230                 235                 240

Leu His Lys Arg Phe Asp Ala Phe Leu Ser Ser Ile Leu Lys Glu His
                245                 250                 255

Glu Met Asn Gly Gln Asp Gln Lys His Thr Asp Met Leu Ser Thr Leu
            260                 265                 270

Ile Ser Leu Lys Gly Thr Asp Leu Asp Gly Asp Gly Ser Leu Thr
        275                 280                 285

Asp Thr Glu Ile Lys Ala Leu Leu Asn Met Phe Thr Ala Gly Thr
    290                 295                 300

Asp Thr Ser Ala Ser Thr Val Asp Trp Ala Ile Ala Glu Leu Ile Arg
305                 310                 315                 320

His Pro Asp Ile Met Val Lys Ala Gln Glu Glu Leu Asp Ile Val Val
                325                 330                 335

Gly Arg Asp Arg Pro Val Asn Glu Ser Asp Ile Ala Gln Leu Pro Tyr
            340                 345                 350

Leu Gln Ala Val Ile Lys Glu Asn Phe Arg Leu His Pro Pro Thr Pro
        355                 360                 365

Leu Ser Leu Pro His Ile Ala Ser Glu Ser Cys Glu Ile Asn Gly Tyr
370                 375                 380

His Ile Pro Lys Gly Ser Thr Leu Leu Thr Asn Ile Trp Ala Ile Ala
385                 390                 395                 400

Arg Asp Pro Asp Gln Trp Ser Asp Pro Leu Ala Phe Lys Pro Glu Arg
                405                 410                 415

Phe Leu Pro Gly Gly Glu Lys Ser Gly Val Asp Val Lys Gly Ser Asp
            420                 425                 430

Phe Glu Leu Ile Pro Phe Gly Ala Gly Arg Arg Ile Cys Ala Gly Leu
        435                 440                 445

Ser Leu Gly Leu Arg Thr Ile Gln Phe Leu Thr Ala Thr Leu Val Gln
450                 455                 460

Gly Phe Asp Trp Glu Leu Ala Gly Gly Val Thr Pro Glu Lys Leu Asn
465                 470                 475                 480

Met Glu Glu Ser Tyr Gly Leu Thr Leu Gln Arg Ala Val Pro Leu Val
                485                 490                 495

Val His Pro Lys Pro Arg Leu Ala Pro Asn Val Tyr Gly Leu Gly Ser
            500                 505                 510

Gly
```

<210> SEQ ID NO 43
<211> LENGTH: 7
<212> TYPE: PRT
<213> ORGANISM: Arabidopsis thaliana

<400> SEQUENCE: 43

```
Arg Pro Pro Asn Ser Gly Ala
 1               5
```

```
<210> SEQ ID NO 44
<211> LENGTH: 17
<212> TYPE: PRT
<213> ORGANISM: Arabidopsis thaliana
<220> FEATURE:
<221> NAME/KEY: UNSURE
<222> LOCATION: (8)
<223> OTHER INFORMATION: Xaa can be any amino acid.
<220> FEATURE:
<221> NAME/KEY: UNSURE
<222> LOCATION: (10)
<223> OTHER INFORMATION: Xaa cab be any amino acid.
<220> FEATURE:
<221> NAME/KEY: UNSURE
<222> LOCATION: (15)
<223> OTHER INFORMATION: Xaa can be any amino acid.

<400> SEQUENCE: 44

Arg Pro Pro Asn Ser Gly Ala Xaa His Xaa Ala Tyr Asn Tyr Xaa Asp
 1               5                  10                  15

Leu
```

```
<210> SEQ ID NO 45
<211> LENGTH: 521
<212> TYPE: PRT
<213> ORGANISM: Arabidopsis thaliana
<220> FEATURE:
<221> NAME/KEY: UNSURE
<222> LOCATION: (8)
<223> OTHER INFORMATION: Xaa can be any amino acid.
<220> FEATURE:
<221> NAME/KEY: UNSURE
<222> LOCATION: (10)
<223> OTHER INFORMATION: Xaa cab be any amino acid.
<220> FEATURE:
<221> NAME/KEY: UNSURE
<222> LOCATION: (15)
<223> OTHER INFORMATION: Xaa can be any amino acid.
<220> FEATURE:
<221> NAME/KEY: UNSURE
<222> LOCATION: (18)..(517)
<223> OTHER INFORMATION: Xaa can be any amino acid. Positions 18-517
      can be 0-500 amino acids.

<400> SEQUENCE: 45

Arg Pro Pro Asn Ser Gly Ala Xaa His Xaa Ala Tyr Asn Tyr Xaa Asp
 1               5                  10                  15

Leu Xaa Xaa Xaa Xaa Xaa Xaa Xaa Xaa Xaa Xaa Xaa Xaa Xaa Xaa
         20                  25                  30

Xaa Xaa Xaa Xaa Xaa Xaa Xaa Xaa Xaa Xaa Xaa Xaa Xaa Xaa Xaa
     35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
             100                 105                 110

Xaa Xaa Xaa Xaa Xaa Xaa Xaa Xaa Xaa Xaa Xaa Xaa Xaa Xaa Xaa
         115                 120                 125

Xaa Xaa Xaa Xaa Xaa Xaa Xaa Xaa Xaa Xaa Xaa Xaa Xaa Xaa Xaa
     130                 135                 140
```

-continued

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
        165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
        245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
        325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
        405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
        485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Gly Gly Glu Lys
        515             520